(12) United States Patent
Honma et al.

(10) Patent No.: US 7,153,622 B2
(45) Date of Patent: Dec. 26, 2006

(54) ELECTROSTATIC CHARGE IMAGE DEVELOPING TONER, PRODUCING METHOD THEREFOR, IMAGE FORMING METHOD AND IMAGE FORMING APPARATUS UTILIZING THE TONER, CONSTRUCT AND METHOD FOR MAKING THE CONSTRUCT

(75) Inventors: Tsutomu Honma, Kanagawa (JP); Tetsuya Yano, Kanagawa (JP); Tsuyoshi Nomoto, Tokyo (JP); Shinya Kozaki, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 14 days.

(21) Appl. No.: 10/827,670

(22) Filed: Apr. 20, 2004

(65) Prior Publication Data

US 2004/0259026 A1   Dec. 23, 2004

Related U.S. Application Data

(63) Continuation-in-part of application No. 10/133,404, filed on Apr. 29, 2002, now abandoned, and a continuation-in-part of application No. 10/133,670, filed on Apr. 29, 2002.

(30) Foreign Application Priority Data

| Apr. 27, 2001 | (JP) | ............................ 2001/131694 |
| Apr. 27, 2001 | (JP) | ............................ 2001/133728 |
| Jul. 10, 2001 | (JP) | ............................ 2001/208704 |
| Jul. 10, 2001 | (JP) | ............................ 2001/210021 |

(51) Int. Cl.
C08G 9/00 (2006.01)
C08G 63/00 (2006.01)
C08F 20/00 (2006.01)

(52) U.S. Cl. .................. 430/105; 528/360; 528/361; 528/364; 525/450; 522/38; 522/30; 522/68; 522/149; 522/165; 430/108.4; 430/108.5; 430/109; 430/109.2; 430/109.3; 430/110.2; 430/120; 430/124; 430/137.1; 430/222; 430/146; 430/148; 430/252.33; 430/252.34; 430/252.4

(58) Field of Classification Search ............... 528/360, 528/361, 364; 525/450; 522/28, 30, 68, 522/149, 165; 430/105, 108.4, 108.5, 109, 430/109.2, 110.2, 120, 124, 137.1, 222, 146, 430/148, 252.33, 252.34, 252.4
See application file for complete search history.

(56) References Cited

U.S. PATENT DOCUMENTS

| 4,393,167 | A | 7/1983 | Holmes et al. ............... 525/64 |
| 4,876,331 | A | 10/1989 | Doi ........................... 528/361 |
| 5,004,664 | A | 4/1991 | Fuller et al. ............. 430/106.6 |
| 5,135,859 | A | 8/1992 | Witholt et al. .............. 435/135 |
| 5,223,370 | A | 6/1993 | Sacripante et al. .......... 430/138 |
| 5,292,860 | A | 3/1994 | Shiotani et al. ............. 528/361 |
| 5,318,871 | A | 6/1994 | Inagaki et al. .............. 430/106 |
| 5,415,963 | A | 5/1995 | Toya et al. ................. 430/106 |
| 5,795,694 | A | 8/1998 | Uchiyama et al. .......... 430/109 |
| 6,025,028 | A | 2/2000 | Asrar et al. ................. 427/358 |
| 6,111,006 | A | 8/2000 | Waddington ................ 524/404 |
| 6,146,665 | A | 11/2000 | Marchessault et al. ...... 424/497 |
| 6,853,477 | B1 | 2/2005 | Nomoto et al. ............. 359/296 |
| 2003/0096115 | A1 | 5/2003 | Kozaki et al. ............. 428/404 |
| 2003/0113368 | A1 | 6/2003 | Nomoto et al. ............. 424/450 |
| 2003/0194443 | A1 | 10/2003 | Yano et al. ................. 424/497 |
| 2003/0203458 | A1 | 10/2003 | Kozaki et al. ............. 435/135 |
| 2003/0203987 | A1 | 10/2003 | Nomoto et al. ............. 523/160 |
| 2003/0224494 | A1 | 12/2003 | Nomoto et al. ............. 435/135 |

FOREIGN PATENT DOCUMENTS

| EP | 0900667 | 3/1999 |
| JP | 55-146786 | 11/1980 |
| JP | 62-17753 | 1/1987 |
| JP | 63-305367 | 12/1988 |
| JP | 5-9304 | 1/1993 |
| JP | 5-74492 | 3/1993 |
| JP | 5-88406 | 4/1993 |
| JP | 5-93049 | 4/1993 |
| JP | 5-119531 | 5/1993 |

| | | |
|---|---|---|
| JP | 5-221112 | 8/1993 |
| JP | 5-249725 | 9/1993 |
| JP | 5-289396 | 11/1993 |
| JP | 5-341574 | 12/1993 |
| JP | 6-15604 | 3/1994 |
| JP | 6-332225 | 12/1994 |
| JP | 7-14352 | 2/1995 |
| JP | 7-265065 | 10/1995 |
| JP | 8-19227 | 2/1996 |
| JP | 8-286416 | 11/1996 |
| JP | 9-43896 | 2/1997 |
| JP | 9-191893 | 7/1997 |
| JP | 2642937 | 8/1997 |
| JP | 9-292735 | 11/1997 |
| JP | 10-78676 | 3/1998 |
| JP | 11-7163 | 1/1999 |
| JP | 11-78221 | 3/1999 |
| JP | 2989175 | 12/1999 |
| JP | 2000-066444 | 3/2000 |
| JP | 2000-112174 | 4/2000 |
| JP | 2000-190631 | 7/2000 |
| JP | 2000-330321 | 11/2000 |
| JP | 2001-069968 | 3/2001 |
| JP | 2001-78753 | 3/2001 |
| WO | WO 99/04948 | 2/1999 |

OTHER PUBLICATIONS

Vogel, et al.; "Acetylornithinase of *Escherichia coli* . . . Properties"; J. Biol. Chem., 218, 97-106 (1956).
Speier, et al.; "The Addition of Silicon Hydrides to Olefinic Double Bonds . . . Tribromosilane"; J.A.C.S., 78, 2278 (1956).
Kraak, et al.; "*In vitro* activities of granule-bound poly[(R)-3-hyroxyalkanoate] . . . *oleovorans*"; Eur. J. Biochem, 250, 432-439, 1997.
Tang, et al.; "Organic electroluminescent diodes" Appl. Phys, Lett. 51 (12) 9, 1987, 913-915.
Yamaguchi, et al.; "Oxidation of ω-(Benzoyloxy)alkanols . . . Salt"; J. Org. Chem. 1990, 55; 1490-1492.
Fritzsche, et al.; "Production of unsaturated polyesters . . . *oleovorans*"; Int. J. Biol. Macromol., 1990, 12, 85-91.
Fritzsche, et al.; "An unusual bacterial polyester . . . group"; Makromal. Chem., 191, 1957-1965 (1990).
Antoun, et al.; "Production of a Chiral Polyester . . . Acid"; Chirality, 3, 6, 492-494 (1991).
Kim, et al.; "Preparation and Characterization of Poly(β-hydroxyalkanoates) . . . and n-Alkanoic Acids"; Macromolecules, 1991, 24, 5256-5260.
Lytle, et al.; "Filtration Sizes . . . Barrier Materials"; Appl. & Environm. Microbiol., 1992, 58, 2, 747-749.
Ritter, et al.; "Bacterial production of polyesters . . . chains, 1"; Macromol. Chem. Phys., 195, 1665-1672 (1994).
Kim, et al.; "Bioengineering of poly(β-hydroxyalkanoates) . . . substituents"; Can. J. Microbiol. 41, (Suppl. 1): 32-43 (1995).
Gerngross, et al.; "Enzyme-catalyzed . . . *in vitro*"; Proc. Natl. Acad. Sci. USA, 92, 6279-6283, 1995.
Curley, et al.; "Production of Poly(3-hydroxyalkanoates) . . . *oleovorans*"; Macromolecules 1996, 29, 1762-1766.

Kim, et al.; "Poly-3-hydroxyalkanoates . . . ω-Phenoxyalkanoates"; Macromolecules, 1996, 29, 3432-3435.
Yamaguchi, et al.; "Kinetics of Depolarization-Induced . . . *In Vitro*"; J. Biochem. 121, 432-439 (1997).
Andújar, et al.; "Polyesters Produced by . . . Cyclohexyl Groups"; Macromolecules, 1997, 30, 1611-1619.
Jossek, et al.; "In vitro synthesis of . . . recycling system"; FEMS Microbiology Letters, 168, (1998) 319-324.
Lenz, et al.; "Extracellular polymerization . . . *eutrophus*"; International Journal of Biological Macromolecules, 25 (1999) 55-60.
Aróstegui, et al.; "Bacterial Polyesters . . . Nitrophenyl Groups"; Macromolecules, 32, 9, (1999) 2889-2895.
Nobes, et al.; "Growth and kinetics of *in vitro* poly([R]-(—)-3-hydroxybutyrate) . . . coalescence"; Macromol. Rapid Commun., 21, 77-84 (2000).
Steinbüchel, et al.; "*In vitro* synthesis of poly(3-hydroxydecanoate) . . . *aeruginosa*"; Appl. Microbiol. Biotechnol., (2000) 54: 37-43.
Pelletier, et al.; 2-Hydroxycyclohexanecarboxyl Coenzyme . . . *palustris*; J. Bact., 182, 10, 2753-2760 (2000).
Ostle, et al.; "Nile Blue A as a Fluorescent Stain for Poly-β-Hydroxybutyrate"; Appl. & Environ. Microbiol., 44, 1982, 238-241.

*Primary Examiner*—Samuel A. Acquah
(74) *Attorney, Agent, or Firm*—Fitzpatrick, Cella, Harper & Scinto

(57) ABSTRACT

A construct that comprises a base material and a polyhydroxyalkanoate, wherein at least a part of the base material is coated with the polyhydroxyalkanoate, and the polyhydroxyalkanoate comprises a 3-hydroxyalkanoic acid unit other than 3-hydroxypropionic acid unit, 3-hydroxy-n-butyric acid unit, and 3-hydroxy-n-valeric acid unit.

In addition, an electrostatic charge image developing toner allows to design the toner characteristics such as chargeability, flowability, stability in time and environmental stability uniform among the toners of different colors. The toner has a small particle size enough for enabling uniform dispersion and being excellent in color saturation and transparency. The toner also shows higher contribution to the environmental security. The toner includes a coloring agent of which at least a part of the surface is covered with polyhydroxyalkanoate (PHA). The toner is produced by dispersing the coloring agent in aqueous medium, then fixing PHA synthesizing enzyme to the coloring agent dispersed in the aqueous medium, then adding 3-hydroxyacyl CoA, and executing a PHA synthesizing reaction to cover at least a part of the surface of the coloring agent with PHA. The toner thus obtained is used for an image forming method.

37 Claims, 12 Drawing Sheets

ELECTROSTATIC CHARGE IMAGE DEVELOPING TONER, PRODUCING METHOD THEREFOR, IMAGE FORMING METHOD AND IMAGE FORMING APPARATUS UTILIZING THE TONER, CONSTRUCT AND METHOD FOR MAKING THE CONSTRUCT

CROSS REFERENCE TO RELATED APPLICATIONS

This application is a continuation-in-part of U.S. application Ser. No. 10/133,404 now abandoned and a continuation-in-part of U.S. application Ser. No. 10/133,670, both filed on Apr. 29, 2002, the contents of which are incorporated herein by reference.

This application is based on Japanese Patent Application Nos. 2001-131694 (filed Apr. 27, 2001), 2001-133728 (filed Apr. 27, 2001), 2001-208704 (filed Jul. 10, 2001), and 2001-210021 (filed Jul. 10, 2001), all filed in Japan, the contents of which are incorporated herein by reference.

BACKGROUND OF THE INVENTION

1. Field of the Invention

The present invention relates to a construct comprising polyhydroxyalkanoate and a base material at least partly coated with the polyhydroxyalkanoate, and to a method for making the construct. More specifically, the present invention relates to a construct which comprises a base material that is at least partly coated with a polyhydroxyalkanoate made with a 3-hydroxyalkanoic acid monomer unit other than 3-hydroxypropionic acid unit, 3-hydroxy-n-butyric acid unit, or 3-hydroxy-n-valeric acid unit. The present invention also relates to a method for making the construct by immobilizing a polyhydroxyalkanoate synthetic enzyme that participates in medium chain length polyhydroxyalkanoate biosynthesis to the base material and carrying out synthesis of polyhydroxyalkanoate from 3-hydroxyacyl coenzyme A to coat at least part of the base material. Further, the construct of the present invention includes a capsule construct that comprises a particulate base material coated with polyhydroxyalkanoate, and a laminated construct that comprises a plate or film base material coated with polyhydroxyalkanoate.

Each construct of the present invention has a wide range of use as a functional construct. For example, the capsule construct can be used as a capsule toner for electrophotography, and the laminated construct can be used as a recording medium such as OHP film or inkjet recording medium.

The present invention also relates to electrostatic charge image developing toner employed in electrophotography, electrostatic recording or the like, a producing method for such toner and an image forming method utilizing such toner.

2. Related Background Art

Polymer materials are indispensable for today's life or industries. Polymer materials are utilized in various fields, for example, as housing materials for home electrics, packing materials, buffer materials and textile materials because of cheapness, light in weight and good formability. On the other hand, various polymer functional materials such as liquid crystals and coating materials have been produced utilizing the stable properties by introducing various functional substituents into polymer chains. These functional materials can expect larger market needs in a smaller production scale due to the higher added value than the bulk polymers as structural materials. Such polymeric functional materials have been produced by organic synthetic chemistry, for example, by introducing substituents during or after synthesis process of the polymer. Most polymers to be the skeleton of functional polymers are produced from petroleum-based raw materials by organic synthetic chemistry. Such polymers include polyethylene, polyethylene terephthalate, polyesters, polystyrene, polyvinylchloride, and polyacrylamide.

As one of the constituent techniques for confer higher added value to the polymer compound, the inventors of the present invention have been focusing on a layered construct in which a base material is coated with a polymer compound. By coating a certain base material a polymer compound, a composite construct having an extremely useful functionality can be obtained. Specific applications of such a construct include, for example, a capsule toner for electrophotography having a microcapsule structure encapsulating toner components in a polymer compound, and a recording medium for inkjet recording, where a sheet of base material is coated with a polymer compound.

Generally, in the electrophotography, an electrostatic latent image is formed by various means on a photosensitive material utilizing a photoconductive substance, then the latent image is developed with a toner, and the toner image is transferred to a transfer material such as paper according to the necessity and then fixed by heat, pressure, heat and pressure, or solvent vapor to obtain a copy image. As a toner used for this purpose, a "pulverized toner" has been used. The pulverized toner is produced by melting and mixing uniformly a colorant such as dyes and pigments in a thermoplastic resin, and then pulverizing the resin mixture by means of a pulverizer and a classifier to obtain a desired particle size. Although such a toner has excellent performance, there are some problems that, for example, the selection range of the materials is limited because brittleness is required the materials due to the making step in the toner production. In order to overcome such problems, Japanese Patent Publication No. 36-10231 or the like have suggested the manufacture of "a polymerized toner" by means of suspension polymerization. In the suspension polymerization, a polymerizable monomer, a colorant, a polymerization initiator, and if necessary a crosslinking agent and a charge controlling agent all of which are uniformly dissolved or dispersed are dispersed into a continuous phase (an aqueous phase, for example) containing a dispersion stabilizer by using an agitator, and polymerization reaction is carried out to obtain a desired toner. This method has advantages that, for example, brittleness is not required for the toner material because this method does not include pulverization step and consequently soft materials can be used. However, with such a polymerized toner of a fine particle size, the colorant and the charge controlling agent tend to be exposed on the toner surface, so that the toner tends to be affected by the colorant and reduction in uniform charging is concerned. In order to solve these problems, so-called "capsule toner" of which surface is coated with a polymer layer or layers has been proposed.

For example, Japanese Patent Application Laid-Open No. 8-286416, for example, discloses a capsule toner for electrostatic development and a production method in which polymerized particles are coated with a shell of a polar resin. In accordance with this method, a shell is formed around a core of a polymerized particle containing toner components by organic synthetic chemistry, by which the above described problem is overcome and an excellent capsule toner is obtained for electrostatic charge development with increased image durability and uniformity and stabilization of charging. In addition, Japanese Patent Application Laid-Open No. 9-292735 discloses a capsule toner for image formation in which a core made of a material of high thermal expansion and a release agent is covered with a hard resin layer. The above-described toner is a functional microcapsule designed such that the thermally expandable material within the core expands at fixation heating to break the shell and release the contained releasing agent out of the shell. Therefore, it can be expected that the above-described toner have such advantages that it can prevent offset when a film heating fixation apparatus is used, or it enables low-pressure fixation and alleviation of paper wrinkling when a roller fixing apparatus is used. Japanese Patent Application Laid-Open Nos. 5-119531, 5-249725, 6-332225, 9-43896, 10-78676, 11-7163, 2000-66444, 2000-112174, and 2000-330321 also disclose capsule constructs having a polymer shell and production methods thereof, all of which produce capsule toners by organic synthetic chemistry such as suspension polymerization, emulsion polymerization, precipitation polymerization, dispersion polymerization, soap-free emulsion polymerization, and seed polymerization.

However, these methods for making the capsule toners have some problems that the making process becomes extremely complicated and a large amount of solvents and surfactants are used in the making process.

On the other hand, the laminated construct comprised of a sheet of a base material coated with a polymer compound is used, for example, as a recording medium for inkjet recording system. In the inkjet recording system, micro-droplets of ink are applied to a recording medium such as paper to record images and characters on it by ejecting droplets on various operation principles. In such recording system, the ink contains a lot of liquid medium such as water and a mixture of water and organic solvents, so that the ink must be applied in a certain amount to obtain a high image density. In addition, since the ink droplets are continuously ejected to the recording medium, there may occur a beading phenomenon where the ejected ink droplets fuse and consequently dots will fuse leading to image distortion. Therefore, high ink-absorbing capacity and high ink-absorption speed are required for the inkjet recording medium.

For this purpose, it has been proposed a recording medium provided with an ink-receiving layer on the base material to increase ink absorption capacity. For example, Japanese Patent Application Laid-Open No. 55-146786 proposes a recording medium of which base material is coated with a water-soluble resin such as polyvinyl alcohol and polyvinyl pyrrolidone. In addition, Japanese Patent Application Laid-Open No. 5-221112 and others propose a recording medium employing a waterproof resin. Further, a recording medium employing an ionic resin as an ink receiving layer is proposed (Japanese Patent Application Laid-Open Nos. 11-78221 and 2000-190631, for example), to provide a recording medium excellent in wettability, water resistance, and dye-fixing properties, as well as the ink-absorption and drying properties and vivid image forming properties.

To form the ink absorbing layer on the base material, conventionally, coating methods have been widely used, for example, blade coating, air knife coating, roll coating, flash coating, gravure coating, kiss coating, die coating, extrusion coating, slide hopper coating, curtain coating, spray coating, etc.

In any of the methods mentioned above, the polymer compounds used for coating the base material are synthesized by organic synthesis, followed by addition of various functions.

Meanwhile, active studies have been done to produce polymer compounds by using biotechnology, and partly in practice. For example, known microbial polymers include polyhydroxyalkanoates (PHAs) such as poly-3-hydroxy-n-butyric acid (PHB), and copolymers of 3-hydroxy-n-butyric acid and 3-hydroxy-n-valeric acid (PHB/V); polysaccharides such as bacterial cellulose and pullulan; and polyamino acids such as poly-γ-glutamic acid and polylysine. Particularly, PHA can be processed into various products by melt-preparation etc., just like other existing plastics. In addition, because of excellent biocompatibility, application of PHA as medical soft materials is also expected.

It has been reported that many microorganisms produce PHA and accumulate it within cells. For example, microbial productions of PHB/V by *Alcaligenes eutrophus* H16 (ATCC No. 17699), *Methylobacterium* sp., *Paracoccus* sp., *Alcaligenes* sp., and *Pseudomonas* sp. have been reported (for example, Japanese Patent Application Laid-Open No. 5-74492, Japanese Patent Publication Nos. 6-15604, 7-14352, and 8-19227). Furthermore, *Comamonas acidovorans* IFO 13852 produces PHA comprised of monomer units of 3-hydroxy-n-butyric acid and 4-hydroxy-n-butyric acid (Japanese Patent Application Laid-Open No. 9-191893), and *Aeromonas caviae* produces a copolymer of 3-hydroxy-n-butyric acid and 3-hydroxyhexanoic acid (Japanese Patent Application Laid-Open Nos. 5-93049 and 7-265065).

Biosynthesis of these PHB and PHB/V is an enzymatic polymerization reaction using as a substrate (R)-3-hydroxybutyryl CoA or (R)-3-hydroxyvaleryl CoA that is synthesized from various carbon sources through various metabolic pathways within a living organism. The enzyme that catalyzes this polymerization reaction is PHB synthetase (this can be referred to as PHB polymerase or PHB synthase). CoA is an abbreviation for coenzyme A, and its chemical structure is represented by the following chemical formula.

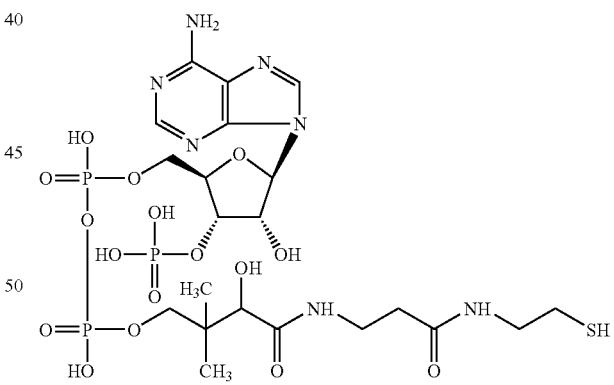

Recently, active studies on polyhydroxyalkanoate comprised of 3-hydroxyalkanoic acid units of medium-chain-length (about 3 to 12 carbon atoms) (mcl-PHA) have been conducted.

For example, Japanese Patent No. 2642937 discloses that *Pseudomonas oleovorans* ATCC 29347 can produce PHA comprised of 3-hydroxyalkanoic acid monomer units of 6 to 12 carbon atoms from non-cyclic aliphatic hydrocarbons. In addition, it has been reported, in Appl. Environ. Microbiol., 58, 746 (1992), that *Pseudomonas resinovorans* produces PHA of which monomer units are 3-hydroxy-n-butyric acid, 3-hydroxyhexanoic acid, 3-hydroxyoctanoic acid, and 3-hydroxydecanoic acid using octanoic acid as a sole carbon source, and it also produces PHA of which monomer units are 3-hydroxy-n-butyric acid, 3-hydroxyhexanoic acid, 3-hydroxyoctanoic acid, and 3-hydroxydecanoic acid using hexanoic acid as sole carbon source. Here, the 3-hydroxy-alkanoic acid monomer units longer than the raw material fatty acid are considered derived from the fatty acid synthesizing pathway described below.

Int. J. Biol. Macromol., 16 (3), 119 (1994) reported that *Pseudomonas* sp. Strain 61-3 produces PHA comprised of monomer units of 3-hydroxyalkanoic acids such as 3-hydroxy-n-butyric acid, 3-hydroxyhexanoic acid, 3-hydroxyoctanoic acid, and 3-hydroxydecanoic acid, and 3-hydroxyalkenoic acids such as 3-hydroxy-5-cis-decenoic acid and 3-hydroxy-5-cis-dodecenoic acid, using sodium gluconate as a sole carbon source.

The above-described PHAs are comprised of monomer units having alkyl groups as the side chain (usual-PHAs). However, when wider application of PHA, e.g., as a functional polymer, is intended, PHA having side chains other than alkyl groups (for example, side chains having substituents such as phenyl group, unsaturated hydrocarbons, ester groups, allyl group, cyano group, halogenated hydrocarbons, and epoxides) is extremely useful (unusual-PHA).

As for biosynthesis of unusual-PHA having phenyl groups, it was reported that *Pseudomonas oleovorans* produced PHA having 3-hydroxy-5-phenylvaleric acid units from 5-phenylvaleric acid (Polymers, 24, 5256–5260 (1991), Macromol. Chem., 191, 1957–1965 (1990); Chirality, 3, 492–494 (1991)). Polymers, 29, 1762–1766 (1996) reported that *Pseudomonas oleovorans* produced PHA having 3-hydroxy-5-(4-tolyl)valeric acid units from 5-(4-tolyl) valeric acid (5-(4-methylphenyl)valeric acid). Further, Polymers, 32, 2889–2895 (1999) reported that *Pseudomonas oleovorans* produced PHA having 3-hydroxy-5-(2,4-dinitrophenyl)valeric acid units and 3-hydroxy-5-(4-nitrophenyl) valeric acid units from 5-(2,4-dinitrophenyl)valeric acid.

As for unusual-PHA having phenoxy groups, Macromol. Chem. Phys., 195, 1665–1672 (1994) reported that *Pseudomonas oleovorans* produced PHA having 3-hydroxy-5-phenoxyvaleric acid units and 3-hydroxy-9-phenoxynonanoic acid units from 11-phenoxyundecanoic acid. Also, Polymers, 29, 3432–3435 (1996) reported that *Pseudomonas oleovorans* produced a PHA having 3-hydroxy-4-phenoxybutyric acid units and 3-hydroxy-6-phenoxyhexanoic acid units from 6-phenoxyhexanoic acid, a PHA having 3-hydroxy-4-phenoxybutyric acid units, 3-hydroxy-6-phenoxyhexanoic acid units, and 3-hydroxy-8-phenoxyoctanoic acid units from 8-phenoxyoctanoic acid, and a PHA having 3-hydroxy-5-phenoxyvaleric acid unit and 3-hydroxy-7-phenoxyheptanoic acid units from 11-phenoxyundecanoic acid. Further, Can. J. Microbiol., 41, 32–43 (1995) reported that *Pseudomonas oleovorans* ATCC 29347 and *Pseudomonas putida* KT 2442 produced PHA having 3-hydroxy-p-cyanophenoxyhexanoic acid units and PHA having 3-hydroxy-p-nitrophenoxyhexanoic acid units from p-cyanophenoxyhexanoic acid and p-nitrophenoxyhexanoic acid respectively. Japanese Patent No. 2989175 describes a homopolymer comprised of 3-hydroxy-5-(monofluorophenoxy)valeric acid units or 3-hydroxy-5-(difluorophenoxy) valeric acid units and a copolymer containing at least 3-hydroxy-5-(monofluorophenoxy)pentanoate unit or 3-hydroxy-5-(difluorophenoxy)pentanoate unit and a method for producing such homopolymer or copolymer, reciting that such homopolymer and copolymer can provide water-repellency and stereoregularity with high melting point and good workability.

As an example of unusual-PHA having a cyclohexyl group, Polymers, 30, 1611–1615 (1997) reported that *Pseudomonas oleovorans* produced such PHA from cyclohexylbutyric acid or cyclohexylvaleric acid.

These mcl-PHA and unusual-PHA are synthesized through an enzymatic polymerization reaction using (R)-3-hydroxyacyl CoA as a substrate. Such 3-hydroxyacyl CoAs are produced through various metabolic pathways (for example, β-oxidation pathway or fatty acid synthesis pathway) in a living organism from different alkanoic acids. The enzyme that catalyzes this polymerization reaction is PHA synthetase (this can be referred to as PHA polymerase or PHA synthase). The following is the reaction route from alkanoic acid to PHA via the β-oxidation pathway and polymerization reaction by PHA synthetase.

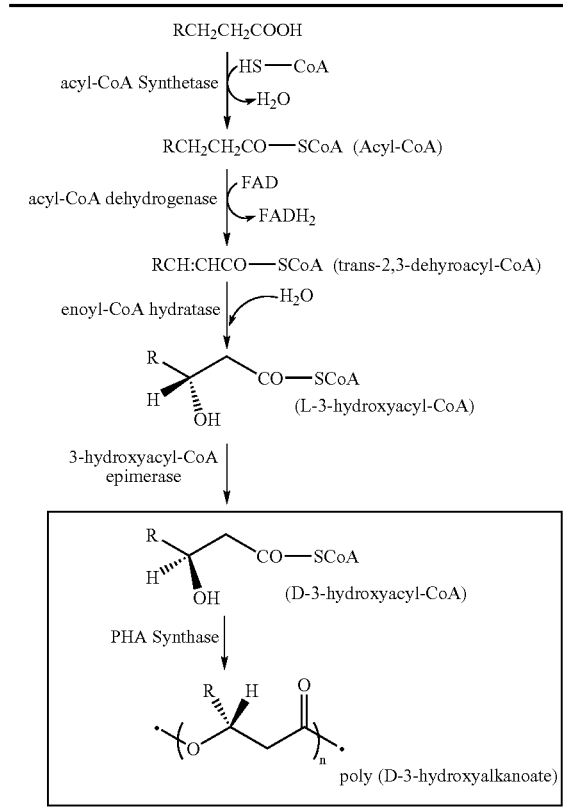

On the other hand, when the production is performed through the fatty acid synthesis pathway, it is considered that (R)-3-hydroxyacyl-ACP (ACP means acyl carrier protein) generated in this pathway is converted to (R)-3-hydroxyacyl CoA from which PHA is synthesized by PHA synthetase.

Recently, attempts have been made to synthesize PHA in vitro using PHB synthetase or PHA synthetase isolated from cells.

For example, Proc. Natl. Acad. Sci. USA, 92, 6279–6283 (1995) describes that PHB comprised of 3-hydroxy-n-butyric acid units has been successfully synthesized by using PHB synthetase derived from *Alcaligenes eutrophus* and 3-hydroxybutyryl CoA as a substrate. In addition, Int. J. Biol. Macromol., 25, 55–60 (1999) describes that PHA comprised of 3-hydroxy-n-butyric acid units or 3-hydroxy-n-valeric acid units has been successfully synthesized by reacting PHB synthetase derived from *Alcaligenes eutro*-

*phus* with 3-hydroxybutyryl CoA or 3-hydroxyvaleryl CoA. Further, this report mentions that, when racemic 3-hydroxybutyryl CoA was reacted with PHB synthetase, PHB comprised of only (R)3-hydroxy-n-butyric acid units was successfully synthesized due to the stereoselectivity of the enzyme. Macromol. Rapid Commun., 21, 77–84 (2000) reported in vitro PHB synthesis using PHB synthetase derived from *Alcaligenes eutrophus*.

FEMS Microbiol. Lett., 168, 319–324 (1998) describes that PHB comprised of 3-hydroxy-n-burytic acid units was successfully synthesized by reacting PHB synthetase derived from *Chromatium vinosum* with 3-hydroxybutyryl CoA.

In Appl. Mircobiol. Biotechnol., 54, 37–43 (2000), PHA comprised of 3-hydroxydecanoic acid is synthesized by reacting PHA synthetase derived from *Pseudomonas aeruginosa* with 3-hydroxydecanoyl CoA.

As described above, application of biotechnological methods to polymer synthesis may enable synthesis of new polymer compounds which can not be made by conventional organic synthesis or enable imparting new functions and constructs to polymer compounds. In addition, there are many cases where conventional multi-step reaction can be replaced with only one step reaction, so that simplification of the production process, cost reduction, and time saving are expected. Further, this enables consumption reduction of organic solvents, acids, alkalis, surfactants, etc., moderate reaction conditions, and synthesis from non-petroleum raw materials or crude raw materials, thus enables a synthesis process of lower environmental burden and of resource-recycling type. In more detail with synthesis from the crude raw materials, the substrate specificity of the enzyme used as a catalyst in biotechnological synthesis is high in general, so that it is possible to selectively promote a desired reaction even when the low purity raw material is used. Thus, use of waste materials or recycled materials can be expected.

On the other hand, as an elemental technical idea for adding values to polymer compounds, the inventors of the present invention has been focusing on a construct in which a base material is coated with a polymer compound as described above. Coating a certain base material with a polymer compound can provide composite constructs having extremely useful functionality. Conventionally, organic synthesis techniques have been used to produce such constructs, but there are certain limits to such techniques.

If such a construct can be manufactured by using a biotechnological method as described above, it is possible to utilize new polymer compounds that can not be realized by conventional organic synthesis techniques or to impart new functions and constructs to polymer compounds. It is also possible to achieve a making process being less burdening environment and of resource-recycling type at a low cost. For example, utilizing the highly strict molecular recognition ability or stereoselectivity specific to biocatalysts, it is possible to produce capsule constructs or laminated constructs coated with a new functional polymer compound or a polymer compound having extremely high chirality that could not be realized through conventional techniques of the synthetic organic chemistry, through a simple process with low environmental burden.

Therefore, the present invention provides a construct of highly functional polymer compound that can be manufactured by a biotechnological method. The present invention also provides an efficient method for making a construct of a base material coated with a polymer compound usable as a functional composite construct.

Meanwhile, in the field of electrophotography, various methods are known but generally consist of utilizing a photoconductive material, forming an electrical latent image on an image bearing member (photosensitive member) by various means, developing such latent image with toner to obtain a visible image, then transferring if necessary the toner image onto a transfer material such as paper, and fixing the toner image onto the transfer material by heat and/or pressure thereby obtaining a copy. For rendering the electrical latent image visible, there are known a cascade development method, a magnetic brush development method, a pressure development method etc. There is also known a method of employing magnetic toner and a rotary developing sleeve having magnetic poles at the center thereof, thereby causing the magnetic toner to fly from the developing sleeve to the photosensitive member. In the development method for developing the electrostatic latent image, there is known a two-component development method employing two-component developer consisting of toner and carrier, and a one-component development method employing one-component developer consisting solely of toner and not employing carrier.

The colorant generally called toner (hereinafter colorant means a substance which contains a coloring agent as the essential component and may contain other components for providing other functions) contains binder resin and a coloring agent (hereinafter coloring agent means carbon black, pigment, dye or other coloring material itself) as the essential components and further contains magnetic powder or the like if necessary. For a monochromatic copying apparatus there is utilized not only black toner but also monochromatic color toner such as of red, blue, green or brown color, and, in such color toner there is utilized a pigment or a dye for developing respective color instead of the black coloring agent (principally carbon black) in the black toner.

In preparing color toner with such pigment or dye, there is widely employed a method kneading such pigment or dye with binder resin, then executing crushing with a mechanical or air collision crusher and executing classification to achieve desired average particle size and particle size distribution. However, such conventional method has been associated with drawbacks that the coloring agent etc. added in the toner may not be uniformly dispersed depending on the component, or that it may be difficult to produce the toner of a small particle size with a narrow particle size distribution whereby such toner of the conventional method may generate image fog because of the significant loss of charge in certain cases, and that the particle size distribution may become wider to result in selective development thereby leading to deterioration in the image.

Also, since the chargeability and the powder flowability are different for each coloring agent, it is generally conducted to adjust the kind and amount of the internally added charge control agent or the externally added materials, in order to obtain uniform characteristics among the color toners. Also in a full-color copying apparatus, there are employed color toners of magenta, cyan and yellow colors in addition to the black color toner, and, also in this case, there is executed adjustment on the kind and amount of the internally added charge control agent or the externally added material as explained above, in order to obtain uniform characteristics among the color toners. However, such adjustment of the kind and amount of the internally or externally added material as explained in the foregoing for obtaining uniform characteristics in the color toners may practically be quite cumbersome and difficult, so that, both for monochromatic toner and full-color toner, there have been drawbacks of fluctuation in the quality of the copy image or difference in behavior of deterioration among the color toners.

Also in recent years, in the image formation with the full-color electrophotography, though the image quality of the full-color copying apparatus has been improved by the expansion of color presenting area by the improvement in the pigment dispersing technology and by the higher resolution of the image based on the toner of smaller average particle size of 7 to 8 μm, the electrophotographic image is still deficient in the uniformity of image luster, uniformity or image height and reproducibility of halftone image area in comparison with the offset printed image.

In order to resolve the aforementioned unevenness of the image, there is being investigated reduction of the toner amount loaded on the transfer medium based on a further reduction of the diameter of the toner. However, in order to reproduce a density same as that of the printed image with the toner of smaller diameter, it becomes necessary to increase the concentration of the coloring agent to be added in the toner, but an increase in the concentration of the coloring agent in the toner renders it difficult to control the charge amount of the toner, whereby the fluctuation in the charge amount may increase particularly under a high temperature-high humidity or low temperature-low humidity condition or in certain coloring agent, resulting in deterioration of the image quality. Also since the coloring agent enhances the influence on the fusing characteristics of the binder resin, there may result difficulty in the fixing ability such as generation of hot offset phenomenon or decrease of image intensity.

In order to alleviate the aforementioned influence of the coloring agent on the characteristics of toner, the Japanese Patent Application Laid-open Nos. 62-17753, 5-88406, 5-289396 and 5-341574 propose, in toner utilizing resin having surface activating effect as an auxiliary dispersant and having a matrix-domain structure formed by fused phase separation of the resins of different compositions, to disperse the coloring agent only in the domain portion, and the Japanese Patent Application Laid-open No. 63-305367 proposes to cover a nucleus particle, prepared by suspension polymerization and containing the coloring agent in a large amount, with resin of a high electrical resistance not containing the coloring agent by two-step polymerization, thereby controlling the electrical resistance of the toner surface, thus balancing the color developing property and the electrical characteristics.

These proposals can control the dispersion area of the coloring agent in the toner to a certain extent and can therefore relax the influence of the coloring agent on the toner characteristics. However, for achieving phase separation of the resins in the former method, the selection range of the resins is limited because the resin to be used in the matrix and that to be used in the domain have to be mutually unmixable, so that there will result drawbacks that the particle size and distribution of the domain is difficult to control and that it is difficult to include the coloring agent only in the domain in case the concentration of the coloring agent is high or in certain types of the coloring agent.

On the other hand, in the latter method, the toner is prepared by preparing the nucleus particle containing the coloring agent in a large amount by suspension polymerization and then by adding a monomer, but, since the nucleus particle and the monomer constituting the covering resin are of similar types and are mutually well soluble, the coloring agent inevitably migrates to the toner surface to result in deterioration of the toner chargeability and the fixing property. Also in the suspension polymerization, since the concentration of the coloring agent that can be introduced into the nucleus particle is limited, it is difficult to attain a high concentration of the coloring agent in the toner and it is not possible to reduce the size of the nucleus particle. Also in the nucleus particle produced by the suspension polymerization, since the polymerization initiator or the surfactant such as the suspension stabilizer used in a large amount remain in the capsule, the type or amount of the surfactant or the polymerization initiator are limited for certain applications and it may become difficult to attain the desired objective.

Also in the aforementioned producing methods, organic solvent is often used for monomer polymerization or for polymer dissolution, so that it is difficult to use the coloring agent soluble in the organic solvent. Also in case the organic solvent is used in a large amount for mass production, there results a large burden on the facility, human body and environment, such methods are not preferred also in such aspect. Further, these methods are associated with a drawback that the reaction conditions are not easily controllable and that the process steps are also complicated.

On the other hand, bioengineering methods for producing polymer compounds are actively investigated in recent years and are partially employed commercially. As examples of microorganism-origin polymer compounds, there are known polyhydroxyalkanoates (which may hereinafter be abbreviated as PHA) such as poly-3-hydroxy-n-butyric acid (which may hereinafter be abbreviated as PHB) or a copolymer of 3-hydroxy-n-butyric acid and 3-hydroxy-n-valeric acid (which may hereinafter be abbreviated as PHB/V), polysaccharides such as bacteria cellulose or purulan, and polyamino acids such as poly-γ-glutamic acid or polylysin. Such PHA produced by the microorganisms can be utilized for producing various products for example by fusion, like the conventional plastics. It also shows satisfactory matching with the living tissues and is expected in the applications as the soft material for medical use.

It has been reported that various microorganisms produce and accumulate PHA. For example, the production of PHB/V by the microorganisms of *Alcaligenes eutropus* H16 (ATCC No. 17699), *Methylobacterium* sp., *Paracoccus* sp., *Alcaligenes* sp. and *Pseudomonas* sp. is reported (Japanese Patent Application Laid-open No. 5-74492, Japanese Patent Publications Nos. 6-15604, 7-14352 and 8-19227 etc.).

It is also disclosed that *Comamonas acidovorans* (IFO 13852) produce PHA having monomer units including 3-hydroxy-n-butyric acid and 4-hydroxy-n-butyric acid (Japanese Patent Application Laid-open No. 9-191893). It is also disclosed that *Aeromonas caviae* produce copolymer of 3-hydroxy-n-butyric acid and 3-hydroxyhexanoic acid (Japanese Patent Application Laid-open Nos. 5-93049 and 7-265065).

The biosynthesis of such PHB or PHB/V is executed by a polymerization reaction by an enzyme utilizing, as the substrate, (R)-3-hydroxybutyryl CoA or (R)-3-hydroxyvaleryl CoA produced from various carbon sources through various metabolism paths in the microorganisms. The enzyme catalyzing such polymerization reaction is PHB synthesizing enzyme (also called PHB polymerase or PHB synthase). CoA means coenzyme A having the following chemical structure:

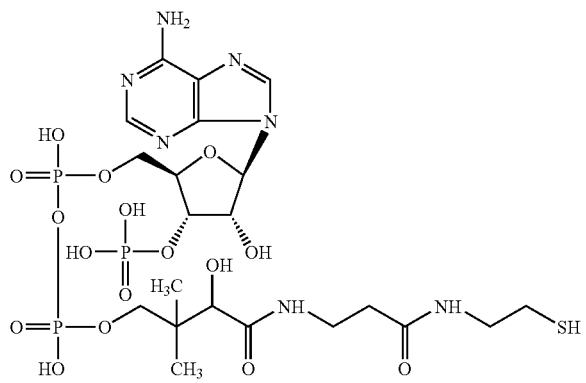

Also in recent years, investigations are actively executed on polyhydroxyalkanoate consisting of 3-hydroxy alkanoic acid unit of a medium-chain-length with 3 to 12 carbon atoms (which may be hereinafter abbreviated as mcl-PHA).

For example, Japanese Patent No. 2642937 discloses that *Pseudomonas oleovorans* ATCC 29347 supplied with acyclic aliphatic hydrocarbon produces PHA including 3-hydroxy alkanoic acid monomer unit with 6 to 12 carbon atoms. Also, Appl. Environ. Microbiol., 58, 746(1992) reports that *Pseudomonas resinovorans* produces PHA including 3-hydroxy-n-butyric acid, 3-hydroxy-hexanoic acid, 3-hydroxy-octanoic acid and 3-hydroxy-decanoic acid as monomer units from octanoic acid as the single carbon source, and PHA including 3-hydroxy-n-butyric acid, 3-hydroxy-hexanoic acid, 3-hydroxy-octanoic acid and 3-hydroxy-decanoic acid as monomer units from hexanoic acid as the single carbon source. In these syntheses, the introduction of a 3-hydroxyalkanoic acid unit having a chain length longer than that of the starting fatty acid is assumed to result from a fatty acid synthesis path to be explained later.

Int. J. Biol. Macromol., 16(3), 119(1994) reports that *Pseudomonas* sp. strain 61-3 produces, from sodium gluconate as a single carbon source, PHA including, as units thereof, 3-hydroxyalkanoic acids such as 3-hydroxy-n-butyric acid, 3-hydroxyhexanoic acid, 3-hydroxyoctanoic acid, 3-hydroxy decanoic acid and 3-hydroxydodecanoic acid, and 3-hydroxyalkenoic acids such as 3-hydroxy-5-cis-decenoic acid and 3-hydroxy-5-cis-dodecenoic acid.

The aforementioned PHA is a PHA consisting of a monomer unit having an alkyl radical in the side chain (which may hereinafter be abbreviated as usual-PHA). However, for wider applications, for example for application as functional polymer, PHA having a substituent other than alkyl radical, such as phenyl radical, unsaturated hydrocarbon radical, ester radical, allyl radical, cyano radical, halogenated hydrocarbon, epoxide etc., in the side chain (such PHA may hereinafter be abbreviated as unusual-PHA) is anticipated to be extremely useful.

As an example of biosynthesis of unusual-PHA containing phenyl radical, Macromolecules, 24, 5256–5260(1991), Macromol. Chem., 191, 1957–1965(1990) and Chirality, 3, 492–494(1991) report that *Pseudomonas oleovorans* produces PHA containing 3-hydroxy-5-phenylvaleric acid as a unit, from 5-phenylvaleric acid. Also Macromolecules, 29, 1762–1766(1996) reports that *Pseudomonas oleovorans* produces PHA containing 3-hydroxy-5-(4-tolyl)valeric acid as a unit, from 5-(4-tolyl)-valeric acid (i.e. 5-(4-methylphenyl)valeric acid). Also Macromolecules, 32, 2889–2895 (1999) reports that *Pseudomonas oleovorans* produces PHA containing 3-hydroxy-5-(2,4-dinitrophenyl)valeric acid and 3-hydroxy-5-(4-nitrophenyl)valeric acid as units, from 5-(2,4-dinitrophenyl)valeric acid.

Also as examples of unusual-PHA containing phenoxy radical, Macromol. Chem. Phys., 195, 1665–1672(1994) reports that *Pseudomonas oleovorans* produces PHA containing 3-hydroxy-5-hydroxyvaleric acid and 3-hydroxy-9-phenoxynonanoic acid as the units, from 11-phenoxyundecanoic acid. Also Macromolecules, 29, 3432–3435(1996) reports that *Pseudomonas oleovolans* produces PHA including 3-hydroxy-4-phenoxybutyric acid unit and 3-hydroxy-6-phenoxyhexanoic acid unit from 6-phenoxyhexanoic acid, also produces PHA including 3-hydroxy-4-phenoxybutyric acid unit, 3-hydroxy-6-phenoxyhexanoic acid unit and 3-hydroxy-8-phenoxyoctanoic acid unit from 8-phenoxyoctanoic acid, and produces PHA including 3-hydroxy-5-phenoxyvaleric acid unit and 3-hydroxy-7-phenoxyheptanoic acid unit from 11-phenoxyundecanoic acid.

Also Can. J. Microbiol., 41, 32–43(1995) reports production of PHA containing 3-hydroxy-6-(p-cyanophenoxy)hexanoic acid or 3-hydroxy-6-(p-nitrophenoxy)hexanoic acid as the monomer unit by *Pseudomonas oleovorans* ATCC 29347 strain and *Pseudomonas putida* KT2442 strain, from p-cyanophenoxy hexanoic acid or p-nitrophenoxy hexanoic acid. The Japanese Patent No. 2989175 discloses homopolymer consisting of 3-hydroxy-5-(monofluorophenoxy) valeric acid unit or 3-hydroxy-5-(difluorophenoxy) valeric acid unit, copolymer including at least 3-hydroxy-5-(monofluorophenoxy)pentanoate unit or 3-hydroxy-5-(difluorophenoxy)pentanoate unit and a producing method therefor, and describes the advantages thereof such as providing stereo regularity and water repellency while maintaining high melting point and satisfactory workability.

Also as examples of unusual-PHA having cyclohexyl radical, Macromolecules, 30, 1611–1615(1997) reports that *Pseudomonas oleovolans* produces such PHA from cyclohexylbutyric acid or cyclohexylvaleric acid.

The biosynthesis of such mcl-PHA or unusual-PHA is executed by a polymerization reaction by an enzyme utilizing, as the substrate, (R)-3-hydroxyacyl CoA produced from various alkanoic acid sources through various metabolism paths (β-oxidation system or fatty acid synthesis path) in the microorganisms. The enzyme catalyzing such polymerization reaction is PHA synthesizing enzyme (also called PHA polymerase or PHA synthase). In the following there are shown reactions from alkanoic acid to PHA through the polymerization reaction by β-oxidation system and PHA synthesizing enzyme.

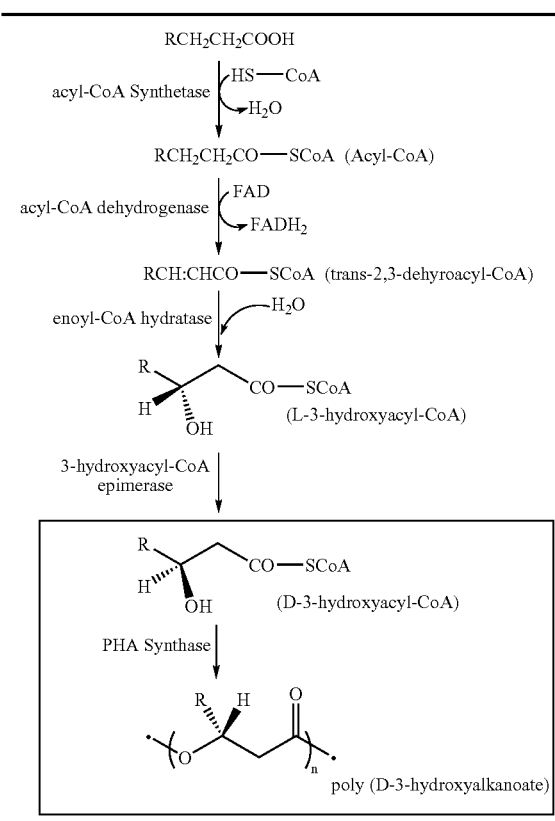

On the other hand, in case through the fatty acid synthesis path, PHA is assumed to be synthesized similarly by the PHA synthesizing enzyme, from (R)-3-hydroxyacyl CoA converted from (R)-3-hydroxyacyl-ACP (ACP means acyl carrier protein) generated in such path as the substrate.

Recently, it is being tried to take out the aforementioned PHB synthesizing enzyme or PHA synthesizing enzyme from the bacteria and to synthesize PHA in cell-free system (in vitro).

For example, Proc. Natl. Acad. Sci. USA, 92, 6279–6283 (1995) reports reacting 3-hydroxybutyryl CoA on PHB synthesizing enzyme derived from *Alcaligenes eutrophus* to produce PHB consisting of 3-hydroxy-n-butyric acid unit. Also Int. J. Biol. Macromol., 25, 55–60(1999) reports reacting 3-hydroxybutyryl CoA or 3-hydroxyvaleryl CoA on PHB synthesizing enzyme derived from *Alcaligenes eutrophus* to produce PHA consisting of 3-hydroxy-n-butyric acid unit or 3-hydroxy-n-valeric acid unit. Also this report describes that reaction of racemic 3-hydroxy-butyryl CoA results in synthesis of PHB consisting solely of (R)-3-hydroxy-n-butyric acid unit by the stereo selectivity of the enzyme. Also Macromol. Rapid Commun., 21, 77–84(2000) reports in vitro PHB synthesis utilizing PHB synthesizing enzyme derived from *Alcaligenes eutrophus*.

Also FEMS Microbiol. Lett., 168, 319–324(1998) reports reacting 3-hydroxybutyryl CoA on PHB synthesizing enzyme derived from Chromatium vinosum to produce PHB consisting of 3-hydroxy-n-butyric acid unit.

Appl. Microbiol. Biotechnol., 54, 37–43(2000) reports synthesis of PHA consisting of 3-hydroxy-decanoic acid unit by reacting 3-hydroxydecanoyl CoA on PHA synthesizing enzyme of *Pseudomonas aeruginosa*.

SUMMARY OF THE INVENTION

As a result of intensive investigation to achieve the above objects, the inventors have found that a construct of a base material coated with PHA can be obtained by immobilizing PHA synthetase to a surface of the base material and adding 3-hydroxyacyl CoA thereto and synthesizing desired PHA on the surface of the base material. Thus, the inventors have accomplished the present invention. Furthermore, the inventors have found that a construct having various improved properties can be obtained by chemically modifying the above-described PHA. More specifically, the inventors have found that, for example, by introducing a graft chain into PHA, one can obtain a construct of which base material is at least partly coated with PHA having properties derived from the introduced graft chains. In addition, the inventors have found that by crosslinking PHA, one can obtain a construct of which base material is at least partly coated with PHA having desired physico-chemical properties (for example, mechanical strength, chemical resistance, heat resistance, etc.). In the present invention, the chemical modification means alteration of the molecular structure of the polymeric material by a chemical reaction within the polymer or between polymer molecules or between the polymer and other chemical substance. The crosslinking means formation of a network structure by chemical or physico-chemical intramolecular or intermolecular bonding of the polymeric materials, and a crosslinking agent means a substance having a certain reactivity with the above described polymeric material to be added for crosslinking reaction.

Thus, according to one aspect of the present invention, there is provided a construct in which at least a part of a base material is coated with polyhydroxyalkanoate which contains 3-hydroxyalkanoic acid units (excluding a 3-hydroxypropionic acid unit, a 3-hydroxy-n-butyric acid unit, or a 3-hydroxy-n-valeric acid unit).

The present invention also relates to a method for making a construct in which at least a part of a base material is coated with polyhydroxyalkanoate by immobilizing a medium chain length of polyhydroxyalkanoate synthetase to a surface of the base material, and then performing polymerization of 3-hydroxyacyl coenzymes A by the above described synthetase to synthesize the polyhydroxyalkanoate.

In addition, the present invention relates to a capsule construct having a base material as a core and mcl-PHA or unusual-PHA as a shell, and more particularly, the present invention relates to a capsule construct in which the core contains colorants at the least, a capsule construct in which the colorants contain pigments at the least, or a capsule construct in which the core is a pigment. Further, the present invention relates to a laminated construct in which at least a part of a plate-like or film-like base material is coated with mcl-PHA or unusual-PHA.

In addition, the present invention relates to a capsule toner for electrophotography comprised of the above described capsule construct or to a recording medium comprised of the above described laminated construct.

Further, the present invention relates to a method of image formation which uses the above described toner and to an image forming apparatus.

Meanwhile, in conventional electrostatic charge image developing toners, as explained in the foregoing, it has often been difficult to provide the electrostatic charge image developing toners having uniform toner characteristics such as chargeability, flowability, stability in time, environmental stability etc. among the toners of different colors including black color. Also in the full-color electrostatic charge image developing toner of small diameter, there may result deterioration of the charging characteristics, powder characteristics, charge amount maintainability and fixing characteristics with an increase in the concentration of the coloring agent.

Also there has been desired electrostatic charge image developing toner of a small particle size, containing the coloring agent dispersed uniformly and finely, excellent in color saturation and transparency, uniformity of charging and durability. Also there has been desired such electrostatic charge image developing toner having low burden on the environment or organisms, low limitation on the material of the coloring agent, and including a capsule structure (colorant) containing the coloring agent at a high concentration and free from contamination of surfactant or polymerization initiator which has been the contamination sources of the conventional capsule structure.

The object of the present invention is to provide electrostatic charge image developing toner capable of resolving the aforementioned drawbacks, a method for producing such electrostatic charge image developing toner, and an image forming method and an image forming apparatus utilizing such electrostatic charge image developing toner.

As a result of intensive investigation for attaining the above-mentioned object, the present inventors have found that the coloring agent can be easily included in minute microcapsules without employing surfactant, by fixing a polyhydroxyalkanoate (hereinafter abbreviated PHA) synthesizing enzyme on the coloring agent and executing reaction by adding 3-hydroxyacyl coenzyme A thereto, also that the coloring agent is included at a high density because PHA directly covers the surface of the coloring agent, and that the mutual solubility of PHA, constituting the covering of the coloring agent, with the binder resin by suitably selecting the type of 3-hydroxyacyl coenzyme A.

It is also found that a structured material improved in various characteristics (particularly control of the aforementioned mutual solubility) by applying chemical modification to such PHA. More specifically, it is found that, by introducing a graft chain to such PHA, there can be obtained colorant in which at least a part of the coloring agent is covered by PHA having various characteristics derived from such graft chain. It is also found that, by crosslinking such PHA, there can be obtained colorant in which at least a part of the coloring agent is covered with PHA provided with the desired physicochemical properties (such as mechanical strength, chemical resistance, heat resistance etc.). In the present invention, chemical modification means a modification of the molecular structure of polymer material by a chemical intramolecular or intermolecular reaction of such polymer material, or by a chemical reaction of the polymer material and another chemical substance. Also crosslinking means intramolecular or intermolecular chemical or physicochemical coupling of the polymer material to form a network structure, and a crosslinking agent means a substance having certain reactivity with the polymer material to be added for forming the aforementioned crosslinking reaction.

It is also found that, by the aforementioned characteristics, the toner characteristics can be made uniform among the toners of different colors, that the high concentration of the coloring agent can be easily attained without deteriorating other functions of the toner, and that the coloring agent can be uniformly and finely dispersed in the toner particle, whereby the present invention is attained.

The electrostatic charge image developing toner of the present invention is featured in that the electrostatic charge image developing toner is at least composed of a colorant at least a part of which is covered with polyhydroxyalkanoate constituting a first resin component, and binder resin constituting a second resin component.

More specifically, the present invention provides, in the electrostatic charge image developer requiring toner of several colors, electrostatic charge image developing toner allowing uniform design of toner characteristics such as chargeability, flowability, stability in time, environmental stability etc. among the toner of different colors including black color. It also provides full-color electrostatic charge image developing toner of small particle size, capable of resolving deterioration in the charging characteristics, powder characteristics, maintenance of charge amount and fixing characteristics resulting from the increase in the concentration of the coloring agent in such toner. It also provides electrostatic charge image developing toner of a small particle size including a coloring agent dispersed uniformly and finely, being excellent in color saturation, transparency, charge uniformity and durability. Also the present invention allows to provide electrostatic charge image developing toner having low burden on the environment or organisms, low limitation on the material of the coloring agent, and including a capsule structure (colorant) containing the coloring agent at a high concentration and free from contamination of surfactant or polymerization initiator which has been the contamination sources of the conventional capsule structure, by utilizing PHA having a variety of functions.

In the electrostatic charge image developing toner of the present invention, the colorant preferably contains a pigment. Also polyhydroxyalkanoate preferably includes at least one selected from the group consisting of monomer units represented by the following formulas (23) to (32):

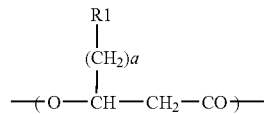

[23]

wherein the monomer unit is at least one selected from the group consisting of monomer units in which the combination of R1 and a is any of the following:

a monomer unit in which R1 is a hydrogen atom (H) and a is an integer from 0 to 10;

a monomer unit in which R1 is a halogen atom and a is an integer from 1 to 10;

a monomer unit in which R1 is a chromophore and a is an integer from 1 to 10;

a monomer unit in which R1 is a carboxyl group or a salt thereof and a is an integer from 1 to 10; and a monomer unit in which R1 is a group represented by the following formula:

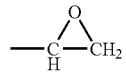

and a is an integer from 1 to 7;

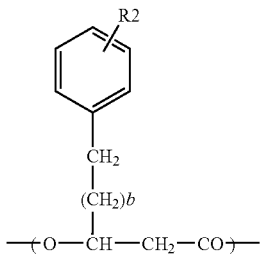
[24]

wherein b is an integer from 0 to 7, and R2 is a substitution selected from the group consisting of a hydrogen atom (H), a halogen atom, —CN, —NO$_2$, —CF$_3$, —C$_2$F$_5$ and —C$_3$F$_7$;

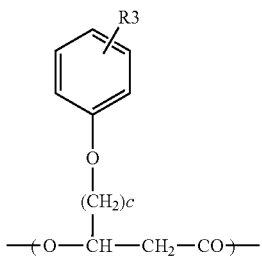
[25]

wherein c is an integer from 1 to 8, and R3 is a substitution selected from the group consisting of a hydrogen atom (H), a halogen atom, —CN, —NO$_2$, —CF$_3$, —C$_2$F$_5$ and —C$_3$F$_7$;

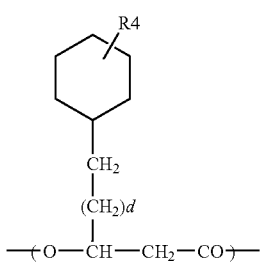
[26]

wherein d is an integer from 0 to 7, and R4 is a substitution selected from the group consisting of a hydrogen atom (H), a halogen atom, —CN, —NO$_2$, —CF$_3$, —C$_2$F$_5$ and —C$_3$F$_7$;

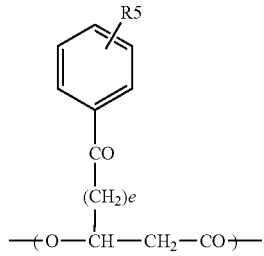
[27]

wherein e is an integer from 1 to 8, and R5 is a substitution selected from the group consisting of a hydrogen atom (H), a halogen atom, —CN, —NO$_2$, —CF$_3$, —C$_2$F$_5$, —C$_3$F$_7$, —CH$_3$, —C$_2$H$_5$ and —C$_3$H$_7$;

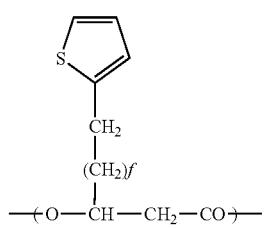
[28]

wherein f is an integer from 0 to 7;

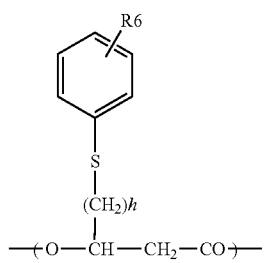
[29]

wherein g is an integer from 1 to 8;

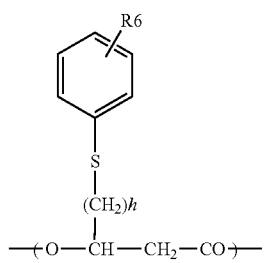
[30]

wherein h is an integer from 1 to 7, R6 is a substitution selected from the group consisting of a hydrogen atom (H), a halogen atom, —CN, —NO$_2$, —COOR', —SO$_2$R'', —CH$_3$, —C$_2$H$_5$, —C$_3$H$_7$, —CH(CH$_3$)$_2$ and —C(CH$_3$)$_3$, R' is a hydrogen atom, Na, K, —CH₃ or —C₂H₅, and R" is —OH, —ONa, —OK, a halogen atom, —OCH₃ or —OC₂H₅;

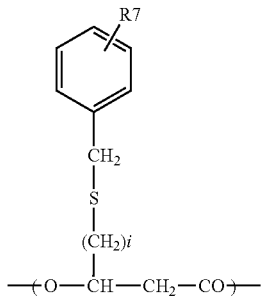

[31]

wherein i is an integer from 1 to 7, R7 is a substitution selected from the group consisting of a hydrogen atom (H), a halogen atom, —CN, —NO₂, —COOR' and —SO₂R", R' is a hydrogen atom, Na, K, —CH₃ or —C₂H₅, and R" is —OH, —ONa, —OK, a halogen atom, —OCH₃ or —OC₂H₅; and

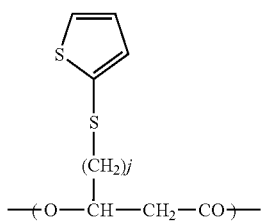

[32]

wherein j is an integer from 1 to 9.

Also polyhydroxyalkanoate preferably has a number-averaged molecular weight within a range from 1,000 to 10,000,000.

Also it is preferred that the monomer unit composition of polyhydroxyalkanoate changes in a direction from the inside to the outside of the colorant.

Also it is preferred that at least a part of polyhydroxyalkanoate is chemically modified polyhydroxyalkanoate, and that the chemically modified polyhydroxyalkanoate includes at least a graft chain. Also the graft chain is preferably a graft chain formed by chemical modification of polyhydroxyalkanoate at least including a monomer unit having an epoxy group, or a graft chain of a compound having an amino group.

The compound having amino group is preferably a compound modified at an end with amino group (referred to as terminal amino-modified compound). The terminal amino-modified compound is preferably at least one selected from the group consisting of polyvinylamine, polyethyleneimine, and polysiloxane modified at the end with amino group. Also at least a part of polyhydroxyalkanoate is preferably crosslinked polyhydroxyalkanoate.

It is also preferred that the crosslinked polyhydroxyalkanoate is obtained by crosslinking polyhydroxyalkanoate at least including a monomer unit having an epoxy group.

The crosslinked polyhydroxyalkanoate is preferably polyhydroxyalkanoate crosslinked by at least one selected from the group consisting of diamine compounds, succinic anhydride, 2-ethyl-4-methylimidazole and electron beam irradiation. In such case, the diamine compound is preferably hexamethylene diamine.

The present invention also provides an image forming method at least including a step of externally applying a voltage to a charging member thereby charging an electrostatic latent image bearing member, a step of forming an electrostatic charge image on the charged electrostatic latent image bearing member, a development step of developing the electrostatic charge image with electrostatic charge image developing toner thereby forming a toner image on the electrostatic latent image bearing member, a transfer step of transferring the toner image on the electrostatic latent image bearing member onto a recording material, and a fixation step of heat fixing the toner image on the recording material, the method being featured by using the aforementioned electrostatic charge image developing toner.

Another embodiment of the image forming method of the present invention at least includes a step of externally applying a voltage to a charging member thereby charging an electrostatic latent image bearing member, a step of forming an electrostatic charge image on the charged electrostatic latent image bearing member, a development step of developing the electrostatic charge image with electrostatic charge image developing toner thereby forming a toner image on the electrostatic latent image bearing member, a first transfer step of transferring the toner image on the electrostatic latent image bearing member onto an intermediate transfer member, a second transfer step of transferring the toner image on the intermediate transfer member onto a recording material, and a fixation step of heat fixing the toner image on the recording material, the method being featured by using the aforementioned electrostatic charge image developing toner.

The present invention further provides an image forming apparatus at least including means for externally applying a voltage to a charging member thereby charging an electrostatic latent image bearing member, means for forming an electrostatic charge image on the charged electrostatic latent image bearing member, development means for developing the electrostatic charge image with electrostatic charge image developing toner thereby forming a toner image on the electrostatic latent image bearing member, transfer means for transferring the toner image on the electrostatic latent image bearing member onto a recording material, and fixation means for heat fixing the toner image on the recording material, the apparatus being featured by using the aforementioned electrostatic charge image developing toner.

Another embodiment of the image forming apparatus of the present invention at least includes means for externally applying a voltage to a charging member thereby charging an electrostatic latent image bearing member, means for forming an electrostatic charge image on the charged electrostatic latent image bearing member, development means for developing the electrostatic charge image with electrostatic charge image developing toner thereby forming a toner image on the electrostatic latent image bearing member, first transfer means for transferring the toner image on the electrostatic latent image bearing member onto an intermediate transfer member, second transfer means for transferring the toner image on the intermediate transfer member onto a recording material, and fixation means for heat fixing the toner image on the recording material, the apparatus being featured by using the aforementioned electrostatic charge image developing toner.

The present invention further provides a method for producing electrostatic charge image developing toner including a colorant obtained by covering at least a part of the surface of a coloring agent with polyhydroxyalkanoate constitute a first resin component, the method being featured by executing a polyhydroxyalkanoate synthesizing reaction utilizing 3-hydroxyacyl CoA as the substrate in the presence of polyhydroxyalkanoate synthesizing enzyme fixed on the surface of the coloring agent dispersed in aqueous medium to cover at least a part of the surface of the coloring agent with polyhydroxyalkanoate thereby producing the aforementioned colorant.

In the aforementioned methods, polyhydroxyalkanoate preferably includes at least one selected from the group consisting of monomer units represented by the following formulas (23) to (32), and the respectively corresponding 3-hydroxyacyl coenzyme A is any of those represented by the chemical formulas (33) to (42):

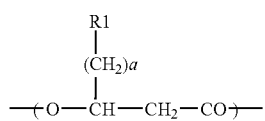  [23]

wherein the monomer unit is at least one selected from the group consisting of monomer units in which the combination of R1 and a is any of the following:

a monomer unit in which R1 is a hydrogen atom (H) and a is an integer from 0 to 10;

a monomer unit in which R1 is a halogen atom and a is an integer from 1 to 10;

a monomer unit in which R1 is a chromophore and a is an integer from 1 to 10;

a monomer unit in which R1 is a carboxyl group or a salt thereof and a is an integer from 1 to 10; and a monomer unit in which R1 is a group represented by the following formula:

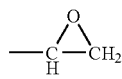

and a is an integer from 1 to 7;

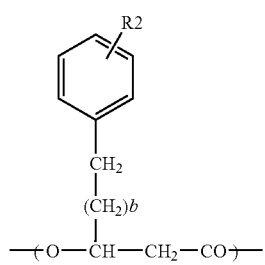  [24]

wherein b is an integer from 0 to 7, and R2 is a substitution selected from the group consisting of a hydrogen atom (H), a halogen atom, —CN, —NO$_2$, —CF$_3$, —C$_2$F$_5$ and —C$_3$F$_7$;

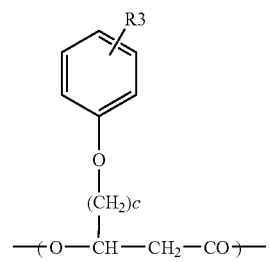  [25]

wherein c is an integer from 1 to 8, and R3 is a substitution selected from the group consisting of a hydrogen atom (H), a halogen atom, —CN, —NO$_2$, —CF$_3$, —C$_2$F$_5$ and —C$_3$F$_7$;

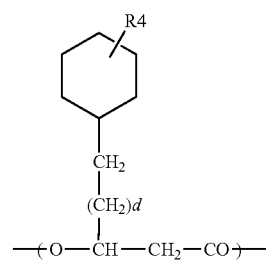  [26]

wherein d is an integer from 0 to 7, and R4 is a substitution selected from the group consisting of a hydrogen atom (H), a halogen atom, —CN, —NO$_2$, —CF$_3$, —C$_2$F$_5$ and —C$_3$F$_7$;

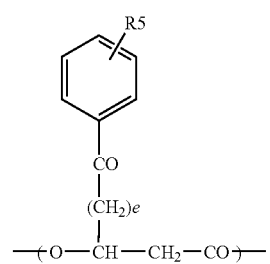  [27]

wherein e is an integer from 1 to 8, and R5 is a substitution selected from the group consisting of a hydrogen atom (H), a halogen atom, —CN, —NO$_2$, —CF$_3$, —C$_2$F$_5$, —C$_3$F$_7$, —CH$_3$, —C$_2$H$_5$ and —C$_3$H$_7$;

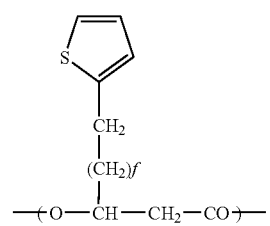  [28]

wherein f is an integer from 0 to 7;

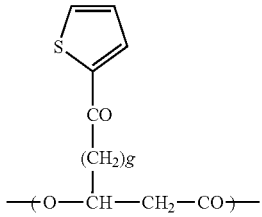
[29]

wherein g is an integer from 1 to 8;

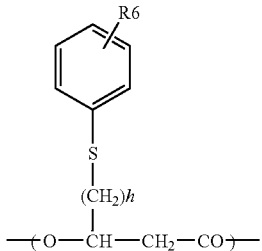
[30]

wherein h is an integer from 1 to 7, R6 is a substitution selected from the group consisting of a hydrogen atom (H), a halogen atom, —CN, —NO$_2$, —COOR', —SO$_2$R", —CH$_3$, —C$_2$H$_5$, —C$_3$H$_7$, —CH(CH$_3$)$_2$ and —C(CH$_3$)$_3$, R' is a hydrogen atom, Na, K, —CH$_3$ or —C$_2$H$_5$, and R" is —OH, —ONa, —OK, a halogen atom, —OCH$_3$ or —OC$_2$H$_5$;

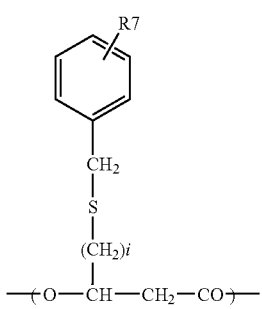
[31]

wherein i is an integer from 1 to 7, R7 is a substitution selected from the group consisting of a hydrogen atom (H), a halogen atom, —CN, —NO$_2$, —COOR' and —SO$_2$R", R' is a hydrogen atom, Na, K, —CH$_3$ or —C$_2$H$_5$, and R" is —OH, —ONa, —OK, a halogen atom, —OCH$_3$ or —OC$_2$H$_5$;

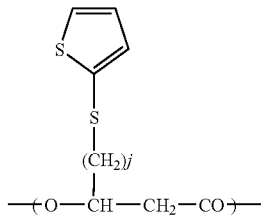
[32]

wherein j is an integer from 1 to 9;

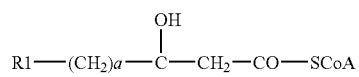
[33]

wherein —SCoA indicates coenzyme A bonded to alkanoic acid, and the combination of R1 and a is any of the following and corresponds to the combination of R1 and a in the foregoing chemical formula (23):

a monomer unit in which R1 is a hydrogen atom (H) and a is an integer from 0 to 10;

a monomer unit in which R1 is a halogen atom and a is an integer from 1 to 10;

a monomer unit in which R1 is a chromophore and a is an integer from 1 to 10;

a monomer unit in which R1 is a carboxyl group or a salt thereof and a is an integer from 1 to 10; and a monomer unit in which R1 is a group represented by the following formula:

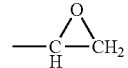

and a is an integer from 1 to 7;

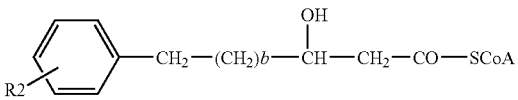
[34]

wherein —SCoA indicates coenzyme A bonded to alkanoic acid, b is an integer from 0 to 7 corresponding to b in the foregoing chemical formula (24), and R2 is a substitution selected from the group consisting of a hydrogen atom (H), a halogen atom, —CN, —NO$_2$, —CF$_3$, —C$_2$F$_5$ and —C$_3$F$_7$, corresponding to R2 in the foregoing chemical formula (24);

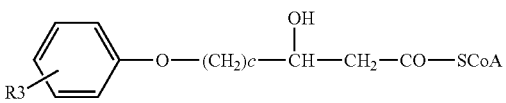
[35]

wherein —SCoA indicates coenzyme A bonded to alkanoic acid, c is an integer from 1 to 8 corresponding to c in the foregoing chemical formula (25), and R3 is a substitution selected from the group consisting of a hydrogen atom (H), a halogen atom, —CN, —NO$_2$, —CF$_3$, —C$_2$F$_5$ and —C$_3$F$_7$, corresponding to R3 in the foregoing chemical formula (25);

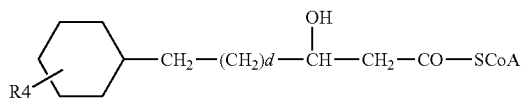

[36]

wherein —SCoA indicates coenzyme A bonded to alkanoic acid, d is an integer from 0 to 7 corresponding to d in the foregoing chemical formula (26), and R4 is a substitution selected from the group consisting of a hydrogen atom (H), a halogen atom, —CN, —NO$_2$, —CF$_3$, —C$_2$F$_5$ and —C$_3$F$_7$, corresponding to R4 in the foregoing chemical formula (26);

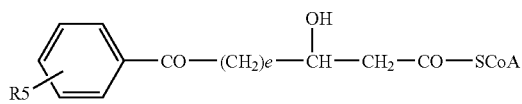

[37]

wherein —SCoA indicates coenzyme A bonded to alkanoic acid, e is an integer from 1 to 8 corresponding to e in the foregoing chemical formula (27), and R5 is a substitution selected from the group consisting of a hydrogen atom (H), a halogen atom, —CN, —NO$_2$, —CF$_3$, —C$_2$F$_5$, —C$_3$F$_7$, —CH$_3$, —C$_2$H$_5$ and —C$_3$H$_7$, corresponding to R5 in the foregoing chemical formula (27);

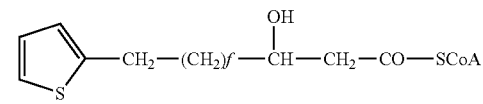

[38]

wherein —SCoA indicates coenzyme A bonded to alkanoic acid, and f is an integer from 0 to 7 corresponding to f in the foregoing chemical formula (28);

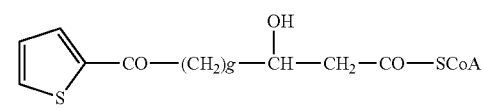

[39]

wherein —SCoA indicates coenzyme A bonded to alkanoic acid, and g is an integer from 1 to 8 corresponding to g in the foregoing chemical formula (29);

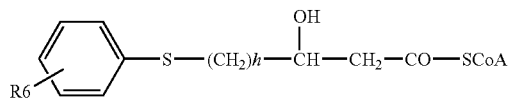

[40]

wherein —SCoA indicates coenzyme A bonded to alkanoic acid, h is an integer from 1 to 7 corresponding to h in the foregoing chemical formula (30), R6 is a substitution selected from the group consisting of a hydrogen atom (H), a halogen atom, —CN, —NO$_2$, —COOR', —SO$_2$R", —CH$_3$, —C$_2$H$_5$, —C$_3$H$_7$, —CH(CH$_3$)$_2$ and —C(CH$_3$)$_3$ corresponding to R6 in the foregoing chemical formula (30), R' is a hydrogen atom, Na, K, —CH$_3$ or —C$_2$H$_5$, and R" is —OH, —ONa, —OK, a halogen atom, —OCH$_3$ or —OC$_2$H$_5$;

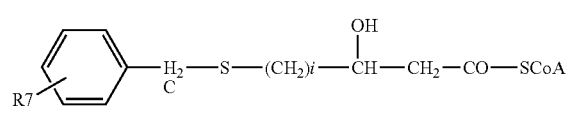

[41]

wherein —SCoA indicates coenzyme A bonded to alkanoic acid, i is an integer from 1 to 7 corresponding to i in the foregoing chemical formula (31), R7 is a substitution selected from the group consisting of a hydrogen atom (H), a halogen atom, —CN, —NO$_2$, —COOR' and —SO$_2$R" corresponding to R7 in the foregoing chemical formula (31), R' is a hydrogen atom, Na, K, —CH$_3$ or —C$_2$H$_5$, and R" is —OH, —ONa, —OK, a halogen atom, —OCH$_3$ or —OC$_2$H$_5$; and

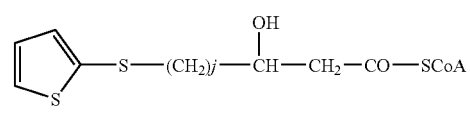

[42]

wherein —SCoA indicates coenzyme A bonded to alkanoic acid, and j is an integer of 1 to 9 corresponding to the foregoing chemical formula (132).

Also it is preferable to change the monomer unit composition of polyhydroxyalkanoate in a direction from the inside to the outside of the colorant, by changing in time the composition of 3-hydroxyacyl coenzyme A.

Also it is preferable to further have a step of applying chemical modification in at least a part of polyhydroxyalkanoate covering the colorant. The aforementioned step of applying chemical modification is preferably a step of adding a graft chain in at least a part of polyhydroxyalkanoate.

Also it is preferable that the aforementioned step of adding the graft chain is a step of reacting at least a part of polyhydroxyalkanoate with a compound having a reactive functional group at the end.

Also polyhydroxyalkanoate preferably includes at least a monomer unit having an epoxy group.

The aforementioned compound having a reactive functional group at the end is preferably a compound having an amino group, and the compound having amino group is preferably a terminal amino-modified compound. The terminal amino-modified compound is preferably at least one selected from the group consisting of polyvinylamine, polyethyleneimine, and polysiloxane modified at the end with amino group.

The aforementioned step of applying chemical modification is preferably a step of crosslinking at least a part of polyhydroxyalkanoate, and the aforementioned crosslinking step is preferably a step of reacting at least a part of polyhydroxyalkanoate with a crosslinking agent.

The aforementioned polyhydroxyalkanoate is preferably polyhydroxyalkanoate at least including a monomer unit having an epoxy group.

The aforementioned crosslinking agent is preferably at least one selected from the group consisting of diamine compounds, succinic anhydride, and 2-ethyl-4-methylimidazole. In such case, the diamine compound is preferably hexamethylene diamine.

The aforementioned crosslinking step can be a step of irradiating polyhydroxyalkanoate with an electron beam.

The aforementioned polyhydroxyalkanoate synthesizing enzyme is preferably polyhydroxyalkanoate synthesizing enzyme produced by microorganism having ability of producing such enzyme, or a transformant obtained by introducing a gene relating to such producing ability into host microorganisms.

The microorganisms having the ability of producing the aforementioned polyhydroxyalkanoate synthesizing enzyme are preferably those of *Pseudomonas* sp. of at least one species selected from the group consisting of *Pseudomonas putida* P91 (FERM BP-7373), *Pseudomonas cichorii* H45 (FERM BP-7374), *Pseudomonas cichorii* YN2 (FERM BP-7375), and *Pseudomonas jessenii* P161 (FERM BP-7376).

The microorganisms having the ability of producing polyhydroxyalkanoate synthesizing enzyme can also be those of *Burkholderia* sp. of at least one species selected from the group consisting of *Burkholderia cepacia* KK01 (FERM BP-4235), *Burkholderia* sp. OK3 (FERM P-17370), and *Burkholderia* sp. OK4 (FERM P-17371).

The microorganisms having the ability of producing polyhydroxyalkanoate synthesizing enzyme can also be those of *Alcaligenes* sp. and can be *Alcaligenes* sp. TL2 (FERM BP-6913).

The microorganisms having the ability of producing polyhydroxyalkanoate synthesizing enzyme can also be those of *Ralstonia* sp. and can be *Ralstonia eutropha* TB64 (FERM BP-6933).

Also the host microorganisms for the transformant having the ability for producing the aforementioned polyhydroxyalkanoate synthesizing enzyme can be *Escherichia coli*.

The present invention enables to provide, in the electrostatic charge image developer requiring toner of several colors, electrostatic charge image developing toner composed of a colorant at least a part thereof is covered with polyhydroxyalkanoate constituting a first resin component, and binder resin constituting a second resin component, thereby allowing uniform design of toner characteristics such as chargeability, flowability, stability in time, environmental stability etc. among the toner of different colors including black color. It also allows to provide full-color electrostatic charge image developing toner of small particle size, capable of resolving deterioration in the charging characteristics, powder characteristics, maintenance of charge amount and fixing characteristics resulting from the increase in the concentration of the coloring agent in such toner.

It also allows to provide electrostatic charge image developing toner of a small particle size including a coloring agent dispersed uniformly and finely, being excellent in color saturation, transparency, charge uniformity and durability. Also the present invention allows to provide electrostatic charge image developing toner having low burden on the environment or organisms, low limitation on the material of the coloring agent, and including a capsule structure (colorant) containing the coloring agent at a high concentration and free from contamination of surfactant or polymerization initiator which has been the contamination sources of the conventional capsule structure.

In addition, the present invention allows to provide a method for producing the aforementioned electrostatic charge image developing toner, and an image forming method and an image forming apparatus utilizing the aforementioned electrostatic charge image developing toner.

The above and other objects, effects, features and advantages of the present invention will become more apparent from the following description of embodiments thereof taken in conjunction with the accompanying drawings.

DESCRIPTION OF THE PREFERRED EMBODIMENTS

Figure 1:
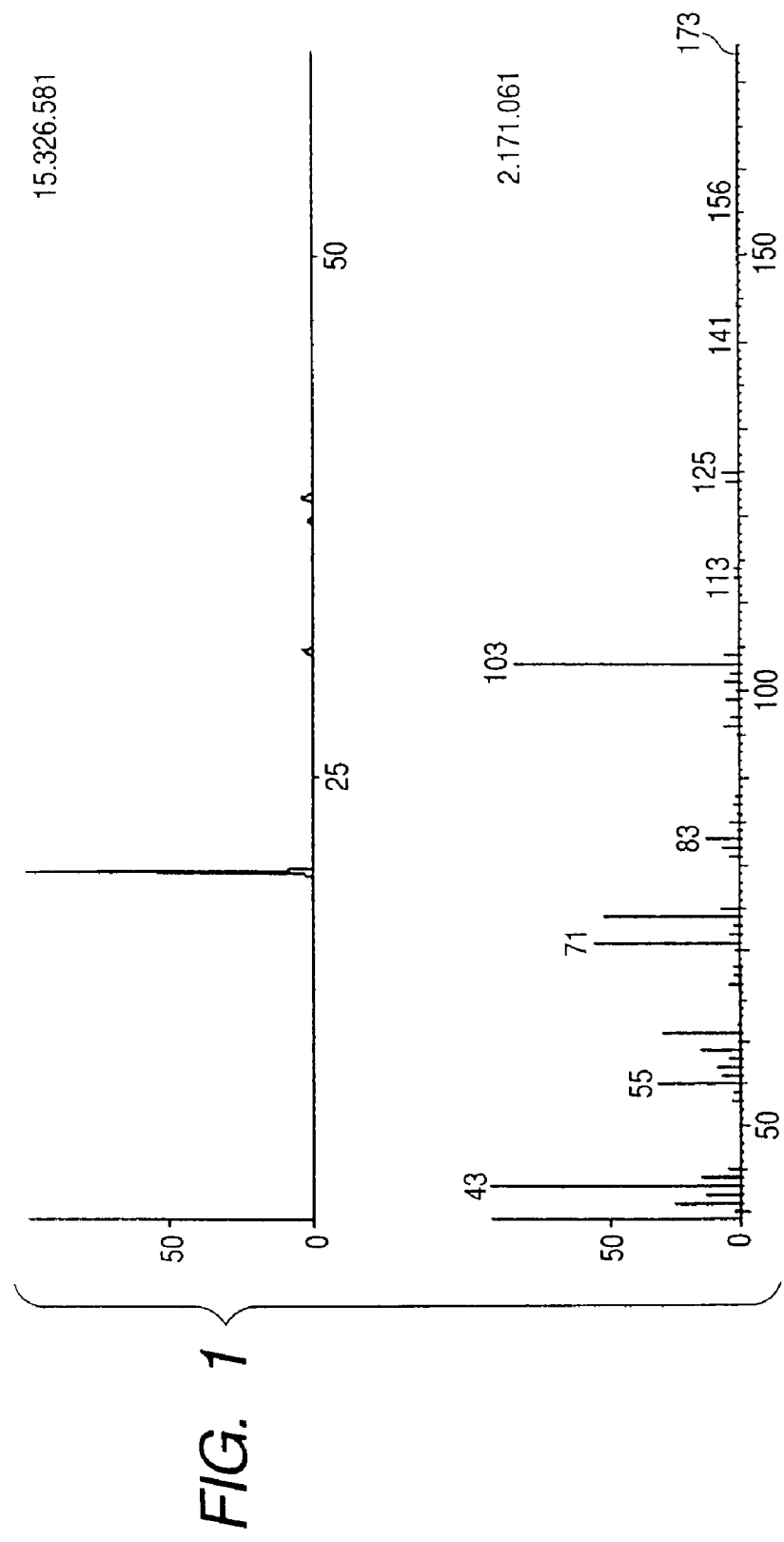
FIG. 1 is a GC-MS analytical result of the shell of a capsule construct in Example 1.

The construct according to the present invention has a configuration in which a base material is coated with PHA comprised of various types of monomer units having a substituent on side chains. Such a construct is extremely useful as a highly functional construct including a capsule toner for electrophotography and a recording medium. The present invention will be described in detail.

<PHA>

PHA which is available for the present invention is not particularly limited as long as the PHA can be synthesized by a PHA synthetase participating with mcl-PHA synthesis, that is, various mcl-PHAs and unusual-PHAs are included in PHA. As described above, PHA synthetase is an enzyme that catalyzes the final step in the in vivo PHA synthesis, so that any PHA known to be synthesized in a living organism is synthesized by the catalytic action of PHA synthetase. Therefore, it is possible to make a construct of which base material is coated with any kind of PHA known to be synthesized in vivo, by reacting 3-hydroxyacyl CoA corresponding to the desired PHA with the enzyme immobilized on the base material.

Such PHA may contain monomer units represented by the following chemical formulae [1] to [10].

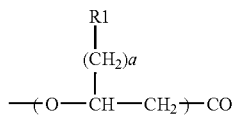
[1]

wherein R1 and a are selected from the group of combinations consisting of:

(1) R1 is a hydrogen atom (H) and a is any of integers from 3 to 10;

(2) R1 is a halogen atom and a is any of integers from 1 to 10;

(3) R1 is a chromophore and a is any of integers from 1 to −10;

(4) R1 is a carboxyl group or a salt thereof and a is any of integers from 1 to 10; and (5) R1 is

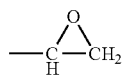

and a is any of integers from 1 to 7.

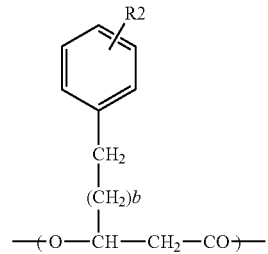
[2]

wherein b represents any of integers from 0 to 7 and R2 represents any one selected from the group consisting of hydrogen atom (H), halogen atoms, —CN, —NO$_2$, —CF$_3$, —C$_2$F$_5$, and —C$_3$F$_7$.

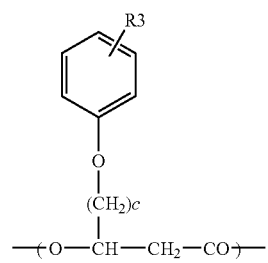
[3]

wherein c represents any of integers from j to 8 and R3 represents any one selected from the group consisting of hydrogen atom (H), halogen atoms, —CN, —NO$_2$, —CF$_3$, —C$_2$F$_5$, and —C$_3$F$_7$.

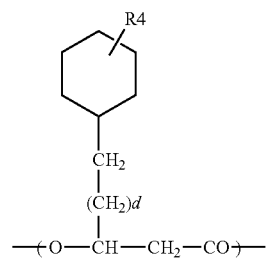
[4]

wherein d represents any of integers from 0 to 7 and R4 represents any one selected from the group consisting of hydrogen atom (H), halogen atoms, —CN, —NO$_2$, —CF$_3$, —C$_2$F$_5$, and —C$_3$F$_7$.

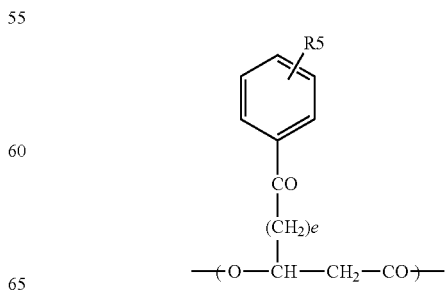
[5]

wherein e represents any of integers from 1 to 8 and R5 represents any one selected from the group consisting of hydrogen atom (H), halogen atoms, —CN, —NO$_2$, —CF$_3$, —C$_2$F$_5$, —C$_3$F$_7$, —CH$_3$, —C$_2$H$_5$, and —C$_3$H$_7$

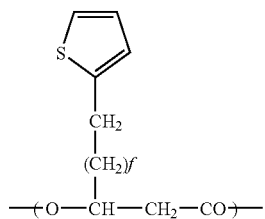

[6]

wherein f represents any of integers from 0 to 7.

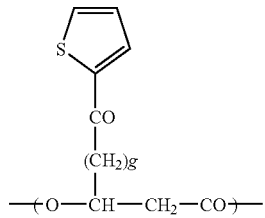

[7]

wherein g represents any of integers from 1 to 8.

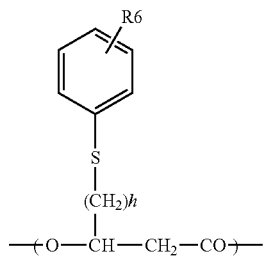

[8]

wherein h represents any of integers from 1 to 7 and R6 represents any one selected from the group consisting of hydrogen atom (H), halogen atoms, —CN, —NO$_2$, —OOOR', —SO$_2$R", —CH$_3$, —C$_2$H$_5$, —C$_3$H$_7$, —CH(CH$_3$)$_2$, and —C(CH$_3$)$_3$, wherein R' is selected from the group consisting of hydrogen atom (H), Na, K, —CH$_3$, and —C$_2$H$_5$, and R" is selected from the group consisting of —OH, —ONa, —OK, halogen atoms, —OCH$_3$, and —OC$_2$H$_5$.

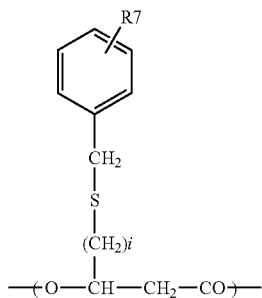

[9]

wherein i represents any of integers from 1 to 7 and R7 represents any one selected from the group consisting of hydrogen atom (H), halogen atoms, —CN, —NO$_2$, —COOR', —SO2R", in which R' is selected from the group consisting of hydrogen atom (H), Na, K, —CH$_3$, and —C$_2$H$_5$, and R" is selected from the group consisting of —OH, —ONa, —OK, halogen atoms, —OCH$_3$, and —OC$_2$H$_5$.

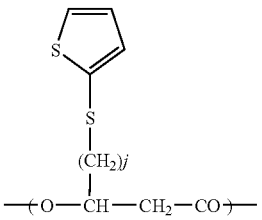

[10]

wherein j represents any of integers from 1 to 9.

In the above formulas 1 to 10, halogen atoms can be fluorine, chlorine, or bromine. The chromophores are not particularly limited as long as the 3-hydroxyacyl CoA having the chromophore is catalyzed by PHA synthetase, but it is preferable that a methylene chain of 1 to 5 carbon atoms is present between the chromophore and the carboxyl group to which CoA is bonded, in view of steric hindrance at the time of polymer synthesis. When the light absorption wavelength of the chromophore is within a visible range, a colored construct can be obtained and when the light absorption wavelength is outside the visible range, the construct may be used as various electronic materials. Such chromophores include nitro so, nitro, azo, diarylmethane, triarylmethane, xanthene, acridine, quinoline, methine, thiazole, indamine, indophenol, lactone, aminoketone, hydroxyketone, stilbene, azine, oxazine, thiazine, anthraquinone, phthalocyanine, and indigoid.

As PHA which is used for the present invention, random copolymers or block copolymers which include a plurality of the above described monomer units can be used. Therefore, it becomes possible to control physical properties of PHA and add some functions to the PHA by utilizing properties of each monomer unit or functional groups included therein, and also possible to manifest new functions obtained by utilizing interaction between functional groups.

Further, it is possible to change a monomer unit composition of the PHA in a radial direction in the case where a shape of the construct is like a particle and in a vertical direction in the case where a shape of the construct is like a plate, by changing the composition with time through alteration of kinds and concentrations of 3-hydroxyacyl CoA which is a base material.

Consequently, in the case of a capsule toner for example, the toner becomes possible to simultaneously possess a plurality of functions such as an excellent blocking resistance at the time of preserving the toner and an excellent low temperature fixing property at the time of the fixing, by forming PHA having a high glass transition temperature as a surface layer of the toner and by forming PHA having a low glass transition temperature as an inner layer of the toner.

In addition, if it requires that a coating construct is formed by PHA which has a less affinity for a base material for example, it becomes possible to form a PHA coating which is strongly bound to the base material by firstly coating the base material with PHA having a high affinity for the base material and then changing a monomer unit composition of the PHA having a high affinity for the base material in its radial direction or in its vertical direction to obtain a desired monomer unit composition of the PHA, for example, a multilayered construct or a gradient construct.

PHA comprising only 3-hydroxypropionic acid unit, 3-hydroxy-n-butyric acid unit, 3-hydroxy-n-valeric acid unit, or 4-hydroxy-n-butyric acid unit is not applicable to mcl-PHA or unusual-PHA, but PHA in which these monomer units are mixed in the previously illustrated monomer units is available for the present invention. In addition, a chemical modification can be performed after synthesizing PHA or during synthesizing PHA, as required. As for the molecular weight of PHA, the number average molecular weight of PHA is about 1,000 to 10 million, and preferably about 3,000 to a million when the above described construct is used as a capsule toner for electrophotography.

In the present invention, the PHA synthesized by PHA synthetase and used for the construct of the present invention is generally isotactic polymer comprised of R bodies alone.

<3-hydroxyacyl CoA>

Specifically, 3-hydroxyacyl CoA usable as the substrate of PHA synthetase in the present invention is represented by the following chemical formulae [11] to [20].

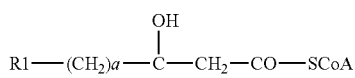

[11]

wherein —SCoA represents coenzyme A bonded to alkanoic acid, and R1 and a are as defined for the above-described chemical formula [1].

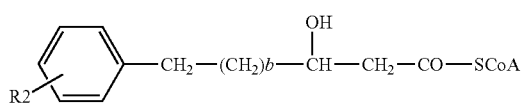

[12]

wherein —SCoA represents coenzyme A bonded to alkanoic acid, R2 and b are as defined for the above-described chemical formula [2],

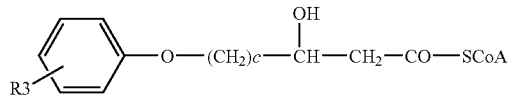

[13]

wherein —SCoA represents coenzyme A bonded to alkanoic acid, R3 and c are as defined for the above-described chemical formula [3].

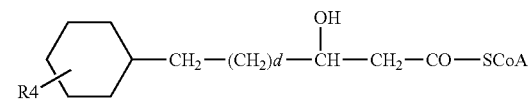

[14]

wherein —SCoA represents coenzyme A bonded to alkanoic acid, R4 and d are as defined for the above-described chemical formula [4].

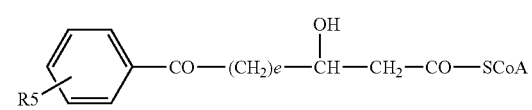

[15]

wherein —SCoA represents coenzyme A bonded to alkanoic acid, R5 and e are as defined for the above-described chemical formula [5].

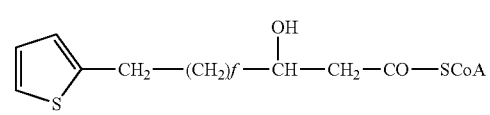

[16]

wherein —SCoA represents coenzyme A bonded to alkanoic acid, and f is as defined for the above-described chemical formula [6].

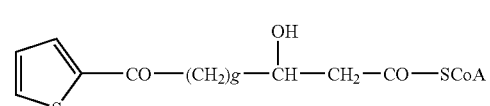

[17]

wherein, —SCoA represents coenzyme A bonded to alkanoic acid, and g represents any of integers from 1 to 8 as defined for the above-described chemical formula [7].

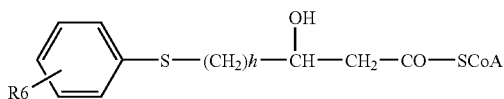
[18]

wherein, —SCoA represents coenzyme A bonded to alkanoic acid, R6 and h are as defined for the above-described chemical formula [8].

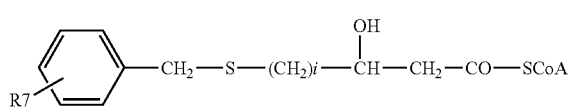
[19]

wherein, —SCoA represents coenzyme A bonded to alkanoic acid, R7 and i are as defined for the above-described chemical formula [9].

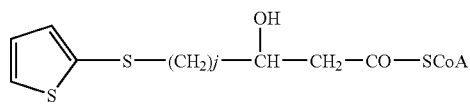
[20]

wherein, —SCoA represents coenzyme A bonded to alkanoic acid, and j represents any of integers from 1 to 9 as defined for the above-described chemical formula [10].

These 3-hydroxyacyl CoAs can be synthesized by a suitable method selected from, for example, in vitro synthesis use an enzyme, in vivo synthesis using living organisms such as microorganisms and plants, and chemical synthesis. Enzymatic synthesis, especially, is commonly used to synthesize these substrates. For example, it is known a method to use a commercially available acyl CoA synthetase (acyl CoA ligase, E. C. 6. 2. 1. 3) to catalyze the following reaction: 3-hydroxyalkanoic acid+CoA→3-hydroxyacyl CoA (Eur. J. Biochem., 250, 432–439 (1997), Appl. Microbiol. Biotechnol., 54, 37–43 (2000) etc.). The synthesis process using enzyme or organism may be a batch process or a continuous process using immobilized enzyme or cells.

<PHA Synthetase and Production Microorganisms>

The PHA synthetase used in the present invention can be produced by using a microorganism selected from the microorganisms known to produce PHA synthetase, or by using a transformant to which the PHA synthetase gene of such a microorganism has been introduced.

For example, mcl-PHA- or unusual-PHA-producing microorganisms can be used as the PHA synthetase-producing microorganism. Such microorganisms include, in addition to the above described *Pseudomonas oleovorans, Pseudomonas resinovorans, Pseudomonas* sp. strain 61-3, *Pseudomonas putida* KT 2442, and *Pseudomonas aeruginosa*, strains of *Pseudomonas* sp. such as *Pseudomonas putida* P91, *Pseudomonas cichorii* H45, *Pseudomonas cichorii* YN2, and *Pseudomonas jessenii* P161 all of which were isolated by the inventors, strains belonging to *Burkholderia* sp. such as *Burkholderia* sp. OK3, FERM P-17370 described in Japanese Patent Application-Laid-Open No. 2001-78753 and *Burkholderia* sp. OK4, FERM P-17371 described in Japanese Patent Application Laid-Open No. 2001-69968. In addition to the above-described microorganisms, it is possible to use microorganisms of genus *Aeromonas* and *Comamonas* that can produce mcl-PHA and unusual-PHA.

Strains P91, H45, YN2 and P161 have been deposited (accession number: FERM BP-7373, FERM BP-7374, FERM BP-7375, and FERM BP-7376 respectively) in International Patent Organism Depositary of Institute of Advanced Industrial Science and Technology (former National Institute of Bioscience and Human Technology, Agency of Industrial Science and Technology), 1–3, Higashi 1-chome, Tsukuba-shi, Ibaraki-ken, 305-0046, Japan, under the Budapest Treaty on the International Recognition of the Deposit of Microorganism for the Purpose of Patent Procedure.

Microbiological properties of the above described P91, H45, YN2 and P161 are as follows. As for the strain P161, the base sequence of 16S rRNA is as SEQ ID NO: 1.

*Pseudomonas putida* P91

(1) Morphology
Form and size of the cell: rod, 0.6 μm×1.5 μm
Polymorphism of the cell: −
Mobility: +
Spore formation: −
Gram stain: negative
Colony shape: circular, smooth edge, low convex, smooth surface, lustrous, cream color (2) Physiological Properties
Catalase: positive
Oxidase: positive
O/F test: oxidizing type
Reduction of nitrate: negative
Production of indole: negative
Acidification of glucose: negative
Arginine dihydrolase: positive
Urease: negative
Esculin hydrolysis: negative
Gelatin hydrolysis: negative
β-galactosidase: negative
Fluorescent dye production on King's B agar: positive (3) Substrate Assimilation
Glucose: positive
L-arabinose: negative
D-mannose: negative
D-mannitol: negative
N-acetyl-D-glucosamine: negative
Maltose: negative
Potassium gluconate: positive
n-capric acid: positive
Adipic acid: negative
dl-malic acid: positive
Sodium citrate: positive
Phenyl acetate: positive

*Pseudomonas cichorii* H45

(1) Morphology
Form and size of the cell: rod, 0.8 μm×1.0 to 1.2 μm
Polymorphism of the cell: −
Mobility: +
Spore formation: −
Gram stain: negative Colony shape: circular, smooth edge, low convex, smooth surface, lustrous, cream color (2) Physiological Properties
Catalase: positive
Oxidase: positive
O/F test: oxidizing type
Reduction of nitrate: negative
Production of indole: negative
Acidification of glucose: negative
Arginine dihydrolase: negative
Urease: negative
Esculin hydrolysis: negative
Gelatin hydrolysis: negative
β-galactosidase: negative
Fluorescent dye production on King's B agar: positive
Growth in 4% NaCl: negative
Accumulation of poly-β-hydroxybutyric acid: negative (3) Substrate Assimilation
Glucose: positive
L-arabinose: negative
D-mannose: positive
D-mannitol: positive
N-acetyl-D-glucosamine: positive
Maltose: negative
Potassium gluconate: positive
n-capric acid: positive
Adipic acid: negative
dl-malic acid: positive
Sodium citrate: positive
Phenyl acetate: positive

*Pseudomonas cichorii* YN2

(1) Morphology
Form and size of the cell: rod, 0.8 μm×1.5 to 2.0 μm
Polymorphism of the cell: −
Mobility: +
Spore formation: −
Gram stain: negative
Colony shape: circular, smooth edge, low convex, smooth surface, lustrous, translucent (2) Physiological Properties
Catalase: positive
Oxidase: positive
O/F test: oxidizing type
Reduction of nitrate: negative
Production of indole: positive
Acidification of glucose: negative
Arginine dihydrolase: negative
Gelatin hydrolysis: negative
β-galactosidase: negative
Fluorescent dye production on King's B agar: positive
Growth in 4% NaCl: positive (weakly growth)
Accumulation of poly-β-hydroxybutyric acid: negative
Hydrolysis of Tween 80: positive (3) Substrate Assimilation
Glucose: positive
L-arabinose: positive
D-mannose: negative
D-mannitol: negative
N-acetyl-D-glucosamine: negative
Maltose: negative
Potassium gluconate: positive
n-capric acid: positive
Adipic acid: negative
dl-malic acid: positive
Sodium citrate: positive
Phenyl acetate: positive

*Pseudomonas jessenii* P161

(1) Morphology
Form and size of the cell: spherical: φ 0.6 μm, rod: 0.6 μm×1.5 to 2.0 μm
Polymorphism of the cell: + (elongation)
Mobility: +
Spore formation: −
Gram stain: negative
Colony shape: circular, smooth edge, low convex, smooth surface, pale yellow (2) Physiological Properties
Catalase: positive
Oxidase: positive
O/F test: oxidizing type
Reduction of nitrate: positive
Production of indole: negative
Arginine dihydrolase: positive
Urease: negative
Esculin hydrolysis: negative
Gelatin hydrolysis: negative
β-galactosidase: negative
Fluorescent dye production on King's B agar: positive (3) Substrate Assimilation
Glucose: positive
L-arabinose: positive
D-mannose: positive
D-mannitol: positive
N-acetyl-D-glucosamine: positive
Maltose: negative
Potassium gluconate: positive
n-capric acid: positive
Adipic acid: negative
dl-malic acid: positive
Sodium citrate: positive
Phenyl acetate: positive For routine culture of the PHA synthetase-producing microorganisms, for example, to prepare cell stocks, to obtain sufficient cells for enzyme production or to maintain active state of the cells, one can select suitable culture medium containing ingredients necessary for the growth of microorganisms. Any culture medium can be used as long as it does not interfere microbial growth or vitality, including common natural media such as nutrient broth and yeast extracts, and synthetic media supplemented with nutrients.

Any culture method, such as liquid culture and solid culture, can be used as long as the subject microorganism can proliferate. It may be batch culture, fed-batch culture, semi-continuous culture, or continuous culture. Liquid batch culture includes a method of shaking a culture flask to supply oxygen, and a method using ajar fermenter that supplies oxygen by aeration. A plurality of these processes may be combined as a multistage method.

To produce PHA synthetase by using the above described PHA-producing microorganism, first the microorganism is grown on an inorganic medium containing alkanoic acid such as octanoic acid and nonanoic acid, and then the cells in the late logarithmic to early stationary growth phase are harvested by centrifugation or the like to extract the enzyme from the cells. When cells are cultured as above, mcl-PHA is synthesized in the cells from added alkanoic acid. In this case, it has been considered that PHA synthetase exists in a bound form to the fine particles of PHA synthesized in the cell. However, the inventors have found that substantial enzyme activity is present in the supernatant when the cultured cells were disrupted and centrifuged. Presumably, a certain amount of free PHA synthetase is present because this enzyme is actively synthesized during this relatively early growth phase of the late logarithmic to early stationary phase.

Any inorganic culture medium can be used for the above described culture process as long as the medium contains ingredients such as phosphorus source (phosphate etc.), and nitrogen source (ammonium salt, nitrate etc.) to support microbial growth. Therefore, MSB medium, E medium (J. Biol. Chem., 218, 97–106 (1956)), or M9 medium can be used as the inorganic salt medium, for example. Composition of M9 medium which is used in Examples is as follows.

| | |
|---|---|
| $Na_2HPO_4$: | 6.2 g |
| $KH_2PO_4$: | 3.0 g |
| NaCl: | 0.5 g |
| $NH_4Cl$: | 1.0 g |

(per liter, pH 7.0)

In addition, it is preferable to add the stock solution of trace ingredients of the following composition to about 0.3% (v/v), for good proliferation and production of PHA synthetase.

Stock Solution of Trace Ingredients

| | |
|---|---|
| Nitrilotriacetic acid: | 1.5 g |
| $MgSO_4$: | 3.0 g |
| $MnSO_4$: | 0.5 g |
| NaCl: | 1.0 g |
| $FeSO_4$: | 0.1 g |
| $CaCl_2$: | 0.1 g |
| $COCl_2$: | 0.1 g |
| $ZnSO_4$: | 0.1 g |
| $CuSO_4$: | 0.1 g |
| $AlK(SO_4)_2$: | 0.1 g |
| $H_3BO_3$: | 0.1 g |
| $Na_2MoO_4$: | 0.1 g |
| $NiCl_2$: | 0.1 g |

(per liter)

Culture temperature is chosen to be favorable for proliferation of the above strains, so that, for example, in the range of 14 to 40° C., preferably about 20 to 35° C.

It is also possible to produce PHA synthetase by using a transformant to which the PHA synthetase gene of the above PHA producing strain has been introduced. Cloning of the PHA synthetase gene, construction of expression vectors and transformants can be done according to the conventional methods. To culture a transformant obtained using a bacterial host such as *Escherichia coli*, natural media such as LB medium or synthetic media such as M9 medium can be used. Cells are cultured with aeration for 8 to 27 hours at 25 to 37° C. After culture, cells are collected to recover PHA synthetase accumulated in the cells. Antibiotics such as kanamycin, ampicillin, tetracycline, chloramphenicol, and streptomycin may be added to the culture as required. In addition, if the an inducible promoter is used in the expression vector, expression may be promoted by adding a corresponding inducer to the culture medium when the transformant is cultured. Such an inducer may be isopropyl-β-D-thiogalactopyranoside (IPTG), tetracycline, or indoleacrylic acid (IAA).

The PHA synthetase may be a crude enzyme such as a cell lysate or protein components precipitated with ammonium sulfate, or a purified enzyme purified by various methods. The enzyme preparation may be added with a stabilizer or activator such as metallic salts, glycerin, dithiothreitol, EDTA, and bovine serum albumin (BSA) as required.

PHA synthetase may be isolated and purified by any method as long as the enzyme activity is maintained. For example, the enzyme can be purified as follows: a crude enzyme or ammonium sulfate precipitate thereof, prepared by disrupting microbial cells by using a French press or ultrasonic homogenizer, lysozyme, or various surfactants and by centrifuging the cell lysate, is purified by affinity chromatography, cation or anion exchange chromatography, gel filtration, or a certain combination thereof. Recombinant proteins, those expressed as a fusion protein having a tag such as histidine residue at N-terminus or C terminus, can be purified easily by binding through this tag to the affinity resin. The protein of interest may be isolated from the fusion protein by treating with protease such as thrombin and blood coagulation factor Xa, by lowering pH, or by adding high concentration imidazole as a binding competitive agent. Alternatively, when pTYBI (made by New England Biolabs Inc.) was used as an expression vector, and the tag contains inteins, the bonding may be broken under reduced conditions by using dithiothreitol. In addition to the histidine tag, glutathione S-transferase (GST), chitin binding domain (CBD), maltose binding protein (MBP), and thioredoxin are known to allow affinity purification of fusion proteins. The GST fusion protein can be purified by a GST affinity resin.

Enzyme activity of PHA synthetase can be measured various known methods. For example, the following method that measures CoA released from 3-hydroxyacyl CoA during PHA polymerization reaction catalyzed by PHA synthetase utilizing color development with 5,5'-dithiobis-(2-nitrobenzoic acid): Reagent 1: a 3.0 mg/ml solution of bovine serum albumin (Sigma) dissolved in 0.1 M Tris-HCl buffer (pH 8.0), Reagent 2: a 3.0 mM solution of 3-hydroxyoctanoyl CoA in 0.1 M Tris-HCl buffer (pH 8.0); Reagent 3: a 1 mg/ml solution of trichloroacetic acid in 0.1 M Tris-HCl buffer (pH 8.0), Reagent 4: a 2.0 mM solution of 5,5'-dithiobis-(2-nitrobenzoic acid) in 0.1 M Tris-HCl buffer (pH 8.0).

First reaction (PHA synthesizing reaction): 100 μl of Reagent 1 is added to and mixed with 100 μl of the sample (enzyme) solution, then the mixture is pre-incubated for one minute at 30° C., to which 100 μl of Reagent 2 is added and mixed. The resultant mixture is incubated for 1 to 30 minutes at 30° C. and the reaction is stopped by adding Reagent 3.

Second reaction (color development of free CoA): The resulting first reaction solution is centrifuged (15,000×g, for 10 minutes). To 500 μl of the supernatant, 500 μl of Reagent 4 is added and incubated for 10 minutes at 30° C. Then the absorbance at 412 nm is measured.

Calculation of enzyme activity: The amount of enzyme that releases 1 μmol of CoA within one minute is defined as one unit (U).

Generally, PHA synthesized by the above described enzyme is an isotactic polymer made with R bodies alone.

<Base Material>

The base material used in the present invention can be appropriately selected from ordinary polymer compounds and inorganic solid materials such as resins, glass, and metals as long as PHA synthetase can be immobilized to it. The type and structure of the base material can be chosen appropriately according to the method for immobilizing PHA synthetase to the base material or application form of the resulting construct.

For example, the following substances can be used as a base material (core) of a capsule construct according to the present invention but are not limited thereto as a matter of course: resin particulates produced by polymerization of polymerizable monomers selected from the group consisting of styrenic polymerizable monomers such as styrene, α-methylstyrene, β-methylstyrene, o-methylstyrene, m-methylstyrene, p-methylstyrene, 2,4-dimethylstyrene, p-n-butylstyrene, p-tert-butylstyrene, p-n-hexylstyrene, p-n-octylstyrene, p-n-nonylstyrene, p-n-decylstyrene, p-n-dodecylstyrene, p-methoxystyrene, and p-phenylstyrene, acrylic polymerizable monomers such as methyl acrylate, ethyl acrylate, n-propyl acrylate, iso-propyl acrylate, n-butyl acrylate, iso-butyl acrylate, tert-butyl acrylate, n-amyl acrylate, n-hexyl acrylate, 2-ethylhexyl acrylate, n-octyl acrylate, n-nonyl acrylate, cyclohexylacrylate, benzyl acrylate, dimethylphosphate ethylacrylate, diethylphosphate ethylacrylate, dibutylphosphate ethylacrylate, and 2-benzoyloxy ethylacrylate, methacrylic polymerizable monomers such as methyl methacrylate, ethyl methacrylate, n-propyl methacrylate, iso-propyl methacrylate, n-butyl methacrylate, iso-butyl methacrylate, tert-butyl methacrylate, n-amyl methacrylate, n-hexyl methacrylate, 2-ethylhexyl methacrylate, n-octyl methacrylate, n-nonyl methacrylate, diethylphosphate ethylmethacrylate, and dibutylphosphate ethylmethacrylate, polymerizable vinyl monomers including methylene aliphatic monocarboxylic esters, vinylesters such as vinyl acetate, vinyl propionate, vinyl benzoate, vinyl butyrate, vinyl benzoate, and vinyl formate, vinyl ethers such as vinyl methyl ether, vinyl ethyl ether, and vinyl isobutyl ether, vinyl ketones such as vinyl methyl ketone, vinyl hexyl ketone, and vinyl isopropyl ketone; resin particulates produced by adding various additives such as polar group polymers and colorants to the above described monomers; particulates including paraffin wax, polyolefin wax, Fisher-Tropsch wax, amide wax, higher fatty acids, ester wax and derivatives thereof or graft and block compounds thereof; clay minerals such as kaolinite, bentonite, talc, and mica; metal oxides such as alumina and titanium oxide; insoluble inorganic salts such as silica gel, hydroxyapatite, and calcium phosphate gel; black pigments such as carbon black, copper oxide, manganese dioxide, aniline black, activated carbon, nonmagnetic ferrite, and magnetite; yellow pigments such as chrome yellow, zinc yellow, yellow iron oxide, cadmium yellow, mineral fast yellow, nickel titanium yellow, navels yellow, naphtol yellow S, Hansa yellow G, Hansa Yellow 10G, benzidine yellow G, benzidine yellow GR, quinoline yellow lake, permanent yellow NCG, and tartrazine lake; orange pigments such as red chrome yellow, molybdenum orange, permanent orange GTR, pyrazolone orange, vulkan orange, benzidine orange G, indanthrene brilliant orange RK, and indanthrene brilliant orange GK; red pigments such as red iron oxide, cadmium red lead, mercury sulfide, cadmium, permanent red 4R, lithol red, pyrazolone red, watching red, calcium salt, lake red C, lake red D, brilliant carmine 6B, brilliant carmine 3B, eosin lake, rhodamine lake B, and alizarin lake; blue pigments such as iron blue, cobalt blue, alkali blue lake, victoria blue lake, copper phthalocyanine blue, metal-free phthalocyanine blue, partly chlorinated phthalocyanine blue compound, fast sky blue, and indanthrene blue BC; purple pigments such as manganese purple, fast violet B, and methyl violet lake; green pigments such as chromium oxide, chrome green, pigment green B, malachite green lake, and final yellow green G; white pigments such as zinc oxide, titanium oxide, and zinc sulfide; extender pigments such as barytes, barium carbonate, clay, white carbon, talc, and alumina white. Although a shape of the core can appropriately varies depending on its intended use, it is preferable that a particle whose particle size is within a range of 0.1 μm to 1.0 mm is used for example. In addition, when the construct is used as a capsule toner for electrophotography, a particle may be selected so that its particle size becomes within a range of 3.0 μm to 10 μm.

On the other hand, as the base material of a laminated construct of the present invention the following substances can be used but not limited thereto: Plastic films of polyethylene terephthalate (PET), diacetate, triacetate, cellophane, celluloid, polycarbonate, polyimide, polyvinyl chloride, polyvinylidene chloride, polyacrylate, polyethylene, polypropylene, or polyester; porous polymer membranes of polyvinyl chloride, polyvinyl alcohol, acetyl cellulose, polycarbonate, nylon, polypropylene, polyethylene, or Teflon; wooden boards; glass plates; fabrics of cotton, rayon, acrylic, silk, or polyester; papers such as wood-free paper, medium-quality paper, art paper, bond paper, recycled paper, baryta paper, cast-coated paper, corrugated fiberboard, and resin-coated paper. The above described base material may have a smooth or uneven surface, and also may be transparent, translucent or opaque. The laminated construct may be made by laminating two or more substances which are selected among the above listed substances.

<Making of a Construct>

The method for making a construct according to the present invention comprises a step of immobilizing a PHA synthetase onto a base material and a step of reacting the immobilized PHA synthetase with 3-hydroxyacyl CoA to synthesize PHA.

As a method for immobilizing the PHA synthetase onto the base material, one can choose and use any conventional method for immobilizing enzymes as long as the method would not affect the activity of the synthetase and is applicable to the intended base material. For example, covalent bonding, ionic adsorption, a hydrophobic adsorption, physical adsorption, affinity adsorption, crosslinking, lattice inclusion can be utilized. In particular, immobilization using ionic adsorption or hydrophobic adsorption is simple for use.

An enzyme protein such as PHA synthetase is a polypeptide made with a plurality of amino acids bonded together. The enzyme protein exhibits properties as an ionic adsorbate due to constituent amino acids having free ionic groups such as lysine, histidine, arginine, aspartic acid, glutamic acid. The enzyme protein also exhibits properties as a hydrophobic adsorbate due to the constituent amino acids having free hydrophobic groups such as alanine, valine, leucine, isoleucine, methionine, tryptophan, phenylalanine, and proline and because protein is organic polymer. Therefore, the PHA synthetase can be adsorbed by any solid surfaces having ionic and/or hydrophobic properties in various degrees.

To immobilize PHA synthetase using mainly ion adsorption, one can use a base material having ionic functional groups on the surface. Such a base material includes clay minerals such as kaolinite, bentonite, talc, and mica; metal oxides such as alumina and titanium oxide; and insoluble inorganic salts such as silica gel, hydroxyapatite, and calcium phosphate gel. In addition, inorganic pigment made with the above-described substance as the principal constituent, a polymer having ionic functional groups such as ion exchange resins, chitosan, and polyamino polystyrene can be used as an ion adsorptive base material.

To immobilize PHA synthetase by mainly hydrophobic adsorption, one can use a base (core) material having a nonpolar surface, including many polymers not having ionic functional groups or having hydrophobic functional groups on the surface, such as styrenic polymers, acrylic polymers, methacrylic polymers, vinyl esters, and vinyl polymers. Also, organic pigments such as azo pigments having a plurality of aromatic rings, phthalocyanine pigments and anthraquinone pigments having condensed polycyclic structure, and carbon black etc. show hydrophobic adsorptivities.

To immobilize PHA synthetase by ionic or hydrophobic adsorption, the above described synthetase and the core material are mixed in a certain reaction solution. In this case, it is desirable to shake the reaction vessel or stir the reaction solution with a suitable strength so that the enzyme may be uniformly adsorbed to the core surface.

Polarity of surface charge, charge amount, and hydrophobicity of the base (core) material and the PHA synthetase will vary depending on pH, a salt concentration, and a temperature of the reaction solution. Thus, it is desirable to adjust the solution in accordance with the properties of the core within an enzymatically acceptable range. For example, if adsorption is ionic nature, lower salt concentration will increase the charge involved in adsorption of the PHA synthetase to the base (core) material. pH change may increase the amount of opposite charges of the core or base material and the PHA synthetase. If the adsorption is basically hydrophobic nature, higher salt concentration will increase hydrophobicity of the base material (core) and PHA synthetase. In addition., it is possible to determine solution conditions suitable for adsorption by investigating the charge condition and hydrophobicity of the base material (core) and PHA synthetase performing electrophoresis or measuring wetting angle. Further, the conditions can be determined by direct measurement of adsorption between base material (core) and PHA synthetase. The measurement of the adsorption amount is carried out, for example, by adding a PHA synthetase solution of a known concentration to a dispersion of the core to allow adsorption in the resultant mixture, and then measuring the concentration of free PHA synthetase in the solution to determine the adsorbed enzyme amount by subtraction.

If it is difficult to immobilize the enzyme to the base material by the ion adsorption method or hydrophobic adsorption method, one may use a covalent bonding method knowing complicated operations and possibility of enzyme inactivation. Some methods for such immobilization will be listed below by way of example: the enzyme is bonded by diazo-coupling to a solid material having diazo group converted from aromatic amino group; a peptide bond is formed between the enzyme and a base material having a carboxyl group or amino group; alkylation using halogen group of the base material and amino group etc. of the enzyme; a polysaccharide base material activated by cyanogen bromide is reacted with an amino group of the enzyme; crosslinking between amino group of the base material and amino group of the enzyme; a base material having a carboxyl group or amino group is reacted with the enzyme in the presence of a compound having aldehyde or ketone group and an isocyanide compound; and exchange reaction between disulfide group of the base material and the thiol group of the enzyme.

Alternatively, the enzyme may be attached to the base material through affinity adsorption. Affinity adsorption is biological adsorption between a biopolymer and a substance having specific affinity to the biopolymer called ligand, e.g., an enzyme and its substrate, an antibody and its antigen, a receptor and its signaling molecule such as acetylcholine, and mRNA and tRNA for example. Generally, to immobilize an enzyme by affinity adsorption, a substrate, a reaction product, a competitive inhibitor, a coenzyme, an allosteric effecter, etc. of the enzyme is bonded to a solid as a ligand, then the enzyme is applied to this solid. In the present invention, if PHA synthetase is immobilized using 3-hydroxyacyl CoA as a ligand, the active site of the PHA synthetase for synthesizing PHA is blocked by the ligand. Thus, to maintain PHA synthesizing activity, the PHA synthetase may be fused to another biopolymer, and then a ligand of the fused biopolymer is employed for affinity adsorption. PHA synthetase may be fused to the biopolymer by genetic engineering procedure, or the biopolymer may be chemically bonded to the PHA synthetase. Although any biopolymers can be used as long as its ligand is readily available and is easily bonded to the base material (core), the biopolymer is preferably a protein when the fusion product is expressed by genetic recombination. For example, a PHA synthetase fused to glutathione S-transferase (GST) is produced by using an *Escherichia coli* transformant in which the PHA synthetase gene is linked to the GST gene for expression, and the fusion protein can adsorb to Sepharose to which glutathione, a ligand of GST, has been bonded.

Alternatively, PHA synthetase can be immobilized to a surface of the base material through binding between the base material and a peptide portion having a binding ability to the base material and being fused to the PHA synthetase.

The amino acid sequence having a binding ability to the base material can be determined by screening a random peptide library for example. Specifically, it is preferably used a phage display peptide library constructed to link random synthetic genes to a gene encoding a surface protein gene of M13 phage (for example, gene III) to be display at the N-terminus of the coat protein. Screening process for the amino acid sequence that binds to the base material is as follows. The phage display peptide library is added to the base material or to at least one constituent of the base material to bring the phages into contact with the base material, then the bound phages are separated from the not bound phages. Phages bound to the base material are eluted with an acid etc. and is neutralized with a buffer solution, then the phages are infected to *Escherichia coli* for phage proliferation. After repeating the screening process more than once, clones having binding ability to the base material are enriched. Then, to isolate single clones, colonies of *E. coli* infected with such clones are formed on a culture plate, and each colony is cultured in a liquid culture medium, and the phages in the culture medium is purified by polyethylene glycol precipitation etc. Consequently, the peptide structure is known by analyzing the base sequence.

Such an amino acid sequence having binding capacity for the base material, obtained as above, is utilized fusing this amino acid sequence to the PHA synthetase by ordinary genetic engineering process. Such a binding peptide can be linked to the N-terminus or C-terminus of the PHA synthetase for expression. In this case, an appropriate spacer sequence can be inserted for expression. Such a spacer sequence has preferably about 3 to 400 amino acids, and the spacer sequence may include any amino acids. Most preferably, the spacer sequence will not prevent the PHA synthetase activity or the binding to the base material.

The immobilized enzyme prepared as above may be used as it is, or may be lyophilized before use.

When the base material is a core of the capsule construct, the amount of PHA synthetase to be immobilized to the base material may be within a range of 10 to 1,000 units (U) per gram of base material, and preferably 50 to 500 units (U) per gram of base material, where the amount of enzyme that releases 1 μmol of CoA within one minute is defined as one unit (U).

When the above described immobilized enzyme is reacted in an aqueous reaction solution containing 3-hydroxyacyl CoA, it synthesizes PHA on the base material to form a construct in which the base material is coated with the PHA on the surface. The aqueous reaction solution should be prepared as a reaction system suitable for PHA synthetase activity. For example, pH is adjusted with a buffer solution to from 5.5 to 9.0 and preferably from 7.0 to 8.5. However, a possibility of setting the solution conditions out of the above described range is not eliminated depending on an optimum pH of the PHA synthetase to be used and on the pH stability thereof. Any buffer solution can be used according to the desired pH range as long as it does not affect the PHA synthetase activity. For example, one can use buffer solutions commonly used for biochemical reactions such as acetate buffer, sodium phosphate buffer, potassium phosphate buffer, 3-(N-morpholino)propanesulfonic acid (MOPS) buffer, N-tris(hydroxymethyl)methyl-3-aminopropanesulfonic acid (TAPS) buffer, Tris-HCl buffer, glycine buffer, and 2-(cyclohexylamino)ethanesulfonic acid (CHES) buffer. The concentration of the buffer solution is not particularly limited to a certain range as long as the PHA synthetase to be used can exhibit its activity, but generally it is from 5.0 mM to 1.0 M, preferably from 0.1 to 0.2 M. The reaction temperature is appropriately set according to characteristics of the PHA synthetase to be used, but generally it may be within a range of 4° C. to 50° C. and preferably within a range of 20° C. to 40° C., but not limited thereto according to the optimum temperature and heat resistance of the PHA synthetase to be used. The reaction time depends on stability of the PHA synthetase to be used, but generally, it may be within a range of one minute to 24 hours and preferably within a range of 30 minutes to 3 hours. The concentration of 3-hydroxyacyl CoA in the reaction solution is appropriately set within a certain range in which the PHA synthetase to be used can be exhibit it activity, but the concentration may be generally set within a range of 0.1 mM to 1.0 M and preferably within a range of 0.2 mM to 0.2 M. When the 3-hydroxyacyl CoA concentration in the reaction solution is high, it is preferable to use a buffer solution of a higher concentration since pH of the reaction system tends to be lowered.

In the above describe process, it is possible to change the monomer unit composition of the coating PHA in a radial direction with a particulate construct, and in a vertical direction with a flat construct, by changing the composition of 3-hydroxyacyl CoA (e.g., species and/or concentration) in the aqueous reaction solution with time.

One example of such a construct of which monomer unit composition is varied is such a construct that the base material is coated with one PHA layer of which composition is continuously changed to form a composition gradient in a radial direction or in a vertical direction. Such a construct may be produced, for example, by adding a different 3-hydroxyacyl CoA composition to the reaction solution during PHA synthesis.

Another example is such a construct that the base material is coated with a plurality of PHA layers of which compositions are different from one another. Such a construct may be produced, for example, by carrying out the reaction with one 3-hydroxyacyl CoA composition and then collecting the construct under making by centrifugation etc. from the reaction solution and transferring it to another reaction solution containing different 3-hydroxyacyl CoA composition for reaction.

The construct obtained by the above described reaction is subjected to a washing process as required. The method for washing is not particularly limited as long as the construct would not be affected undesirably in view of production purpose of the construct. If the construct is a capsule construct comprised of a core of the base material and a shell of PHA, unwanted constituents contained in the reaction solution may be removed by centrifuging the reaction solution and removing the supernatant therefrom, for example. Further washing nay be carried out by adding to the pellet a washing agent such as water, a buffer solution, and methanol that would not dissolve the PHA, and by repeating centrifugation. Also, other operations such as filtration may be used instead of centrifugation. On the other hand, if the construct is a construct in which a plate-like base material is coated with PHA, washing can be performed by soaking the construct in the above-described washing agent, for example. Further, the construct can be subjected to a drying process as required. Furthermore, the construct may be subjected to various secondary processing or chemical modifications before use.

For example, a construct provided with more useful functions and characteristics can be obtained by performing chemical modification on the PHA coating.

For example, introducing a graft chain to the PHA, one can obtain a construct in which at least part of the base material is coated with the PHA having various characteristics owing to the graft chain. In addition, it is possible to control mechanical strength, chemical resistance, heat resistance, etc. of the construct by cross-linking the PHA.

Although the method of chemical modification is not particularly limited as long as an object of obtaining the desired function and construct is achieved, it is preferably used a method to synthesize PHA having reactive functional groups on the side group and to utilize the reactivity of the functional group for chemical modification.

Although a kind of the above described reactive functional groups is not particularly limited as long as an object of obtaining the desired function and construct is achieved, the reactive functional groups include the above described epoxy group for example. In PHA having the epoxy groups on the side chains, chemical conversion can be performed as in the case of a common polymer having epoxy groups. Specifically, it is possible to convert epoxy to hydroxyl group or to introduce sulfone group. In addition, it is possible to add a compound having thiol or amine. For example, a compound having a reactive functional group at an end thereof, specifically a compound having at an end thereof an amino group having high reactivity with epoxy can be added and reacted to form a graft polymer.

The compounds having an amino group at the end include amino modified polymers such as polyvinyl amine, polyethylene imine, and amino modified polysiloxane (amino modified silicone oil). Among these, commercially available modified silicone oil may be used as the amino modified polysiloxane. Such amino modified polysiloxane can be also synthesized by a method described in J. Amer. Chem. Soc., 78, 2278 (1956). Improvement in properties such as the heat resistance is expected due to the addition of graft chains to the polymer.

Another example of chemical conversion of polymers having epoxy groups is the crosslinking reaction using diamine compounds such as hexamethylenediamine, succinic anhydride, 2-ethyl-4-methylimidazole, or electron beam irradiation. For example, the reaction of PHA having epoxy group on the side chain with hexamethylenediamine proceeds as shown below to form a crosslinked polymer.

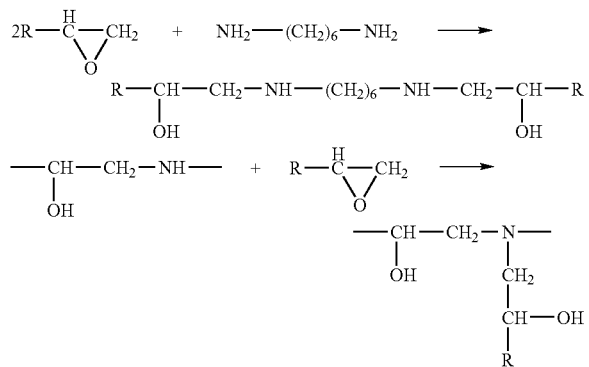

To confirm that the base material is coated with PHA in the obtained construct, one can use a combination of composition analysis by gas chromatography etc. and morphological observation by electron microscopy etc.; or a method for determining the structure from the mass spectra of constituent layers by means of time-of-flight secondary ion mass spectroscopy (TOF-SIMS) and ion sputtering technology. It is also possible to use a method newly developed by the inventors as a more simple and direct confirmation method in which Nile blue A staining is combined with a fluorescence microscopic observation. As a result of intensive study on the method for simply determining the in vitro PHA synthesis by PHA synthetase, the inventors have found that the Nile blue A that fluoresces specifically when it binds to PHA and is applicable to calling in vivo microbial production of PHA (Appl. Environ. Microbiol., 44, 238–241 (1982)) can also be used for calling the in vitro PHA synthesis if an appropriate method and conditions are determined. That is, in this method, a Nile blue A solution of a certain concentration is filtered and mixed with a reaction solution containing PHA, and when the sample is irradiated with an excitation light of a certain wavelength and observed under a fluorescence microscope, fluorescence is observed only from the synthesized PHA, allowing simple calling of in vitro PHA synthesis. PHA coating on the surface of the base material can be directly observed and evaluated by applying this method to the manufacture of the construct of the present invention, as long as the used base material itself does not fluoresce under the above-described conditions.

The composition distribution of PHA coating the base material along inside-to-outside or vertical direction can be evaluated by combining the ion sputtering technology with TOF-SIMS.

<Use of Construct>

One of features of the present invention is that it enables production of constructs of which production has been difficult by conventional organic synthetic chemistry. Therefore, it is possible to obtain a construct having excellent properties that could not have been conferred to the capsule constructs or laminated constructs manufactured by conventional organic synthetic chemistry. For example, it enables utilization of new polymer compounds or it can provide new functions or construct, which have been difficult by the conventional organic synthetic chemistry. More specifically, by utilizing highly strict molecule-recognition ability or stereo selectivity specific to a biological catalyst derived from a living organism, it is possible to produce a new functional polymer compound not obtainable by the conventional synthetic chemistry, or a capsule or laminated construct coated with a polymer compound having extremely high chirality through a significantly simple process.

An exemplary application of the above described constructs is a highly functionalized capsule toner for electrophotography. As described above, the capsule toner for electrophotography has some problems that the production process is significantly complicated and a large amount of solvents and surfactants are used in the production process. In accordance with a method of the present invention, such problems are solved and the capsule toner can be produced by a simple method. In addition, the thickness of the shell and the monomer unit composition, for example, can be relatively easily controlled. Japanese Patent Application Laid-Open No. 8-286416 teaches that inclusion of polar polymers such as polyester in the shell of a capsule toner improves image durability and provides charging uniformity and stability. Such advantages are expected for the shell of PHA of a capsule toner produced by the method of the present invention. Further, in the method of the present invention, PHA having various functional groups can be used as a shell. Thus, it is possible to control physical properties of the toner surface by these functional groups or to confer new functionalities to the toner. This method uses little or no organic solvents or surfactants except for the production process of the core and the reaction conditions are extremely mild, so that it is possible to reduce the environmental loads in making to a great extent.

Another exemplary application of the construct according to the present invention is, for example, a recording medium for inkjet recording. As described above, in general, various coating methods have been used to form an ink absorption layer on the base material of the conventional recording medium. According to the present invention, it is possible to produce a recording medium without using such a method. That is, a base material to which an enzyme has been immobilized is allowed to react with, for example, 3-hydroxypimelyl CoA represented by the following chemical formula [21].

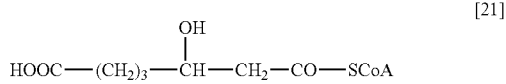

[21]

As a result, a recording medium having PHA represented by the following chemical formula [22] as an ink receiving layer is produced, where the PHA has an anionic functional group, i.e., carboxyl group, on the side group.

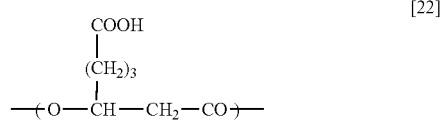

[22]

In accordance with the method of the present invention, it becomes possible to manufacture a novel functional recording medium as described above which has been difficult to be manufactured by the conventional techniques. There has been no report on making a recording medium by such techniques.

According to the present invention, the construct, usage thereof or the method for making thereof is not limited to those described above.

EXAMPLES

Now the present invention will be described in more detail with reference to Examples. Although each of the examples described below is the best mode of the present invention, the technical scope of the present invention is not limited to these examples. "%" or "part" herein is based on the weight unless otherwise specified.

Reference Example 1

Construction of Transformant Having PHA Synthetase Production Capacity

Strain YN2 was cultured in 100 ml of LB medium (1% polypeptone (NIPPON SEIYAKU CO., LTD.), 0.5% yeast extract (Difco), 0.5% sodium chloride, pH 7.4) overnight at 30° C., then the chromosomal DNA was isolated by the method of Marmar et al. The obtained DNA was completely digested by a restriction enzyme HindIII. A vector pUC18 was also cut by HindIII. After terminal dephosphorylation (Molecular Cloning, 1, 572, (1989); Cold Spring Harbor Laboratory Press), complete HindIII digestion fragments of the chromosomal DNA were ligated to the HindIII cleavage site of the vector (a cloning site) using a DNA ligation kit Ver. II (TAKARA SHUZO CO., LTD.). With these plasmid vectors containing chromosomal DNA fragments, *Escherichia coli* HB 101 was transformed to construct a DNA library of strain YN2. Next, to select DNA fragments covering the PHA synthetase gene of strain YN2, a probe for colony hybridization was prepared by synthesizing an oligonucleotide comprised of the base sequences of SEQ ID NO: 2 and SEQ ID NO: 3 (Amersham Pharmacia Biotech). Then PCR was carried out by using the chromosomal DNA as a template. The PCR-amplified DNA fragments were used as a probe. Labeling of the probe was conducted by employing a commercially available labeling enzyme Alk Phos Direct (Amersham Pharmacia Biotech). Using the obtained labeled probe for colony hybridization, a clone carrying the recombinant plasmid containing the PHA synthetase gene was selected from the chromosomal DNA library of YN2. The plasmid was recovered from the selected clone by the alkali process to give DNA fragment including the PHA synthetase gene. This gene fragment was inserted into a vector pBBR122 having a wide-host-replication range (Mo Bi Tec) not belonging to any of IncP, IncQ, or IncW incompatibility group. When *Pseudomonas cichorii* YN2 ml (a PHA synthesis negative strain) was transformed with this recombinant plasmid by electroporation, the PHA synthesizing capacity of the YN2 ml strain was recovered to show complementarity. Consequently, it was confirmed that the selected gene fragment contains PHA synthetase gene region which can be translated into PHA synthetase within *Pseudomonas cichorii* YN2 ml.

The base sequence of this DNA fragment was determined by the Sanger method. As a result, it was shown that there are base sequences represented by SEQ ID NO: 4 and SEQ ID NO: 5 each encoding a polypeptide in the determined base sequence. With respect to these PHA synthetase genes, PCR was carried out by using the chromosomal DNA as a template to produce the complete PHA synthetase gene. More specifically, an upstream primer (SEQ ID NO: 6) and a downstream primer (SEQ ID NO: 7) corresponding to the PHA synthetase gene of SEQ ID NO:4, and an upstream primer (SEQ ID NO: 8) and a downstream primer (SEQ ID NO: 9) corresponding to the PHA synthetase gene of SEQ ID NO: 5 were synthesized respectively (Amersham Pharmacia Biotech).

Using these primers, PCR was carried out for each of the base sequences shown by SEQ ID NO: 4 and SEQ ID NO: 5, then a full length of PHA synthetase gene was amplified (an LA-PCR kit; TAKARA SHUZO CO., LTD.). Next, the obtained PCR amplified fragment and an expression vector pTrc99A were digested by the restriction enzyme HindIII and dephosphorylated (Molecular Cloning, vol. 1, p. 572, (1989); Cold Spring Harbor Laboratory Press), then the DNA fragment including a full length PHA synthetase gene excluding unnecessary base sequences at both terminuses was linked to a restriction site of the expression vector pTrc99A by using a DNA ligation kit Ver. II (TAKARA SHUZO CO., LTD.).

An *E. coli* strain (*Escherichia coli* HB 101: TAKARA SHUZO) was transformed with each of the obtained recombinant plasmids by the calcium chloride method. The obtained recombinants were cultured and the recombinant plasmids were amplified, then the recombinant plasmids were respectively recovered. The recombinant plasmid having a DNA of SEQ ID NO: 4 was designated as pYN2-C1, and the recombinant plasmid having a DNA of SEQ ID NO: 5 was designated as pYN2-C2. An *E. coli* strain (*Escherichia coli* HB101fB fadB deletion strain) was transformed with pYN2-C1 and pYN2-C2 respectively by the calcium chloride method to obtain recombinant *E. coli* strains having respective recombinant plasmids, i.e., a pYN2-C1 recombinant strain and a pYN2-C2 recombinant strain.

Reference Example 2

Production of PHA Synthetase (1)

For the pYN2-C1, an upstream primer (SEQ ID NO: 10) and a downstream primer (SEQ ID NO: 11) were designed and synthesized respectively (Amersham Pharmacia Biotech). PCR was carried out with LA-PCR kit (TAKARA SHUZO CO., LTD.) using these primers and template pYN2-C1 to synthesize a full length PHA synthetase gene having a BamHI restriction site upstream and a XhoI restriction site downstream.

Similarly, for pYN2-C2, an upstream primer (SEQ ID NO: 12) and a downstream primer (SEQ ID NO: 13) were designed and synthesized respectively (Amersham Pharmacia Biotech). PCR was carried out with an LA-PCR kit (TAKARA SHUZO CO., LTD.) using these primers and the template pYN2-C2 to amplify the full length PHA synthetase gene having a BamHI restriction site upstream and a XhoI restriction site downstream.

Respective purified PCR amplification products were digested by BamHI and XhoI, then inserted into the corresponding restriction sites of plasmid pGEX-6P-1 (Amersham Pharmacia Biotech). An *E. coli* strain JM109 was transformed with these vectors, and consequently a strain expressing PHA synthetase was obtained. For confirmation, the plasmid DNA was prepared by Miniprep (Wizard Minipreps DNA Purification Systems, PROMEGA) in a large amount and digested by BamHI and XhoI, and the resulting DNA fragment was identified. The PHS synthetase was expressed and purified as follows: The obtained strain was pre-cultured in 10 ml of LB-Amp medium overnight, and then an 0.1 ml culture was transferred to 10 ml of LB-Amp medium and cultured at 37° C., 170 rpm for 3 hours with shaking. Then, IPTG was added to the culture to a concentration of 1 mM, then the culture was continued for 4 to 12 hours at 37° C.

The E. coli cells induced with IPTG were collected (8,000×g, 2 min., 4° C.) and resuspended in a 1/10 volume of phosphate buffer physiological saline PBS; 8 g NaCl, 1.44 g $Na_2HPO_4$, 0.24 g $KH_2PO_4$, 0.2 g, KCl, 1,000 ml purified water) at 4° C. The cells were disrupted by freeze and thawing and sonication, and subjected to centrifugation (8,000×g, 10 min., 4° C.) to remove solid impurities. Confirming that the aimed recombinant protein was present in the supernatant by SDS-PAGE, the induced and expressed GST fusion protein was purified by using Glutathione Sepharose 4B (Amersham Pharmacia Biotech). The Glutathione Sepharose was previously treated to avoid nonspecific adsorption, that is, the Glutathione Sepharose was washed with an equivalent amount of PBS for three times (8,000×g, 1 min., 4° C.), and then an equivalent amount of 4% bovine serum albumin PBS was added thereto at 4° C. for one hour. After that, the Sepharose was washed with an equivalent amount of PBS twice, and re-suspended in an 1/2 amount of PBS. The pre-treated 40 µl of Glutathione Sepharose was added to 1 ml of the above cell free extract, and gently stirred at 4° C. to adsorb fusion protein GST-YN2-C1 and GST-YN2-C2 onto Glutathione Sepharose respectively. After centrifugation (8,000×g, 1 min., 4° C.) to collect the Glutathione Sepharose, it was washed with 400 µl of PBS for three times. After the washing, 10 mM of glutathione was added thereto and stirred for one hour at 4° C. to elute the adsorbed fusion protein. After centrifugation (8,000×g, 2 min., 4° C.), the supernatant was recovered and dialyzed against PBS to purify the GST fusion protein. Single band was recognized by SDS-PAGE.

Then 500 µg of each GST fusion protein was digested by PreScission protease (Amersham Pharmacia Biotech, 5U), the protease and the GST were removed therefrom by passing through Glutathione Sepharose. The flow-through fraction was further loaded to Sephadex G200 column equilibrated with PBS, then expression proteins YN2-C1 and YN2-C2 were obtained as final purified products. By SDS-PAGE, single bands (60.8 kDa and 61.5 kDa, respectively) were confirmed.

The above described enzymes were concentrated with a bioliquid concentrating agent (Mizubutorikun AB-1100, Atto Corp.) to obtain 10 U/ml of purified enzyme solutions.

The enzyme activity was measured by the above-described method. The protein concentration of the sample was determined by using a micro BCA protein assay reagent kit (Pierce Chemical Co.). The results are shown in Table 1.

TABLE 1

| | Specific activity |
|---|---|
| pYN2-C1 | 4.1 U/mg protein |
| pYN2-C2 | 3.6 U/mg protein |

Reference Example 3

Production of PHA Synthetase (2)

Each of E coli strains P91, H45, YN2, and P161 was inoculated in 200 ml of an M9 medium containing 0.5% of yeast extract (Difco) and 0.1% of octanoic acid, and incubated at 30° C., with shaking at 125 strokes/min. After 24 hours, the cells were harvested by centrifugation (10,000×g, 4° C., for 10 min.), then the cells were re-suspended in 200 ml of 0.1M Tris-HCl buffer (pH 8.0) and further subjected to centrifugation for washing. The cells were re-suspended in 2.0 ml of 0.1M Tris-HCl buffer (pH 8.0) and disrupted by an ultrasonic homogenizer and then centrifuged (12,000×g, 4° C., for 10 min.) to collect the supernatant to obtain the crude enzyme.

Each crude enzyme activity was measured by the above described method, and the result is shown in Table 2.

TABLE 2

| | Activity |
|---|---|
| P91 | 0.1 U/ml |
| H45 | 0.2 U/ml |
| YN2 | 0.4 U/ml |
| P161 | 0.2 U/ml |

Example 1

Preparation of Capsule Construct (1)

One part of alumina particles (particle size: 0.12 µm to 135 µm) and 39 parts of PBS were added to 10 parts of a PHA synthetase solution (10 U/ml) derived from a pYN2-C1 recombinant strain, and the mixture was reacted with mild shaking for 30 minutes at 30° C. to adsorb PHA synthetase onto the surface of the alumina particles. Then the mixture was centrifuged at 10,000×g, 4° C., for 10 min, and the precipitate was suspended in a PBS solution and centrifuged again (10,000×g, 4° C., for 10 min.) to obtain the immobilized enzyme.

The immobilized enzyme was suspended in 48 parts of a 0.1M phosphate buffer solution (pH 7.0), to which one part of (R)-3-hydroxyoctanoyl CoA (prepared according to the method described in Eur. J. Biochem., 250, 432–439 (1997)) and 0.1 part of bovine serum albumin (Sigma) were added, and incubated with mild shaking for 2 hours at 30° C.

A 10 µl aliquot of the above reaction solution was put on a slide glass, to which 10 µl of a 1% solution of Nile blue A in water was added. These solutions were mixed on the slide glass, covered with a cover glass, and observed under a fluorescence microscope (330 to 380 nm excitation filter, 420 nm long pass absorption filter, Nikon Corp.). As a result, fluorescence from the surface of the alumina particles was observed to confirm that the alumina particles were coated with PHA on the surface.

As a control, one part of alumina particles was added to 49 parts of a 0.1M phosphate buffer (pH 7.0), and incubated with mild shaking for 2.5 hours at 30° C. Observation under a fluorescence microscope after Nile blue A staining showed the surface of the alumina particle did not fluoresce at all.

Further, part of the above coated particles was collected by centrifugation (10,000×g, 4° C., for 10 min.), dried in vacuum, suspended in chloroform, and stirred for 20 hours at 60° C. to extract the PHA coating. The extract was filtered through a membrane filter of 0.45 µm pore size and concentrated under a reduced pressure by using a rotary evaporator. Then the extract was subjected to methanolysis by a conventional method and analyzed by gas chromatography-mass spectroscopy (GC-MS, Shimadzu QP-5050, an EI method) to identify the methyl-esterified PHA monomer unit. As a result, it was confirmed that the PHA was made from 3-hydroxyoctanoic acid monomer unit as shown in FIG. 1.

In addition, the molecular weight of the above PHA was determined by gel permeation chromatography (GPC; TOSOH HLC-8020, column; Polymer Laboratories Ltd. PL gel MIXED-C (5 μm), solvent; chloroform, column temperature; 40° C., polystyrene base conversion). As a result, Mn=21,000, Mw=40,000.

Example 2

Preparation of Capsule Construct (2)

One part of alumina particles (particle size: 0.12 μm to 135 μm) and 39 parts of PBS were added to 10 parts of a PHA synthetase solution (10 U/ml) derived from a pYN2-C2 recombinant strain, and the mixture was reacted with mild shaking for 30 minutes at 30° C. to adsorb PHA synthetase onto the surface of the alumina particles. Then the mixture was centrifuged at 10,000×g, 4° C., for 10 min, and the precipitate was suspended in a PBS solution and centrifuged again (10,000×g, 4° C., for 10 min.) to obtain the immobilized enzyme.

The immobilized enzyme was suspended in 48 parts of a 0.1M phosphate buffer solution (pH 7.0), to which one part of (R)-3-hydroxyoctanoyl CoA (prepared according to the method described in Eur. J. Biochem., 250, 432–439 (1997)) and 0.1 part of bovine serum albumin (Sigma) were added, and incubated with mild shaking for 2 hours at 30° C.

A 10 μl aliquot of the above reaction solution was put on a slide glass, to which 10 μl of a 1% solution of Nile blue A in water was added. These solutions were mixed on the slide glass, covered with a cover glass, and observed under a fluorescence microscope (330 to 380 nm excitation filter, 420 nm long pass absorption filter, Nikon Corp.). As a result, fluorescence from the surface of the alumina particles was observed to confirm that the alumina particles were coated with PHA on the surface.

Further, part of the above coated particles was collected by centrifugation (10,000×g, 4° C., for 10 min.), dried in vacuum, suspended in chloroform, and stirred for 20 hours at 60° C. to extract the PHA coating. The extract was filtered through a membrane filter of 0.45 μm pore size and concentrated under a reduced pressure by using a rotary evaporator. Then the extract was subjected to methanolysis by a conventional method and analyzed by gas chromatography-mass spectroscopy (GC-MS, Shimadzu QP-5050, an EI method) to identify the methyl-esterified PHA monomer unit. As a result, as in Example 1, it was confirmed that the PHA was made from 3-hydroxyoctanoic acid monomer unit.

Example 3

Preparation of Capsule Construct (3)

One part of alumina particles (particle size: 0.12 μm to 135 μm) was added to 99 parts of crude PHA synthetase preparations derived from strains YN2, H45, P91 and P161 respectively, and each mixture was reacted with mild shaking for 30 minutes at 30° C. to adsorb PHA synthetase onto the surface of the alumina particles. Then each mixture was centrifuged at 10,000×g, 4° C., for 10 min, and the precipitate was suspended in a PBS solution and centrifuged again (10,000×g, 4° C., for 10 min.) to obtain the immobilized enzyme.

Each immobilized enzyme was suspended in 48 parts of a 0.1M phosphate buffer solution (pH 7.0), to which one part of (R)-3-hydroxyoctanoyl CoA (prepared according to the method described in Eur. J. Biochem., 250, 432–439 (1997)) and 0.1 part of bovine serum albumin (Sigma) were added, and incubated with mild shaking for 2 hours at 30° C.

A 10 μl aliquot of each above reaction solution was put on a slide glass, to which 10 μl of a 1% solution of Nile blue A in water was added. These solutions were mixed on the slide glass, covered with a cover glass, and observed under a fluorescence microscope (330 to 380 nm excitation filter, 420 nm long pass absorption filter, Nikon Corp.). As a result, fluorescence from the surface of the alumina particles was observed to confirm that the alumina particles were coated with PHA on the surface with each immobilized enzyme reaction.

Further, part of the above coated particles was collected by centrifugation (10,000×g, 4° C., for 10 min.), dried in vacuum, suspended in chloroform, and stirred for 20 hours at 60° C. to extract the PHA coating. The extract was filtered through a membrane filter of 0.45 μm pore size and concentrated under a reduced pressure by using a rotary evaporator. Then the extract was subjected to methanolysis by a conventional method and analyzed by gas chromatography-mass spectroscopy (GC-MS, Shimadzu QP-5050, an EI method) to identify the methyl-esterified PHA monomer unit. As a result, as in Example 1, it was confirmed that the PHA was made from 3-hydroxyoctanoic acid monomer unit.

Example 4

Preparation of Capsule Construct (4)

One part of alumina particles (particle size: 0.12 μm to 135 μm) and 39 parts of PBS were added to 10 parts of a PHA synthetase solution (10 U/ml) derived from a pYN2-C1 recombinant strain, and the mixture was reacted with mild shaking for 30 minutes at 30° C. to adsorb PHA synthetase onto the surface of the alumina particles. Then the mixture was centrifuged at 10,000×g, 4° C., for 10 min, and the precipitate was suspended in a PBS solution and centrifuged again (10,000×g, 4° C., for 10 min.) to obtain the immobilized enzyme.

The immobilized enzyme was suspended in 48 parts of a 0.1M phosphate buffer solution (pH 7.0), to which one part of (R)-3-hydroxy-5-phenylvaleryl CoA and 0.1 part of bovine serum albumin (Sigma) were added, and incubated with mild shaking for 2 hours at 30° C. The (R)-3-hydroxy-6-phenylvaleryl CoA was prepared from 3-hydroxy-5-phenylvaleric acid according to the method described in Eur. J. Biochem., 250, 432–439 (1997), where first 3-hydroxy-5-phenylvaleriate was prepared by the Reformatsky reaction, and then hydrolyzed to give 3-hydroxy-5-phenylvaleric acid.

A 10 μl aliquot of the above reaction solution was put on a slide glass, to which 10 μl of a 1% solution of Nile blue A in water was added. These solutions were mixed on the slide glass, covered with a cover glass, and observed under a fluorescence microscope (330 to 380 nm excitation filter, 420 nm long pass absorption filter, Nikon Corp.). As a result, fluorescence from the surface of the alumina particles was observed to confirm that the alumina particles were coated with PHA on the surface.

Figure 2:
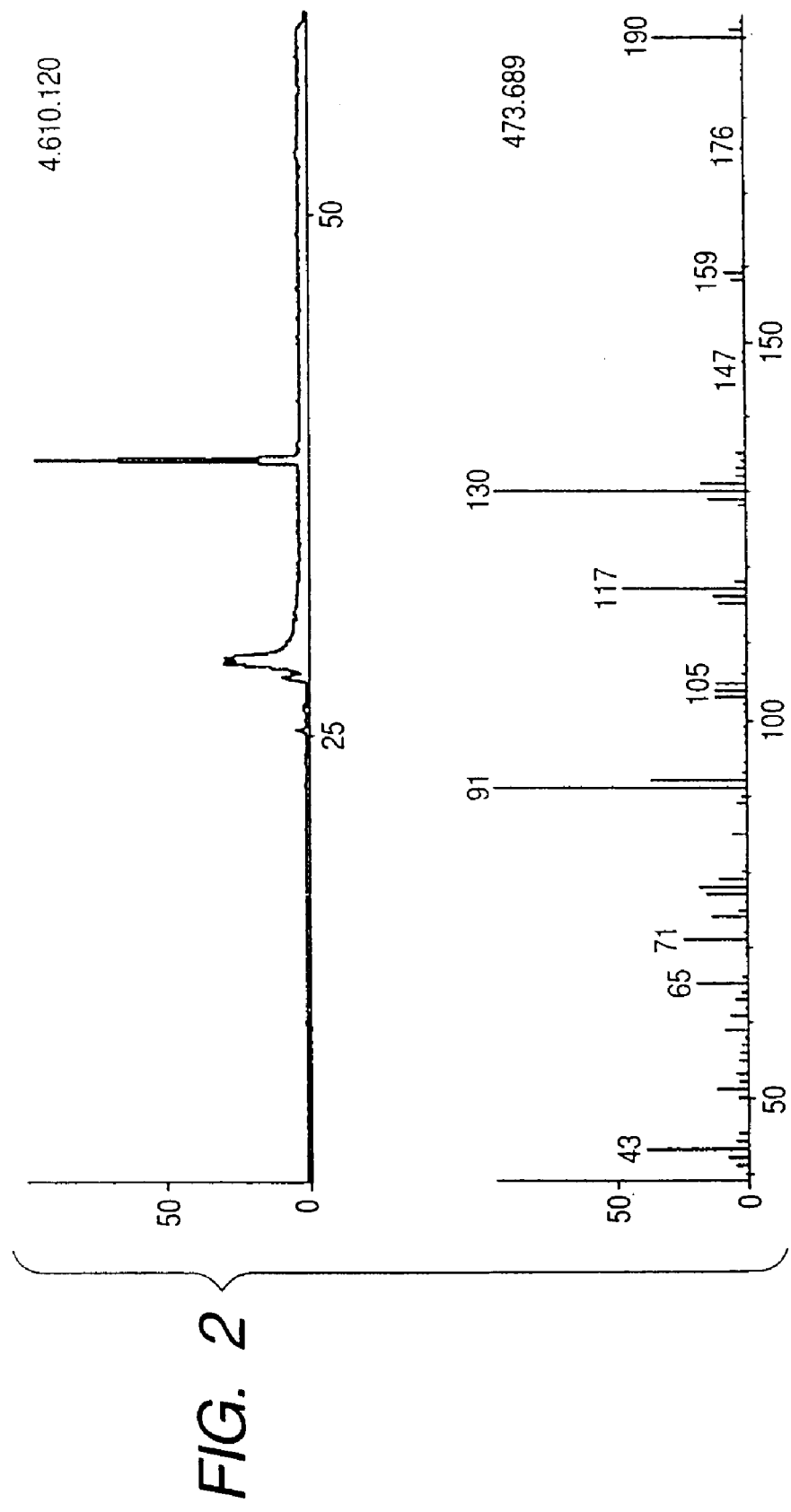
FIG. 2 is a GC-MS analytical result of the shell of a capsule construct in Example 4.

Further, part of the above coated particles was collected by centrifugation (10,000×g, 4° C., for 10 min.), dried in vacuum, suspended in chloroform, and stirred for 20 hours at 60° C. to extract the PHA coating. The extract was filtered through a membrane filter of 0.45 μm pore size and concentrated under a reduced pressure by using a rotary evaporator. Then the extract was subjected to methanolysis by a conventional method and analyzed by gas chromatography-mass spectroscopy (GC-MS, Shimadzu QP-5050, an EI method) to identify the methyl-esterified PHA monomer unit. As a result, it was confirmed that the PHA was made from 3-hydroxy-5-phenylvaleric acid monomer unit as shown in FIG. 2.

In addition, the molecular weight of the above PHA was determined by gel permeation chromatography (GPC; TOSOH HLC-8020, column; Polymer Laboratories Ltd. PL gel MIXED-C (5 μm), solvent; chloroform, column temperature; 40° C., polystyrene base conversion) to give a result of Mn=16,000, and Mw=36,000.

Example 5

Preparation of Capsule Construct (5)

One part of alumina particles (particle size: 0.12 μm to 135 μm) and 39 parts of PBS were added to 10 parts of a PHA synthetase solution (10 U/ml) derived from a pYN2-C1 recombinant strain, and the mixture was reacted with mild shaking for 30 minutes at 30° C. to adsorb PHA synthetase onto the surface of the alumina particles. Then the mixture was centrifuged at 10,000×g, 4° C., for 10 min, and the precipitate was suspended in a PBS solution and centrifuged again (10,000×g, 4° C., for 10 min.) to obtain the immobilized enzyme.

The immobilized enzyme was suspended in 48 parts of a 0.1M phosphate buffer solution (pH 7.0), to which one part of (R)-3-hydroxy-5-(4-fluorophenyl)valeryl CoA and 0.1 part of bovine serum albumin (Sigma) were added, and incubated with mild shaking for 2 hours at 30° C. The (R)-3-hydroxy-6-phenylvaleryl CoA was prepared from 3-hydroxy-5-(4-fluorophenyl)valeric acid according to the method described in Eur. J. Biochem., 250, 432–439 (1997), where first 3-hydroxy-5-(4-fluorophenyl)valeriate was prepared by the Reformatsky reaction, and then hydrolyzed to give 3-hydroxy-5-(4-fluorophenyl)valeric acid.

A 10 μl aliquot of the above reaction solution was put on a slide glass, to which 10 μl of a 1% solution of Nile blue A in water was added. These solutions were mixed on the slide glass, covered with a cover glass, and observed under a fluorescence microscope (330 to 380 nm excitation filter, 420 nm long pass absorption filter, Nikon Corp.). As a result, fluorescence from the surface of the alumina particles was observed to confirm that the alumina particles were coated with PHA on the surface.

Figure 3:
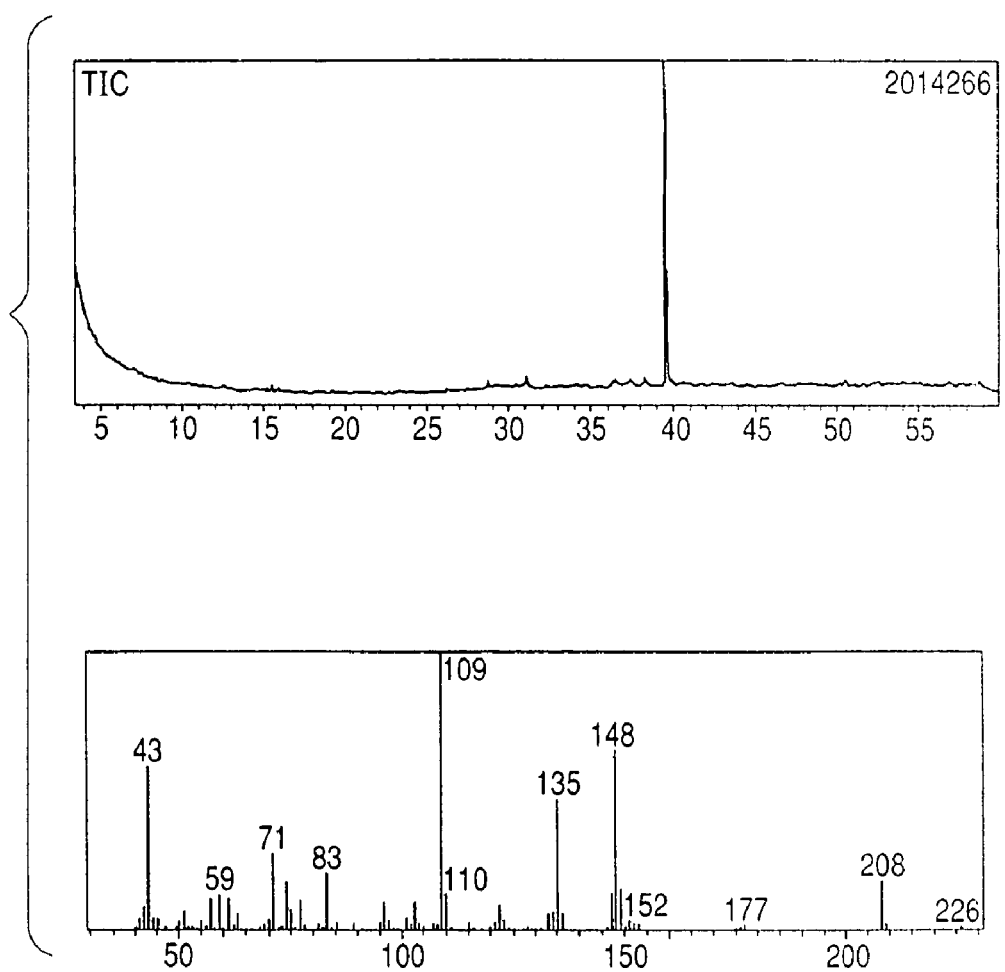
FIG. 3 is a GC-MS analytical result of the shell of a capsule construct in Example 5.

Further, part of the above coated particles was collected by centrifugation (10,000×g, 4° C., for 10 min.), dried in vacuum, suspended in chloroform, and stirred for 20 hours at 60° C. to extract the PHA coating. The extract was filtered through a membrane filter of 0.45 μm pore size and concentrated under a reduced pressure by using a rotary evaporator. Then the extract was subjected to methanolysis by a conventional method and analyzed by gas chromatography-mass spectroscopy (GC-MS, Shimadzu QP-5050, an EI method) to identify the methyl-esterified PHA monomer unit. As a result, it was confirmed that the PHA was made from 3-hydroxy-5-(4-fluorophenyl)valeric acid monomer unit as shown in FIG. 3.

Example 6

Preparation of Capsule Construct (6)

To 10 parts of a PHA synthetase solution (10 U/ml) derived from a pYN2-C1 recombinant strain, one part of alumina particles of which particle size was adjusted by precipitation to an volume average particle size of 1.45 μm and 39 parts of PBS were added and the mixture was reacted with mild shaking for 30 minutes at 30° C. to adsorb PHA synthetase onto the surface of the alumina particles. Then the mixture was centrifuged at 10,000×g, 4° C., for 10 min, and the precipitate was suspended in a PBS solution and centrifuged again (10,000×g, 4° C., for 10 min.) to obtain the immobilized enzyme.

The immobilized enzyme was suspended in 48 parts of a 0.1M phosphate buffer solution (pH 7.0), to which one part of (R)-3-hydroxyoctanoyl CoA (prepared according to the method described in Eur. J. Biochem., 250, 432–439 (1997)) and 0.1 part of bovine serum albumin (Sigma) were added, and incubated with mild shaking for 2 hours at 30° C.

A 10 μl aliquot of the above reaction solution was put on a slide glass, to which 10 μl of a 1% solution of Nile blue A in water was added. These solutions were mixed on the slide glass, covered with a cover glass, and observed under a fluorescence microscope (330 to 380 nm excitation filter, 420 nm long pass absorption filter, Nikon Corp.). As a result, fluorescence from the surface of the alumina particles was observed to confirm that the alumina particles were coated with PHA on the surface.

Further, part of the above coated particles was collected by centrifugation (10,000×g, 4° C., for 10 min.) After drying treatment, the mass of the polymer formed on the particle surface was determined by using a time-flight secondary ion mass spectroscope (TOF-SIMS IV, CAMEMA). The obtained mass spectrum showed that the surface of the construct was made of polyhydroxyoctanoate homopolymer. Furthermore, mass spectrum was taken by using TOF-SIMS scraping the construct surface little by little by ion spattering. In this case also, only polyhydroxyoctanoate homopolymer was detected showing that in the capsule construct a hydrophilic inorganic particle is directly coated with hydrophobic polyhydroxyoctanoate homopolymer.

In addition, the molecular weight of the above PHA was determined by gel permeation chromatography (GPC; TOSOH HLC-8020, column; Polymer Laboratories Ltd. PL gel MIXED-C (5 μm), solvent; chloroform, column temperature; 40° C., polystyrene base conversion) to give a result of Mn=23,000, and Mw=42,000.

Example 7

Preparation of a Capsule Construct 7

To 10 parts of a PHA synthetase solution (10 U/ml) derived from a pYN2-C1 recombinant strain, one part of alumina particles of which particle size was adjusted by precipitation to an volume average particle size of 1.45 μm and 39 parts of PBS were added and the mixture was reacted with mild shaking for 30 minutes at 30° C. to adsorb PHA synthetase onto the surface of the alumina particles. Then the mixture was centrifuged at 10,000×g, 4° C., for 10 min, and the precipitate was suspended in a PBS solution and centrifuged again (10,000×g, 4° C., for 10 min.) to obtain the immobilized enzyme.

The immobilized enzyme was suspended in 48 parts of a 0.1M phosphate buffer solution (pH 7.0), to which one part of (R)-3-hydroxypimelyl CoA prepared according to the method described in J. Bacteriol., 182, 2753–2760 (2000) and 0.1 part of bovine serum albumin (Sigma) were added, and incubated with mild shaking for 2 hours at 30° C. Then, to this reaction solution, a 0.1M phosphate buffer solution (pH 7.0) containing one part of (R)-3-hydroxyoctanoyl CoA prepared according to the method described in Eur. J. Biochem., 250, 432–439 (1997)) and 0.1 part of bovine serum albumin was added by using a micro tube pump (TOKYO RIKAKIKAI Co., MP-3N) at a rate of one part per minute, with mild shaking at 30° C. After one and a half hours of incubation, the produced particles were collected by centrifugation (10,000×g, 4° C., for 10 min.). After the supernatant was removed, the particles were suspended in 25 parts of a 0.1M phosphate buffer (pH 7.0) including one part of (R)-3-hydroxyoctanoyl CoA (prepared by a method described in Eur. J. Biochem., 250, 432–439 (1997)) and 0.1 part of bovine serum albumin (Sigma) and incubated with mild shaking for 20 minutes at 30° C.

After reaction, a 10 µl aliquot of the above reaction solution was put on a slide glass, to which 10 µl of a 1% solution of Nile blue A in water was added. These solutions were mixed on the slide glass, covered with a cover glass, and observed under a fluorescence microscope (330 to 380 nm excitation filter, 420 nm long pass absorption filter, Nikon Corp.). As a result, fluorescence from the surface of the alumina particles was observed to confirm that the alumina particles were coated with PHA on the surface.

Further, the capsule constructs were collected by centrifugation (10,000×g, 4° C., for 10 min.) After drying treatment, the mass of the polymer formed on the particle surface was determined by using a time-flight secondary ion mass spectroscope (TOF-SIMS IV, CAMEMA). The obtained mass spectrum showed that the surface of the construct was made of polyhydroxyoctanoate homopolymer. Furthermore, spectrum was taken by using TOF-SIMS scraping the construct surface little by little by ion spattering. First appeared a copolymer of 3-hydroxyactanoic acid and 3-hydroxypimelic acid at a molar ratio of 21:1, and this ratio gradually changed as the scraping proceeded inward the particle, with decreasing 3-hydroxyoctanoic acid and increasing 3-hydroxypimelic acid, and finally a homopolymer of polyhydroxypimelate appeared. This result shows that the capsule construct of this example was constructed in such a manner that a hydrophilic particulate base material was coated with polyhydroxypimelate having hydrophilic functional groups, and the surface of this polyhydroxypimelate was coated with a copolymer of 3-hydroxypimelic acid having a hydrophilic functional group and 3-hydroxyoctanoic acid having a hydrophobic functional group with a gradually increasing ratio of 3-hydroxyoctanoic acid toward the surface, and the outmost surface was coated with polyhydroxyoctanoate homopolymer.

In addition, the molecular weight of the above PHA was determined by gel permeation chromatography (GPC; TOSOH HLC-8020, column; Polymer Laboratories Ltd. PL gel MIXED-C (5 µm), solvent; chloroform, column temperature; 40° C., polystyrene base conversion) to give a result of Mn=21,000, and Mw=40,000.

Example 8

Evaluation of Example 6 and Example 7

The respective capsule constructs of Example 6 and Example 7, and alumina particles of which particle size had been adjusted uniform by precipitation (the volume average particle size: 1.45 µm) as, Comparative Example A were evaluated. Each of them was added one part to 10 parts of purified water. Each suspension was stored for 30 days at room temperature, with or without vigorous shaking of 5 minutes by using a vortex mixer before storage, and the volume average particle size was measured before and after the storage. The measurement was performed by a laser Doppler type of particle size distribution measuring instrument (UPA-150; a product of Nikkiso). Table 3 shows the result without shaking, and Table 4 shows the result with shaking.

TABLE 3

|  | Example 6 | Example 7 | Comparative Example A |
|---|---|---|---|
| Volume average particle size (before storage) | 1.58 | 1.68 | 1.45 |
| Volume average particle size (after storage, µm) | 1.60 | 1.71 | 3.42 |

(µm)

TABLE 4

|  | Example 6 | Example 7 | Comparative Example A |
|---|---|---|---|
| Volume average particle size (before storage) | 1.47 | 1.65 | 1.41 |
| Volume average particle size (after storage) | 2.05 | 1.71 | 3.56 |

(µm)

As a result, when the shaking was not performed, the volume average particle size of capsule constructs from Example 6 and Example 7 did not change before and after storage, showing the excellent storage stability of these constructs. On the other hand, the volume average particle size of particles of Comparative Example A increased after storage.

When shaking was performed before storage, the volume average particle size of the capsule construct of Example 7 almost did not change before and after storage, but the volume average particle size of the capsule construct of Example 6 increased slightly after storage. The volume average particle size of the particles of Comparative Example A showed the same change as with the above case without shaking.

The capsule constructs of Example 6 and Example 7 after storage with shaking were observed under a light microscope. As a result, it was observed that the capsule constructs of Example 7 were in a good dispersion condition, but those of Example 6 were agglomerated and the PHA coating of some capsule constructs had come off.

From the above described results, it was found that a hydrophobic PHA capsule encapsulating an inorganic base material stably can be produced by coating the inorganic base material with a PHA having a hydrophilic functional group having high affinity to the inorganic base material, and then coating the particle surface with PHA copolymer made with a hydrophilic PHA monomer unit and a hydrophobic PHA monomer unit increasing the percentage of the hydrophobic PHA monomer unit toward the surface.

Example 9

Preparation of capsule Construct (8)

To 10 parts of a PHA synthetase solution (10 U/ml) derived from a pYN2-C1 recombinant strain, one part of alumina particles of which particle size was adjusted by precipitation to an volume average particle size of 1.45 μm and 39 parts of PBS were added and the mixture was reacted with mild shaking for 30 minutes at 30° C. to adsorb PHA synthetase onto the surface of the alumina particles. Then the mixture was centrifuged at 10,000×g, 4° C., for 10 min, and the precipitate was suspended in a PBS solution and centrifuged again (10,000×g, 4° C., for 10 min.) to obtain the immobilized enzyme.

The immobilized enzyme was suspended in 48 parts of a 0.1M phosphate buffer solution (pH 7.0), to which 0.8 parts of (R,S)-3-hydroxy-5-phenoxyvaleryl CoA, 0.2 parts of (R,S)-3-hydroxy-7,8-epoxyoctanoyl CoA and 0.1 part of bovine serum albumin (Sigma) were added, and incubated with mild shaking for 2 hours at 30° C. to obtain Sample 1. Here, (R, S)-3-hydroxy-5-phenoxyvaleryl CoA was prepared from 3-hydroxy-5-phenylvaleric acid according to the method described in Eur. J. Biochem., 250, 432–439 (1997), and 3-hydroxy-5-phenylvalerylate was prepared by first preparing 3-hydroxy-5-phenylvaleriate from. 3-phenoxypropanal and ethyl bromoacetate by the Reformatsky reaction, and they hydrolyzing it. (R,S)-3-hydroxy-7,8-epoxyoctanoyl CoA was prepared by the method described in Eur. J. Biochem., 250, 432–439 (1997) from 3-hydroxy-7,8-epoxyoctanoic acid synthesized by epoxidizing the unsaturated part of 3-hydroxy-7-octenoic acid synthesized by the method described in Int. J. Biol. Macromol., 12, 85–91 (1990) with 3-chlorobenzoic acid.

Separately, Sample 2 was obtained by the above described method except that 3-hydroxyoctanoyl CoA was used in the place of (R,S)-3-hydroxy-7,8-epoxyoctanoyl CoA.

A 10 μl aliquot of the above sample was put on a slide glass, to which 10 μl of a 1% solution of Nile blue A in water was added. These solutions were mixed on the slide glass, covered with a cover glass, and observed under a fluorescence microscope (330 to 380 nm excitation filter, 420 nm long pass absorption filter, Nikon Corp.). As a result, fluorescence from the surface of the alumina particles was observed to confirm that the alumina particles were coated with PHA on the surface.

As a control, one part of alumina particles was added to 49 parts of a 0.1M phosphate buffer (pH 7.0), and incubated with mild shaking for 2.5 hours at 30° C. Observation under a fluorescence microscope after Nile blue A staining showed the surface of the alumina particle did not fluoresce at all.

Further, part of the above coated particles was collected by centrifugation (10,000×g, 4° C., for 10 min.), dried in vacuum, suspended in chloroform, and stirred for 20 hours at 60° C. to extract the PHA coating. The extract was subjected to 1H-NMR analysis (equipment: FT-NMR (Bruker DPX400); measured nuclide: 1H; solvent: $CDCl_3$ including TMS). The calculated unit percentage of respective units are shown in Table 5.

TABLE 5

Composition of shell PHA of capsule construct (1H- NMR, %)

| Monomer unit | Sample 1 | Sample 2 |
|---|---|---|
| 3-hydroxy-5-phenoxyvaleric acid | 83% | 77% |
| 3-hydroxy-7,8-epoxyoctanoic acid | 17% | — |
| 3-hydroxyoctanoic acid | — | 23% |

The capsule construct of the above-described Sample 1 was washed three times by repeating centrifugation (10,000×g, 4° C., for 10 min.) and suspending the capsule construct in the equivalent volume of purified water. Then to 50 parts of the resulting suspension, was dissolved 0.5 part of hexamethylenediamine as a crosslinking agent. After confirming that the crosslinking agent was dissolved in the suspension, water was removed by lyophilization to give Sample 3. Then Sample 3 was reacted for 12 hours at 70° C. to give Sample 4.

The above described Sample 3 and Sample 4 were suspended in chloroform respectively and stirred for 20 hours at 60° C. to extract PHA coating, then chloroform was removed by vacuum drying. The extracts were analyzed by using a differential scanning calorimeter (DSC; Perkin Elmer, Pyris 1, temperature rise: 10° C./min.). As a result, Sample 3 showed prominent exothermal peak at about 90° C. indicating that epoxy groups in the polymer were reacting with the hexamethylenediamine and the crosslinking between polymers were proceeding during heating. On the other hand, Sample 4 did not show marked heat flow indicating that the crosslinking reaction had been completed.

Further, the infrared absorption was measured with Samples 3 and 4 (FT-IR; Perkin Elmer, 1720×). As a result, peaks indicating amine (at about 3340 $cm^{-1}$) and epoxy (at about 822 $cm^{-1}$) were observed with Sample 3, but not with Sample 4.

From the above described results, it was shown that the crosslinked polymer were obtained by reacting PHA having epoxy on the side group with hexamethylenediamine.

On the other hand, when Sample 2 was treated in the same manner, clear evidence to show crosslinking between polymers was not obtained.

Example 10

Preparation of Capsule Construct (9)

To 10 parts of a PHA synthetase solution (10 U/ml) derived from a pYN2-C1 recombinant strain, one part of alumina particles of which particle size was adjusted by precipitation to an volume average particle size of 1.45 μm and 39 parts of PBS were added and the mixture was reacted with mild shaking for 30 minutes at 30° C. to adsorb PHA synthetase onto the surface of the alumina particles. Then the mixture was centrifuged at 10,000×g, 4° C., for 10 min, and the precipitate was suspended in a PBS solution and centrifuged again (10,000×g, 4° C., for 10 min.) to obtain the immobilized enzyme.

The immobilized enzyme was suspended in 48 parts of a 0.1M phosphate buffer solution (pH 7.0), to which 0.8 parts of (R,S)-3-hydroxy-5-phenoxyvaleryl CoA, 0.2 parts of (R,S)-3-hydroxy-7,8-epoxyoctanoyl CoA and 0.1 part of bovine serum albumin (Sigma) were added, and incubated with mild shaking for 2 hours at 30° C. to obtain Sample 5. Here, (R,S)-3-hydroxy-5-phenoxyvaleryl CoA was prepared from 3-hydroxy-5-phenylvaleric acid according to the method described in Eur. J. Biochem., 250, 432–439 (1997), and 3-hydroxy-5-phenylvalerylate was prepared by first preparing 3-hydroxy-5-phenylvaleriate from 3-phenoxypropanal and ethyl bromoacetate by the Reformatsky reaction, and they hydrolyzing it. (R,S)-3-hydroxy-7,8-epoxyoctanoyl CoA was prepared by the method described in Eur. J. Biochem., 250, 432–439 (1997) from 3-hydroxy-7,8-epoxyoctanoic acid synthesized by epoxidizing the unsaturated part of 3-hydroxy-7-octenoic acid synthesized by the method described in Int. J. Biol. Macromol., 12, 85–91 (1990) with 3-chlorobenzoic acid.

A 10 μl aliquot of the above Sample 5 was put on a slide glass, to which 10 μl of a 1% solution of Nile blue A in water was added. These solutions were mixed on the slide glass, covered with a cover glass, and observed under a fluorescence microscope (330 to 380 nm excitation filter, 420 nm long pass absorption filter, Nikon Corp.). As a result, fluorescence from the surface of the alumina particles was observed to confirm that the alumina particles were coated with PHA on the surface.

As a control, one part of alumina particles was added to 49 parts of a 0.1M phosphate buffer (pH 7.0), and incubated with mild shaking for 2.5 hours at 30° C. Observation under a fluorescence microscope after Nile blue A staining showed the surface of the alumina particle did not fluoresce at all.

Further, part of the above coated particles was collected by centrifugation (10,000×g, 4° C., for 10 min.), dried in vacuum, suspended in chloroform, and stirred for 20 hours at 60° C. to extract the PHA coating. The extract was subjected to 1H-NMR analysis (equipment: FT-NMR (Bruker DPX400); measured nuclide: 1H; solvent: $^2$H chloroform including TMS). The calculated unit percentages were: 3-hydroxy-5-phenoxyvaleric acid 83% and 3-hydroxy-7,8-epoxyoctanoic acid 17%.

The capsule construct of the above-described Sample 5 was washed three times by repeating centrifugation (10,000×g, 4° C., for 10 min.) and suspending the capsule construct in the equivalent volume of purified water. Then the resulting suspension was lyophilized to remove water, and then 10 parts of terminal amino modified polysiloxane (modified silicone oil TSF4700, GE Toshiba Silicones) was added to the capsule constructs to react for two hours at 70° C. The reaction product was washed three times by suspending in methanol and subjecting to centrifugation (10,000×g, 4° C., for 20 min.) and dried. Thus, PHA having a graft chain of polysiloxane was obtained.

Example 11

Preparation of Laminated Construct

A porous glass sheet of 10 mm×10 mm×1 mm was dipped into 1% glutaraldehyde for one hour and washed with purified water, then the glass sheet was dipped into a PHA synthetase solution (10 U/ml) derived from the recombinant strain pYN2-C1 for 30 minutes at 30° C. in order to immobilize the above described enzyme to the glass sheet. Unreacted PHA synthetase was removed by washing with PBS, and consequently an immobilized enzyme was obtained.

The above described immobilized enzyme was dipped into 0.1M phosphate buffer (pH 7.0) containing 30 mM (R)-3-hydroxyoctanoyl CoA (prepared by a method described in Eur. J. Biochem., 250, 432–439 (1997)) and 0.1% bovine serum albumin (Sigma), then moderately shaken for two hours at 30° C. After completing the reaction, the immobilized enzyme was washed with 0.1M phosphate buffer (pH 7.0) to remove unreacted substances or the like.

The glass sheet after being subjected to the reaction was stained with a 1% solution of Nile blue A in water and observed by a fluorescence microscope (330 to 380 nm excitation filter, 420 nm long pass absorption filter, Nikon Corp.). As a result, fluorescence was observed on the surface of the glass sheet to show that the glass sheet was coated with a layer of PHA forming a laminated construct.

Figure 4:
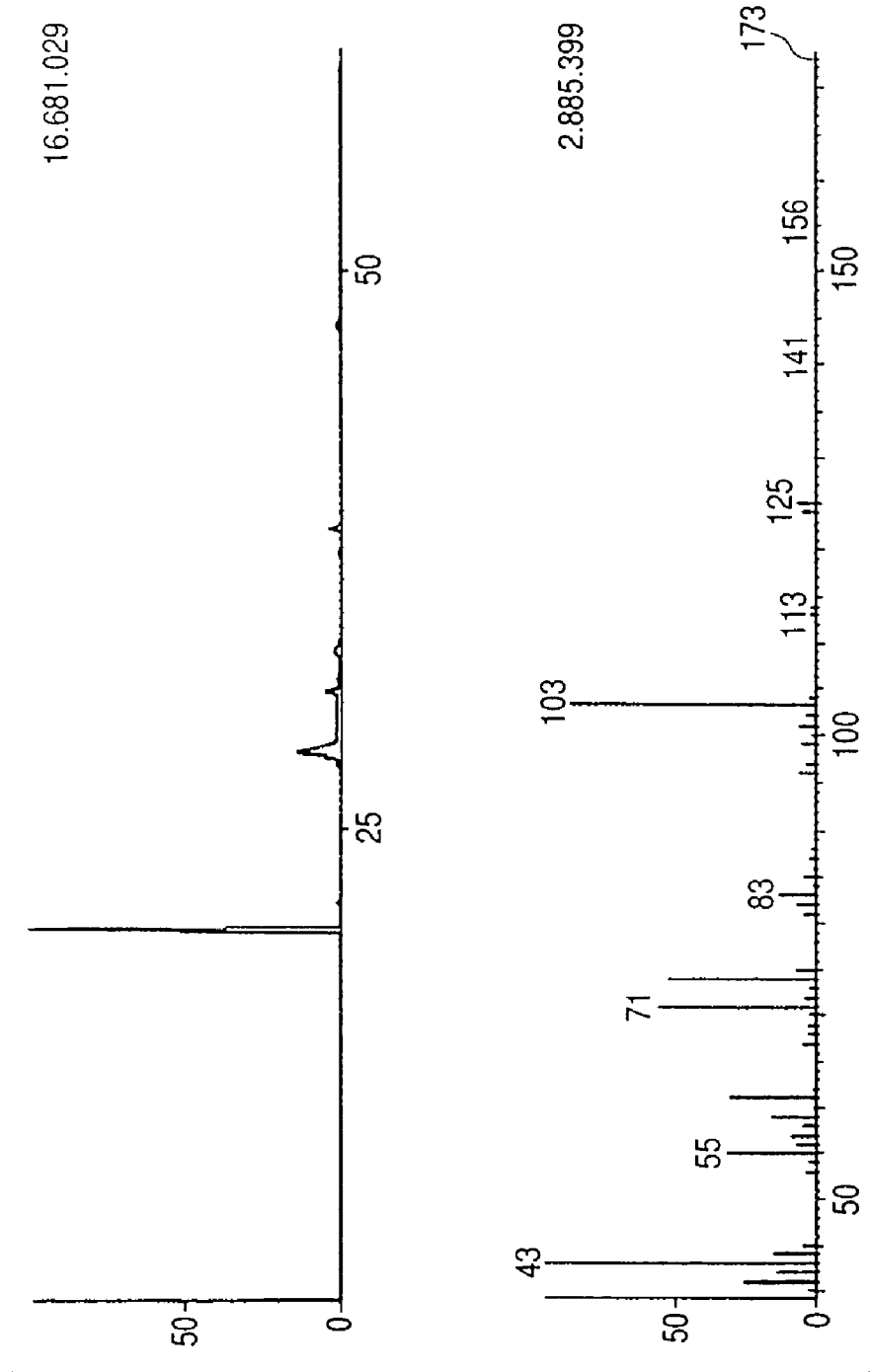
FIG. 4 is a GC-MS analytical result of the coating layer of a laminated construct in Example 11.

Next, the above described laminated construct was dried in a vacuum, and dipped into chloroform with stirring for 20 hours at 60° C. to extract PHA coating. After the extract was filtered through a membrane filter of 0.45 μm pore size, and concentrated under a reduced pressure by a rotary evaporator, methanolysis was performed according to the conventional method and analysis was performed by a gas chromatography-mass spectroscope (GC-MS, Shimadzu QP-5050, an EI method), and the methyl-esterified PHA monomer units were identified. As a result of the identification, it was confirmed that the above described PHA was a PHA made with 3-hydroxyoctanoic acid monomer unit as shown in FIG. 4.

Example 12

Capsule Toner Production

First, a polymer particulate was produced as a core by the method described below. After 450 parts of a 0.1M solution of $Na_3PO_4$ in water were added to 710 parts of ion exchange water and heated to 60° C., this mixture was stirred at 12,000 rpm by a TK homomixer (TOKUSHU KIKA KOGYO CO., LTD.). Then, 68 parts of a 1.0M solution of $CaCl_2$ in water were gradually added to the mixture to obtain an aqueous medium containing $Ca_3(PO_4)_2$. Next, 165 parts of styrene monomer, 35 parts of n-butyl acrylate, 12 parts of copper phthalocyanine pigment, 10 parts of unsaturated polyester (fumaric acid-propylene oxide modified bisphenol A), and 60 parts of ester wax. 10 parts of a polymerization initiator, 2,2'-azobis(2,4-dimethylvaleronitrile), were dissolved in the above mixture to prepare a polymeric monomer composition and heated to 60° C., then uniformly dissolved and dispersed in the mixture at 12,000 rpm by using a TK homomixer (TOKUSHU KIKA KOGYO CO., LTD). The above described polymeric monomer composition was added to the above describe aqueous medium and stirred for 10 minutes at 10,000 rpm by the TK homomixer under nitrogen atmosphere at 60° C. in order to perform granulation. After the granulation, the temperature was raised to 80° C. while stirring with paddle stirring blades, then the reaction was performed for 10 hours. After the polymerization reaction was completed, the suspension was cooled down, and 3.6 parts of $Na_2CO_3$ were added to the suspension to make pH to 11. Then, a solution in which 0.3 part of potassium persulfate as a polymerization initiator was added to and dissolved in a polymeric monomer system comprised of 82 parts of styrene monomer, 12 parts of n-butyl acrylate, and 0.05 part of unsaturated polyester (fumaric acid-propylene oxide modified bisphenol A) was dropped into the above described suspension. The temperature of the solution was increased to 80° C., then the reaction was allowed to be conducted for further 6 hours. Then, the suspension was cooled to room temperature, and hydrochloric acid was added thereto for dissolving and removing calcium phosphate. Then, a filtration process and a drying process were conducted to obtain a core component particulate of a toner.

10 parts of the above described particulate and 390 parts of PBS were added to 100 parts of a PHA synthetase solution (10 U/ml) derived from pYN2-C1 recombinant strain, and moderately shaken for 30 minutes at 30° C. to allow adsorption of the PHA synthetase to the surface of the above described particulate. This was subjected to centrifugation (10,000×g, 4° C., for 10 min.), and the precipitate was suspended in a PBS solution and again subjected to centrifugation (10,000×g, 4° C., for 10 min.) to obtain an immobilized enzyme.

Then 10 parts of the above described immobilized enzyme was suspended in 480 parts of a 0.1M phosphate buffer (pH 7.0), then 10 parts of (R)-3-hydroxy-5-(4-fluorophenyl)valeryl CoA (prepared by a method described in Eur. J. Biochem., 250, 432–439 (1997) after obtaining 3-hydroxy-5-(4-fluorophenyl)valeric acid by hydrolyzing 3-hydroxyphenyl valeric acid ester obtained by a Reformatsky reaction) and one part of bovine serum albumin (Sigma) were added to the suspension, and this suspension was moderately shaken for two hours at 30° C.

After the reaction was completed, the suspension was subjected to centrifugation (10,000×g, 4° C., for 10 min.), and the precipitate was suspended in 1000 parts of a 0.1M phosphate buffer (pH 7.0) and again subjected to centrifugation. This operation was repeated three times to recover the precipitate. After filtration and drying, a capsule construct was obtained. Then 0.12 parts of hydrophobic titanium oxide fine powder was added to 10 parts of the obtained capsule construct to obtain a capsule toner A having titanium oxide fine powder on the surface of the capsule construct.

Meanwhile, 0.12 parts of hydrophobic titanium oxide fine powder was added to 10 parts of the above described core component particulate to obtain, as a control, toner B having titanium oxide fine powder on the surface of the toner.

Six parts of each capsule toner were mixed with 144 parts of a ferrite carrier coated with acrylic resin to obtain a two-component developer.

With these developers, an image was copied by using a commercially available copying machine NP6000 (Canon) in an environment where the temperature was 23° C. and the humidity was 60% RH, to estimate running durability, toner scattering, fogging, etc. As a result, with the developer using capsule toner A, image defects such as decrease in the image density, toner scattering, fog, etc., were not observed even after 100,000 copies were produced as shown in Table 6. In addition, when the triboelectricity was measured as an electrostatic property, the initial value was −33 mC/kg and the value after the durability test was −31 mC/kg, indicating stable electrostatic properties. Further, no problem was observed with fixing. On the other hand, with the developer using the capsule toner B, image defects such as lowering of image density, toner scattering, fog, etc. were observed when only 200 sheets of copies were made so that images of high precision and fidelity were not obtained. In addition, triboelectricity varied from initial −24 mC/kg to −18 mC/kg after durability test, indicating unstable chargeability. Further, as a result of the fixing test, it was inferior in offset resistance at high temperature.

TABLE 6

|  | Production property | Image density | Image quality | Electrostatic property | Fixing property |
| --- | --- | --- | --- | --- | --- |
| Capsule toner A | A | A | A | A | A |
| Capsule Toner B | A | B | B | A | B |

A: good,
B: somewhat inferior,
C: no good

Example 13

Production of Capsule Toner (2)

Ten parts of core particles prepared in the same manner as in Example 12 and 390 parts of PBS were added to 100 parts of a PHA synthetase solution (10 U/ml) derived from pYN2-C1 recombinant strain, and moderately shaken for 30 minutes at 30° C. to allow adsorption of the PHA synthetase to the surface of the particles. The reaction was subjected to centrifugation (10,000×g, 4° C., for 10 min.), then the precipitate was suspended in a PBS solution and again subjected to centrifugation (10,000×g, 4° C., for 10 min.) for obtaining an immobilized enzyme.

Ten parts of the above described immobilized enzyme was suspended in 480 parts of a 0.1M phosphate buffer (pH 7.0), then 10 parts of (R)-3-hydroxy-5-(4-fluorophenyl)valeryl CoA (prepared by a method described in Eur. J. Biochem., 250, 432–439 (1997) after obtaining 3-hydroxy-5-(4-fluorophenyl)valeric acid by hydrolyzing 3-hydroxyphenylvaleric acid ester obtained by a Reformatsky reaction) and one part of bovine serum albumin (Sigma) were added to the suspension and moderately shaken for one and a half hours at 30° C. After the reaction was completed, centrifugation was performed for 10 minutes at 10,000×g to recover the pellet.

Then, the pellet was suspended in 480 parts of a 0.1M phosphate buffer (pH 7.0), and 5 parts of (R)-3-hydroxy-5-phenoxyvaleryl CoA (prepared by a method described in Eur. J. Biochem., 250, 432–439 (1997) after obtaining 3-hydroxy-5-phenoxyvaleric acid by hydrolyzing 3-hydroxy-5-phenoxylvaleric acid ester obtained by a Reformatsky reaction using zinc, in which 3-phenoxypropanal synthesized by a method described in J. Org. Chem., 55, 1490–1492 (1990) and ethyl bromoacetate were used as raw materials) and one part of bovine serum albumin (Sigma) were added to the suspension before moderately shaking the suspension for 30 minutes at 30° C.

After the reaction was completed, centrifugation was performed for 10 minutes at 10,000×g, then the precipitate was suspended in 1000 parts of a 0.1M phosphate buffer (pH 7.0) and again subjected to centrifugation. This operation was repeated three times to recover the precipitate. From this precipitate, a capsule construct was obtained through a filtration process and a drying process.

Weight of the polymer formed on the surface of the capsule construct was measured by a time-of-flight secondary ion mass spectroscope (TOF-SIMS IV, CAMECA). From the obtained mass spectrum, it was confirmed that the surface of the capsule construct was made of poly-3-hydroxy-5-phenoxyvaleric acid. In addition, mass spectra were further taken by the TOF-SIMS as described above while scraping the surface of the capsule construct little by little by ion sputtering, and consequently, it was confirmed that the polymer of the capsule construct was made with poly-3-hydroxy-5-(4-fluorophenyl)valeric acid from a certain point. As a result of the above measurement, it was found that the capsule construct of this example was an intended capsule construct in which poly-3-hydroxy-5-(4-fluorophenyl)valeric acid having a low glass transition temperature was coated with poly-3-hydroxy-5-phenoxyvaleric acid having a relatively high glass transition temperature.

0.12 part of hydrophobic titanium oxide fine powder was added to 10 parts of the capsule construct to obtain a capsule toner C having titanium oxide fine powder on a surface of the capsule construct.

144 parts of ferrite carrier coated with an acrylic resin were mixed with 6 parts of the capsule toner C to obtain a two-component developer.

Using the above described developer, an image was copied by a commercially available copying machine NP6000 (Canon Inc.) as described in Example 7 in an environment where the temperature was 23° C. and the humidity was 60% RH, then the running durability, toner scattering, fog, etc. were evaluated. According to the evaluation, this toner exhibited the same good performance as with the capsule toner A of Example 7.

In addition, to evaluate fixing properties of the capsule toners A and C at a low temperature, a fixing test was performed by an external fixing device having the same arrangement as the NP6000. In this fixing test, a strip of 2 cm×10 cm carrying an unfixed image on it was passed between rollers along a longitudinal direction of the strip while monitoring the temperature of the upper roller of the external fixing devise, then fixing property was determined by checking whether the offset was seen or not at the rear part of the strip. From this result, it was found that the lowest fixation temperature was as low as 95° C. in both cases of capsule toner A and capsule toner C, so that these toners were excellent in the fixing property at low temperature.

Further, to evaluate the blocking resistance of the capsule toners A and C, the cohesiveness was observed by allowing the above described capsule toners to stand for 3 days at every degree from 50° C. to 70° C. Then, using these toners, images were developed and evaluated as described above. A point at which roughness in a highlight region changed was defined as a blocking resistance temperature. According to the evaluation, it was found that the blocking resistance of the capsule toner C was 61° C. and the blocking resistance of the capsule toner A was 58° C., so that the capsule toner C was excellent in the blocking resistance.

As described above, the low-temperature fixing property is realized by capsulating a toner with a PHA of low glass transition temperature, and further by coating a capsule toner coated with a PHA of low glass transition temperature, with a PHA of high glass transition temperature, both low temperature fixation and blocking resistance can be achieved at the same time.

Example 14

Production of Capsule Toner (3)

A 3 liter four-neck separable flask was equipped with a reflux condenser, a thermometer, a nitrogen introducing tube, and a stirrer. Next, a mixture of 1200 parts of ion exchange water, 15 parts of polyvinyl alcohol, 0.1 part of dodecyl sodium sulfate, 75 parts of styrene monomer, 25 part of n-butyl acrylate, 5 parts of chromium di-tert-butyl-salicylate complex salt, 5 parts of copper phthalocyanine, and 6 parts of 2,2-azobis(2,4-dimethylvaleronitrile) was charged into this flask, then the mixture was stirred by a high-speed stirrer, TK-homomixer, for 10 minutes at 10,000 rpm for granulation. Then, the revolutions per minute was decreased to 1,000 rpm and bubbling with nitrogen gas was sufficiently performed. Next, substituting the stirring blades of crescent-shape for the above homomixer, polymerization was performed for 16 hours in an oil bath at 80° C. with mild stirring.

After the polymerization reaction was completed, the reaction vessel was cooled to room temperature, then the dispersion was washed by decantation for 5 times, filtered, washed with water, and dried to obtain core particles as blue powder. The PHA synthetase derived from pYN2-C1 recombinant strain was immobilized to the above described core particles by the method described in Example 12, to obtain an immobilized enzyme.

Ten parts of the above described immobilized enzyme were suspended in 480 parts of a 0.1M phosphate buffer (pH 7.0), then 8 parts of (R,S)-3-hydroxy-5-phenoxyvaleryl CoA (prepared by a method described in Eur. J. Biochem., 250, 432–439 (1997) after obtaining 3-hydroxy-5-phenoxyvaleric acid by hydrolyzing 3-hydroxy-5-phenoxyvaleric acid ester obtained by a Reformatsky reaction of 3-phenoxypropanal with ethyl bromoacetate), 2 parts of (R,S)-3-hydroxy-7,8-epoxyoctanoyl CoA (prepared by a method described in Eur. J. Biochem., 250, 432–439 (1997) after epoxidizing an unsaturated part of 3-hydroxy-7-octenoic acid with 3-chlorobenzoic acid, the 3-hydroxy-7-octenoic acid being synthesized by a method described in Int. J. Biol. Macromol., 12, 85–91 (1990)), and 1 part of bovine serum albumin (Sigma) were added to the suspension and moderately shaken for 2 hours at 30° C.

After the reaction was completed, the above described reaction solution was subjected to centrifugation (10,000×g, 4° C., for 10 min.) to collect capsule constructs and the capsule constructs were suspended in 100 parts of purified water. This operation was repeated 3 times to recover precipitate. From the precipitate, a blue capsule construct D was obtained through a filtration process and a drying process. Then 0.2 part of ground hydrophobic silica having 362 m$^2$/g BET was mixed with 10 parts of capsule constructs D by a Henschel mixer to obtain a toner D.

Further, 10 parts of the above described capsule toners D was suspended in purified water and 5 parts of hexamethylenediamine were dissolved therein as a crosslinking agent. After confirming that the crosslinking agent was dissolved, water was removed by lyophilization and the reaction was performed for 12 hours at 70° C. After the reaction was completed, the above described reaction solution was subjected to centrifugation for 10 minutes at 10,000×g, and the precipitate was suspended in 1000 parts of a 0.1M phosphate buffer (pH 7.0) and again subjected to centrifugation. This operation was repeated 3, times to recover precipitate. From the precipitate, a blue capsule construct E was obtained after filtration and drying. Then 0.2 part of ground hydrophobic silica whose BET value was 362 m$^2$/g was added to 10 parts of capsule constructs E and mixed by a Henschel mixer to obtain a toner E.

To evaluate the image developed with the above prepared toners, 6 parts of the toner and 94 parts of ferrite carrier of 35 μm in particle size and coated with a silicone resin were charged into a polyethylene bottle and mixed with each other, then the mixture was stirred by a tumbler mixer to prepare a two-component developer. And this developer was set in a modified color laser copying machine CLC-500 (Canon Inc.), and the initial image and the image after ten thousand sheet copying at 23° C. and 60% RH were observed by SEM, then the image quality and the deterioration of developer were evaluated.

The evaluation of the image quality was performed by a multivalue recording with the pulse width modulation (PWM) of laser within one pixel and the reproducibility of a minimum spot was evaluated by a microscopic observation. In addition, the developer after copying a ten thousand times was observed by a scanning electron microscope.

Further, to evaluate the blocking resistance of the toner, agglomeration was observed after standing the toner for 3 days under different temperature conditions. Then, using each toner sample for the developer as above, the image evaluation was carried out.

In addition, to evaluate the fixing properties, a fixing test was performed by an external fixing device having the same arrangement as the CLC-500. In this fixing test, a strip of 2 cm wide by 10 cm long was made, and the unfixed image on the strip was fixed by passing the strip between rollers along a longitudinal direction of the strip while monitoring the temperature of the upper roller of the external fixing devise, then the fixing property was determined by checking whether the offset was seen or not at the rear part of the strip.

Meanwhile, the above described capsule construct was replaced with the core particle without capsulation to form toner F, and the same evaluation as described above was performed. The results are shown in Table 7.

TABLE 7

|         | Image quality | Blocking resistance | Fixing property |
|---------|---------------|---------------------|-----------------|
| Toner D | AA            | A                   | AA              |
| Toner E | AA            | AA                  | AA              |
| Toner F | A             | A                   | B               |

Notes: Symbols in Table; AA: very good, A: good, B: somewhat inferior, C: no good (the above symbols AA, A, B and C do not correspond to the symbols in Example 12)

Example 15

Production of Capsule Toner (4)

A core particulate was produced in the same manner as in Example 14 and the PHA synthetase derived from pYN2-C1 recombinant strain was immobilized to obtain an immobilized enzyme. Then 10 parts of the immobilized enzyme were suspended in 480 parts of a 0.1M phosphate buffer (pH 7.0), then 8 parts of (R, S)-3-hydroxy-5-phenoxyvaleryl CoA (prepared as with Example 14), 2 parts of (R,S)-3-hydroxy-7,8-epoxyoctanoyl CoA (prepared as with Example 14), and one part of bovine serum albumin (Sigma) were added to the suspension, and moderately shaken for 2 hours at 30° C.

After the reaction was completed, the above described reaction solution was subjected to centrifugation (10,000×g, 4° C., for 10 min.) to recover capsule constructs and the capsule constructs were suspended in 100 parts of purified water. This operation was repeated 3 times to recover precipitate. From the precipitate, a blue capsule construct G was obtained after filtration and drying. Then 0.2 part of ground hydrophobic silica whose BET value was 362 m²/g was added to 10 parts of capsule constructs G and mixed by a Henschel mixer to obtain a toner G.

Further, 100 parts of terminal amino modified polysiloxane (modified silicone oil TSF4700, GE Toshiba Silicones) was added to 10 parts of the capsule construct G for reaction of two hours at 70° C. The reaction product was suspended in methanol and subjected to centrifugation (10,000×g, 4° C., for 20 min.) several times for washing and dried to give a blue capsule construct H having a graft chain of polysiloxane. Then 0.2 part of ground hydrophobic silica whose BET value was 362 m²/g was added to 10 parts of capsule construct H and mixed by a Henschel mixer to obtain a toner H.

With these toners, the image quality and the deterioration of developer were evaluated as with Example 14.

Meanwhile, instead of the above described capsule construct, the core particle without capsulation was used for a toner I, and the same evaluation as described above was performed. The results are shown in Table 8.

TABLE 8

|         | Image quality | Blocking resistance | Fixing property |
|---------|---------------|---------------------|-----------------|
| Toner G | AA            | A                   | AA              |
| Toner H | AA            | AA                  | AA              |
| Toner I | A             | A                   | B               |

Note: Symbols in Table 8; AA: very good, A: good, B: somewhat inferior, C: no good (wherein the above described symbols do not correspond to symbols in Example 12)

Example 16

Preparation of Recording Medium (1)

A PET film (100Q80D, TORAY Inc.) was dipped into a 1% glutaraldehyde solution for one hour and washed by purified water, then the film was dipped into a PHA synthetase solution (10 U/ml) derived from pYN2-C1 recombinant strain for 30 minutes at 30° C. to immobilized the enzyme to the film. Unreacted PHA synthetase was removed by washing with PBS, then an immobilized enzyme was obtained.

The above described PET film was dipped into a 0.1M phosphate buffer (pH 7.0) including 30 mM (R)-3-hydroxypimelyl CoA (prepared by a method described in J. Bacteriol., 182, 2735–2760 (2000)) and 0.1% bovine serum albumin (Sigma), and moderately shaken for 30 minutes at 30° C. After the reaction was completed, the film was washed with a 0.1M phosphate buffer (pH 7.0) to remove unreacted substances, and air-dried. Consequently, a desired recording medium having an ionic polymer of poly-(R)-3-hydroxypimelic acid as an ink receiving layer was obtained.

As a comparative example, a PET film was made by the similar treatment as described above, except that PHA synthetase was not used.

Using these recording media respectively, a black image and a colored image were printed thereon by an inkjet printer (BJC-4301, Canon Inc.). Then, whether the feathering or beading of the ink were present or not on the recording medium was checked. As a result, such feathering or beading could hardly be seen and excellent images were obtained with the recording medium of the present invention, while heavy feathering or beading were observed with the comparative recording medium.

Example 17

Preparation of Recording Medium (2)

As described in Example 16, a PET film (100Q80D, TORAY Inc.) was dipped into a 1% glutaraldehyde solution for one hour and washed with purified water, then the film was dipped into a PHA synthetase solution (10 U/ml) of pYN2-C1 recombinant strain for 30 minutes at 30° C. to immobilized the enzyme to the film. Unreacted PHA synthetase was washed away with PBS, then an immobilized enzyme was obtained.

The PET film to which this enzyme was immobilized was dipped into 100 parts of a 0.1M phosphate buffer (pH 7.0) including 30 mM (R)-3-hydroxyoctanoyl CoA (prepared by a method described in Eur. J. Biochem., 250, 432–439 (1997)) and 0.1% bovine serum albumin (Sigma). Then, 0.1M phosphate buffer (pH 7.0) including 30 mM (R)-3-hydroxypimelyl CoA (prepared by a method described in J. Bacteriol., 182, 2735–2760 (2000)) and 0.1% bovine serum albumin (Sigma) was added to the above reaction solution by the use of a micro-tube pump (TOKYO RIKAKIKAI Co., MP-3N) at a rate of 25 parts per minute while moderately shaken at 30° C.

After shaking for 30 minutes, the film was washed with a 0.1M phosphate buffer (pH 7.0) to remove unreacted substances or the like, and air-dried. Consequently, a recording medium was prepared.

The amount of the polymer formed on the surface of the recording medium was measured by a time-of-flight secondary ion mass spectroscope (TOF-SIMS IV, CAMECA). The obtained mass spectrum showed that the surface of the recording medium was made up by a copolymer of 3-hydroxypimelic acid and 3-hydroxyoctanoic acid (the molar ratio was 17:1). In addition, mass spectra were taken by the TOF-SIMS as described above while scraping the surface of the glass sheet little by little by ion sputtering. As a result, the percentage of 3-hydroxypimelic acid in the copolymer gradually decreased in an inward direction while the percentage of 3-hydroxyoctanoic acid gradually increased. As a result, it was shown that the recording medium of this example was an intended recording medium having the outer surface of polyhydroxypimelate having hydrophilic functional groups, and under the polyhydroxypimelate layer a layer of a copolymer of 3-hydroxypimelic acid having a hydrophilic functional group and 3-hydroxyoctanoic acid having a hydrophobic functional group where the percentage of the 3-hydroxyoctanoic acid gradually increased in a direction toward the lower part of this layer.

Using this recording medium, a black image and a colored image were printed thereon by an inkjet printer (BJC-4301, Canon Inc.) as described in Example 16. Then, whether the blots or beading of the ink were present or not on the recording medium was checked, and this result was compared to that of the recording medium prepared in Example 16. As a result, it was found that the recording medium of this example had less blots in the ink receiving layer compared to the recording medium of Example 16. The reason of this can be considered as follows: the PHA coating of the recording medium of this example gradually becomes hydrophobic in a direction toward the lower part of this layer, so that the diffusion of the absorbed ink at the surface is gradually suppressed in the layer.

In addition, the electrostatic charge image developing toner of the present invention is composed of a colorant covered in at least a part thereof by polyhydroxyalkanoate constituting a first resin component, and binder resin constituting a second resin component. As the polyhydroxyalkanoate constituting the first resin component, there can be advantageously employed at least one selected from the group consisting of monomer units represented by the following formulas (23) to (32):

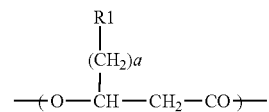

[23]

wherein the monomer unit is at least one selected from the group consisting of monomer units in which the combination of R1 and a is any of the following:

a monomer unit in which R1 is a hydrogen atom (H) and a is an integer from 0 to 10;

a monomer unit in which R1 is a halogen atom and a is an integer from 1 to 10;

a monomer unit in which R1 is a chromophore and a is an integer from 1 to 10;

a monomer unit in which R1 is a carboxyl group or a salt thereof and a is an integer from 1 to 10; and a monomer unit in which R is a group represented by the following formula:

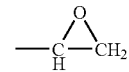

and a is an integer from 1 to 7;

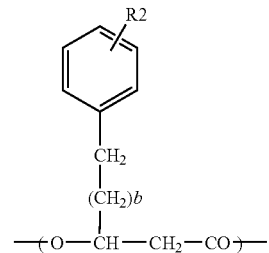

[24]

wherein b is an integer from 0 to 7, and R2 is a substitution selected from the group consisting of a hydrogen atom (H), a halogen atom, —CN, —NO$_2$, —CF$_3$, —C$_2$F$_5$ and —C$_3$F$_7$;

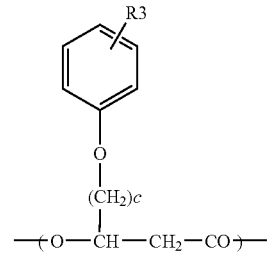

[25]

wherein c is an integer from 1 to 8, and R3 is a substitution selected from the group consisting of a hydrogen atom (H), a halogen atom, —CN, —NO$_2$, —CF$_3$, —C$_2$F$_5$ and —C$_3$F$_7$;

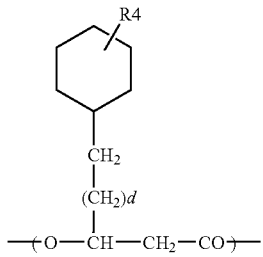

[26]

wherein d is an integer from 0 to 7, and R4 is a substitution selected from the group consisting of a hydrogen atom (H), a halogen atom, —CN, —NO$_2$, —CF$_3$, —C$_2$F$_5$ and —C$_3$F$_7$;

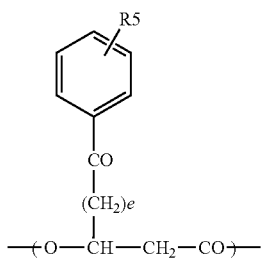

[27]

wherein e is an integer from 1 to 8, and R5 is a substitution selected from the group consisting of a hydrogen atom (H), a halogen atom, —CN, —NO$_2$, —CF$_3$, —C$_2$F$_5$, —C$_3$F$_7$, —CH$_3$, —C$_2$H$_5$ and —C$_3$H$_7$;

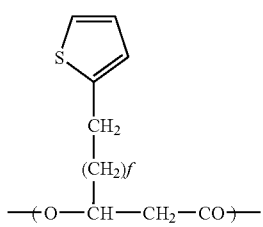

[28]

wherein f is an integer from 0 to 7;

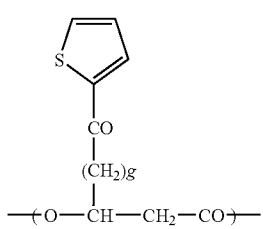

[29]

wherein g is an integer from 1 to 8;

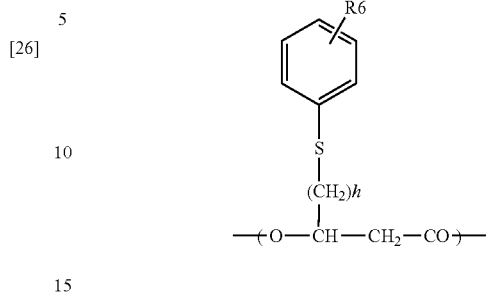

[30]

wherein h is an integer from 1 to 7, R6 is a substitution selected from the group consisting of a hydrogen atom (H), a halogen atom, —CN, —NO$_2$, —COOR', —SO$_2$R", —CH$_3$, —C$_2$H$_5$, —C$_3$H$_7$, —CH(CH$_3$)$_2$ and —C(CH$_3$)$_3$, R' is a hydrogen atom, Na, K, —CH$_3$ or —C$_2$H$_5$, and R" is —OH, —ONa, —OK, a halogen atom, —OCH$_3$ or —OC$_2$H$_5$;

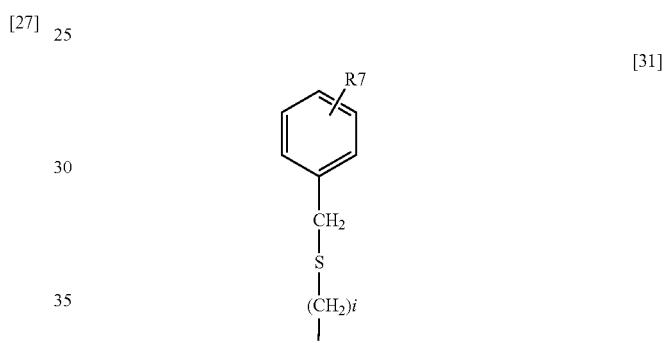

[31]

wherein i is an integer from 1 to 7, R7 is a substitution selected from the group consisting of a hydrogen atom (H), a halogen atom, —CN, —NO$_2$, —COOR' and —SO$_2$R", R' is a hydrogen atom, Na, K, —CH$_3$ or —C$_2$H$_5$, and R" is —OH, —ONa, —OK, a halogen atom, —OCH$_3$ or —OC$_2$H$_5$; and

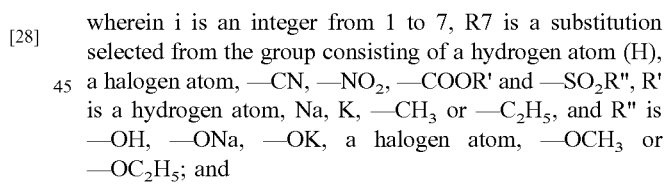

[32]

wherein j is an integer from 1 to 9.

Such PHA can be synthesized with the respectively corresponding 3-hydroxyacyl coenzyme A, namely 3-hydroxyacyl coenzymes A of a necessary number selected from those represented by the following chemical formulas (33) to (42):

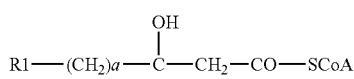

wherein —SCoA indicates coenzyme A bonded to alkanoic acid, and the combination of R1 and a is any of the following and corresponds to the combination of R1 and a in the foregoing chemical formula (23):

a monomer unit in which R1 is a hydrogen atom (H) and a is an integer from 0 to 10;

a monomer unit in which R1 is a halogen atom and a is an integer from 1 to 10;

a monomer unit in which R1 is a chromophore and a is an integer from 1 to 10;

a monomer unit in which R1 is a carboxyl group or a salt thereof and a is an integer from 1 to 10; and a monomer unit in which R1 is a group represented by the following formula:

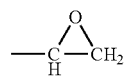

and a is an integer from 1 to 7;

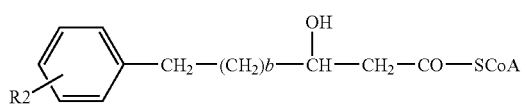

wherein —SCoA indicates coenzyme A bonded to alkanoic acid, b is an integer from 0 to 7 corresponding to b in the foregoing chemical formula (24), and R2 is a substitution selected from the group consisting of a hydrogen atom (H), a halogen atom, —CN, —NO$_2$, —CF$_3$, —C$_2$F$_5$ and —C$_3$F$_7$, corresponding to R2 in the foregoing chemical formula (24);

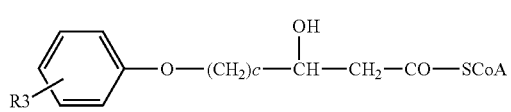

wherein —SCoA indicates coenzyme A bonded to alkanoic acid, c is an integer from 1 to 8 corresponding to c in the foregoing chemical formula (25), and R3 is a substitution selected from the group consisting of a hydrogen atom (H), a halogen atom, —CN, —NO$_2$, —CF$_3$, —C$_2$F$_5$ and —C$_3$F$_7$, corresponding to R3 in the foregoing chemical formula (25);

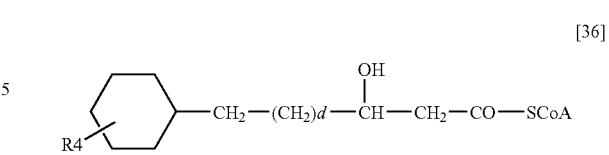

wherein —SCoA indicates coenzyme A bonded to alkanoic acid, d is an integer from 0 to 7 corresponding to d in the foregoing chemical formula (26), and R4 is a substitution selected from the group consisting of a hydrogen atom (H), a halogen atom, —CN, —NO$_2$, —CF$_3$, —C$_2$F$_5$ and —C$_3$F$_7$, corresponding to R4 in the foregoing chemical formula (26);

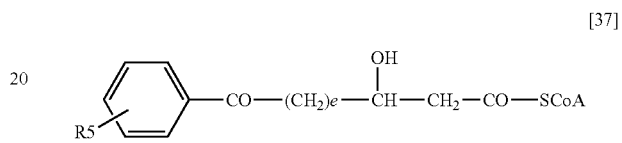

wherein —SCoA indicates coenzyme A bonded to alkanoic acid, e is an integer from 1 to 8 corresponding to e in the foregoing chemical formula (27), and R5 is a substitution selected from the group consisting of a hydrogen atom (H), a halogen atom, —CN, —NO$_2$, —CF$_3$, —C$_2$F$_5$, —C$_3$F$_7$, —CH$_3$, —C$_2$H$_5$ and —C$_3$H$_7$, corresponding to R5 in the foregoing chemical formula (27);

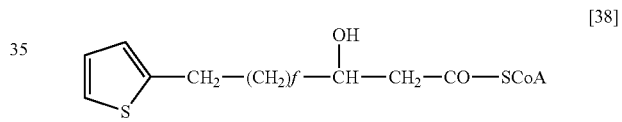

wherein —SCoA indicates coenzyme A bonded to alkanoic acid, and f is an integer from 0 to 7 corresponding to f in the foregoing chemical formula (28);

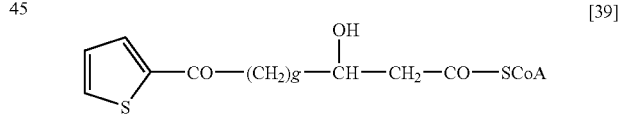

wherein —SCoA indicates coenzyme A bonded to alkanoic acid, and g is an integer from 1 to 8 corresponding to g in the foregoing chemical formula (29);

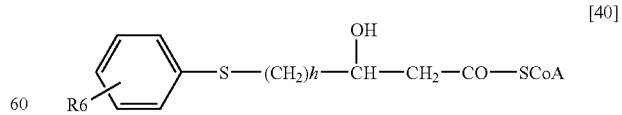

wherein —SCoA indicates coenzyme A bonded to alkanoic acid, h is an integer from 1 to 7 corresponding to h in the foregoing chemical formula (30), R6 is a substitution selected from the group consisting of a hydrogen atom (H), a halogen atom, —CN, —NO$_2$, —COOR', —SO$_2$R'', —$CH_3$, —$C_2H_5$, —$C_3H_7$, —$CH(CH_3)_2$ and —$C(CH_3)_3$ corresponding to R6 in the foregoing chemical formula (30), R' is a hydrogen atom, Na, K, —$CH_3$ or —$C_2H_5$, and R" is —OH, —ONa, —OK, a halogen atom, —$OCH_3$ or —$OC_2H_5$;

[41]

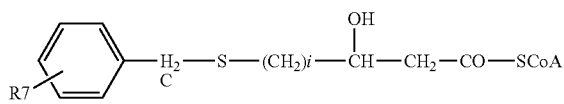

wherein —SCoA indicates coenzyme A bonded to alkanoic acid, i is an integer from 1 to 7 corresponding to i in the foregoing chemical formula (31), R7 is a substitution selected from the group consisting of a hydrogen atom (H), a halogen atom, —CN, —$NO_2$, —COOR' and —$SO_2R"$ corresponding to R7 in the foregoing chemical formula (31), R' is a hydrogen atom, Na, K, —$CH_3$ or —$C_2H_5$, and R" is —OH, —ONa, —OK, a halogen atom, —$OCH_3$ or —$OC_2H_5$; and

[42]

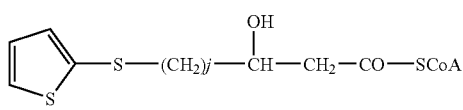

wherein —SCoA indicates coenzyme A bonded to alkanoic acid, and j is an integer of 1 to 9 corresponding to the foregoing chemical formula (32).

Figure 12:
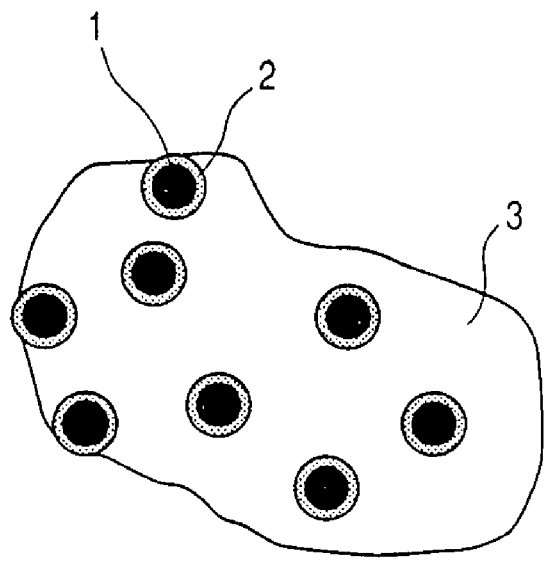
FIG. 12 is a schematic cross-sectional view of a toner particle of the present invention.
Figure 13:
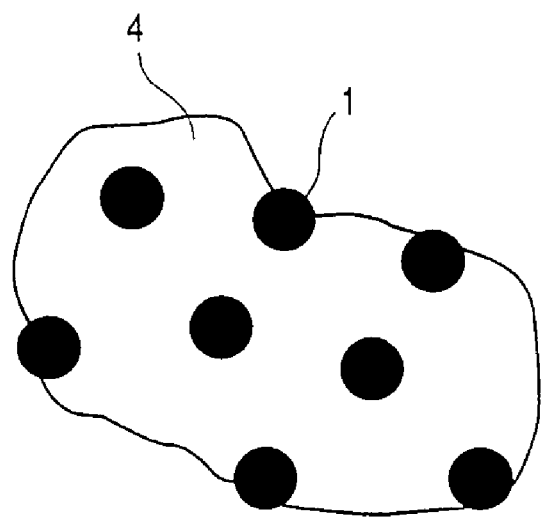
FIG. 13 is a schematic cross-sectional view of a conventional toner particle.

As explained in the foregoing, the electrostatic charge image developing toner of the present invention is featured by, instead of directly dispersing the coloring agent such as pigment into the toner, dispersing colorant, covered with outer shell resin consisting of PHA constituting the first resin, in the binder resin containing thermoplastic resin. FIG. 12 is a schematic cross-sectional view of a toner particle in which the colorant is dispersed in the toner binder resin, while FIG. 13 is a cross-sectional view of a conventional toner particle. In case of the conventional toner, pigment 1 is dispersed in binder resin 4, but, in case of the present invention, pigment 1 is covered with first resin component 2 and is further dispersed in second resin component 3.

In the toner of the present invention, since the colorant covered with the outer shell resin is bound by the thermoplastic resin, the combination of the coloring agent contained in the colorant and the resin for binding the colorant is not limited and there can be obtained large freedom in the material selection. Also the coloring agent, for example pigment particles cause less migration to the exterior of the colorant (exposure to the surface of the colorant). Besides, the colorant, covered with the outer shell, can be produced with a sharper particle size distribution even in case of containing the coloring agent at a higher concentration. The interior of the colorant covered with polyhydroxyalkanoate generally consists of the coloring agent itself, and the coloring agent is preferably composed of pigment in consideration of the light fastness and antibleeding resistance of the coloring agent.

In the following there will be given a detail explanation on the aforementioned colorant.

<PHA>

The PHA to be employed in the present invention can be any PHA that can be synthesized by a PHA synthesizing enzyme relating to the PHA biosynthesizing reaction.

The biosynthesis of PHA is executed from various alkanoic acids as starting material by a polymerization reaction by an enzyme, utilizing, as the substrate, (R)-3-hydroxyacyl CoA generated through various metabolic paths (for example β-oxidation system or fatty acid synthesis path) in the organisms. The enzyme catalyzing such polymerization reaction is PHA synthesizing enzyme (also called PHA polymerase or PHA synthase).

CoA is an abbreviation for coenzyme A, having the aforementioned chemical structure. Also the reaction path from alkanoic acid to PHA through the β-oxidation system and polymerization reaction by the PHA synthesizing enzyme is as explained in the foregoing. On the other hand, in case of synthesis through the fatty acid synthesis path, PHA is assumed to be synthesized similarly by the PHA synthesizing enzyme, utilizing, as the substrate, (R)-3-hydroxyacyl CoA converted from (R)-3-hydroxyacyl ACP (ACP meaning acyl carrier protein) generated in such path. It is already known and reported, as explained in the foregoing, that PHA can be synthesized in a cell-free system (in vitro) by taking out the aforementioned PHB synthesizing enzyme or PHA synthesizing enzyme from the bacteria. As explained in the foregoing, the PHA synthesizing enzyme catalyzes the final stage in the PHA synthesizing reaction system in the organisms, so that any PHA known to be synthesizable in the organisms is synthesized by the catalyzing effect of such enzyme. Therefore, it is possible to prepare microcapsules formed by covering the coloring agent with any PHA known to be synthesizable in the organisms, by reacting 3-hydroxyacyl CoA corresponding to the desired PHA on the aforementioned enzyme fixed on the coloring agent of the present invention.

Specific examples of the PHA employable in the present invention include the aforementioned PHA. Specific examples of the aforementioned halogen atom include fluorine, bromine and chlorine. Also the aforementioned chromophore is not particularly limited as long as its 3-hydroxyacyl CoA bonding form can be catalyzed by the PHA synthesizing enzyme, but, in consideration of steric hindrance in the polymer systhesis, it is desirable, in the 3-hydroxyacyl CoA molecule, that a methylene chain with 1 to 5 carbon atoms is present between the carboxyl group bonded to CoA and the chromophore. Also the colored composition consisting of microcapsule pigment based on the PHA having such chromophore is expected, for example, to exhibit more effective color development by a composite action with the color developing component of the pigment.

Also as the PHA to be employed in the present invention, there can be utilized random copolymer or block copolymer including a plurality of the aforementioned monomer units, and there can be achieved control of the physical properties, realization of plural functions and realization of novel functions utilizing the properties of the monomer units or the functional groups contained therein or the interaction of such functional groups. It is also possible to synthesize, on the surface of the coloring agent, a block copolymer of arbitrary sequence and composition by suitably controlling the amount and order of addition of 3-hydroxyacyl CoA constituting the substrate. It is also possible, if necessary, to execute chemical modification after or during the PHA synthesis.

For example, it is possible to vary the monomer unit composition of PHA in a direction from the inner side to the outer side of the colorant, by changing in time the type and concentration of 3-hydroxyacyl CoA constituting the substrate. In this manner it is possible to form PHA showing higher mutual solubility with the binder resin in the outer surfacial layer of the colorant and to form PHA showing higher affinity with the coloring agent in the inner surfacial layer of the colorant, thereby enhancing the effect of the present invention. More specifically, in case PHA having mutual solubility with the binder resin shows low affinity with the coloring agent, there can be employed a process of at first covering the coloring agent with PHA showing higher affinity therewith and changing the monomer unit of the PHA toward higher mutual solubility with the binder resin from the inner side of the colorant to the outer side thereof for example in a multi-layered or gradient structure, thereby producing colorant showing stronger bonding with the coloring agent and having a PHA covering mutually soluble with the binder resin.

Also by introducing a graft chain in the PHA on the surface of the colorant, there can be obtained the colorant showing mutual solubility with the binder resin, based on such graft chain. Also there can be obtained colorant of superior mechanical strength by crosslinking the PHA on the surface of the colorant.

The PHA synthesized by the PHA synthesizing enzyme and employed in the structured material of the present invention is generally an isotactic polymer consisting solely of R-isomer.

The method for synthesizing 3-hydroxyacyl CoA, serving as the PHA synthesizing substrate, can be suitably selected for example from in vitro synthesis utilizing enzyme, in vivo synthesis utilizing organisms such as microorganisms or plants, and chemical synthesis. In particular, the enzyme synthesis method is generally employed for synthesizing such substrate, and there is for example known a method based on the following reaction:

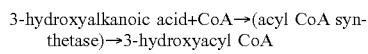

3-hydroxyalkanoic acid+CoA→(acyl CoA synthetase)→3-hydroxyacyl CoA utilizing the commercially available acyl CoA synthetase (acyl CoA ligase, E.C.6.2.1.3) (Eur. J. Biochem., 250, 432–439(1997); Appl. Microbiol. Biotechnol., 54, 37–43 (2000), etc). The synthesis utilizing enzyme or organisms can be executed in batch or in continuous manner utilizing fixed enzyme or fixed cells.

<PHA Synthesizing Enzyme and Producing Bacteria Therefor>

The PHA synthesizing enzyme to be employed in the present invention can be produced by microorganisms suitably selected from those capable of producing such enzyme, or produced by a transformant obtained by introducing a PHA synthesizing enzyme gene of such microorganisms into host microorganisms.

The microorganisms producing the PHA synthesizing enzyme can be PHB or PHB/V producing bacteria, and include those of *Aeromonas* sp., *Alcaligenes* sp., *Chromatium* sp., *Comamonas* sp., *Methylobacterium* sp., *Paracoccus* sp. and *Pseudomonas* sp., and there can also be utilized *Burkholderia* cepacia KK01, Ralstonia eutropha TB64 or *Alcaligenes* sp. TL2 separated by the present inventors. The KK01 strain, TB64 strain and TL2 strain are deposited, respectively under deposition numbers FERM BP-4235, BP-6933 and BP-6913, at the International Patent Organism Depositary (IPOD), National Institute of Advanced Industrial Science and Technology (AIST), Japan.

The microorganisms producing the PHA synthesizing enzyme can also be mcl-PHA or unusual-PHA producing bacteria, and include *Pseudomonas oleovolans, Pseudomonas resinovolans, Pseudomonas* sp. 61-3, *Pseudomonas putida* KT2442 and *Pseudomonas aeruginosa*, and there can also be utilized the microorganisms of *Pseudomonas* species such as *Pseudomonas putida* P91, *Pseudomonas cichorii* H45, *Pseudomonas cichorii* YN2 and *Pseudomonas jessenii* P161 separated by the present inventors, those of *Burkholderia* species such as *Burkholderia* sp. OK3 (FERM P-17370) described in the Japanese Patent Application Laid-open 2000-78753, or *Burkholderia* sp. OK4 (FERM P-17371) described in the Japanese Patent Application Laid-open 2001-69968. In addition, there can also be employed microorganisms of *Aeromonas* sp. or *Comamonas* sp. capable of producing mcl-PHA or unusual-PHA.

The P91 strain, H45 strain, YN2 strain and P161 strain are deposited, under the Budapest Treaty on the International Recognition of the Deposit of Microorganisms for the Purposes of Patent Procedure and respectively assigned deposition numbers FERM BP-7373, BP-7374, BP-7375 and BP-7376, at the IPOD, AIST.

For the ordinary culture of the microorganisms to be utilized in the production of PHA synthesizing enzyme of the present invention, for example for preparation of reserve strain or for proliferation for securing the number and active state of bacteria required for production of the PHA synthesizing enzyme, there is suitably selected a culture medium containing components necessary for the proliferation of the microorganisms. For example, unless detrimental to the growth or living of the microorganisms, there can be employed any culture medium, such as usual natural culture medium (broth culture medium, yeast extract etc.) or chemically defined culture medium in which nutrition sources are added.

The culture can be executed in any culture method such as liquid culture or solid culture. Also there may be employed any of batch culture, fed batch culture, semi-continuous culture or continuous culture. For example for liquid batch culture, there can be employed oxygen supply method by shaking in a shaking flask or by agitated aeration in a jar fermenter.

In case of producing the PHA synthesizing enzyme with the aforementioned PHA producing microorganisms, there can be employed, for example, a method of proliferating such microorganisms in an inorganic culture medium containing alkanoic acid such as octanoic acid or nonanoic acid and recovering the microorganisms in the logarithmic proliferation stage to the initial stage of the stationary stage for example by centrifuging thereby extracting the desired enzyme. In case of the culture under the aforementioned condition, the mcl-PHA resulting from the added alkanoic acid is synthesized in the bacteria, and, in such case, the PHA synthesizing enzyme is generally considered to be bonded to the fine PHA particles formed in the bacteria. However, the investigation by the present inventors indicates that a considerable enzyme activity is present also in the supernatant after the centrifuging separation of the bacteria cultured in the aforementioned methods. Such phenomenon is presumably ascribable to a fact that the PHA synthesizing enzyme in free state is also present in a considerable amount, since such enzyme is actively produced in the bacteria in the relatively early stage of culture, from the logarithmic proliferation stage to the early stage of stationary stage as mentioned above.

Also in the aforementioned culture methods, there may be employed any inorganic culture medium containing components necessary for the proliferation of the microorganisms, such as phosphor source (for example phosphate salt) and nitrogen source (for example ammonium salt or nitrate salt), such as MSB culture medium, E culture medium (J. Biol. Chem., 218 97–106(1956)) or M9 culture medium. In the following there will be shown the composition of the inorganic salt M9 culture medium employed in the examples of the present invention to be explained later:

| | |
|---|---|
| $Na_2HPO_4$ | 6.2 g |
| $KH_2PO_4$ | 3.0 g |
| NaCl | 0.5 g |
| $NH_4Cl$ | 1.0 g |

(in 1 liter of culture medium; pH 7.0)

For satisfactory proliferation and resulting PHA production, the above-mentioned inorganic culture medium has to be replenished with the essential minor elements by adding the following minor component solution by about 0.3%(w/v).

| (Minor component solution) | |
|---|---|
| nitrilotriacetic acid | 1.5 g; |
| $MgSO_4$ | 3.0 g; |
| $MnSO_4$ | 0.5 g; |
| NaCl | 1.0 g; |
| $FeSO_4$ | 0.1 g; |
| $CaCl_2$ | 0.1 g; |
| $CoCl_2$ | 0.1 g; |
| $ZnSO_4$ | 0.1 g; |
| $CuSO_4$ | 0.1 g; |
| $AlK(SO_4)_2$ | 0.1 g; |
| $H_3BO_3$ | 0.1 g; |
| $Na_2MoO_4$ | 0.1 g; |
| $NiCl_2$ | 0.1 g; |

(in 1 liter).

The culture temperature can be any temperature at which the aforementioned strains can satisfactorily proliferate, for example 14 to 40° C., preferably 20 to 35° C.

It is also possible to produce the desired PHA synthesizing enzyme utilizing a transformant in which introduced is the PHA synthesizing enzyme gene of the aforementioned PHA producing bacteria. The cloning of the PHA synthesizing enzyme gene, preparation of expression vector and preparation of transformant can be executed according to the known methods. In the transformant obtained by utilizing *Escherichia coli* or the like as the host bacteria, there can be employed a natural or chemically defined culture medium such as LB culture medium or M9 culture medium for the culture. The proliferation of the microorganisms is executed by the aerobic culture for 8 to 27 hours at 25 to 37° C. Then the bacteria are collected and the PHA synthesizing enzyme accumulated therein can be recovered. In the culture medium, there may be added, if necessary, antibiotics such as kanamycin, ampicillin, tetracycline, chloramphenicol, streptomycin etc. Also in case an inductive promoter is employed in the expression vector, an inductive substance corresponding to such promoter may be added to the culture medium in the culture of the transformant in order to accelerate expression. Examples of such inductive substance includes isopropyl-β-thiogalactopyranoside (IPTG), tetracycline and indole acrylic acid (IAA).

As the PHA synthesizing enzyme, there can be utilized crude enzyme such as bacteria crushed extract of the microorganisms or salted-out substance in which the protein component is precipitated and recovered with ammonium sulfate or the like, or pure enzyme purified with various methods. Such enzyme may be suitably added with a stabilizer or an activator such as a metal salt, glycerin, dithiothreitol, EDTA or bovine serum albumin (BSA).

The separation and purification of the PHA synthesizing enzyme can be executed in any method as long as the enzyme activity thereof can be conserved. For example the pure enzyme can be obtained by crushing the bacteria with French press, ultrasonic crusher, lysozyme or various surfactants, and subjecting crude enzyme obtained by centrifuging or salted-out substance prepared therefrom to affinity chromatography, cation or anion exchange chromatography, or gel permeation chromatography singly or in a suitable combination. Particularly a gene recombinant protein can be more simply purified by expressing it in the form of a fusion protein in which a "tag" such as a histidine residue is bonded to the N- or C-end and bonding it to resin having affinity through such tag. The desired protein can be separated from the fused protein by breakage with protease such as thrombin or blood coagulating factor Xa, by pH decrease or by addition of imidazole at a high concentration as a competitive binding agent. Otherwise, in case the tag contains intein, as in the case of utilizing pTYB1 (New England Biolab. Inc.) as the expression vector, breakage is executed under a reducing condition for example with dithiothreitol. As the fused protein enabling purification by affinity chromatography, there are known, in addition to the histidine tag, glutathione s-transferase (GST), chitin-binding domain (CBD), maltase-binding protein (MBP) and thioredoxin (TRX). The GST fused protein can be purified with GST affinity resin.

The activity of the PHA synthesizing enzyme can be measured by various known methods, for example by the following method, based on a principle of measuring the color, developed by 5,5'-dithiobis-(2-nitrobenzoic acid), of CoA released in the course of polymerization of 3-hydroxyacyl CoA to form PHA by the catalytic action of the PHA synthesizing enzyme. Reagent 1: bovine serum albumin (Sigma Co.) being dissolved in 0.1 M tris hydrochloric acid buffer (pH 8.0) in 3.0 mg/mL; Reagent 2: 3-hydroxyoctanoyl CoA being dissolved in 0.1 M tris hydrochloric acid buffer (pH 8.0) in 3.0 mM; Reagent 3: trichloroacetic acid being dissolved in 0.1 M tris hydrochloric acid buffer (pH 8.0) in 10 mg/mL; Reagent 4: 5,5'-dithiobis-(2-nitrobenzoic acid) being dissolved in 0.1 M tris hydrochloric acid buffer (pH 8.0) in 2.0 mM. First reaction (PHA synthesizing reaction): 100 μL of the reagent 1 is added and mixed to 100 μL of specimen (enzyme) solution, and the mixture is pre-incubated for 1 minute at 30° C. Then 100 μL of the reagent 2 is added and mixed, and the mixture is pre-incubated for 1 to 30 minutes at 30° C., and then the reaction is terminated by adding the reagent 3. Second reaction (color developing reaction of free CoA): The first reaction mixture after termination of reaction is centrifuged (147,000 m/s² (15,000 G), 10 minutes), and 500 μL of the supernatant is added with 500 μL of the reagent 4 and, after incubation for 10 minutes at 30° C., the optical absorbance at 412 nm is measured. Calculation of enzyme activity: An enzyme amount causing release of CoA of 1 μmol in 1 minute is defined as 1 unit (U).

<Colorant Producing Method>

As an example of the method for producing the electrostatic charge image developing toner utilizing the colorant of the present invention, there can be employed a method for producing the colorant, at least including the following preparation steps:

Preparation Steps of Colorant a step of dispersing a coloring agent in aqueous medium;

a step of fixing polyhydroxyalkanoate syinthesizing agent to the coloring agent dispersed in the aqueous medium;

a step of adding 3-hydroxyacyl CoA serving as the substrate; and a step of executing polyhydroxyalkanoate synthesizing reaction to cover at least a part of the surface of the coloring agent with polyhydroxyalkanoate.

The step of dispersing the coloring agent in the aqueous medium is executed by adding one or plural selected coloring agents, for example pigment, in the aqueous medium, and executing dispersion, if necessary followed by classification into a desired particle size range.

In the following there will be given a more detailed explanation in case the coloring agent consists of pigment.

The pigment to be employed in the present invention can be organic or inorganic, but is desirably of pigment excellent in heat resistance and light fastness. Examples of organic pigment include those of azo, phthalocyanine, benzimidazolone, quinacridone, isoindolinone, pyranthrone, dibromanthanthrone, indanthrone, anthrapyrimidine, flavanthrone, perylene, perinone, quinophthalone, phthalone, thioindigo, indigo, dioxazine, anthraquinone, xanthene, methine and azomethine types and other condensed polycyclic pigments including metal complex system. Examples of the inorganic pigment includes Miroli blue, iron oxide, cobalt violet, manganese violet, Prussian blue, ultramarine, cobalt blue, celurian blue, billidian, emerald green and cobalt green, and one or more can be suitably selected. Such pigment may be used after known surface treatments. Examples of such surface treatment include treatment with surfactant, coupling treatment or pigment derivative treatment.

The dispersion can be executed for example by a homomixer, a horizontal mini mill, a ball mill, a roll mill, a sand grinder, a crusher or ultrasonic treatment. There can also be utilized a method of passing the mixture through multiple nozzles under a liquid pressure at least equal to 1000 psi (about 70.3 kg/cm$^2$) in a liquid jet interaction chamber.

The dispersed pigment preferably has, from the standpoint of light transmittance and uniformity of the printed surface, a particle size at least not exceeding 0.7 µm, more preferably 0.01 to 0.4 µm, and is preferably in a monodisperse state. If the dispersed pigment is not in the desired particle size range, the particle size can be regulated by classification for example by filtration or precipitation.

The particle size of the dispersed pigment can be measured by known methods such as optical absorption, static light scattering, dynamic light scattering or centrifugal precipitation, and there can be utilized a particle size measuring apparatus such as Coulter Counter Multisizer for this purpose.

The aqueous medium for the synthesizing reaction in the present step can have any composition capable of dispersing the pigment in a desired dispersed state and not hindering the succeeding steps of fixing the enzyme to the pigment and executing PHA synthesis, but, in order to simplify the succeeding steps, the aqueous medium of the present step may have a composition allowing to exhibit the activity of the PHA synthesizing enzyme. As such composition, the aqueous medium can be composed for example of buffer. For such buffer, there can be advantageously employed ordinary buffer utilized in the biochemical reactions, such as acetic acid buffer, phosphoric acid buffer, potassium phosphate buffer, 3-(N-morpholino)propanesulfonic acid (MOPS) buffer, N-tris(hydroxymethyl)methyl-3-aminopropane sulfonic acid (TAPS) buffer, tris hydrochloric acid buffer, glycin buffer, 2-(cyclohexylamino)ethanesulfonic acid (CHES) buffer etc. The aqueous medium allowing to exhibit the PHA synthesizing enzyme can be employed in an ordinary concentration, namely 5 mM to 1.0 M, but preferably in a range of 10 to 200 mM. The buffer is so prepared that pH comes into a range of 5.5 to 9.0, preferably 7.0 to 8.5, but the condition may be set outside the aforementioned range, depending on the optimum pH or pH stability of the PHA synthesizing enzyme to be employed.

Also in order to maintain the dispersed state of the pigment in the aqueous medium, there may be added surfactant in type and concentration not hindering the succeeding steps and not hindering the objects of the colored composition of the present invention. Examples of such surfactant include anionic surfactants such as sodium oleate, sodium dodecylsulfonate, sodium dodecylsulfate, sodium dodecyl-N-sarcosinate, sodium cholate, sodium deoxycholate or sodium taurodeoxycholate; cationic surfactants such as cetyl trimethyl ammonium bromide or dodecyl pyridinium chloride; amphoteric surfactants such as 3-[(cholamidopropyl)dimethylammonio]-1-propane sulfonic acid (CHAPS) 3-[(3-cholamidopropyl)dimethylammonio]-2-hydroxy-1-propane sulfonic acid (CHAPSO), palmitoyl lysolecithin or dodecyl-β-alanine; and nonionic surfactants such as octyl glucoside, octyl thioglucoside, heptyl thioglucoside, decanoyl-N-methylglucamide (MEGA-10), polyoxyethylene dodecyl ether (Brij, Lubrol), polyoxyethylene i-octylphenyl ether (Triton X), polyoxyethylene nonylphenyl ether (Nonidet P-40, Triton N), polyoxyethylene fatty acid ester (Span) or polyoxyethylene sorbitol ester (Tween).

Also in order to maintain the dispersed state of the pigment in the aqueous medium, there may be added suitable auxiliary solvent in type and concentration not hindering the succeeding steps and not hindering the objects of the colored composition of the present invention. Such auxiliary solvent can be one or more selected from straight-chain aliphatic hydrocarbons such as hexane, monovalent alcohols such as methanol or ethanol, polyvalent alcohols such as glycerin, fatty acid esters and carboxylic acid esters.

The step of fixing the PHA synthesizing enzyme to the pigment can be executed by adding PHA synthesizing enzyme to the aforementioned pigment dispersion and executing fixation treatment. The fixation can be arbitrarily selected from the ordinary enzyme fixation methods as long as the enzyme activity can be retained and it is applicable to the desired pigment. Examples of such fixation method include covalent bonding, ionic adsorption, hydrophobic adsorption, physical adsorption, affinity adsorption, crosslinking and lattice inclusion, but particularly simple is the fixation utilizing ionic adsorption or hydrophobic adsorption.

The enzyme protein such as the PHA synthesizing enzyme is a polypeptide formed by a plurality of amino acids, and shows the property as ionically adsorbable substance by the amino acids having free ionic group such as lysine, histidine, arginine, aspartic acid or glutamic acid, and also shows the property as hydrophobically adsorbable substance by the amino acids having free hydrdophobic group such as alanine, valine, isoleucine, methionine, tryptophan, phenylalanine or proline and also by being an organic polymer. It can therefore be adsorbed by pigment showing ionic character and/or hydrophobicity in variable levels.

In the method of fixing the PHA synthesizing enzyme principally by ionic adsorption, there can be employed pigment having ionic functional group on the surface, such as inorganic pigment principally composed of clay minerals or metal oxides.

Also in the method of fixing the PHA synthesizing enzyme principally by hydrophobic adsorption, there can be employed pigment having non-polar surface, for example organic pigments such as azo pigment including plural aromatic rings, phthalocyanine pigment including condensed polycyclic structure, or anthraquinone pigment, or inorganic pigments composed of carbon crystals such as carbon black.

The fixation of the PHA synthesizing enzyme onto the pigment by ionic adsorption or hydrophobic adsorption can be achieved by mixing the pigment and the PHA synthesizing enzyme at predetermined concentrations in predetermined aqueous medium. In this operation, it is desirable to shake or agitate the reaction vessel at suitable intensity, in order that the enzyme can be uniformly adsorbed on the pigment surface.

In such fixation treatment, the aqueous medium containing the pigment and the enzyme in mixture desirably has a composition determined in consideration of a fact that the polarity of surface charge, charge amount and hydrophobicity of the pigment and the PHA synthesizing enzyme change depending on the pH and salt concentration of the aqueous medium. For example, if the pigment is principally ionically adsorbable, a decrease in the salt concentration allows to increase the charge amount contributing to the adsorption between the pigment and the PHA synthesizing enzyme. Also a change in pH allows to increase the opposite charges of the two. In case the pigment is principally hydrophobically adsorbable, an increase in the salt concentration allows to increase the hydrophobicity of the two. It is also possible to select a composition suitable for adsorption by executing in advance electrophoresis or measuring the wetting angle to determine the charge state or hydrophobicity of the pigment and the PHA synthesizing enzyme. Also the composition can be determined by directly measuring the adsorption amount of the pigment and the PHA synthesizing enzyme. The adsorption amount can be measured, for example, by adding solution of PHA synthesizing enzyme of a known concentration to pigment dispersion, then executing adsorption process, measuring the concentration of the PHA synthesizing enzyme in the mixture and determining the adsorbed enzyme amount by subtraction.

In case of pigment for which it is difficult to fix the enzyme by ionic adsorption or hydrophobic adsorption, there may be employed covalent bonding method in consideration of the cumbersomeness of the operations or the possibility of deactivation of the enzyme. For example there can be utilized a method of converting pigment having an aromatic amino group into a diazo compound and executing diazo coupling of the enzyme thereto, a method of forming a peptide bond between pigment having a carboxyl group or an amino group and the enzyme, a method of executing alkylation between pigment having a halogen atom and the enzyme, a method of crosslinking an amino group of a solid particle and an amino group of the enzyme, a method of reacting pigment having a carboxyl group and an amino group and the enzyme in the presence of a compound having an aldehyde group or a ketone group and an isocyanide compound, or a method of executing exchange reaction between pigment having a disulfide group and a thiol group of the enzyme.

Also the enzyme may be fixed by affinity adsorption to the pigment in which a ligand is introduced.

In such case, there may be employed any ligand capable of executing affinity adsorption while maintaining the activity of the PHA synthesizing enzyme. The enzyme fixation may also be executed by bonding another organism-origin polymer such as protein to the PHA synthesizing enzyme and affinity adsorbing the thus bonded organism-origin polymer. Also the bonding of the PHA synthesizing enzyme and the organism-origin polymer can be executed either by gene recombination or by a chemical method. For example, as described later in the examples, fixation can be achieved by fusing glutathione S-transferase with PHA synthesizing enzyme by transformation and executing affinity adsorption of the fused protein by sepharose in which introduced is glutathione which is a ligand of glutathione-S-transferase.

Also fixation of polyhydroxyalkanoate onto the pigment surface can be achieved by having a peptide, including an amino acid sequence having bonding ability to the pigment, expressed with polyhydroxyalkanoate synthesizing enzyme, and fixing the PHA synthesizing enzyme to the pigment surface based on the bonding property of such peptide portion to the pigment.

The amino acid sequence having bonding ability to the pigment can be determined for example by screening of random peptide library. For example there can be advantageously employed a phage display peptide library prepared by linking a randomly synthesized gene to the N-end side gene of the surface protein (for example gene III protein) of M13 phage, and, in such case, the amino acid sequence having bonding ability to the pigment is determined by the following procedure. The phage display peptide library is added to and contacted with the pigment, and then the coupled phage and uncoupled phage are separated by rinsing. The phage coupled with the pigment is dissolved out with an acid, then neutralized with buffer and infected on *Escherichia coli* for phage amplification. Such selection is repeated plural times whereby plural clones having the bonding ability to the desired pigment are concentrated. In order to obtain a single clone, a colony is formed on the culture medium plate in a state infected again on *Escherichia coli*. Each single colony is cultured in liquid culture medium, and the phage present in the supernatant of the culture medium is purified by precipitation with polyethylene glycol etc. and the base sequence thereof is analyzed to know the structure of the peptide.

Thus obtained amino acid sequence of the peptide having the bonding ability to the pigment is utilized by fusing with the PHA synthesizing enzyme by an ordinary genetic engineering method. The peptide having the bonding ability to the pigment can be expressed by linking the N-end or C-end of the PHA synthesizing enzyme. It can also be expressed by inserting a suitable spacer sequence. The spacer sequence is preferably composed of 3 to 400 amino acids, and may contain any amino acid. There is most preferred is a spacer sequence that does not hinder the function of the PHA synthesizing enzyme nor coupling of the PHA synthesizing enzyme to the pigment.

The enzyme-fixed pigment prepared by the aforementioned method can be utilized in such state or after lyophilization etc.

By defining 1 unit (U) of the amount of the PHA synthesizing enzyme releasing 1 μmol/minute of CoA in the PHA synthesis reaction by polymerization of 3-hydroxyacyl CoA, the amount of enzyme fixed on the pigment is within a range of 10 to 1,000 U per 1 g of pigment, preferably 50 to 500 U.

The enzyme fixation process is executed desirably within a time of 1 minute to 24 hours, more desirably 10 minutes to 1 hour. Excessively long standing is undesirable because it results in coagulation of pigment and deterioration of enzyme activity.

It is also possible to omit the initial step of pigment dispersion but to directly add the pigment, prior to dispersion in the aqueous medium, to the enzyme solution and to fix the enzyme to the pigment under dispersion in the enzyme solution. In such case it is rendered possible, by the electrical repulsion or steric hindrance by the ionic functional groups contained in the enzyme fixed to the pigment, to facilitate dispersion of the pigment into the aqueous medium, thereby dispensing with the addition of surfactant to the aqueous medium or reducing the amount of such surfactant.

The step of adding 3-hydroxyacyl CoA as the substrate can be achieved by adding separately prepared reserve liquid of 3-hydroxyacyl CoA so as to attain a desired concentration. The 3-hydroxyacyl CoA serving as the substrate is added so as to attain an end concentration of 0.1 mM to 1.0 M, preferably 0.2 mM to 0.2 M, more preferably 0.2 mM to 1.0 mM.

Also in the above-mentioned step, by varying in time the composition such as type and concentration of the 3-hydroxyacyl CoA in the aqueous reaction mixture, the monomer unit composition of the PHA covering the coloring agent can be varied in a direction from the inner side to the outer side if the coloring agent has a spherical shape.

In such colorant showing change in the monomer unit composition, there can be assumed a configuration in which the PHA covering layer shows continuous change in the composition, and PHA of a single layer involving a gradient composition in the radial direction covers the coloring agent. Such configuration can be realized, in the course of synthesis of PHA, by adding 3-hydroxyacyl CoA of different composition.

There can also be another configuration, in which the PHA layer has stepwise changes in the composition and the coloring agent is covered by plural layers of PHA with different compositions. Such configuration can be realized for example by synthesizing PHA with a certain composition of 3-hydroxyacyl CoA, then recovering the colorant under preparation from the reaction mixture for example by centrifuging, and adding again reaction mixture having a different composition of 3-hydroxyacyl CoA.

The step of PHA synthesizing reaction is executed by regulating the reaction time and the reaction temperature and also regulating so as to obtain a composition capable of exhibiting the activity of the PHA synthesizing enzyme, in case the composition of the reaction mixture is not regulated in the preceding step, in order to obtain the microcapsule (colorant) of a desired shape by the synthesized PHA.

The concentration of the reaction solution capable of exhibiting the activity of the PHA synthesizing enzyme can be an ordinary concentration, namely within a range of 5 mM to 1.0 M, more preferably 10 to 200 mM. The pH is adjusted within a range of 5.5 to 9.0, preferably 7.0 to 8.5, but the condition may be outside the aforementioned range depending on the optimum pH or pH stability of the PHA synthesizing enzyme to be used.

The reaction temperature is suitably set according to the characteristics of the PHA synthesizing enzyme to be used, usually within a range of 4 to 50° C., preferably 20 to 40° C., but the condition may be outside the aforementioned range depending on the optimum temperature or heat resistance of the PHA synthesizing enzyme to be used.

The reaction time varies depending on the stability etc. of the PHA synthesizing enzyme to be used, but is usually selected within a range of 1 minute to 24 hours, preferably 30 minutes to 3 hours.

The present step provides microcapsules, and the monomer unit structure of PHA constituting such microcapsule (colorant) can be determined, after extracting PHA from the microcapsule (colorant) with chloroform, by composition analysis with gas chromatography or by time of flight type secondary ion mass spectrometer (TOF-SIMS) and ion sputtering.

The molecular weight of PHA is not particularly limited, but the number average molecular weight is preferably selected within a range of 1,000 to 10,000,000, more preferably 10,000 to 1,000,000 in order to maintain the strength of the microcapsule (colorant) and to realize the glass transition point to be explained later. The molecular weight of PHA can be measured by GPC (gel permeation chromatography) after PHA extraction from the microcapsule (colorant) with chloroform.

For sufficiently attaining the objects of the present invention, it is desirable that the number average molecular weight satisfies the following relationship:

(number average molecular weight of first resin component)>(number average molecular weight of second resin component).

In case the first and second resin components satisfy the aforementioned relationship, in obtaining the toner by crushing the kneaded substance, the probability of crack generation in the second resin component or in the interface between the first and second resin components becomes high, so that the almost entire toner surface is covered with the first and second resin components. Stated differently, there is lowered the probability that the coloring agent such as pigment is directly exposed to the surface of the toner particle. It is therefore rendered possible to resolve the drawbacks of low charge amount, a large difference in the charge amount under a high temperature/high humidity condition or a low temperature/low humidity condition (environmental dependence), and fluctuation in the charge amount among the toners of different colors utilizing pigments of cyan, magenta, yellow and black colors depending on the pigment types, for example in case of full-color image recording. Also it becomes possible to use the external addition material of a same type or a same amount for the toners of different colors.

Also the colorant of the present invention reduces the distribution of toner composition and improves the flowability of powder even in case the coloring agent such as pigment is used in a large amount. Particularly in case of adding the coloring agent such as pigment in a large amount to the small-sized toner not exceeding 5 μm, it is rendered possible to maintain the charging characteristics, fixing characteristics and powder characteristics that cannot be attained in the conventional methods. In the method of the present invention for producing the microcapsule (colorant), since the coloring agent such as pigment is directly covered with PHA, the density of the coloring agent can be elevated in the microcapsule. On the other hand, as the covering amount of PHA is requested to be increased in order to improve the dispersibility and mechanical strength of the microcapsule (colorant), it is within a range of 1 to 30 mass % in mass ratio with respect to the coloring agent, preferably 1 to 20 mass % and more preferably 1 to 15 mass %.

The conventional matrix-domain structure formed by fused phase separation of different resins is associated with the drawbacks of small selection range of the usable resins and difficulty in controlling the particle size and distribution of the domain, but, in the toner of the present invention, since the coloring agent covered with outer shell resin is bound by the thermoplastic resin, there is no limitation in the combination of the coloring agent and the binder resin and the concentration of the coloring agent in the colorant and the particle size thereof can be easily controlled.

The particle size of the microcapsule (colorant) obtained by the aforementioned steps is normally not exceeding 1 μm, preferably not exceeding 0.7 μm and more preferably 0.01 to 0.4 μm. The particle size of the microcapsule pigment can be measured by known methods such as optical absorption, static light scattering, dynamic light scattering or centrifugal precipitation, and there can be utilized a particle size measuring apparatus such as Coulter Counter Multisizer for this purpose.

Also the microcapsule (colorant) obtained in the aforementioned steps can be used after various secondary processes or chemical modification.

For example, by applying chemical modification to the PHA on the surface of the colorant, there can be obtained the colorant having more useful functions and characteristics. For example by introducing a graft chain, there can be obtained colorant improved in various characteristics, for example mutual solubility with the binder resin, derived from such graft chain. Also by crosslinking the PHA on the surface of the colorant, there can be improved the mechanical strength, chemical resistance, heat resistance etc. of the colorant.

The method of chemical modification is not particularly limited as long as it can attain the desired functions and structure, but there can be advantageously employed a method of synthesizing PHA having reactive functional group in the side chain and executing chemical modification utilizing the chemical reaction of such functional group.

The type of the aforementioned reactive functional group is not particularly limited as long as it can attain the desired functions and structure, but the aforementioned epoxy group can be cited as an example. The PHA having an epoxy group in the side chain can be subjected to chemical conversion as in the ordinary polymer having an epoxy group. More specifically, there can be executed conversion into a hydroxyl group or introduction of a sulfon group. It is also possible to add a compound having thiol or amine, and, more specifically, the graft chain of the polymer can be formed by reaction under addition of a compound having an end amino group highly reactive with the epoxy group.

Examples of the compound having an amino group at the end include amino modified polymers such as polyvinylamine, polyethylenimine or amino-modified polysiloxane (amino-modified silicone oil). Among these, amino-modified polysiloxane can be commercially available modified silicone oil or can be synthesized by the method described for example in J. Amer. Chem. Soc., 78, 2278(1956), and is expected to provide effects by the addition of graft chain in the polymer, such as improvement in the mutual solubility with the binder resin.

Other examples of chemical conversion of the polymer having an epoxy group include crosslinking reaction with a diamine compound such as hexamethylene diamine, succinic anhydride or 2-ethyl-4-methylimidazole, and examples of physicochemical conversion include crosslinking reaction by electron beam irradiation. Among these, the reaction between PHA having an epoxy group in the side chain and hexamethylene diamine proceeds in the following manner to produce crosslinked polymer:

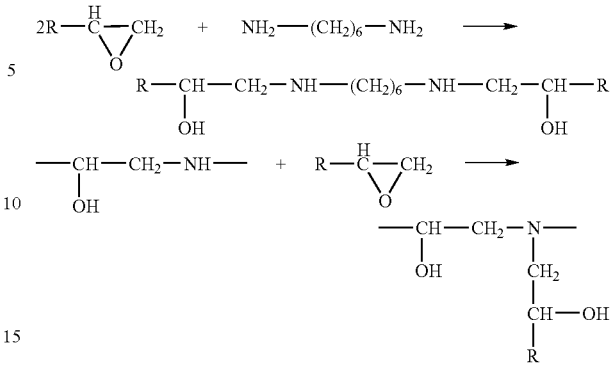

Since the microcapsule (colorant) of the present invention is featured by a high concentration of the coloring agent as explained in the foregoing and also by the small size thereof, the electrostatic charge image developing toner containing such microcapsule (colorant) allows to form an image excellent in transparency, color development and contrast.

<Examples of Coloring Agent>

The coloring agent constituting the electrostatic charge image developing toner of the present invention is not particularly limited and can be any coloring agent ordinarily employed in the toner manufacture. A coloring agent effectively employable in the present invention is pigment.

As the pigment, there can be utilized known organic or inorganic pigments. Examples of black pigment include inorganic ones such as carbon black and triiron tetraoxide, and organic ones such as cyanine black. Examples of white pigment include zinc white, titanium oxide, antimony white and zinc sulfide.

Examples of yellow pigment include inorganic ones such as lead yellow, cadmium yellow, yellow iron oxide, titanium yellow and ochre.

Also examples of monoazo pigment of acetoacetic acid anilide type which is a low-soluble metal salt (azo rake) include Hanza yellow G (C.I. Pigment Yellow 1), Hanza yellow 10G (C.I. Pigment Yellow 3), Hanza yellow RN(C.I. Pigment Yellow 65), Hanza brilliant yellow 5GX (C.I. Pigment Yellow 74), Hanza brilliant yellow 10GX (C.I. Pigment Yellow 98), Permanent yellow FGL (C.I. Pigment Yellow 97), Shimura rake fast yellow 6G (C.I. Pigment Yellow 133), and Rionol yellow K-2R(C.I. Pigment Yellow 169). Also examples of acetoacetic acid anilide type disazo pigment include disazo yellow G (C.I. Pigment Yellow 12), disazo yellow GR (C.I. Pigment Yellow 13), disazo yellow 5G (C.I. Pigment Yellow 14), disazo yellow 8G (C.I. Pigment Yellow 17), disazo yellow R(C.I. Pigment Yellow 55), and permanent yellow HR(C.I. Pigment Yellow 83).

Also examples of condensed azo pigment include chromophthal yellow 3G (C.I. Pigment Yellow 93), chromophthal yellow 6G (C.I. Pigment Yellow 94), and chromophthal yellow GR (C.I. Pigment Yellow 95). Also examples of benzimidazolone type monoazo pigment include hostapalm yellow H3G (C.I. Pigment Yellow 154), hostapalm yellow H4G (C.I. Pigment Yellow 151), hostapalm yellow H2G (C.I. Pigment Yellow 120), hostapalm yellow H6G (C.I. Pigment Yellow 175) and hostapalm yellow HLR (C.I. Pigment Yellow 156). Also examples of isoindolinone type pigment include irgazin yellow 3RLTN (C.I. Pigment Yellow 110), irgazin yellow 2RLT, irgazin yellow 2GLT (C.I. Pigment Yellow 109), fastgen super yellow GROH (C.I.

Pigment Yellow 137), fastgen super yellow GRO(C.I. Pigment Yellow 110), and sandrin yellow 6GL (C.I. Pigment Yellow 173). There can also be utilized threne type pigments such as flavanthrone yellow (C.I. Pigment Yellow 24), anthrapyrimidine (C.I. Pigment Yellow 108), phthaloylamide type anthraquinone (C.I. Pigment Yellow 123) and heliofast yellow E3R (C.I. Pigment Yellow 99); metal complex pigments such as azo nickel complex pigment (C.I. Pigment Green 10), nitroso nickel complex pigment (C.I. Pigment Yellow 153) and azomethine copper complex pigment (C.I. Pigment Yellow 117), or quinophtharone yellow (C.I. Pigment Yellow 138) which is a phthalimide type pigment.

Examples of magenta pigment include inorganic ones such as cadmium red, Indian red, silver vermilion, red lead and antimony vermilion. Also examples of azo rake of azo pigment include brilliant carmine 6B (C.I. Pigment Red 57:1), rake red (C.I. Pigment Red 53:1), permanent red F5R(C.I. Pigment Red 48), lysol red (C.I. Pigment Red 49), persian orange (C.I. Pigment Orange 17), chrosay orange (C.I. Pigment Orange 18), helio orange TD (C.I. Pigment Orange 19), pigment scarlet (C.I. Pigment Red 60:1), brilliant scarlet G (C.I. Pigment Red 64:1), helio red RMT (C.I. Pigment Red 51), bordeaux 10B (C.I. Pigment Red 63) and helio bordeaux (C.I. Pigment Red 54). Also examples of insoluble azo (monoazo, disazo, condensed azo) pigment include para red (C.I. Pigment Red 1), rake red 4R(C.I. Pigment Red 3), permanent orange (C.I. Pigment Orange 5), permanent red FR2 (C.I. Pigment Red 2), permanent red FRLL (C.I. Pigment Red 9), permanent red FGR (C.I. Pigment Red 112), brilliant carmine BS (C.I. Pigment Red 114), permanent carmine FB (C.I. Pigment Red 5), P.V. carmine HR(C.I. Pigment Red 150), permanent carmine FBB (C.I. Pigment Red 146), nova palm red F3RK-F5RK (C.I. Pigment Red 170), nova palm red HFG (C.I. Pigment Orange 38), nova palm red HF4B (C.I. Pigment Red 187), nova palm orange HL.HL-70 (C.I. Pigment Orange 86), P.V. carmine HF4C(C.I. Pigment Red 185), hosta balm brown HFR (C.I. Pigment Brown 25), Vulcan orange (C.I. Pigment Orange 16), pyrazolone orange (C.I. Pigment Orange 13) and pyrazolone red (C.I. Pigment Red 36). Examples of condensed azo pigment include chromophthal orange 4R(C.I. Pigment Orange 31), chromophthal scarlet R(C.I. Pigment Red 166) and chromophthal red BR (C.I. Pigment Red 144).

Also among anthraquinone pigments which are condensed polycyclic pigments, there can be used pyranthrone orange (C.I. Pigment Orange 40), anthanthrone orange (C.I. Pigment Orange 168), and dianthraquinonyl orange (C.I. Pigment Red 177). Among thioindigo pigment there can be used thioindigo magenta (C.I. Pigment Violet 38), thioindigo violet (C.I. Pigment Violet 36) and thioindigo Red (C.I. Pigment Red 88). Among perinone pigments there can be used perinone orange (C.I. Pigment Orange 43). Among perylene pigments there can be used perylene red (C.I. Pigment Red 190), perylene vermilion (C.I. Pigment Red 123), perylene maroon (C.I. Pigment Red 179), perylene scarlet (C.I. Pigment Red 149), and perylene red (C.I. Pigment Red 178). Among quinacridone pigment there can be used quinacridone red (C.I. Pigment Violet 19), quinacridone magenta (C.I. Pigment Red 122), quinacridone maroon (C.I. Pigment Red 206) and quinacridone scarlet (C.I. Pigment Red 207). Also there can be used pyrrocoline pigment, red fluorobin pigment and vat rake pigments (soluble dye+precipitator=fixed rake) as condensed polycyclic pigment.

Among cyan pigments there can be used inorganic ones such as Prussian blue, ultramarine, cobalt blue, and celurian blue. Also among phthalocyanine pigments there can be used fastgen blue BB (C.I. Pigment Blue 15), sumiton cyanine blue HB (C.I. Pigment Blue 15), cyanine blue 5020 (C.I. Pigment Blue 15:1), Simikaprint cyanine blue GN-O (C.I. Pigment Blue 15), fast sky blue A-612 (C.I. Pigment Blue 17), cyanine Green GB (C.I. Pigment Green 7), cyanine green S537-2Y (C.I. Pigment Green 36) and Sumiton fast violet RL (C.I. Pigment Violet 23). There can also be used indanthrone blue (PB-60P, PB-22, PB-21, PB-64) which is threne pigment, and methyl violet phosphor molybdenate rake (PV-3) which is a basic dye rake pigment. Also as base pigment, there can be used baryte powder, barium carbonate, clay, silica, white carbon, talc and alumina white. In addition there can be used pigments obtained by resin coating on the surface of the aforementioned pigments.

The aforementioned pigments can be used singly or in an arbitrary mixture for obtaining desired color of the toner. Also in consideration of the environmental security or safety to human body, there can be advantageously utilized various edible rakes, such as edible red 40 aluminum rake, edible red 2 aluminum rake, edible red 3 aluminum rake, edible red 106 aluminum rake, edible yellow 5 aluminum rake, edible yellow 4 aluminum rake, edible blue 1 aluminum rake, or edible blue 2 aluminum rake.

The content of the aforementioned coloring agent in the toner can be widely variable according to the desired coloring effect. Ordinarily, in order to obtain optimum toner characteristics, namely in consideration of the print coloring power, shape stability of toner, and toner scattering, such coloring agent is contained in a proportion of 0.1 to 60 mass parts, preferably 0.5 to 20 mass parts with respect to 100 mass parts of the binder resin.

<Post Treatment of Colorant>

The capsule structure (colorant) obtained by the producing method of the present invention can be utilized in the state of aqueous dispersion in the reaction mixture, or after recovery of the colorant by mild centrifuging or suction filtration followed by dispersion in another aqueous medium. It is also possible to use as solvent dispersion by dispersing the recovered capsule structure (colorant) in organic solvent in which PHA is insoluble, or as dispersion in organic solvent in which PHA is insoluble obtained by solvent replacement. It is furthermore possible to rinse the capsule structure (colorant) by the above-mentioned method.

The capsule structure (colorant) in powder state can be obtained, in case the particle size is large, by obtaining a wet cake through mild centrifuging or suction filtration, followed by drying by vacuum drying or jet mill. Also in case the particle size is small, drying can be executed by spray drying.

The particle size of the produced capsule structure (colorant) can be made uniform to a certain extent by employing the coloring agent of uniform particle size, but classification may be executed after the preparation of the capsule structure (colorant) in order to obtain more uniform particle size.

<Toner Constituting Materials>

In the following there will be explained other constituents of the electrostatic charge image developing toner of the present invention. The electrostatic charge image developing toner of the present invention includes at least the aforementioned colorant and the binder resin, and further contains a charge control agent and other additives if necessary.

(Binder Resin)

The binder resin is not particularly limited, and there can be used any binder resin usually employed in the toner preparation. Examples of the binder resin include styrenic polymers such as polystyrene, polyacrylate ester and styrene-acrylate ester copolymer; polyvinyl chloride, polyvinyl acetate, polyvinylidene chloride, phenolic resin, epoxy resin, polyester resin etc.

(Biodegradable Plastics)

In the present invention, the commercially available biodegradable plastics can also be used advantageously. Examples of the biodegradable plastics include "Ecostar", "Ecostar plus" (Hagiwara Kogyo), "Biopol" (ICI Japan), "Azicoat" (Ajinomoto), "Placcel", "Polycaprolactone" "Daicel Chemical", "Sholex", "Bionolle" (Showa Denko), "Lacty" (Shimadzu Mfg.), and "Lacea" (Mitsui Chemical).

(Other Resins)

Examples of the styrene polymer include copolymer of styrene and (meth)acrylate ester, copolymer thereof with another monomer capable of copolymerizing therewith, copolymer of styrenic and dienic monomer (butadiene, isoprene etc.) and copolymer thereof with another monomer capable of copolymerizing therewith. Examples of polyester polymer include condensation product of an aromatic dicarboxylic acid and addition product of aromatic diol with alkylene oxide. Examples of epoxy polymer include reaction product of aromatic diol and epichlorohydrin and modified products thereof. Examples of polyolefin polymer include polyethylene, polypropylene and a copolymerized chain with another monomer capable of copolymerizing therewith. Examples of polyurethane polymer include poly addition product of aromatic diisocyanate and alkylene oxide addition product of aromatic diol.

Specific examples of the binder resin employed in the present invention include polymers of following polymerizable monomers, mixtures thereof, and copolymerization products obtained by using at least two of the following polymerizable monomers. Specific examples of such compounds include styrenic copolymers such as styrene-acrylic acid copolymer or styrene-methacrylic acid copolymer, polyester polymers, epoxy polymers, polyolefin polymers and polyurethane polymers.

(Polymerizable Monomer)

Specific examples of the polymerizable monomer include styrene and derivatives thereof such as styrene, o-methylstyrene, m-methylstyrene, p-methylstyrene, p-methoxystyrene, p-phenylstyrene, p-chlorostyrene, 3,4-dichlorostyrene, p-ethylstyrene, 2,4-dimethylstyrene, p-n-butylstyrene, p-tert-butylstyrene, p-n-hexylstyrene, p-n-octylstyrene, p-n-nonylstyrene, p-n-decylstyrene or p-n-dodecylstyrene; ethylenic unsaturated monoolefins such as ethylene, propylene, butylene or isobutylene; unsaturated polyenes such as butadiene; halogenated vinyls such as vinyl chloride, vinylidene chloride, vinyl bromide or vinyl fluoride; vinyl esters such as vinyl acetate, vinyl propionate or vinyl benzoate; aliphatic α-methylene monocarboxylic acid esters such as methyl methacrylate, ethyl methacrylate, propyl methacrylate, n-butyl methacrylate, isobutyl methacrylate, n-octyl methacrylate, dodecyl methacrylate, 2-ethylhexyl methacrylate, stearyl methacrylate, phenyl methacrylate, dimethylaminoethyl methacrylate or diethylaminoethyl methacrylate; acrylate esters such as methyl acrylate, ethyl acrylate, n-butyl acrylate, isobutyl acrylate, propyl acrylate, n-octyl acrylate, dodecyl acrylate, 2-ethylhexyl acrylate, stearyl acrylate, 2-chloroethyl acrylate or phenyl acrylate; vinyl ethers such as vinylmethyl ether, vinylethyl ether or vinylisobutyl ether; vinyl ketones such as vinylmethyl ketone, vinylhexyl ketone or methylisopropenyl ketone; N-vinyl compounds such as N-vinylpyrrol, N-vinylcarbazole, N-vinylindole or N-vinylpyrrolidone; vinylnaphthalenes; acrylic or methacrylic acid derivatives such as acrylonitrile, methacrylonitrile acrylamide; esters of the aforementioned α,β unsaturated acids or diesters of dibasic acids; dicarboxylic acids such as maleic acid, methyl maleate, butyl maleate, dimethyl maleate, phthalic acid, succinic acid or terephthalic acid; polyols such as ethylene glycol, diethylene glycol, triethylene glycol, 1,2-propylene glycol, 1,3-propylene glycol, 1,4-butanediol, 1,6-hexanediol, bisphenol-A, hydrogenated bisphenol-A or polyoxyethylenated bisphenol-A; isocyanates such as p-phenylene diisocyanate, p-xylylene diisocyanate or 1,4-tetramethylene diisocyanate; amines such as ethylamine, butylamine, ethylenediamine, 1,4-diaminobenzene, 1,4-diaminobutane or monoethanolamine; and epoxy compounds such as diglycidyl ether, ethyleneglycol diglycidyl ether, bisphenol-A glycidyl ether or hydroquinone glycidyl ether.

(Crosslinking Agent)

In the formation of the binder resin to be used in the present invention, there may be employed the following crosslinking agent if necessary. Examples of the crosslinking agent with two functional groups include divinylbenzene, bis(4-acryloxy-polyethoxyphenyl)propane, ethyleneglycol diacrylate, 1,3-butyleneglycol diacrylate, 1,4-butanediol diacrylate, 1,5-pentanediol diacrylate, 1,6-hexanediol diacrylate, neopentylglycol diacrylate, diethyleneglycol diacrylate, triethyleneglycol diacrylate, tetraethyleneglycol diacrylate, diacrylates of polyethyleneglycol #200, #400 and #600, dipropyleneglycol diacrylate, polypropyleneglycol diacrylate, polyester type diacrylate, and methacrylates corresponding to the foregoing acrylates.

Examples of the crosslinking agent with more than two functional groups include pentaerythritol triacrylate, trimethyrolethane triacrylate, trimethyrolpropane triacrylate, tetramethyrolmethane tetraacrylate, oligoester acrylate and methacrylate, 2,2-bis(4-methacryloxy-polyethoxyphenyl) propane, diallyl phthalate, triallyl cyanurate, triallyl isocyanurate, triallyl trimellitate, and diaryl chlorendate.

(Polymerization Starter)

In the formation of the binder resin to be used in the present invention, there may be employed the following polymerization starter if necessary. Examples of the polymerization starter include t-butylperoxy-2-ethyl hexanoate, cumin perpivarate, t-butyl peroxylaurate, benzoyl peroxide, lauroyl peroxide, octanoyl peroxide, di-t-butyl peroxide, t-butylcumyl peroxide, dicumyl peroxide, 2,2'-azobisisobutylonitrile, 2,2'-azobis(2-methylbutylonitrile), 2,2'-azobis(2, 4-dimethyl-valeronitrile), 2,2'-azobis(4-methoxy-2,4-dimethyl-valeronitrile), 1,1-bis(t-butylperoxy)-3,3,5-trimethylcyclohexane, 1,1-bis(t-butylperoxy) cyclohexane, 1,4-bis(t-butylperoxycarbonyl)cyclohexane, 2,2-bis(t-butylperoxy) octane, n-butyl-4,4-bis(t-butylperoxy) valylate, 2,2-bis(t-butylperoxy)butane, 1,3-bis(t-butylperoxy-isopropyl)benzene, 2,5-dimethyl-2,5-di(t-butylperoxy) hexane, 2,5-dimethyl-2,5-di(benzoylperoxy)hexane, di-t-butyldiperoxy isophthalate, 2,2-bis(4,4-di-t-butylperoxycyclohexyl) propane, di-t-butylperoxy-α-methyl succinate, di-t-butylperoxydimethyl glutarate, di-t-butylperoxy hexahydroterephthalate, di-t-butylperoxy azelate, 2,5-dimethyl-2,5-di(t-butylperoxy)hexane, diethyleneglycol-bis(t-butylperoxycarbonate), di-t-butylperoxy trimethyladipate, tris(t-butylperoxy)triazine, and vinyltris(t-butylperoxy) silane.

These materials can be used singly or in combination. These materials are used at a concentration of at least 0.05 mass parts (preferably 0.1 to 15 mass parts) with respect to 100 mass parts of the monomer.

(Charge Control Agent)

There can be employed a charge control agent employed conventionally. Specific examples thereof include nigrosin dyes, quaternary ammonium salts and monoazo metal complex salt dyes. The amount of the charge control agent is determined in consideration of the charging property of the binder resin, the producing method including the amount and dispersing method of the colorant and the charging ability of other additives, but is generally employed in an amount of 0.1 to 20 mass parts, preferably 0.5 to 10 mass parts with respect to 100 mass parts of the binder resin. There may also be employed inorganic particles such as metal oxide or an inorganic substance surfacially treated with the aforementioned organic materials. Such charge control agent may be mixed in the binder resin or attached to the surface of the toner particles.

(Other Components of Toner)

The electrostatic charge image developing toner of the present invention may include, in addition to the aforementioned binder resin, colorant and charge control agent, the following compounds. Examples of such compound include silicone resin, polyester, polyurethane, polyamide, epoxy resin, polyvinylbutyral, rosin, denatured rosin, terpene resin, phenolic resin, aliphatic or alicyclic hydrocarbon resin such as low molecular weight polyethylene or low molecular weight polypropylene, aromatic petroleum resin, chlorinated paraffin and paraffin wax. Among these, there is preferably employed wax, and the examples thereof include low molecular weight polypropylene and byproducts thereof, low molecular weight polyester, ester wax and aliphatic derivatives. Wax classified by the molecular weight by various methods is also preferably employed in the present invention. After the classification, there may be also executed oxidation, block copolymerization or graft modification.

The electrostatic charge image developing toner of the present invention provides particularly excellent characteristics in case the toner includes the aforementioned wax component and such wax component is dispersed in substantially spherical- and/or spindle-shaped islands in the binder resin in the observation of the toner section under the transmission electron microscope (TEM).

(Method of Toner Preparation)

The electrostatic charge image developing toner of the present invention, having the above-described configuration, can be prepared by any known method. The dispersion of the colorant of the present invention into the binder resin can be achieved by fused kneading of the dried colorant into the binder resin under such a shearing force as not to break the colorant, or by melt flushing method in which a water-containing cake in the colorant preparing process, in which the colorant can be relatively easily dispersed into primary particles, is replaced by the fused binder resin.

(Crushing Method)

The electrostatic charge image developing toner of the present invention can be prepared by so-called crushing method for obtaining the toner by the following steps. More specifically, the electrostatic charge image developing toner of the present invention can be prepared by sufficiently mixing the aforementioned colorant of the present invention, resins such as the binder resin, charge control agent and wax to be added if necessary by a mixer such as a Henshell mixer or a ball mill, then mutually dissolving the resins by fusion kneading with a heat kneader such as heated rollers, a kneader or an extruder, then dispersing or dissolving therein additives such as a magnetic material and a metallic compound if necessary, then solidifying the mixture by cooling, crushing the solidified mixture with a crusher such as a jet mill or a ball mill and executing classification to a desired particle size.

In the classifying step, there is preferably employed a multi-division classifier in consideration of the production efficiency. In the present invention, in the fused kneading, there can be obtained electrostatic charge image developing toner in which the coloring agent such as pigment in a state covered by the first resin component is dispersed in the second resin component, without dissolving of the coloring agent such as pigment, covered by the first resin component, into the second resin component or without recoagulation of the coloring agent.

The electrostatic charge image developing toner of the present invention can also be obtained by mixing the binder resin, the charge control agent etc. in solution, utilizing solvent (for example aromatic hydrocarbon such as toluene or xylene, halogenated solvent such as chloroform or ethylene dichloride, ketone such as acetone or methylethylketone, or amide such as dimethylformamide), putting the solution into water after agitation to achieve re-precipitation, then filtering and drying the precipitate, crushing the solid with a crusher such as a jet mill or a ball mill and executing classification to obtain the desired particle size. In the classifying step, there is preferably employed a multi-division classifier in consideration of the production efficiency.

(Polymerization Method)

The electrostatic charge image developing toner of the present invention can also be obtained by so-called polymerization method explained in the following. In this case, a polymerizable monomer, the colorant of the present invention, a magnetic material, a crosslinking agent, a polymerization starter, wax and other additives if necessary are mixed and dispersed and are subjected to suspension polymerization in aqueous dispersion medium in the presence of a surfactant to obtain polymerized colored resin particles, which are then separated from the liquid phase, dried and subjected to classification if necessary to obtain the electrostatic charge image developing toner of the present invention.

(Externally Added Silica)

In the present invention, it is preferable to externally add, to the toner prepared in the above-described methods, fine silica powder in order to improve the charge stability, developability, flowability and durability. The fine silica powder to be employed for this purpose provides satisfactory result in case the specific surface area measured by the nitrogen adsorption by the BET method is at least equal to 20 $m^2/g$ (particularly 30 to 400 $m^2/g$). In such case, the fine silica powder is used in an amount of 0.01 to 8 mass parts, preferably 0.1 to 5 mass parts, with respect to 100 mass parts of toner particles. The fine silica powder to be used is preferably processed, in necessary in order to control the hydrophobicity and charging ability, with silicone varnish, modified silicon varnish, silicone oil, modified silicone oil, silane coupling agent, silane coupling agent containing functional groups, or other organic silicon compounds. These processing agents may be used as a mixture.

(Inorganic Powder)

It is also preferable to add the following inorganic powder in order to improve the developability and durability of the toner. Examples of such inorganic powder include oxides of metals such as magnesium, zinc, aluminum, cerium, cobalt, iron, zirconium, chromium, manganese, strontium, tin or antimony; complex metal oxides such as calcium titanate, magnesium titanate or strontium titanate; metal salts such as calcium carbonate, magnesium carbonate or aluminum carbonate; clay minerals such as caolin; phosphate compounds such as apatite; silicon compounds such as silicon carbide or silicon nitride; and carbon powder such as carbon black or graphite. Among these, particularly preferred is fine powder of zinc oxide, aluminum oxide, cobalt oxide, manganese dioxide, strontium titanate or magnesium titanate.

(Lubricant)

It is also possible to add following lubricant powder to the toner. Examples of such lubricant include fluorinated resins such as teflon polyfluoro-vinylidene; fluorinated compounds such as carbon fluoride; metal salts of fatty acids such as zinc stearate; fatty acid derivatives such as fatty acid or fatty acid ester; and molybdenum sulfide.

In the toner of the present invention, the surface thereof is almost covered by the first resin component and the second resin component, so that the charging property of the toner is not influenced by the type of the pigment. Consequently, the externally added material of a same type or amount can be used in various toner.

Such binder resin, charge control agent and other additive employed if necessary are preferably composed of biodegradable ones if possible, in consideration of the situation after discarding.

<Carrier>

The electrostatic charge image developing toner of the present invention can be used singly as the non-magnetic one-component developer, or applied to the conventionally known various toners such as non-magnetic toner constituting the magnetic two-component developer together with magnetic carrier or magnetic toner to be singly used as the magnetic one-component toner. In case of use in the two-component developing method, there can be utilized any known carrier. More specifically, the carrier particles can be constituted by particles of an average particle size of 20 to 300 μm composed of a surfacially oxidized or unoxidized metal such as iron, nickel, cobalt, manganese, chromium or a rare earth metal, or alloys or oxides thereof. The carrier to be employed in the present invention is preferably covered, on the surface of the carrier particles, with styrene resin, acrylic resin, silicone resin, fluorinated resin, polyester resin or the like.

<Magnetic Toner>

The electrostatic charge image developing toner of the present invention can also be formed as magnetic toner by including a magnetic material in the toner particles. In such case, the magnetic material may also serve as a coloring agent. Examples of such usable magnetic material include iron oxides such as magnetite, hematite or ferrite; metals such as iron, cobalt or nickel; and alloys of such metals with other metals such as aluminum, cobalt, copper, lead, magnesium, tin, zinc, antimony, beryllium, bismuth, cadmium, calcium, manganese, selenium, titanium, tungsten or vanadium; and mixtures thereof. Such magnetic material to be used in the present invention has an average particle size not exceeding 2 μm, preferably 0.1 to 0.5 μm. The content in the toner is preferably 20 to 200 mass parts, more preferably 40 to 150 mass parts with respect to 100 mass parts of the binder resin.

Also for achieving higher image quality, it is necessary to enable faithful development of smaller latent image dots, and, for this purpose, it is preferable that the electrostatic charge image developing toner of the present invention has a weight-averaged particle size within a range of 4 to 9 μm. The toner particles with a weight-averaged particle size less than 4 μm is undesirable because the transfer efficiency becomes lower to increase the toner amount remaining on the photosensitive member thereby resulting in image fog and uneven image caused by defective transfer. Also the toner particles with a weight-averaged particle size exceeding 9 μm tends to cause scattering of characters and line images.

In the present invention, the average particle size and the particle size distribution of the toner were measured with the Coulter Counter TA-II or Coulter Multisizer (supplied by Coulter Inc.) connected to an interface (supplied by Nippon Kagaku Kikai Co.) and a personal computer PC9801 (supplied by NEC) for outputting the number distribution and the volume distribution. As the electrolyte used in the measurement, there was prepared 1% NaCl aqueous solution with 1st grade sodium chloride. The electrolyte can also be for example composed of commercially available ISOTON R-II (supplied by Coulter Scientific Japan Inc.). In the measurement, a surfactant (preferably alkylbenzene sulfonate salt) as the dispersant was added in an amount of 0.1 to 5 ml in 100 to 150 ml of the aforementioned aqueous electrolyte solution, and a specimen for measurement was added by 2 to 20 mg to obtain the measurement sample. At the measurement, the electrolyte solution in which the measurement specimen was suspended was subjected to dispersion for 1 to 3 minutes by an ultrasonic disperser, and was subjected to the measurement of volume and number of toner of 2 μm or larger in the Coulter Counter TA-II with an aperture of 100 μm, thereby calculating the volume distribution and the number distribution. Then there were determined the weight average particle size (D4) based on the volume calculated from the volume distribution of the present invention, and the number average particle size (D1) based on the number calculated from the number distribution.

<Charge Amount>

The electrostatic charge image developing toner of the present invention preferably has a charge amount per unit mass (two component method) of −10 to −80 μC/g, preferably −15 to −70 μC/g in order to improve the transfer efficiency in the transfer method utilizing a voltage-applied transfer member.

Figure 11:
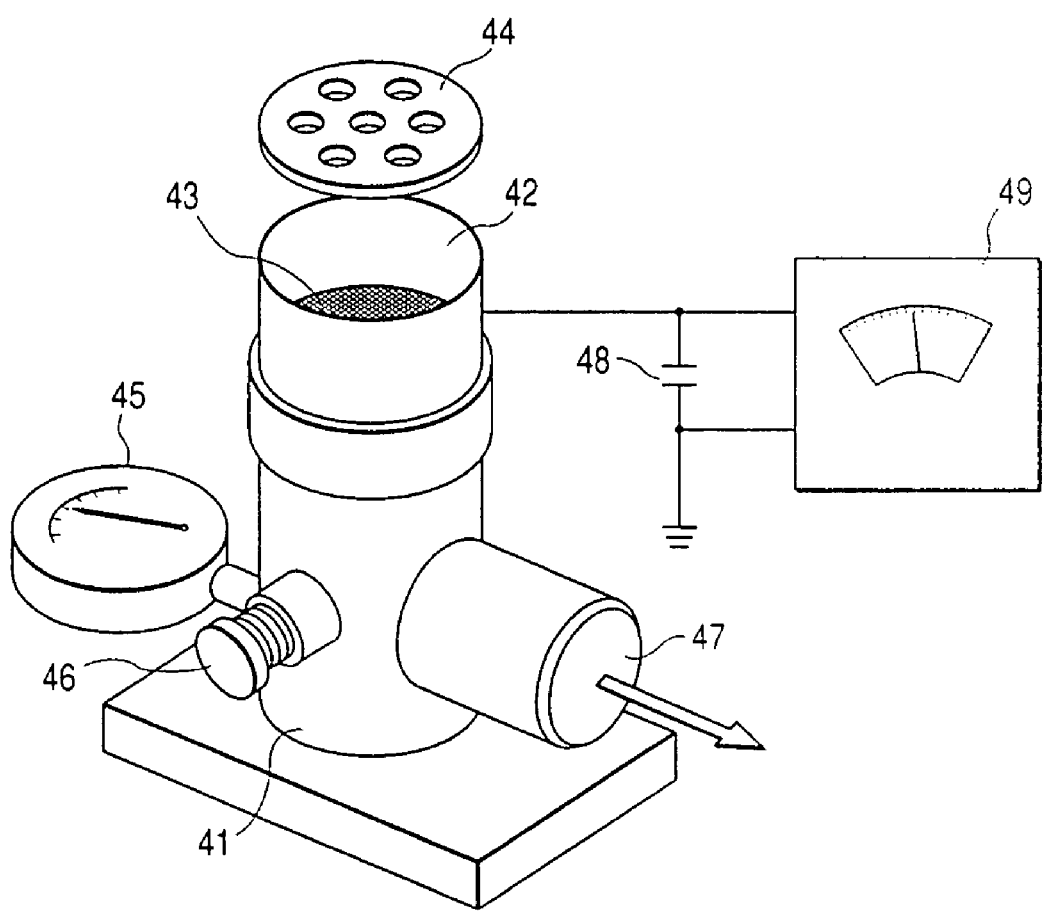
FIG. 11 is a schematic view showing a blow-off charge amount measuring apparatus for measuring the charge amount of toner.

In the following there will be explained the method for measuring the charge amount by the two-component method (two-component tribo) employed in the present invention. For the measurement, there was employed a charge amount measuring apparatus shown in FIG. 11. At first, a mixture consisting of 9.5 g of carrier, composed of EFV 200/300 (supplied by Powdertech Inc.) and 0.5 g of the toner to be measured, was put in a polyethylene bottle of 50 to 100 ml, then placed on a shaker of a constant amplitude and was shaked for a predetermined time under an amplitude of 100 mm and a shaking speed of 100 cycle/minute. Then 1.0 to 1.2 g of the aforementioned mixture was put in a metallic measurement container 42 of the charge amount measuring apparatus shown in FIG. 11, having a screen 43 of 500 mesh at the bottom, and a metal cover 44 was placed. The mass of the entire measurement container 42 was measured as W1 (g). Then suction was executed with an unrepresented suction device (made insulating at least in a portion in contact with the measurement container 22) from a suction aperture 47, and an air amount adjusting valve 46 was so adjusted that a vacuum meter 45 indicated a pressure of 2450 Pa (250 mm Aq). The suction was executed for 1 minute in this state to eliminate the toner by suction. The potential indicated by a potential meter 49 was selected as V (volt). A capacitor 48 had a capacity C (µF). The tribocharge amount of the toner (µC/g) was calculated from these measured values according to the following formula:

$$\text{Tribocharge amount } (\mu C/g) = C \times V/(W1 - W2).$$

<Molecular Weight of Binder Resin>

In the present invention, the molecular weight of the binder resin was measured by GPC (gel permeation chromatography). More specifically, the molecular weight measurement by the GPC was executed by employing a sample obtained by extracting the toner with THF (tetrahydrofurane) for 20 hours in a Soxlet extractor, also employing a column configuration formed by connecting A-801, 802, 803, 804, 805, 806 and 807 supplied by Showa Denko Co. and utilizing a calibration line of standard polystyrene resin. Also in the present invention, it is preferable to use binder resin having a ratio (Mw/Mn) of the weight-average molecular weight (Mw) and the number-averaged molecular weight (Mn), measured as explained in the foregoing, within a range of 2 to 100.

<Glass Transition Point of Toner>

Furthermore, the toner of the present invention is so prepared, with suitable materials, as to have a glass transition point Tg preferably within a range of 30 to 80° C., more preferably 50 to 70° C. in consideration of the fixability and storability. The glass transition point Tg can be measured, for example, by a highly precise scanning differential thermal analyzer of internal input compensation type such as Perkin Elmer DSC-7. The measurement is executed according to ASTM D3418-82. In the present invention, the measurement of the glass transition point is preferably executed by once heating the specimen to eliminate the prior hysteresis, then rapidly cooling the specimen and utilizing a DSC curve obtained heating the specimen again within a range of 0 to 200° C. with a heating rate of 10° C./min.

<Image Forming Method and Apparatus>

The electrostatic charge image developing toner of the present invention having the aforementioned configuration is particularly preferably applied to an image forming method at least including a charging step of externally applying a voltage to a charging member thereby charging an electrostatic latent image bearing member, a step of forming an electrostatic charge image on the charged electrostatic latent image bearing member, a development step of developing the electrostatic charge image with electrostatic charge image developing toner thereby forming a toner image on the electrostatic latent image bearing member, a transfer step of transferring the toner image on the electrostatic latent image bearing member onto a recording material, and a heat fixation step of heat fixing the toner image on the recording material, or an image forming method in which the above-mentioned transfer step consists of a first transfer step of transferring the toner image on the electrostatic latent image bearing member onto an intermediate transfer member and a second transfer step of transferring the toner image on the intermediate transfer member onto the recording material.

Also the apparatus to be employed in this method is preferably provided means respectively corresponding to the aforementioned steps, namely charging means, electrostatic charge image forming means, developing means, transfer means and heat fixing means.

In the following, the present invention will be clarified further by examples thereof, in which (%) is based on mass unless otherwise specified.

Reference Example 4

Preparation of Transformant Capable of Producing PHB Synthesizing Enzyme

The method for preparing a transformant capable of producing TB64 strain-originated PHB synthesizing enzyme was already applied for patent by the present inventors, and a specific example of such method will be explained in the following. After the TB64 strain was cultured overnight at 30° C. in 100 mL of LB culture medium (1% polypeptone, 0.5% yeast extract, 0.5% sodium chloride, pH 7.4), the chromosomal DNA was separated and recovered by the method of Marmer et. al. The obtained chromosomal DNA was partially decomposed by restriction enzyme Sau3AI. Vector pUC18 was digested with restriction enzyme BamHI, and, after dephosphorylation process (Molecular Cloning, Vol. 1, p572 (1989): Cold Spring Harbor Laboratory), it was ligated with the fragment of the chromosomal DNA obtained by partial decomposition with Sau3AI, utilizing a DNA ligation kit Ver. II (Takara Shuzo). Then *Escherichia Coli* HB101 strain was transformed with the ligated DNA fragments to obtain a chromosomal DNA library of the TB 64 strain.

Then there was executed pheno-type screening for obtaining the DNA fragment of the TB64 strain including the genes for the PHB synthesizing enzyme group. An LB culture medium containing 2% glucose was employed as the selection culture medium, and, when the colonies on the flat agar culture medium grew to an appropriate size, Sudan black B solution was sprayed and colonies emitting fluorescence under the UV light irradiation were acquired. Plasmid was recovered from the acquired colonies by the alkali method to obtain the DNA fragment containing the genes of the PHB synthesizing enzyme group.

The acquired gene fragment was recombined to a vector pBBR 122(Mo Bi Tec) including a broad host range replication origin not belonging to the incompatibility group IncP, IncQ or IncW, and the recombinant plasmid was used to transforme Ralstogna eutropha TB64m1 strain (lacking PHB synthesizing ability) by electroporation in whereby the PHB synthesizing ability of the TB64 m1 strain was restored and complementary character was shown.

Then there was designed and synthesized an oligonucleotide having a base sequence in the region around the starting codon of the PHB synthesizing enzyme gene (Amasham Pharmacia Biotech), and PCR was executed utilizing such oligonucleotide as the primer to amplify the fragment including the PHB synthesizing enzyme genes (LA-PCR kit: Takara Shuzo).

Then thus obtained PCR amplified fragment was completely decomposed by restriction enzyme BamHI and ligated with an expression vector pTrc99A, which was completely decomposed by restriction enzyme BamHI and dephosphorylated (Molecular Cloning, Vol. 1, 5.7.2 (1989): Cold Spring Harbor Laboratory), with DNA ligation kit Ver. II (Takara Shuzo). Then *Escherichia coli* HB101 strain was transformed with the obtained recombinant plasmid by calcium chloride method (Takara Shuzo), and a recombinant plasmid recovered from the obtained transformant was named pTB64-PHB.

*Escherichia coli* HB101 was transformed with pTB64-PHB by calcium chloride method to obtain a pTB64-PHB recombinant strain.

Reference Example 5

Preparation of Transformant Capable of Producing GST-Fused PHA Synthesizing Enzyme The pTB64-PHB recombinant strain was inoculated in 200 mL of LB culture medium, and was subjected to shaking culture for 12 hours at 37° C. and 125 stroke/minute. Thus obtained bacteria was recovered by centrifuging, and the plasmid DNA was recovered by an ordinary method.

Oligonucleotide (sequence number 14) constituting an upstream primer for the pTB64-PHB and oligonucleotide (sequence number 15) constituting a downstream primer were designed and synthesized (Amasham Pharmacia Biotech). PCR was executed utilizing the oligonucleotides as the primers and pTB64-PHB as the template to amplify the entire length of the PHB synthesizing enzyme gene having the BamHI restriction site at the upstream side and the Xhol restriction site at the downstream side (LA-PCR kit: Takara Shuzo).

The purified PCR amplification product was digested with BamHI and Xhol and was inserted into a corresponding restriction site in a plasmid pGEX-6P-1 (Amasham Pharmacia Biotech Inc.). Escherichia coli JM109 strain was transformed with the recombinant plasmid to obtain a strain for the enzyme expression. The confirmation of the recombinant strain was executed by a DNA fragment obtained by digesting the plasmid DNA, prepared in large scale with Miniprep (Wizard Minipreps DNA Purification System, PROMEGA Inc.) with BamHI and Xhol.

Reference Example 6

Preparation of PHB Synthesizing Enzyme

The obtained recombinant strain for the enzyme expression was pre-cultured overnight at 30° C. in 100 mL of 2×YT culture medium (polypeptone 16 g/L, yeast extract 10 g/L, NaCl 5 g/L, pH 7.0) added with ampicillin (100 µg/L).

Then it was added to 10 liters of 2×YT culture medium (polypeptone 16 g/L, yeast extract 10 g/L, NaCl 5 g/L, pH 7.0) added with ampicillin (100 µg/L) and culture was executed for 3 hours at 30° C. Then isopropyl-β-D-thiogalactopyranocide (IPTG) was added to obtain a final concentration of 1 mM, and the culture was executed for 3 hours at 30° C.

The recovered culture medium was centrifuged for 10 minutes at 4° C., 78000 M/s$^2$ (=8000 G), and, after the elimination of supernatant, the bacterial pellet was re-suspended in 500 mL of PBS solution at 4° C. The bacterial suspension was poured, 40 mL each time, in a vessel cooled to 4° C. in advance, and, under pressurization of 216 MPA (=2200 kg/cm$^2$) by a French press, the bacterial liquid was released little by little from the nozzle, thereby executing crushing process. The crushed bacterial suspension was centrifuged for 10 minutes at 4° C., 78000 M/S2 (=8000 G), and the supernatant was recovered. The supernatant was filtered with a filter of 0.45 µm to eliminate the debris. The expression of the desired PHB synthesizing enzyme fused with glutathione S transferase (GST) in the supernatant was confirmed by SDS-PAGE.

Then the GST-fused PHB synthesizing enzyme was purified with glutathione sepharose 4B (Amasham Pharmacia Biotech Inc.). 6.65 mL of 75% slurry of glutathione sepharose 4B was centrifuged for 5 minutes at 4° C., 4900 m/s$^2$ (=500 G), and, after the elimination of supernatant, it was re-suspended in 200 mL of PBS solution at 4° C. Centrifuging was executed again for 5 minutes at 4° C., 4900 m/s$^2$ (=500 G), and the supernatant was eliminated. Then it was re-suspended in 5 mL of PBS solution at 4° C. to obtain 50% slurry of glutathione sepharose 4B.

The entire amount of the supernatant prepared before was added to 10 mL of thus obtained 50% slurry of glutathione sepharose 4B, and the mixture was mildly shaken to cause the desired fused protein in the supernatant to be adsorbed by affinity onto glutathione sepharose 4B. The mixture was centrifuged for 5 minutes at 4° C., 4900 m/s$^2$ (=500 G), and, after the elimination of supernatant, it was re-suspended in 5 mL of PBS solution at 4° C., and subjected to similar centrifuging again and the supernatant was eliminated. The glutathione sepharose 4B on which GST-fused PHB synthesizing enzyme was adsorbed was rinsed by repeating re-suspension in PBS solution and centrifuging twice, and was finally suspended in 5 mL of Cleavage buffer (Tris-HCl 50 mM, NaCl 150 mM, EDTA 1 mM, dithiothreitol 1 mM, pH 7). Then 0.5 mL of 4% solution of prescission protease (Amasham Pharmacia Biotech) in cleavage buffer was added, and the mixture was mildly shaken for 4 hours at 5° C. The mixture was centrifuged for 5 minutes at 4° C., 4900 m/s$^2$ (=500 G), and the supernatant was recovered. Then 1 mL of 50% slurry of glutathione sepharose 4B prepared as explained in the foregoing was centrifuged for 5 minutes at 4° C., 4900 m/s$^2$ (=500 G), and the above recovered supernatant was added to glutathione sepharose 4B after the elimination of supernatant, and the mixture was mildly agitated to cause glutation sepharose 4B to adsorb prescission protease remaining in the supernatant. Then centrifuging was executed for 5 minutes at 4° C., 4900 m/s$^2$ (=500 G), and, the supernatant was recovered. The supernatant had a single band by SDS-PAGE, indicating the purification.

The activity of the PHB synthesizing enzyme was measured in the following manner. At first bovine serum albumin (Sigma Co.) was dissolved in 0.1 M tris hydrochloric acid buffer (pH 8.0) in 3.0 mg/mL, and 100 µL of thus obtained solution was added to 100 µL of enzyme solution and the mixture was pre-incubated for 1 minute at 30° C. Then 100 µL of solution of 3-hydroxybutyryl CoA dissolved in 0.1 M tris hydrochloric acid buffer (pH 8.0) in 3.0 mM was added, then the mixture was incubated for 1 to 30 minutes at 30° C., and then the reaction is terminated by adding solution of trichloroacetic acid dissolved in 0.1 M tris hydrochloric acid buffer (pH 8.0) at 10 mg/mL. The solution after termination of reaction was centrifuged (147,000 m/s$^2$ (15,000 G), 10 minutes), and 500 µL of 2 mM solution of 5,5'-dithiobis-(2-nitrobenzoic acid) dissolved in 0.1 M tris hydrochloric acid buffer (pH 8.0) was added to 500 µL of the supernatant. After incubation for 10 minutes at 30° C., the optical absorbance at 412 nm was measured. The enzyme activity was calculated by taking an enzyme amount causing release of CoA of 1 µmol in 1 minute as 1 unit (U). As a result there was obtained a relative activity of 7.5 U/mL. The obtained solution was concentrated by ultrafiltration under the addition of Reiho gel to 10 U/mL, thereby obtaining purified enzyme solution (1).

Reference Example 7

Preparation of Crude Enzyme Solution Containing PHB Synthesizing Enzyme

The KK01 and TL2 strains were cultured for 24 hours at 30° C. in 10 liters of M9 culture medium (following composition) containing 0.5% of yeast extract and 0.3% of mineral solution (see following), and the recovered culture medium was centrifuged for 10 minutes at 4° C., 78000 M/s² (=8000 G), and, after the elimination of supernatant, the bacterial pellet was re-suspended in 500 mL of PBS solution at 4° C. The bacterial suspension was poured, 40 mL each time, in a vessel cooled to 4° C. in advance, and, under pressurization of 2200 kg/cm² by a French press, the bacterial suspension was released little by little from the nozzle, thereby executing crushing process. The crushed bacterial suspension was centrifuged for 10 minutes at 4° C., 78000 m/s² (=8000 G), and the supernatant was recovered. The supernatant was filtered with a filter of 0.45 μm to eliminate the debris, and the activity of the PHB synthesizing enzyme was measured by the aforementioned method. As a result there were obtained relative activities of 1.6 U/mL for the KK01 strain and 1.2 U/mL for the TL2 strain. The solution was concentrated by ultrafiltration under the addition of a biological sample condenser (trade name: Mizubutorikun; Ato Co.) to 10 U/mL, thereby obtaining crude enzyme solution (1) derived from the KK01 strain and (2) derived from the TL2 strain.

| (M9 culture medium) | |
| --- | --- |
| Na₂HPO₄ | 6.2 g |
| KH₂PO₄ | 3.0 g |
| NaCl | 0.5 g |
| NH₄Cl | 1.0 g |

(in 1 liter of culture medium; pH 7.0)
(Mineral Solution)

| | |
| --- | --- |
| nytrilotriacetic acid | 1.5 g; |
| MgSO₄ | 3.0 g; |
| MnSO₄ | 0.5 g; |
| NaCl | 1.0 g; |
| FeSO₄ | 0.1 g; |
| CaCl₂ | 0.1 g; |
| CoCl₂ | 0.1 g; |
| ZnSO₄ | 0.1 g; |
| CuSO₄ | 0.1 g; |
| AlK(SO₄)₂ | 0.1 g; |
| H₃BO₃ | 0.1 g; |
| Na₂MoO₄ | 0.1 g; |
| NiCl₂ | 0.1 g; |

(in 1 liter).

Reference Example 8

Preparation of Transformant Capable of Producing PHA Synthesizing Enzyme

Transformant capable of producing PHA synthesizing enzyme was prepared in the following manner.

The YN2 strain was cultured overnight at 30° C. in 100 mL of LB culture medium (1% polypeptone (Nippon Pharmaceuticals), 0.5% yeast extract (Difco), 0.5% sodium chloride, pH 7.4), and the chromosomal DNA was separated and recovered by the method of Marmer et. al. The obtained chromosomal DNA was completely decomposed by restriction enzyme Hind III. Vector pUC18 was digested with restriction enzyme Hind III, and, after dephosphorylation process (Molecular Cloning, Vol. 1, p572 (1989): Cold Spring Harbor Laboratory), the digested site (cloning site) of the vector was ligated with the Hind III-decomposed fragments of the chromosomal DNA, utilizing a DNA ligation kit Ver. II (Takara Shuzo). Then *Escherichia coli* HB101 strain was transformed with the plasmid vector incorporating the ligated DNA fragment to obtain the DNA library of the YN2 strain.

Then there was prepared a probe for colony hybridization, for selecting the DNA fragment of the YN2 strain including the PHA synthesizing enzyme genes. Oligonucleotides of sequence number 16 and sequence number 17 were synthesized (Amasham Pharmacia Biotech), and PCR was executed utilizing such oligonucleotides as the primers and chromosomal DNA of the YN2 strain as the template. The DNA fragment obtained by PCR amplification was used as a probe. The probe was labeled with a commercial labeling kit AlkPhosDirect (Amasham Pharmacia Biotech Inc.).

The obtained labeled probe was used for colony hybridization method to select the *Escherichia coli* strain having a recombinant plasmid including the PHA synthesizing enzyme genes from the chromosomal DNA library of the YN2 strain. Plasmid was recovered by the alkali method from the selected strain to obtain a DNA fragment containing the PHA synthesizing enzyme genes.

The acquired DNA fragment was recombined to a vector pBBR 122(Mo Bi Tec) including a broad host range replication origin not belonging to the incompatibility group IncP, IncQ or IncW, and such recombinant plasmid was used to transform *Pseudomonas chicorii* YN2 mL strain (lacking PHA synthesizing ability) by electroporation whereby the PHA synthesizing ability of the YN2 mL strain was restored and complementary character was shown. Consequently it was confirmed that the selected DNA fragment includes a PHA synthesizing enzyme gene region that can be translated into the PHA synthesizing enzyme.

The base sequence of the DNA fragment was determined by Sanger method. As a result, it was confirmed that the determined base sequence contained sequences of a sequence number 18 and a sequence number 19 respectively coding peptide chains. PCR was executed on such PHA synthesizing enzyme genes utilizing the chromosomal DNA as the template to prepare the entire fragment containing the PHA synthesizing enzyme genes.

More specifically, an upstream primer (sequence number 20) and a downstream primer (sequence number 21) for the PHA synthesizing enzyme gene represented by the sequence number 18, and an upstream primer (sequence number 22) and a downstream primer (sequence number 23) for the PHA synthesizing enzyme gene represented by the sequence number 19 were respectively synthesized (Amasham Pharmacia Biotech). PCR was executed respectively for the base sequence of the number 18 and that of the number 19, utilizing such primers to amplify the entire fragment containing the PHA synthesizing enzyme genes (LA-PCR kit: Takara Shuzo).

Then the obtained PCR amplified fragments and the expression vector pTrc99A were digested with restriction enzyme Hind III, and, after dephosphorylation process (Molecular Cloning, Vol. 1, 5.7.2 (1989): Cold Spring Harbor Laboratory), the DNA fragments, including the entire region of the PHA synthesizing enzyme genes excluding the unnecessary base sequences on both ends, was ligated to the cloning site of the expression vector pTrc99A by the DNA ligation kit Ver. II (Takara Shuzo).

Then *Escherichia coli* HB101 strain (Takara Shuzo) were transformed with the obtained recombinant plasmids by calcium chloride method (Takara Shuzo). The obtained recombinant plasmids were amplified by culture and were recovered. The recombinant plasmids having the gene of sequence number 18 and 19 were respectively named as pYN2-C1 and pYN2-C2. *Escherichia coli* HB101 fB, lacking fadB, was transformed with pYN2-C1, pNY2-C2 by the calcium chloride method to obtain recombinant strains respectively having each recombinant plasmid.

Reference Example 9

Production 1 of PHA Synthesizing Enzyme

Oligonucleotide (sequence number 24) constituting an upstream primer for the pYN2-C1 and oligonucleotide (sequence number 25) constituting a downstream primer were designed and synthesized (Amasham Pharmacia Biotech). PCR was executed utilizing such oligonucleotides as the primers and pYN2-C1 as the template to amplify the entire fragment containing the PHA synthesizing enzyme gene having the BamHI restriction site at the upstream side and the XhoI restriction site at the downstream side (LA-PCR kit: Takara Shuzo).

Similarly, Oligonucleotide (sequence number 26) constituting an upstream primer for the pYN2-C2 and oligonucleotide (sequence number 27) constituting a downstream primer were designed and synthesized (Amasham Pharmacia Biotech). PCR was executed utilizing such oligonucleotides as the primers and pYN2-C2 as the template to amplify the entire fragment containing the PHA synthesizing enzyme gene having the BamHI restriction site at the upstream side and the XhoI restriction site at the downstream side (LA-PCR kit: Takara Shuzo).

The purified PCR amplification products were digested with BamHI and XhoI and were inserted in a corresponding site of a plasmid pGEX-6P-1 (Amasham Pharmacia Biotech Inc.). *Escherichia coli* JM109 strain was transformed with the recombinant plasmids to obtain a strain for the enzyme expression. The confirmation of the recombinant strain was executed by a DNA fragment obtained by digesting the plasmid DNA, prepared in large scale Miniprep (Wizard Minipreps DNA Purification System, PROMEGA Inc.) with BamHI and XhoI. The obtained recombinant strain was pre-cultured overnight at 30° C. in 10 mL of LB-Amp culture medium, and 0.1 mL of the culture medium was added to 10 mL of LB-Amp culture medium and shaking culture was executed for 3 hours at 37° C., 170 rpm. Then IPTG was added (final concentration 1 mM), and the culture was executed for 4 to 12 hours at 37° C.

*Escherichia coli* induced by IPTG was collected (78000 m/s$^2$ (=8000 G), 2 minutes, 4° C.), and was re-suspended in phosphate buffer physiological saline solution (PBS; 8 g NaCl, 1.44 g NaHPO$_4$, 0.24 g KH$_2$PO$_4$, 0.2 g KCl, 1,000 mL purified water) of 1/10 amount, 4° C. The bacterial cells were crushed by freeze/thawing and sonication, and the debris was eliminated by centrifuging (78000 m/s$^2$ (=8000 G), 2 minutes, 4° C.). After the expression of the desired protein in the supernatant was confirmed by SDS-PAGE, the induced and expressed GST fused protein was purified with glutathione sepharose 4B (Amasham Pharmacia Biotech).

The glutathione sepharose used was subjected in advance to a treatment for suppressing non-specific adsorption. More specifically glutathione sepharose was rinsed three times with PBS of a same amount (78000 m/s$^2$ (=8000 G), 2 minutes, 4° C.) and then processed for 1 hour at 4° C. by adding PBS containing 4% bovine serum albumin of a same amount. After the processing, it was rinsed twice with PBS of a same amount, and was re-suspended in PBS of a ½ amount.

40 μL of pre-processed glutathione sepharose was added to 1 mL of cell-free extract and was gently agitated at 4° C. In this manner the fused proteins GST-YN2-C1 and GST-YN2-C2 were adsorbed by glutathione sepharose. After the adsorption, glutathione sepharose was recovered by centrifuging (78000 m/s$^2$ (=8000 G), 2 minutes, 4° C.) and was rinsed with PBS of 400 μL. Then 40 μL of 10 mM glutathione was added and the mixture was agitated for 1 hour at 4° C. to dissolve out the adsorbed fused protein. After the recovery of the supernatant by centrifuging (78000 m/s$^2$ (=8000 G), 2 minutes, 4° C.), dialysis was executed for PBS to purify the GST fused protein. A single band was confirmed by SDS-PAGE.

500 μg of each GST-fused protein was digested with Prescission protease (5U, Amasham Pharmacia Biotech), and it was passed by glutathione sepharose to eliminate protease and GST. The flow-through fraction was further passed through a sephadex G200 column equilibrized with PBS to obtain the final products of the expression proteins YN2-C1 and YN2-C2. Single band was confirmed by SDS-PAGE respectively at 60.8 kDa and 61.5 kDa.

Such enzyme was concentrated with a biological sample condenser (trade name: Mizubutorikun; Ato Co.) to obtain the purified enzyme solution of 10 U/mL.

The activity of each purified enzyme was measured by the aforementioned method. Also the protein concentration in the specimen was measured by a micro BCA protein analyzing reagent kit (Pierce Chemical Inc.). The measured activities of the purified enzymes are shown in Table 9.

TABLE 9

| Origin | Activity | Relative activity |
|---|---|---|
| Purified enzyme solution (2) pYN2-C1 | 2.1 U/mL | 4.1 U/mg protein |
| Purified enzyme solution (3) pYN2-C2 | 1.5 U/mL | 3.6 U/mg protein |

Reference Example 10

Production 2 of PHA Synthesizing Enzyme

The P91, H45, YN2 and P161 strains were inoculated in 200 mL of M9 culture medium containing 0.5% of yeast extract (Difco Inc.) and 0.1% of octanoic acid, and were subjected to shaking culture at 30° C., 125 stroke/minute. After 24 hours, the bacterial cells were recovered by centrifuging (98000 m/s$^2$ (=10000 G), 10 minutes, 4° C.), and rinsed by re-suspending in 200 mL of 0.1M tris hydrochloric acid buffer (pH 8.0) and centrifuging again. The bacterial cells were re-suspended in 2.0 mL of 0.1M tris hydrochloric acid buffer (pH 8.0) and crushed with an ultrasonic crusher, then centrifuging (118000 m/s$^2$ (=12000 G), 10 minutes, 4° C.) was executed to recover the supernatant, thereby obtaining crude enzyme solution.

The activity of each crude enzyme was measured by the aforementioned method, and the results are shown in Table 10.

TABLE 10

| | Origin | Activity |
|---|---|---|
| Crude enzyme solution(3) | P91 strain | 0.1 U/mL |
| Crude enzyme solution(4) | H45 strain | 0.2 U/mL |
| Crude enzyme solution(5) | YN2 strain | 0.4 U/mL |
| Crude enzyme solution(6) | P161 strain | 0.2 U/mL |

Such enzyme was concentrated with a biological sample condenser (trade name: Mizubutorikun; Ato Co.) to obtain the crude enzyme solution of 10 U/mL.

Example 18

The purified PHB synthesizing enzyme solution was employed in preparing the colorant of the present invention, utilizing phthalocyanine blue (C.I. Pigment Blue 15:3), in the following manner.

Phthalocyanine blue was dispersed by a sand mill to obtain a particle size not exceeding 0.1 µm, and 1 mass part thereof was added with 10 mass parts of the purified enzyme solution (1) and 39 mass parts of PBS, and mild shaking was executed for 30 minutes at 30° C. to cause the PHB synthesizing enzyme to be adsorbed on the pigment surface. Then centrifuging (98000 m/s$^2$ (=10000 G), 10 minutes, 4° C.) was executed, then the precipitate was suspended in PBS solution and again centrifuged (98000 m/s$^2$ (=10000 G), 10 minutes, 4° C.) to adsorb PHB synthesizing enzyme on phthalocyanine blue.

The aforementioned adsorbed enzyme was suspended in 48 mass parts of 0.1M phosphate buffer (pH 7.0), then added with 1 mass part of (R)-3-hydroxybutyryl CoA (Sigma Aldrich Japan Co.) and 0.1 mass parts of bovine serum albumin (Sigma Co.) and the mixture was mildly shaken for 2 hours at 30° C. The generated blue microencapsulated pigment (hereinafter represented as colorant) was filtered, rinsed and dried to obtain colorant 1.

0.01 parts of the aforementioned reaction mixture was placed on a slide glass, and added and mixed with 0.01 parts of 1% Nile blue A aqueous solution on the slide glass, and the mixture was covered with a cover glass and was observed under a fluorescent microscope (330 to 380 nm excitation filter, 420 nm long-path absorption filter; Nikon Co.). As a result, fluorescence from the surface of the colorant 1 was confirmed. It was therefore identified that the surface of the colorant was covered with PHB. As a reference, 10 mass parts of phthalocyanine blue, added to 100 mass parts of 0.1M sodium phosphate buffer (pH 7.0), then mildly shaken for 2.5 hours at 30° C. and was observed under the fluorescent microscope with similar dyeing with Nile blue A. As a result, the surface of the reference phthalocyanine blue did not emit any fluorescence.

Also the colorant 1, after vacuum drying, was suspended in 20 mL of chloroform and agitated for 20 hours at 60° C. to extract PHB constituting the outer shell. The extract was filtered with a membrane filter of a pore size of 0.45 µm, then vacuum concentrated in a rotary evaporator, subjected to methanolysis in the ordinary manner and analyzed in a gas chromatography mass-spectrometer (GC-MS, Shimadzu QP-5050, EI method) to identify the methyl esterified substance of the PHB monomer unit. As a result, since the main peak in the obtained chromatogram showed a retention time same as that of a standard methylated compound of hydroxybutyric acid, the principal component of the outer shell of the obtained colorant 1 was confirmed as PHB.

Further, the molecular weight of PHB was evaluated by gel permeation chromatography (GPC: Toso HLC-8020, column: Polymer Laboratory PLgel MIXED-C (5 µm), solvent: chloroform, column temp.: 40° C., converted as polystyrene) to obtain a result Mn=75,000.

Also the volume-averaged particle size of the pigment before and after covering was measured by a laser Doppler particle size distribution measuring apparatus (UPA-150: Nikkiso Co.). The particles sizes before and after were respectively 0.064 and 0.082 µm and it was presumed that the pigment was covered by PHB.

Example 19

The example 18 was reproduced except that the phthalocyanine pigment in the example 18 was replaced by carmine 6B (C.I. Pigment Red 57:1) and that the purified enzyme solution (1) was replaced by the crude enzyme solution (1), to obtain colorant 2.

Evaluation as in the example 18 confirmed the fluorescent emission from the surface of the colorant 2. It was therefore confirmed that the surface of the colorant 2 was covered with PHB. Also the analysis with gas chromatography mass-spectrometer confirmed that the principal component of the outer shell of the colorant 2 was PHB. Also the analysis by gel permeation chromatography indicated that the number-averaged molecular weight of the obtained colorant 2 was 73,000. Also the particle size before and after covering was respectively 0.071 and 0.086 µm.

Example 20

The example 18 was reproduced except that the phthalocyanine pigment in the example 18 was replaced by disazo yellow (C.I. Pigment Yellow 12) and that the purified enzyme solution (1) was replaced by the crude enzyme solution (2), to obtain colorant 3.

Evaluation as in the example 18 confirmed the fluorescent emission from the surface of the colorant 3. It was therefore confirmed that the surface of the colorant 3 was covered with PHB. Also the analysis with gas chromatography mass-spectrometer confirmed that the principal component of the outer shell of the colorant 3 was PHB. Also the analysis by gel permeation chromatography indicated that the number-averaged molecular weight of the obtained colorant 3 was 69,000. Also the particle size before and after covering was respectively 0.073 and 0.085 µm.

Example 21

The example 18 was reproduced except that the purified enzyme solution (1) was replaced by the purified enzyme solution (2) and that (R)-3-hydroxybutyryl CoA was replaced by (R)-3-hydroxyoctanoyl CoA (prepared by the method described in Eur. J. Biochem., 250, 432–439(1997)) to obtain colorant 4.

Evaluation as in the example 18 confirmed the fluorescent emission from the surface of the colorant 4. It was therefore confirmed that the surface of the colorant 4 was covered with PHA. Also the analysis with gas chromatography mass-spectrometer confirmed that the principal component of the outer shell of the colorant 4 was PHA consisting of 3-hydroxyoctanoic acid unit. Also the analysis by gel permeation chromatography indicated that the number-averaged molecular weight of the obtained colorant 4 was 27,000. Also the particle size before and after covering was respectively 0.064 and 0.080 µm.

Example 22

The example 21 was reproduced except that the phthalocyanine pigment in the example 21 was replaced by carmine 6B (C.I. Pigment Red 57:1) and that the purified enzyme solution (3) was replaced by the purified enzyme solution (3), to obtain colorant 5.

Example 23

The example 21 was reproduced except that the phthalocyanine pigment in the example 21 was replaced by disazo yellow (C.I. Pigment Yellow 12) and that the purified enzyme solution (2) was replaced by the crude enzyme solution (3), to obtain colorant 6.

Evaluation as in the example 18 confirmed the fluorescent emission from the surface of the colorant 6. It was therefore confirmed that the surface of the colorant 6 was covered with PHA. Also the analysis with gas chromatography mass-spectrometer confirmed that the principal component of the outer shell of the colorant 6 was PHA consisting of 3-hydreoxyoctanoic acid unit. Also the analysis by gel permeation chromatography indicated that the number-averaged molecular weight of the obtained colorant 6 was 25,000. Also the particle size before and after covering was respectively 0.073 and 0.088 μm.

Example 24

The example 21 was reproduced except that the purified enzyme solution (2) was replaced by the crude enzyme solution (4), to obtain colorant 7.

Evaluation as in the example 18 confirmed the fluorescent emission from the surface of the colorant 7. It was therefore confirmed that the surface of the colorant 7 was covered with PHA. Also the analysis with gas chromatography mass-spectrometer confirmed that the principal component of the outer shell of the colorant 7 was PHA consisting of 3-hydroxyoctanoic acid unit. Also the analysis by gel permeation chromatography indicated that the number-averaged molecular weight of the obtained colorant 7 was 24,000. Also the particle size before and after covering was respectively 0.064 and 0.079 μm.

Example 25

The example 21 was reproduced except that the phthalocyanine pigment in the example 21 was replaced by carmine 6B (C.I. Pigment Red 57:1) and that the purified enzyme solution (2) was replaced by the crude enzyme solution (5), to obtain colorant 8.

Evaluation as in the example 18 confirmed the fluorescent emission from the surface of the colorant 8. It was therefore confirmed that the surface of the colorant 8 was covered with PHA. Also the analysis with gas chromatography mass-spectrometer confirmed that the principal component of the outer shell of the colorant 8 was PHA consisting of 3-hydreoxyoctanoic acid unit. Also the analysis by gel permeation chromatography indicated that the number-averaged molecular weight of the obtained colorant 8 was 27,000. Also the particle size before and after covering was respectively 0.071 and 0.088 μm.

Evaluation as in the example 18 confirmed the fluorescent emission from the surface of the colorant 5. It was therefore confirmed that the surface of the colorant 5 was covered with PHA. Also the analysis with gas chromatography mass-spectrometer confirmed that the principal component of the outer shell of the colorant 5 was PHA consisting of 3-hydroxyoctanoic acid unit. Also the analysis by gel permeation chromatography indicated that the number-averaged molecular weight of the obtained colorant 5 was 24,000. Also the particle size before and after covering was respectively 0.071 and 0.085 μm.

Example 26

The example 21 was reproduced except that the phthalocyanine pigment in the example 21 was replaced by disazo yellow (C.I. Pigment Yellow 12) and that the purified enzyme solution (2) was replaced by the crude enzyme solution (6), to obtain colorant 9.

Evaluation as in the example 18 confirmed the fluorescent emission from the surface of the colorant 9. It was therefore confirmed that the surface of the colorant 9 was covered with PHA. Also the analysis with gas chromatography mass-spectrometer confirmed that the principal component of the outer shell of the colorant 9 was PHA consisting of 3-hydroxyoctanoic acid unit. Also the analysis by gel permeation chromatography indicated that the number-averaged molecular weight of the obtained colorant 9 was 25,000. Also the particle size before and after covering was respectively 0.073 and 0.086 μm.

Example 27

The example 21 was reproduced except that (R)-3-hydroxyoctanoyl CoA was replaced by (R)-3-hydroxy-5-phenylvaleryl CoA (prepared by hydrolyzing 3-hydroxy-5-phenylvaleric acid ester obtained by a Reformatsky reaction to obtain 3-hydroxy-5-phenylvaleric acid and then by the method described in Eur. J. Biochem., 250, 432–439(1997)) to obtain colorant 10.

Evaluation as in the example 18 confirmed the fluorescent emission from the surface of the colorant 10. It was therefore confirmed that the surface of the colorant 10 was covered with PHA. Also the analysis with gas chromatography mass-spectrometer confirmed that the principal component of the outer shell of the colorant 10 was PHA consisting of 3-hydroxy-5-phenoxylvaleric acid unit. Also the analysis by gel permeation chromatography indicated that the number-averaged molecular weight of the obtained colorant 10 was 27,000. Also the particle size before and after covering was respectively 0.064 and 0.081 μm.

Example 28

The example 21 was reproduced except that (R)-3-hydroxyoctanoyl CoA was replaced by (R,S)-3-hydroxy-5-phenoxylvaleryl CoA (prepared by starting from ethyl bromoacetate and 3-phenoxypropanal synthesized by the method described in J. Org. Chem., 55, 1490–1492(1990), then hydrolyzing 3-hydroxy-5-phenoxyvaleric acid ester obtained by a Reformatsky reaction to obtain 3-hydroxy-5-phenoxyvaleric acid and then by the method described in Eur. J. Biochem., 250, 432–439(1997)) to obtain colorant 11.

Evaluation as in the example 18 confirmed the fluorescent emission from the surface of the colorant 11. It was therefore confirmed that the surface of the colorant 11 was covered with PHA. Also the analysis with gas chromatography mass-spectrometer confirmed that the principal component of the outer shell of the colorant 11 was PHA consisting of 3-hydroxy-5-phenoxyvaleric acid unit. Also the analysis by gel permeation chromatography indicated that the number-averaged molecular weight of the obtained colorant 11 was 29,000. Also the particle size before and after covering was respectively 0.064 and 0.080 μm.

Example 29

The example 27 was reproduced to obtain colorant 10 covered with PHA consisting of 3-hydroxy-5-phenylvaleric acid unit.

Then the example 28 was reproduced except that the colorant 10 was used as a core, to obtain colorant 12.

The mass of the polymer formed on the surface of such capsule structure was measured with a flight time secondary ion mass spectrometer (TOF-SIMS IV, Cameca Inc.). Based on the obtained mass spectrum, it was confirmed that the PHA on the capsule surface consisted of 3-hydroxy-5-phenoxyvaleric acid unit. Also a similar mass spectrum measurement with TOF-SIMS under successive scraping of the capsule surface by ion sputtering, it was confirmed that the monomer unit of PHA constituting the capsule structure was replaced, at a certain point, by 3-hydroxy-5-phenylvaleric acid unit. This result confirmed that the capsule structure of the present example was a desired capsule structure in which poly(3-hydroxy-5-phenylvaleric acid) covering phthalocyanine blue (C.I. Pigment Blue 15:3) was covered by poly(3-hydroxy-5-phenoxyvaleric acid). Also the analysis by gel permeation chromatography indicated that the number-averaged molecular weight of the obtained colorant 12 was 23,000. Also the particle size before and after covering was respectively 0.064 and 0.096 µm.

Example 30

The example 21 was reproduced except that (R)-3-hydroxyoctanoyl CoA was replaced by 0.8 mass parts of (R,S)-3-hydroxy-5-phenylvaleryl CoA and 0.2 mass parts of (R,S)-3-hydroxy-7,8-epoxyoctanoyl CoA (prepared by epoxylating unsaturated portion of 3-hydroxy-7-octenoic acid, synthesized by the method described in Int. J. Biol. Macromol., 12, 85–91(1990), with 3-chlorobenzoic acid, and then by the method described in Eur. J. Biochem., 250, 432–439(1997)) to obtain colorant 13.

Evaluation as in the example 18 confirmed the fluorescent emission from the surface of the colorant 13. It was therefore confirmed that the surface of the colorant 13 was covered with PHA. Also an analysis by $^1$H-NMR (FT-NMR: Bruker DPX400, measured nucleus: $^1$H, solvent: heavy chloroform (containing TMS)) indicated that the outer shell of the obtained colorant 13 consisted of PHA consisting of 3-hydroxy-5-phenylvaleric acid unit by 75% and 3-hydroxy-7,8-epoxyoctanoic acid unit by 25%. Also the analysis by gel permeation chromatography indicated that the number-averaged molecular weight of the obtained colorant 13 was 22,000. Also the particle size before and after covering was respectively 0.064 and 0.079 µm.

Example 31

On 50 mass parts of the aforementioned colorant 13, there were repeated three times a process of recovering by centrifuging (10,000×g, 4° C., 10 minutes) and suspension in 50 mass parts of purified water, and 0.5 mass parts of hexamethylene diamine were dissolved as a crosslinking agent in such suspension. After confirmation of dissolution, water was eliminated by lyophilizing, and reaction was executed for 12 hours at 70° C. to obtain colorant 14.

Infrared absorption measurement (FT-IR: Perkin-Elmer Inc., 1720x) on the colorant 14 indicated that the peaks of amine (about 3340 cm$^{-1}$) and epoxy (about 822 cm$^{-1}$) observed prior to heating vanished in the colorant 14. It was therefore identified that the reaction between PHA having an epoxy unit in the side chain with hexamethylene diamine provided the colorant 14 covered with the crosslinked polymer.

Example 32

On 50 mass parts of the aforementioned colorant 13, there were repeated three times a process of recovering by centrifuging (10,000×g, 4° C., 10 minutes) and suspension in 50 mass parts of purified water, and water was eliminated by lyophilizing. Then 10 mass parts of terminal amino-modified polysiloxane (modified silicone oil TSF4700, GE-Toshiba Silicone Co.) and reaction was executed for 2 hours at 70° C. The product was rinsed by repeating suspension in methanol and centrifuging (10,000×g, 4° C., 20 minutes) and dried to obtain colorant 15 having polysiloxane graft chain.

Infrared absorption measurement (FT-IR: Perkin-Elmer Inc., 1720x) on the colorant 15 indicated that the peaks of amine (about 3340 cm$^{-1}$) and epoxy (about 822 cm$^{-1}$) observed prior to heating vanished in the colorant 15. It was therefore identified that the reaction between PHA having an epoxy unit in the side chain with terminal amino-modified polysiloxane provided the colorant 15 having polysiloxane graft chain.

Example 33

Following composition:
styrene-butyl acrylate copolymer (glass transition temperature: 70° C.): 100 mass parts
colorant 1 (example 18): 5 mass parts
charge control agent (Hoechst NXVP 434): 2 mass parts
was mixed and fusion kneaded in a two-axis extruder (L/D=30). After cooling, there were executed crude crushing with a hammer mill, fine crushing with a jet mill and classification to obtain cyan colored particles (1), which shows a weight-averaged particle size of 7.1 µm and a fine powder amount of 6.0 number %.

100 mass parts of thus prepared cyan colored particles (1) were dry mixing by a Henshell mixer, with 1.5 mass parts of hydrophobic silica powder (BET: 250 m$^2$/g) treated with hexamethyl disilazane as the flowability improving agent, to obtain cyan toner (1) of the present example. Further, 7 mass parts of the cyan toner (1) and 93 mass parts of resin-coated magnetic ferrite carrier (average particle size 45 µm) to obtain two-component cyan developer (1) for magnetic brush development.

Examples 34 to 41

Cyan toners (2) to (9) of the examples 34 to 41 were obtained by a method similar to that in the example 33 except that the colorant 1 was respectively replaced by 5 mass parts of colorant 4, 7, 10 to 15. The characteristics of these toners were measured as in the example 33, and the results are shown in Table 11. Also these toners were used as in the example 33 to respectively obtain two-component cyan developers (2) to (9).

Comparative Example 1

Cyan toner (10) of the comparative example 1 was obtained by a method similar to that of the example 33, except that the colorant 1 was replaced by 15 mass parts of phthalocyanine blue (C.I. Pigment Blue 15:3). The characteristics of such toner were measured as in the example 33, and the results are shown in Table 11. Also such toner was used as in the example 33 to obtain two-component cyan developer 10 of the comparative example 1.

Examples 42 to 44

Magenta toners (1) to (3) of the examples 42 to 44 were obtained by a method similar to that in the example 33 except that the colorant 1 was respectively replaced by 5 mass parts of the colorant 2, 5 and 8. The characteristics of these toners were measured as in the example 33, and the results are shown in Table 11. Also these toners were used as in the example 33 to respectively obtain two-component magenta developers (1) to (3).

Comparative Example 2

Magenta toner (4) of the comparative example 2 was obtained by a method similar to that of the example 33, except that the colorant 1 was replaced by 5 mass parts of carmine 6B (C.I. Pigment Red 57:1). The characteristics of such toner were measured as in the example 33, and the results are shown in Table 11. Also such toner was used as in the example 33 to obtain two-component magenta developer (4) of the comparative example 2.

Examples 45 to 47

Yellow toners (1) to (3) of the examples 45 to 47 were obtained by a method similar to that in the example 33 except that the colorant 1 was respectively replaced by 5.0 mass parts of the colorant 3, 6 and 9. The characteristics of these toners were measured as in the example 33, and the results are shown in Table 11. Also these toners were used as in the example 33 to respectively obtain two-component yellows developers (1) to (3).

Comparative Example 3

Yellow toner (4) of the comparative example 3 was obtained by a method similar to that of the example 33, except that the colorant 1 was replaced by disazo yellow (C.I. Pigment Yellow 12). The characteristics of such toner were measured as in the example 33, and the results are shown in Table 11. Also such toner was used as in the example 33 to obtain two-component yellow developer (4) of the comparative example 3.

<Evaluation>

The two-component cyan developers (1) to (9), magenta and yellow developers (1) to (3) obtained in the examples 33 to 47, and the two-component cyan developer (10), magenta and yellow developers (4) obtained in the comparative examples 1 to 3 were subjected to the measurement of toner charge amount after agitation for 10 or 300 seconds, by the aforementioned charge amount measuring method, respectively under an environment of normal temperature and normal humidity (25° C., 60% RH) and an environment of high temperature and high humidity (30° C., 80% RH). The results are summarized in Table 11:

TABLE 11

| Example | Coloring agent No. | Toner No | Particle size distribution wt. ave. part. size (μm) | Fine powder amount (No. %) | Charge amount (μC/g) Normal temp, Normal humidity (Q/M) 10 sec. agit. | 300 sec agit. | High temp. high humidity (Q/M) 10 sec agit. | 300 sec agit. |
|---|---|---|---|---|---|---|---|---|
| 33 | 1 | blue 1 | 7.1 | 6.0 | −23.5 | −27.6 | −22.5 | −26.5 |
| 34 | 4 | blue 2 | 7.3 | 4.5 | −23.3 | −27.7 | −22.2 | −26.1 |
| 35 | 7 | blue 3 | 7.7 | 4.6 | −23.9 | −27.3 | −22.4 | −26.3 |
| 36 | 10 | blue 4 | 7.9 | 4.6 | −23.0 | −27.0 | −22.0 | −26.1 |
| 37 | 11 | blue 5 | 7.2 | 5.0 | −23.5 | −27.8 | −22.3 | −26.9 |
| 38 | 12 | blue 6 | 7.3 | 4.9 | −23.3 | −27.9 | −22.3 | −26.8 |
| 39 | 13 | blue 7 | 7.7 | 4.5 | −22.7 | −27.0 | −22.0 | −26.0 |
| 40 | 14 | blue 8 | 7.2 | 4.6 | −23.2 | −27.2 | −22.2 | −26.1 |
| 41 | 15 | blue 9 | 7.4 | 5.1 | −23.4 | −27.9 | −22.9 | −26.9 |
| 42 | 2 | red 1 | 7.1 | 5.6 | −23.3 | −27.7 | −22.1 | −26.3 |
| 43 | 5 | red 2 | 7.9 | 3.7 | −23.0 | −27.9 | −22.2 | −26.9 |
| 44 | 8 | red 3 | 7.6 | 4.9 | −23.2 | −27.3 | −22.1 | −26.6 |
| 45 | 3 | yellow 1 | 7.2 | 5.0 | −23.0 | −27.3 | −22.0 | −26.2 |
| 46 | 6 | yellow 2 | 7.5 | 4.7 | −23.1 | −27.2 | −22.1 | −26.3 |
| 47 | 9 | yellow 3 | 7.8 | 4.5 | −23.4 | −27.0 | −22.8 | −26.7 |
| Comp. ex. 1 | — | blue 10 | 7.0 | 4.9 | −17.5 | −25.6 | −13.4 | −19.9 |
| 2 | — | red 4 | 7.3 | 5.1 | −21.5 | −26.6 | −19.5 | −24.5 |
| 3 | — | yellow4 | 7.2 | 5.3 | −14.0 | −19.6 | −11.2 | −16.5 |

Examples 48 to 62 and Comparative Examples 4 to 6

Figure 5:
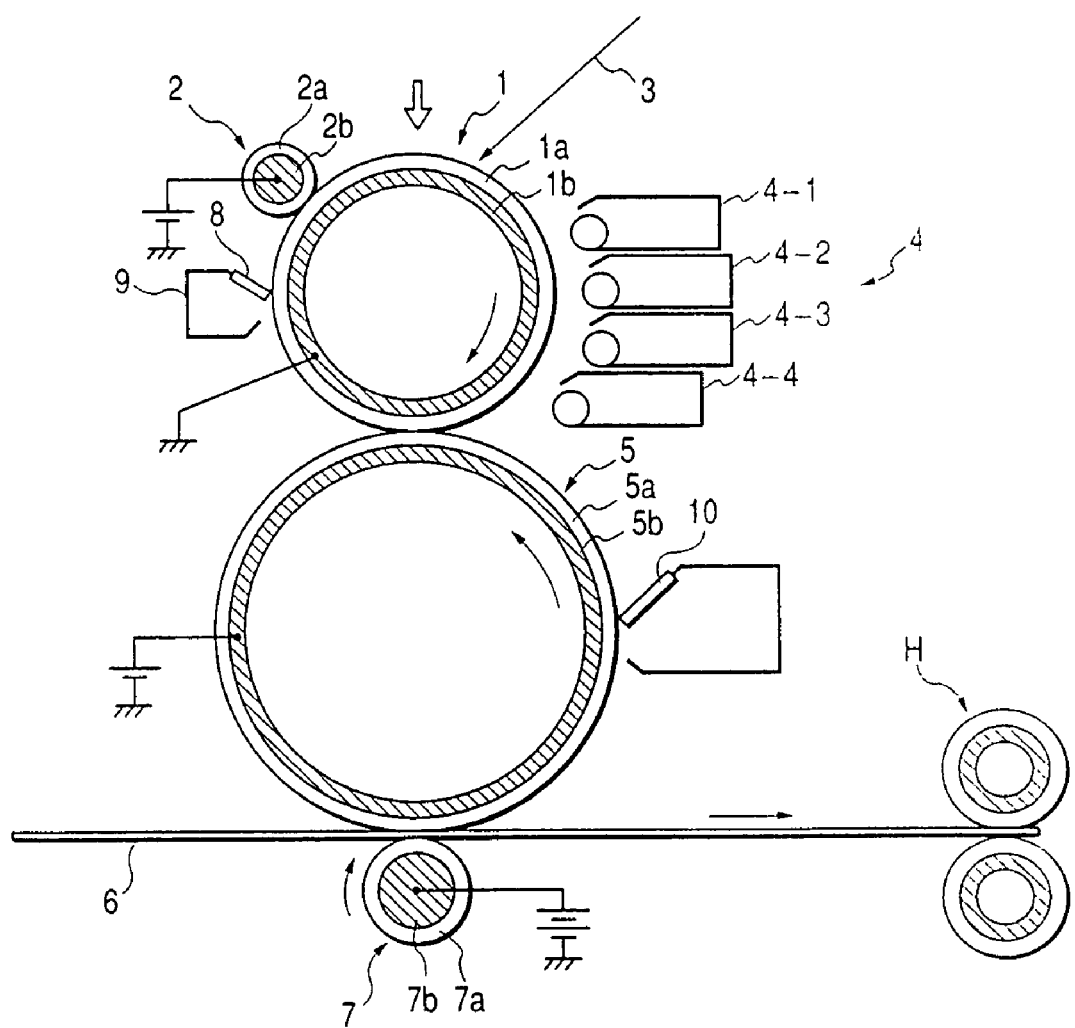
FIG. 5 is a schematic view of an image forming apparatus.

At first there will be explained an image forming apparatus employed in the image forming method of the examples 48 to 62 and the comparative examples 4 to 6. FIG. 5 is a schematic cross-sectional view of an image forming apparatus for executing the image forming method of the examples of the present invention and the comparative examples. Referring to FIG. 5, a photosensitive drum 1 is provided with a photosensitive layer 1a containing organic photoconductor on a substrate 1b, is rendered rotatable in the direction of arrow, and is surfacially charged at a surface potential of about −600 V by a charging roller 2 constituting a charging member opposed to the photosensitive drum 1 and rotated by contact therewith. As shown in FIG. 5, the charging roller 2 is composed of a conductive elastic layer 2a provided on a core metal 2b.

Figure 6:
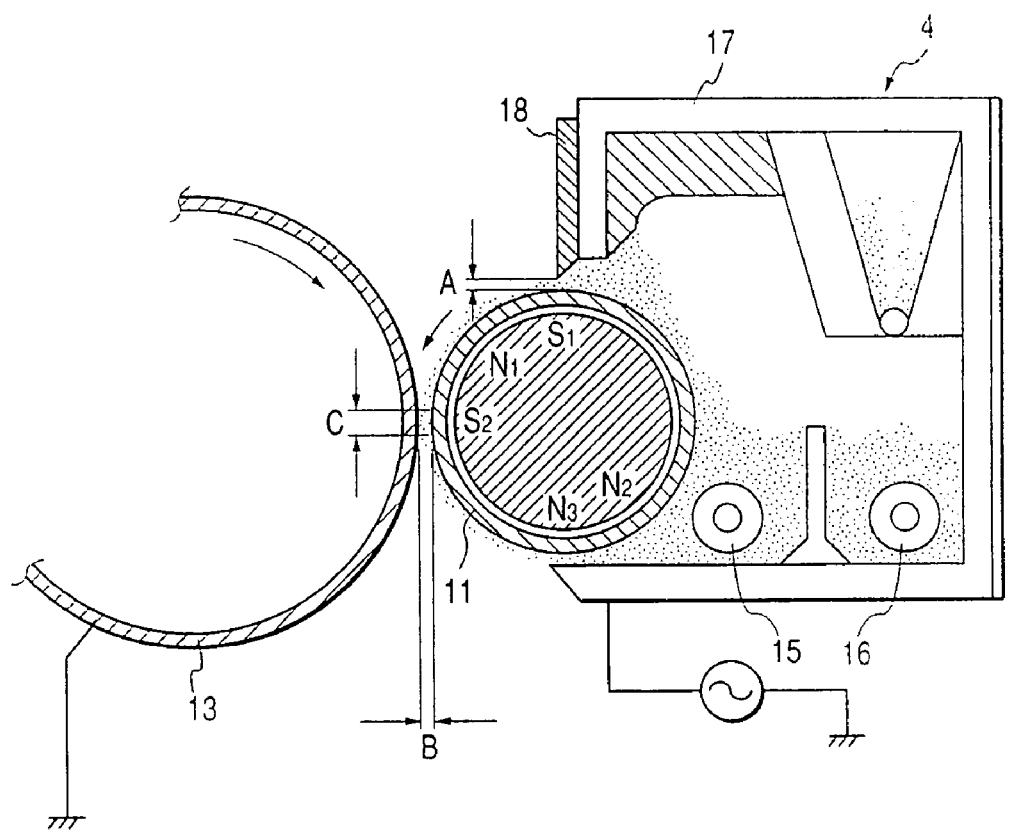
FIG. 6 is a partial cross-sectional view of a developing device for two-component developer.

Then exposure 3 is made toward the surfacially charged photosensitive drum 1 in on-off mode according to the digital image information by a polygon mirror to form an electrostatic charge image of an exposed potential of −100 V and a dark potential of −600 v. Then the electrostatic charge image on the photosensitive drum 1 is reversal developed and rendered visible with plural developing devices 4-1, 4-2, 4-3, 4-4 to form a toner image on the photosensitive drum 1. In this operation, there were respectively employed the two-component developers obtained in the examples 33 to 47 and comparative examples 1 to 3 to form toner images with yellow, magenta and cyan toner. FIG. 6 is a magnified partial cross-sectional view of each developing device 4 for two-component developer, employed in the development. Then the toner image on the photosensitive drum 1 is transferred onto an intermediate transfer member 5 rotated in contact with the photosensitive drum 1. As a result, superposed visible images of four colors are formed on the intermediate transfer member 5. The remaining toner, not transferred and remaining on the photosensitive drum 1, is recovered by a cleaner member 8 into a remaining toner container 9.

As shown in FIG. 5, the intermediate transfer member 5 is composed of a metal core 5b constituting a support member, and an elastic layer 5a laminated thereon. In the present example, there was employed an intermediate transfer member 5 formed by coating a pipe-shaped core metal 5b with an elastic layer 5b composed of carbon black as conductivity providing material sufficiently dispersed in nitrile-butadiene rubber (NBR). The elastic layer 5b had a hardness of 30 degrees measured according to JIS K 6301, and a volume resistivity of $10^9$ Ωcm. The transfer current required for transfer from the photosensitive drum 1 to the intermediate transfer member 5 was about 5 μA and was obtained by providing the core metal 5b with a voltage of +500 V from a power source.

The superposed toner images of four colors formed on the intermediate transfer member 5 were transferred by a transfer roller 7 to a transfer material such as paper, and then fixed by a heat fixing device H. The transfer roller 7 was formed by coating, on a core metal 7b of an external diameter of 10 mm, an elastic layer 7b composed of carbon as conductivity providing material sufficiently dispersed in ethylene-propylene-diene three-dimensional foamed copolymer (EPDM). It had a volume resistivity of $10^6$ Ωcm and a hardness of 35 degrees measured according to JIS K 6301. The transfer roller 7 was given a voltage to obtain a transfer current of 15 μA.

Figure 9:
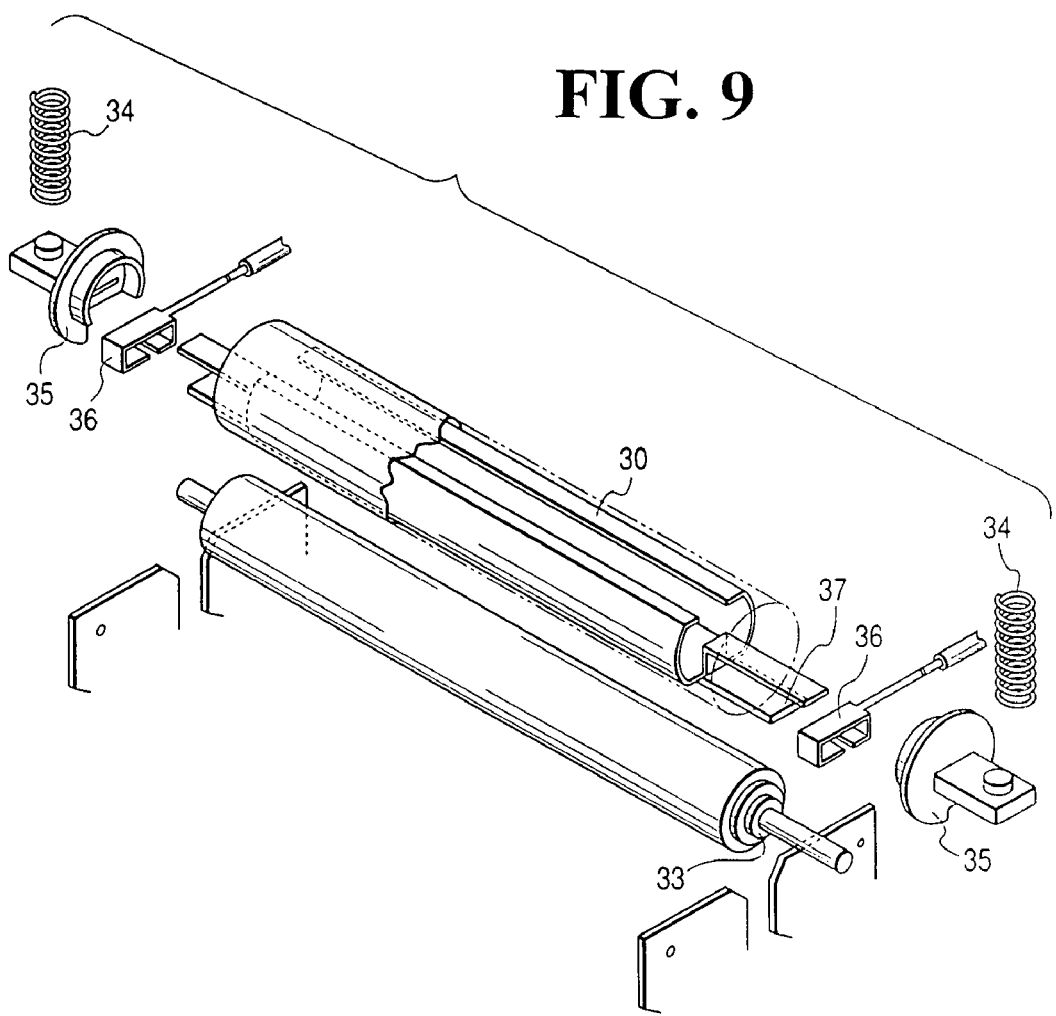
FIG. 9 is a partial exploded perspective view of a fixing device.
Figure 10:
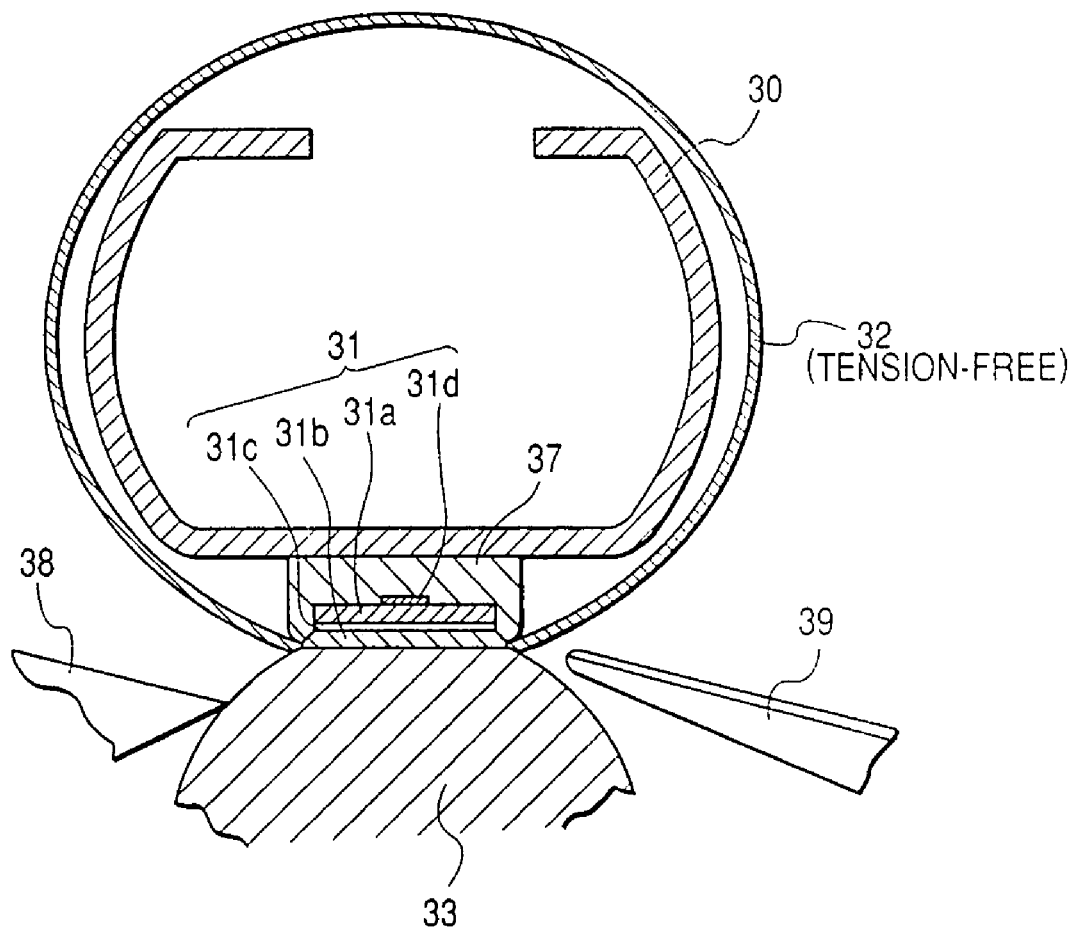
FIG. 10 is a magnified cross-sectional view showing the film state of the fixing device in a non-driven state.

In the apparatus shown in FIG. 5, the heat fixing device H was of heated roller type without oil coating mechanism as shown in FIGS. 9 and 10. Both the upper and lower rollers were provided with surface layers of fluorinated resin. The rollers had a diameter of 60 mm. The fixing temperature was selected as 160° C., and the nip width was selected as 7 mm. The toner remaining on the photosensitive drum 1 and recovered by cleaning was conveyed by a reuse mechanism to the developing device and was reused.

<Evaluation>

Printout test was conducted with the above-described configuration, under the environments of normal temperature and normal humidity (25° C., 60% RH) and high temperature and high humidity (30° C., 80% RH) and at a printout speed of 8 (A4 size) sheet/minute, respectively utilizing the two-component developers prepared with the toners of examples 33 to 47 and those prepared with the toners of comparative examples 1 to 3 under successive replenishment, in a monocolor intermittent mode (developing device being stopped for 10 seconds after each printout to accelerate the deterioration of the toner by the preparatory operation at the re-start), and the obtained printout image was evaluated for the following items. The results of evaluation are summarized in Table 12.

(Printout Image Evaluation)

1. Image Density

Printouts of a predetermined number were made on ordinary copying plain paper (75 g/m²), and there was evaluated the level of image density maintained in the image at the end of printing with respect to the initial image. The image density was measured with a Macbeth reflective densitometer (supplied by Macbeth Inc.), and the evaluation was made on the relative density of the printout image corresponding to a white portion of the original having a density of 0.00 by the following criteria:

⊚: excellent (image density at end at least equal to 1.4)

○: good (image density at end at least equal to 1.35 but less than 1.40)

□: fair (image density at end at least equal to 1.00 but less than 1.35)

X: poor (image density at end less than 1.00).

2. Image Fog

Printouts of a predetermined number were made on ordinary copying plain paper (75 g/m²), and the evaluation was made by a solid white image at the end of the printouts. More specifically, the worst reflective density Ds of the white portion after printout, measured with a reflective densitometer (Reflectometer Model TC-6DS supplied by Tokyo Denshoku Co., Ltd.) and the average reflective density Dr of the sheet before printing were used to calculate (Ds−Dr) as the fog amount, which was evaluated according to the following criteria:

⊚: excellent (fog amount at least equal to 0% but less than 1.5%)

○: good (fog amount at least equal to 1.5% but less than 3.0%)

□: fair (fog amount at least equal to 3.0% but less than 5.0%)

Δ: poor (fog amount at least equal to 5.0%).

3. Transfer Ability

A solid-black image was printed for a predetermined number on ordinary copying plain paper (75 g/m²), and the amount of image lacking amount at the end of printouts was observed visually and evaluated according to the following criteria:

⊚: excellent (almost none)

○: good (slight)

Δ: practically acceptable

X: practically unacceptable

Also after image outputs of 5000 sheets in the examples 48 to 62 and comparative examples 4 to 6, the surfacial scars on the photosensitive drum and the intermediate transfer member, generation of fixing of the remaining toner and influence on the printout image (matching with image forming apparatus) were visually inspected. In the systems utilizing the two-component developers of both the examples 48 to 62 and the comparative example 4 to 6, the surfacial scars on the photosensitive drum and the intermediate transfer member and generation of fixing of the remaining toner were not at all observed, and the matching with image forming apparatus was very satisfactory.

TABLE 12

| Example/ Comp. Ex. | 2-comp developer | Normal temp/normal humidity | | | High temp/high humidity | | |
|---|---|---|---|---|---|---|---|
| | | Image density | Image fog | Transfer | Image density | Image fog | Transfer |
| Ex. 48 | blue 1 | ◎ | ◎ | ◎ | ◎ | ◎ | ◎ |
| 49 | blue 2 | ◎ | ◎ | ◎ | ◎ | ◎ | ◎ |
| 50 | blue 3 | ◎ | ◎ | ◎ | ◎ | ◎ | ◎ |
| 51 | blue 4 | ◎ | ◎ | ◎ | ◎ | ◎ | ○ |
| 52 | blue 5 | ◎ | ◎ | ◎ | ◎ | ◎ | ◎ |
| 53 | blue 6 | ◎ | ◎ | ◎ | ◎ | ◎ | ◎ |
| 54 | blue 7 | ◎ | ◎ | ◎ | ◎ | ◎ | ○ |
| 55 | blue 8 | ◎ | ◎ | ◎ | ◎ | ◎ | ◎ |
| 56 | blue 9 | ◎ | ◎ | ◎ | ◎ | ◎ | ◎ |
| 57 | red 1 | ◎ | ◎ | ◎ | ◎ | ◎ | ◎ |
| 58 | red 2 | ◎ | ◎ | ◎ | ◎ | ◎ | ◎ |
| 59 | red 3 | ◎ | ◎ | ◎ | ◎ | ◎ | ◎ |
| 60 | yellow 1 | ◎ | ◎ | ◎ | ◎ | ◎ | ◎ |
| 61 | yellow 2 | ◎ | ◎ | ◎ | ◎ | ◎ | ◎ |
| 62 | yellow 3 | ◎ | ◎ | ◎ | ◎ | ◎ | ◎ |
| Comp. Ex. 4 | blue 10 | ◎ | ◎ | ◎ | ◎ | ○ | ○ |
| 5 | red 4 | ◎ | ◎ | ◎ | ◎ | ◎ | ◎ |
| 6 | yellow 4 | ◎ | ○ | ○ | ◎ | ○ | ○ |

Examples 63 to 65 and Comparative Examples 7 to 9

Figure 7:
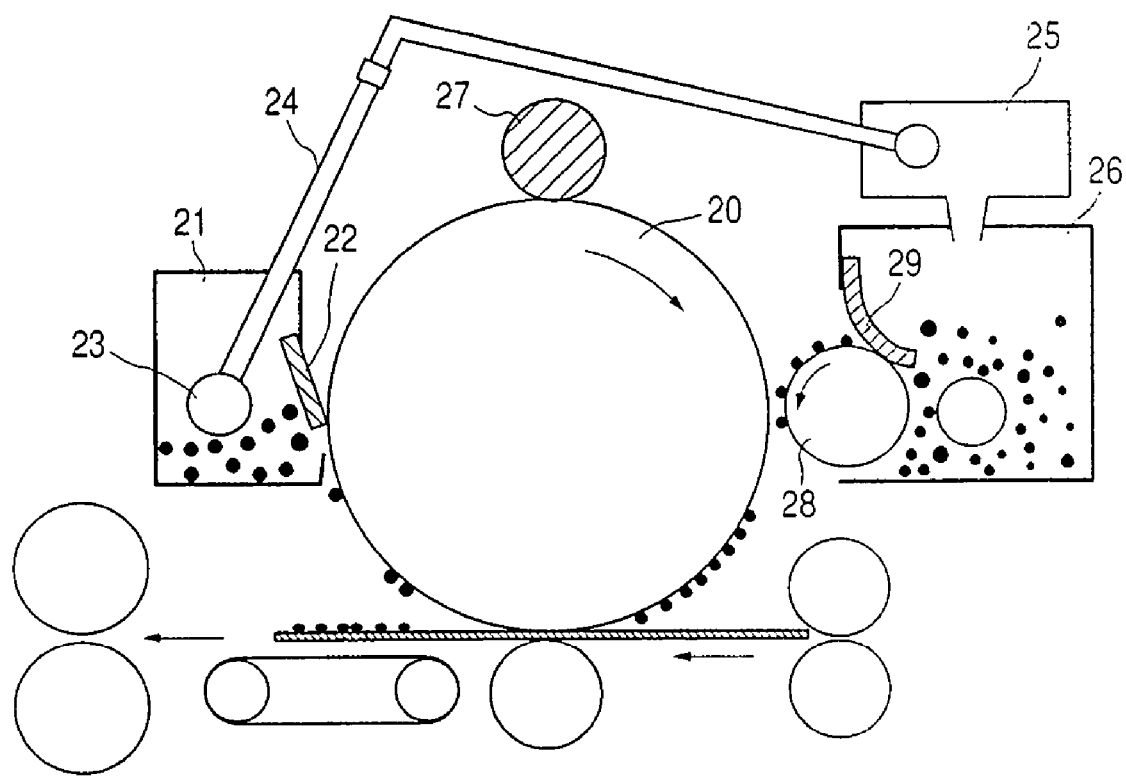
FIG. 7 is a schematic view of an image forming apparatus having a toner reuse mechanism.

In the execution of the image forming method of the examples 63 to 65 and the comparative examples 7 to 9, there were respectively employed toners obtained in the examples 33, 42, 45 and the comparative examples 1 to 3 as the developer. Also as image forming means, there was employed an image forming apparatus obtained by modifying and resetting a commercially available laser beam printer LBP-EX (Canon Inc.) by mounting a reuse mechanism as shown in FIG. 7. More specifically, in the image forming apparatus shown in FIG. 7, there is provided a system for reusing the recovered toner, in which the untransferred toner remaining on the photosensitive drum 20 after the transfer is scraped off by an elastic blade 22 of a cleaner 21 maintained in contact with the photosensitive drum 20, then fed into the cleaner 21 by a cleaner roller, further conveyed by a cleaner reuse mechanism 23 and returned by a supply pipe 24 having a feed screw to a developing device 26 through a hopper 25.

In the image forming apparatus shown in FIG. 7, the photosensitive drum 20 is surfacially charged by a primary charging roller 27. The primary charging roller 27 was composed of a rubber roller (diameter 12 mm, contact pressure 50 g/cm) containing conductive carbon dispersed therein and covered with nylon resin. By laser exposure (600 dpi, not shown), an electrostatic latent image with a dark potential VD=−700 V and a light potential VL=−200 V was formed on the electrostatic latent image bearing member (photosensitive drum 20). The toner bearing member was composed of a developing sleeve 28 having a surface coarseness Ra of 1.1 and surfacially coated with resin containing carbon black dispersed therein.

Figure 8:
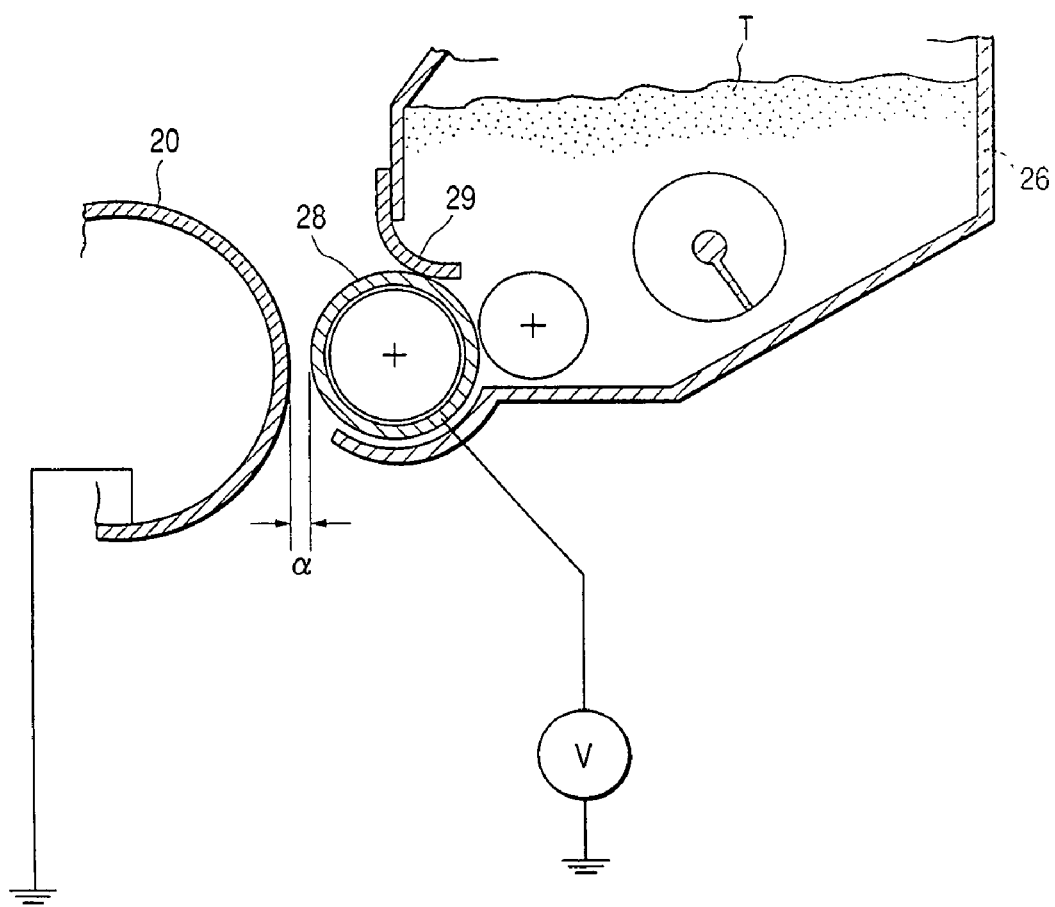
FIG. 8 is a partial cross-sectional view of a developing device for one-component developer.

FIG. 8 is a partial magnified cross-sectional view of a developing device for one-component developer, employed in the examples 63 to 65 and the comparative examples 7 to 9. As the developing conditions for the electrostatic latent image, the speed of the developing sleeve was selected as 1.1 times of the surface moving speed of the opposed photosensitive drum 20, and the gap α (S-D) between the photosensitive drum 20 and the developing sleeve 28 was selected as 270 μm. For regulating the toner layer thickness, an urethane rubber blade 29 was employed in contact state. Also the heat fixing device for fixing the toner image was set at a temperature of 160° C. The employed fixing device was as shown in FIGS. 9 and 10.

Printout test was conducted up to 30,000 prints with the above-described configuration, under the environments of normal temperature and normal humidity (25° C., 60% RH), at a printout speed of 8 (A4 size) sheet/minute and under successive toner replenishment, in a continuous mode (developing device being operated without stopping to accelerate the consumption of the toner), and the image density was measured on the obtained printout image and the durability of the image density was evaluated by the following criteria. Also the image of the 10,000th print was observed and the image fog was evaluated by the following criteria. Also, observation was made on the state of the components constituting the image forming apparatus after the durability test, and evaluation was made also on the matching between each component and each toner. The results of evaluation are summarized in Tab. 5.

(Image Density Change in Durability Test)

Printouts of a predetermined number were made on ordinary copying plain paper (75 g/m²), and there was evaluated the level of image density maintained in the image at the end of printing with respect to the initial image. The image density was measured with a Macbeth reflective densitometer (supplied by Macbeth Inc.), and the evaluation was made on the relative density of the printout image corresponding to a white portion of the original having a density of 0.00 by the following criteria:

⊚: excellent (image density at end at least equal to 1.4)

○: good (image density at end at least equal to 1.35 but less than 1.40)

Δ: fair (image density at end at least equal to 1.00 but less than 1.35)

X: poor (image density at end less than 1.00).

2. Image Fog

Printouts of a predetermined number were made on ordinary copying plain paper (75 g/m$^2$), and the evaluation was made by a solid white image at the end of the printouts. More specifically, the worst reflective density Ds of the white portion after printout, measured with a reflective densitometer (Reflectometer Model TC-6DS supplied by Tokyo Denshoku Co., Ltd.) and the average reflective density Dr of the sheet before printing were used to calculate (Ds−Dr) as the fog amount, which was evaluated according to the following criteria:

⊚: excellent (fog amount at least equal to 0% but less than 1.5%)

Δ: practically acceptable (toner fixation and scars present but little influence on the image)

X: practically unacceptable (toner fixation present in a large amount to cause image defects in streaks).

3. Matching with Fixing Device

The state of the surface of the fixing film was observed, and the durability thereof was evaluated in consideration of the surface state and the fixation of the remaining toner.

(1) Surface State

After the printout test, scars and peeling on the surface of the fixing film were visually observed and evaluated:

⊚: excellent (none)

○: good (almost none)

Δ: practically acceptable

X: practically unacceptable.

(2) Fixation of Remaining Toner

After the printout test, the state of fixation of the remaining toner on the surface of the fixing film was visually observed and evaluated:

⊚: excellent (none)

○: good (almost none)

Δ: practically acceptable

X: practically unacceptable.

TABLE 13

| | | Printout image evaluation | | | | Apparatus matching evaluation | | | |
| --- | --- | --- | --- | --- | --- | --- | --- | --- | --- |
| | | Image density change in durability test | | | | | | Fixing device | |
| | | | | | Image fog | | | | |
| Example | Toner | Initial | 1000 sheets | 10000 sheets | 30000 sheets | 10000 sheets | Developing sleeve | Photosensitive drum | Surface | Toner fix |
| Ex. 63 | blue 1 | ⊚ | ⊚ | ⊚ | ⊚ | ⊚ | ⊚ | ⊚ | ⊚ | ⊚ |
| 64 | red 1 | ⊚ | ⊚ | ⊚ | ⊚ | ⊚ | ⊚ | ⊚ | ⊚ | ⊚ |
| 65 | yellow 1 | ⊚ | ⊚ | ⊚ | ⊚ | ⊚ | ⊚ | ⊚ | ⊚ | ⊚ |
| Comp. ex. 7 | blue 10 | ⊚ | ⊚ | ⊚ | ○ | Δ | ⊚ | ○ | ⊚ | ⊚ |
| 8 | red 4 | ⊚ | ⊚ | ○ | ○ | ○ | ⊚ | ○ | ⊚ | ⊚ |
| 9 | yellow 4 | ⊚ | ⊚ | ⊚ | ○ | Δ | ○ | ○ | ⊚ | ⊚ |

○: good (fog amount at least equal to 1.5% but less than 3.0%)

Δ: fair (fog amount at least equal to 3.0% but less than 5.0%)

X: poor (fog amount at least equal to 5.0%).

(Evaluation of Matching with Image Forming Apparatus)

1. Matching with Developing Sleeve

After the printout test, the state of fixation of the remaining toner to the developing sleeve surface and the influence thereof on the printout image were evaluated visually:

⊚: excellent (none)

○: good (almost none)

Δ: practically acceptable (toner fixation present but little influence on the image)

X: practically unacceptable (toner fixation present in a large amount to cause unevenness in the image).

2. Matching with Photosensitive Drum

The scars on the photosensitive drum surface, the state of fixation of the remaining toner thereto and the influence thereof on the printout image were evaluated visually:

⊚: excellent (none)

○: good (slight scar generated but no influence on the image)

Example 66

Printout test was executed in the same manner as in the example 63, except that the toner reuse device was detached from the image forming apparatus shown in FIG. 7 and the printout speed was changed to 16 (A4 size) sheet/minute, under successive replenishment of the blue toner 1 of the example 33, in a continuous mode (developing device being operated without stopping to accelerate the consumption of the toner). The obtained printout image and the matching with the image forming apparatus were evaluated on the items same as those in the examples 63 to 65 and the comparative examples 7 to 9. Satisfactory results could be obtained in all the items.

The present invention has been described in detail with respect to preferred embodiments, and it will now be that changes and modifications may be made without departing from the invention in its broader aspects, and it is the invention, therefore, in the appended claims to cover all such changes and modifications as fall within the true spirit of the invention.

What is claimed is:

1. A construct comprising a base material and a polyhydroxyalkanoate, wherein at least a part of said base material is coated with said polyhyroxyalkanoate, and said polyhydroxyalkanoate comprises a 3-hydroxyalkanoic acid unit other than 3-hydroxypropionic acid unit, 3-hydroxy-n-butyric acid unit, and 3-hydroxy-n-valeric acid unit, and wherein said base material is a particle.

2. The construct according to claim 1, wherein said polyhydroxyalkanoate comprises at least one selected from the group consisting of monomer units represented by a chemical formula [1] to a chemical formula [10]:

[1]

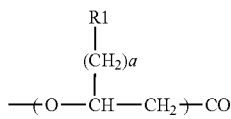

wherein R1 and a are selected from the group of combinations consisting of:

R1 is hydrogen atom (H) and a is any of integers from 3 to 10;

R1 is a halogen atom and a is any of integers from 1 to 10;

R1 is a chromophore and a is any of integers from 1 to 10;

R1 is a carboxyl group or a salt thereof and a is any of integers from 1 to 10; and R1 is

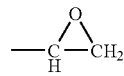

and a is any of integers from 1 to 7;

[2]

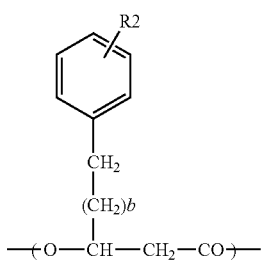

wherein b represents any of integers from 0 to 7 and R2 is selected from the group consisting of hydrogen atom (H), halogen atoms, —CN, —NO$_2$, —CF$_3$, —C$_2$F$_5$, and —C$_3$F$_7$);

[3]

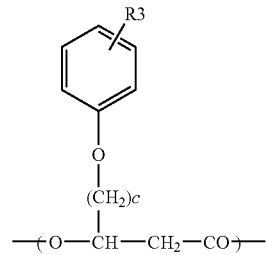

wherein c represents any of integers from 1 to 8 and R3 is selected from the group consisting of hydrogen atom (H), halogen atoms, —CN, —NO$_2$, —CF$_3$, —C$_2$F$_5$, and —C$_3$F$_7$;

[4]

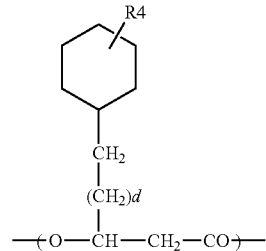

wherein d represents any of integers from 0 to 7 and R4 is selected from the group consisting of hydrogen atom (H), halogen atoms, —CN, —NO$_2$, —CF$_3$, —C$_2$F$_5$, and —C$_3$F$_7$;

[5]

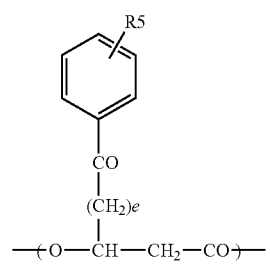

wherein e represents any of integers from 1 to 8 and R5 is selected from the group consisting of hydrogen atom (H), halogen atoms, —CN, —NO$_2$, —CF$_3$, —C$_2$F$_5$, —C$_3$F$_7$, —CH$_3$, —C$_2$H$_5$, and —C$_3$H$_7$;

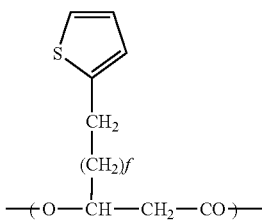
[6]

wherein f represents any of integers from 0 to 7;

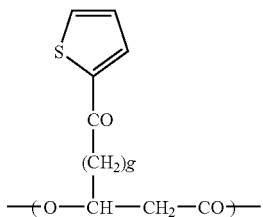
[7]

wherein g represents any of integers from 1 to 8;

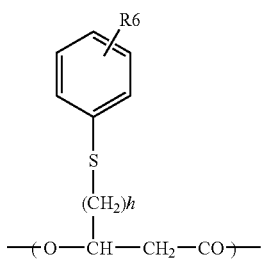
[8]

wherein h represents any of integers from 1 to 7 and R6 is selected from the group consisting of hydrogen atom (H), halogen atoms, —CN, —NO$_2$, —COOR', —SO$_2$R", —CH$_3$, —C$_2$H$_5$, —C$_3$H$_7$, —CH(CH$_3$)$_2$, and —C(CH$_3$)$_3$, wherein R' is selected from the group consisting of hydrogen atom (H), Na, K, —CH$_3$, and —C$_2$H$_5$, and R" is selected from the group consisting of —OH, —ONa, —OK, halogen atoms, —OCH$_3$, and —OC$_2$H$_5$;

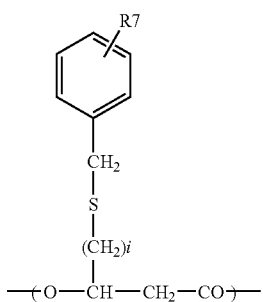
[9]

wherein i represents any of integers from 1 to 7 and R7 is selected from the group consisting of hydrogen atom (H), halogen atoms, —CN, —NO$_2$, —COOR', —SO$_2$R", wherein R' is selected from the group consisting of hydrogen atom (H), Na, K, —CH$_3$, and —C$_2$H$_5$, and R" is selected from the group consisting of —OH, —ONa, —OK, halogen atoms, —OCH$_3$, and —OC$_2$H$_5$; and

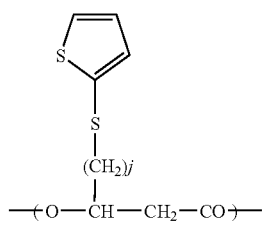
[10]

wherein j represents any of integers from 1 to 9.

3. The construct according to claim 1, wherein at least part of said polyhydroxyalkanoate is chemically modified.

4. The construct according to claim 3, wherein said chemical modification is a graft chain.

5. The construct according to claim 4, wherein said graft chain is introduced by chemically modifying a monomer unit having an epoxy group of the polyhydroxyalkanoate.

6. The construct according to claim 4, wherein said graft chain is made with a compound having an amino group.

7. The construct according to claim 6, wherein said compound having an amino group is a terminal amino-modified compound.

8. The construct according to claim 7, wherein said terminal amino-modified compound is selected from the group consisting of polyvinylamine, polyethyleneimine, and terminal amino-modified polysiloxane.

9. The construct according to claim 3, wherein at least a part of said polyhydroxyalkanoate is crosslinked.

10. The construct according to claim 9, wherein said polyhydroxyalkanoate is crosslinked between monomer units having an epoxy group.

11. The construct according to claim 1, wherein said base material is a particle.

12. The construct according to claim 11, wherein said colorant contains a pigment.

13. The construct according to claim 11, wherein said colorant contains a dye.

14. The construct according to claim 11, wherein said base material is a pigment.

15. The construct according to claim 11, wherein said polyhydroxyalkanoate is made with a composition of monomer units varying in an outward direction of said construct.

16. The construct according to claim 1, wherein a molecular weight of said polyhydroxyalkanoate is 1,000 to 10,000,000.

17. The construct according to claim 16, wherein a molecular weight of said polyhydroxyalkanoate is 3,000 to 1,000,000.

18. The construct according to claim 1, wherein a polyhydroxyalkanoate synthetase is immobilized to said base material.

19. A method for making a construct comprising the steps of:
    immobilizing a medium chain length polyhydroxyalkanoate synthetase to a base material, and reacting 3-hydroxyacyl coenzymes A with the synthetase to synthesize a polyhydroxyalkanoate and to coat at least a part of said base material with the polyhdroxyalkanoate, wherein said polyhydroxyalkanoate comprises a 3-hydroxyalkanoic acid unit other than 3-hydroxypropionic acid unit, 3-hydroxy-n-butyric acid unit, and 3-hydroxy-n-valeric acid unit.

20. The method for making a construct according to claim 19, wherein said polyhydroxyalkanoate comprises at least a monomer unit selected from the group consisting of monomer units represented by chemical formulas [1] to [10], and said monomer units are derived from corresponding 3-hydroxyacyl coenzyme As represented by chemical formulas [11] to [20] in this order:

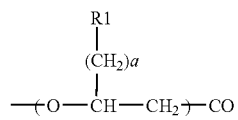

[1]

wherein R1 and a are selected from the group of combinations consisting of:
- R1 is hydrogen atom (H) and a is any of integers from 3 to 10;
- R1 is a halogen atom and a is any of integers from 1 to 10;
- R1 is a chromophore and a is any of integers from 1 to 10;
- R1 is a carboxyl group or a salt thereof and a is any of integers from 1 to 10; and
- R1 is

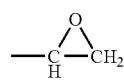

and a is any of integers from 1 to 7;

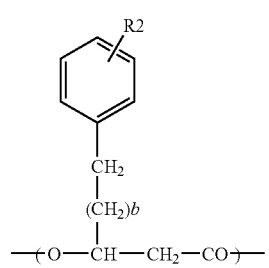

[2]

wherein b represents any of integers from 0 to 7 and R2 is selected from the group consisting of hydrogen atom (H), halogen atoms, —CN, —NO$_2$, —CF$_3$, —C$_2$F$_5$, and —C$_3$F$_7$;

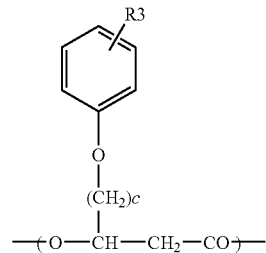

[3]

wherein c represents any of integers from 1 to 8 and R3 is selected from the group consisting of hydrogen atom (H), halogen atoms, —CN, —NO$_2$, —CF$_3$, —C$_2$F$_5$, and —C$_3$F$_7$;

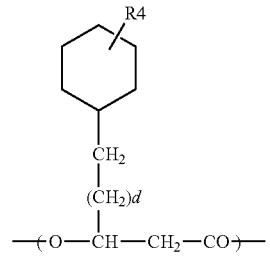

[4]

wherein d represents any of integers from 0 to 7 and R4 is selected from the group consisting of hydrogen atom (H), halogen atoms, —CN, —NO$_2$, —CF$_3$, —C$_2$F$_5$, and —C$_3$F$_7$;

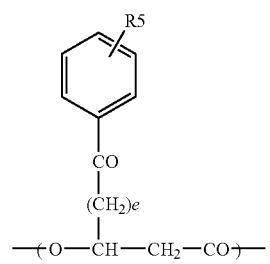

[5]

wherein e represents any of integers from 1 to 8 and R5 is selected from the group consisting of hydrogen atom (H), halogen atoms, —CN, —NO$_2$, —CF$_3$, —C$_2$F$_5$, —C$_3$F$_7$, —CH$_3$, —C$_2$H$_5$, and —C$_3$H$_7$;

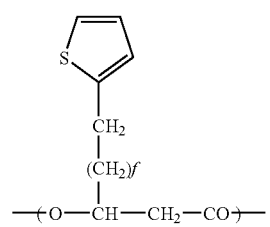

[6]

wherein f represents any of integers from 0 to 7;

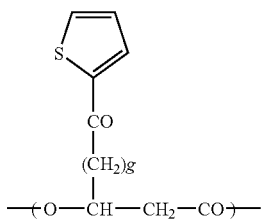

wherein g represents any of integers from 1 to 8;

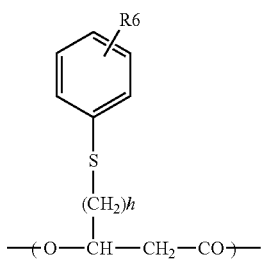

wherein h represents any of integers from 1 to 7 and R6 is selected from the group consisting of hydrogen atom (H), halogen atoms, —CN, —NO$_2$—COOR', —SO$_2$R", —CH$_3$, —C$_2$H$_5$, —C$_3$H$_7$, —CH(CH$_3$)$_2$, and —C(CH$_3$)$_3$, wherein R' is selected from the group consisting of hydrogen atom (H), Na, K, —CH$_3$, and —C$_2$H$_5$, and R" is selected from the group consisting of —OH, —ONa, —OK, halogen atoms, —OCH$_3$, and —OC$_2$H$_5$;

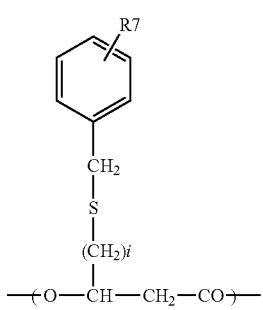

wherein i represents any of integers from 1 to 7 and R7 is selected from the group consisting of hydrogen atom (H), halogen atoms, —CN, —NO$_2$, —COOR', —SO$_2$R", wherein R' is selected from the group consisting of hydrogen atom (H), Na, K, —CH$_3$, and —C$_2$H$_5$, and R" is selected from the group consisting of —OH, —ONa, —OK, halogen atoms, —OCH$_3$, and —OC$_2$H$_5$; and

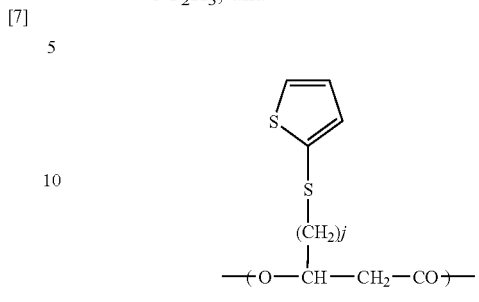

wherein j represents any of integers from 1 to 9,

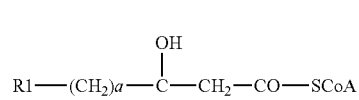

wherein —SCoA represents coenzyme A bound to an alkanoic acid, and R1 and a are the same as in the monomer unit represented by chemical formula (1);

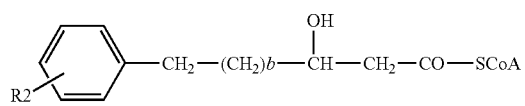

wherein —SCoA represents coenzyme A bound to alkanoic acid, R2 and b are the same as chemical formula [2];

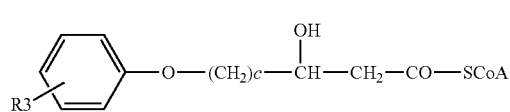

wherein —SCoA represents coenzyme A bound to an alkanoic acid, R3 and c are the same as in the monomer unit represented chemical formula [3];

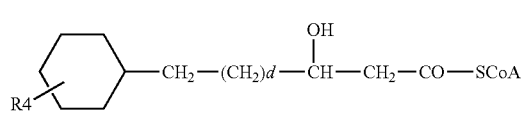

wherein —SCoA represents coenzyme A bound to an alkanoic acid, and R4 and d are the same as with the monomer unit represented by chemical formula [4];

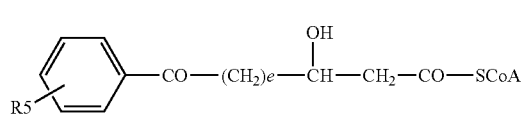

wherein —SCoA represents coenzyme A bound to alkanoic acid, and R5 and e are the same as in the monomer unit represented by chemical formula [5];

[16]
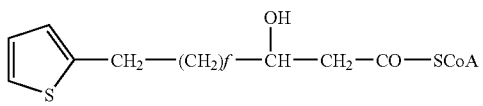

wherein —SCoA represents coenzyme A bound to an alkanoic acid, and f is the same as in the monomer unit represented by chemical formula [6];

[17]
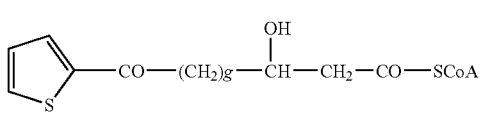

wherein —SCoA represents coenzyme A bound to an alkanoic acid, g is the same as in the monomer unit represented by chemical formula [7];

[18]
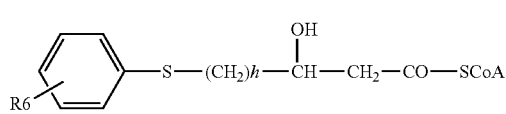

wherein —SCoA represents coenzyme A bound to an alkanoic acid, and R6 and h are the same as with the monomer unit represented by chemical formula [8];

[19]
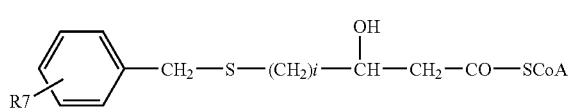

wherein —SCoA represents coenzyme A bound to an alkanoic acid, and R7 and i are the same as with the monomer unit represented by chemical formula [9]; and

[20]
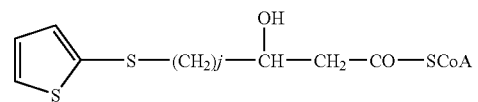

wherein —SCoA represents coenzyme A bound to an alkanoic acid, and j is the same as in the monomer unit represented by chemical formula [10].

21. The method for making a construct according to claim 19, further comprising a step of chemically modifying at least a part of said polyhydroxyalkanoate coating the base material.

22. The method for making a construct according to claim 21, wherein said step of chemically modifying is a step of adding a graft chain to at least a part of said polyhydroxyalkanoate.

23. The method for making a construct according to claim 22, wherein said step of adding the graft chain is a step of reacting at least a part of said polyhydroxyalkanoate with a compound having a reactive functional group at a terminus thereof.

24. The method for making a construct according to claim 21, wherein said step of chemically modifying is a step of crosslinking at least a part of said polyhydroxyalkanoate.

25. The method for making a construct according to claim 24, wherein said crosslinking step is a step of reacting at least a part of said polyhydroxyalkanoate with a crosslinking agent.

26. The method for making a construct according to claim 25, wherein said crosslinking agent is selected from the group consisting of a diamine compound, succinic anhydride, and 2-methyl-4-methylimidazole.

27. The method for making a construct according to claim 26, wherein said diamine compound is hexamethylenediamine.

28. The method for making a construct according to claim 24, wherein said crosslinking step is a step of irradiating said polyhydroxyalkanoate with an electron beam.

29. The method for making a construct according to claim 19, further comprising a step of changing the 3-hydroxyacyl coenzymes A in composition with time to change said polyhydroxyalkanoate in composition of monomer units along an inside-to-outside direction of said construct.

30. The method for making a construct according to claim 19, wherein said polyhydroxyalkanoate synthetase is produced by using a microorganism having a production capability of the synthetase.

31. The method for making a construct according to claim 19, wherein said polyhydroxyalkanoate synthetase is produced by a transformant into which a gene participating in the production capability of the synthetase has been introduced.

32. The method for making a construct according to claim 31, wherein said gene is obtained from a microorganism having a production capability of a polyhydroxyalkanoate synthetase.

33. The method for making a construct according to claim 30, wherein the microorganism is *Pseudomonas* sp.

34. The method for making a construct according to claim 33, wherein the microorganism of *Pseudomonas* sp. is selected from the group consisting of *Pseudomonas putida* P91, FERM BP-7373, *Pseudomonas cichorii* H45, FERM BP-7374, *Pseudomonas cichorii* YN2, FERM BP-7375, and *Pseudomonas jessenii* P161, FERM BP-7376.

35. The method for making a construct according to claim 30, wherein the microorganism is *Burkholderia* sp.

36. The method for making a construct according to claim 35, wherein said microorganism of *Burkholderia* sp. is selected from the group consisting of *Burkholderia* sp. OK3, FERM P-17370 and *Burkholderia* sp. OK4, FERM P-17371.

37. The method for making a construct according to claim 31, wherein the transformant having a production capability of said polyhydroxyalkanoate synthetase is *Escherichia coli*.

* * * * *

SEQUENCE LISTING

<160> NUMBER OF SEQ ID NOS: 27

<210> SEQ ID NO 1
<211> LENGTH: 1501
<212> TYPE: DNA
<213> ORGANISM: Pseudomonas jessenii 161 strain

<400> SEQUENCE: 1

```
tgaacgctgg cggcaggcct aacacatgca agtcgagcgg atgacgggag cttgctcctg      60
aattcagcgg cggacgggtg agtaatgcct aggaatctgc ctggtagtgg gggacaacgt     120
ctcgaaaggg acgctaatac cgcatacgtc ctacgggaga aagcagggga ccttcgggcc     180
ttgcgctatc agatgagcct aggtcggatt agctagttgg tgaggtaatg gctcaccaag     240
gcgacgatcc gtaactggtc tgagaggatg atcagtcaca ctggaactga gacacggtcc     300
agactcctac gggaggcagc agtggggaat attggacaat gggcgaaagc ctgatccagc     360
catgccgcgt gtgtgaagaa ggtcttcgga ttgtaaagca ctttaagttg ggaggaaggg     420
cattaaccta atacgttagt gttttgacgt taccgacaga ataagcaccg gctaactctg     480
tgccagcagc cgcggtaata cagagggtgc aagcgttaat cggaattact gggcgtaaag     540
cgcgcgtagg tggtttgtta agttggatgt gaaagccccg ggctcaacct gggaactgca     600
ttcaaaactg acaagctaga gtatggtaga gggtggtgga atttcctgtg tagcggtgaa     660
atgcgtagat ataggaagga acaccagtgg cgaaggcgac cacctggact gatactgaca     720
ctgaggtgcg aaagcgtggg gagcaaacag gattagatac cctggtagtc cacgccgtaa     780
acgatgtcaa ctagccgttg ggagccttga gctcttagtg gcgcagctaa cgcattaagt     840
tgaccgcctg gggagtacgg ccgcaaggtt aaaactcaaa tgaattgacg ggggcccgca     900
caagcggtgg agcatgtggt ttaattcgaa gcaacgcgaa gaaccttacc aggccttgac     960
atccaatgaa ctttccagag atggatgggt gccttcggga acattgagac aggtgctgca    1020
tggctgtcgt cagctcgtgt cgtgagatgt tgggttaagt cccgtaacga gcgcaaccct    1080
tgtccttagt taccagcacg taatggtggg cactctaagg agactgccgg tgacaaaccg    1140
gaggaaggtg gggatgacgt caagtcatca tggcccttac ggcctgggct acacacgtgc    1200
tacaatggtc ggtacagagg gttgccaagc cgcgaggtgg agctaatccc acaaaaccga    1260
tcgtagtccg gatcgcagtc tgcaactcga ctgcgtgaag tcggaatcgc tagtaatcgc    1320
gaatcagaat gtcgcggtga atacgttccc gggccttgta cacaccgccc gtcacaccat    1380
gggagtgggt tgcaccagaa gtagctagtc taaccttcgg gaggacggtt accacggtgt    1440
gattcatgac tggggtgaag tcgtaccaag gtagccgtag gggaacctgc ggctggatca    1500
c                                                                    1501
```

<210> SEQ ID NO 2
<211> LENGTH: 20
<212> TYPE: DNA
<213> ORGANISM: Artificial Sequence
<220> FEATURE:
<223> OTHER INFORMATION: Primer for PCT multiplication

<400> SEQUENCE: 2

```
tgctggaact gatccagtac                                                   20
```

<210> SEQ ID NO 3
<211> LENGTH: 23

```
<212> TYPE: DNA
<213> ORGANISM: Artificial Sequence
<220> FEATURE:
<223> OTHER INFORMATION: Primer for PCR multiplication

<400> SEQUENCE: 3
gggttgagga tgctctggat gtg                                              23

<210> SEQ ID NO 4
<211> LENGTH: 1680
<212> TYPE: DNA
<213> ORGANISM: Pseudomonas cichorii YN2 ; FERM P 17411

<400> SEQUENCE: 4
atgagtaaca agagtaacga tgagttgaag tatcaagcct ctgaaaacac         50
cttgggcctt aatcctgtcg ttgggctgcg tggaaaggat ctactggctt        100
ctgctcgaat ggtgcttagg caggccatca agcaaccggt gcacagcgtc        150
aaacatgtcg cgcactttgg tcttgaactc aagaacgtac tgctgggtaa        200
atccgggctg caaccgacca gcgatgaccg tcgcttcgcc gatccggcct        250
ggagccagaa cccgctctat aaacgttatt tgcaaaccta cctggcgtgg        300
cgcaaggaac tccacgactg gatcgatgaa agtaacctcg cccccaagga        350
tgtggcgcgt gggcacttcg tgatcaacct catgaccgaa gccatggcgc        400
cgaccaacac cgcggccaac ccggcggcag tcaaacgctt tttcgaaacc        450
ggtggcaaaa gcctgctcga cggcctctcg cacctggcca aggatctggt        500
acacaacggc ggcatgccga gccaggtcaa catgggtgca ttcgaggtcg        550
gcaagagcct gggcgtgacc gaaggcgcgg tggtgtttcg caacgatgtg        600
ctggaactga tccagtacaa gccgaccacc gagcaggtat acgaacgccc        650
gctgctggtg gtgccgccgc agatcaacaa gttctacgtt ttcgacctga        700
gcccggacaa gagcctggcg cggttctgcc tgcgcaacaa cgtgcaaacg        750
ttcatcgtca gctggcgaaa tcccaccaag gaacagcgag agtggggcct        800
gtcgacctac atcgaagccc tcaaggaagc ggttgatgtc gttaccgcga        850
tcaccggcag caaagacgtg aacatgctcg gcgcctgctc cggcggcatc        900
acttgcaccg cgctgctggg ccattacgcg gcgattggcg aaaacaaggt        950
caacgccctg accttgctgg tgagcgtgct tgataccacc ctcgacagcg       1000
atgttgccct gttcgtcaat gaacagaccc ttgaagccgc caagcgccac       1050
tcgtaccagg ccggcgtact ggaaggccgc gacatggcga aggtcttcgc       1100
ctggatgcgc cccaacgatc tgatctggaa ctactgggtc aacaattacc       1150
tgctaggcaa cgaaccgccg gtgttcgaca tcctgttctg gaacaacgac       1200
accacacggt tgcccgcggc gttccacggc gacctgatcg aactgttcaa       1250
aaataaccca ctgattcgcc cgaatgcact ggaagtgtgc ggcacccca        1300
tcgacctcaa gcaggtgacg gccgacatct ttccctggc cggcaccaac       1350
gaccacatca ccccgtggaa gtcctgctac aagtcggcgc aactgtttgg       1400
cggcaacgtt gaattcgtgc tgtcgagcag cgggcatatc cagagcatcc       1450
tgaacccgcc gggcaatccg aaatcgcgct acatgaccag caccgaagtg       1500
gcggaaaatg ccgatgaatg caagcgaat gccaccaagc ataccgattc       1550
```

| | |
|---|---|
| ctggtggctg cactggcagg cctggcaggc ccaacgctcg ggcgagctga | 1600 |
| aaaagtcccc gacaaaactg ggcagcaagg cgtatccggc aggtgaagcg | 1650 |
| gcgccaggca cgtacgtgca cgaacggtaa | 1680 |

<210> SEQ ID NO 5
<211> LENGTH: 1683
<212> TYPE: DNA
<213> ORGANISM: Pseudomonas cichorii YN2 ; FERM P 17411

<400> SEQUENCE: 5

| | |
|---|---|
| atgcgcgata aacctgcgag ggagtcacta cccacccccg ccaagttcat | 50 |
| caacgcacaa agtgcgatta ccggcctgcg tggccgggat ctggtttcga | 100 |
| cttttgcgcag tgtcgccgcc catggcctgc gccaccccgt gcacaccgcg | 150 |
| cgacacgcct tgaaactggg tggtcaactg ggacgcgtgt tgctgggcga | 200 |
| caccctgcat cccaccaacc cgcaagaccg tcgcttcgac gatccggcgt | 250 |
| ggagtctcaa tccctttttat cgtcgcagcc tgcaggcgta cctgagctgg | 300 |
| cagaagcagg tcaagagctg gatcgacgaa agcaacatga gcccggatga | 350 |
| ccgcgcccgt gcgcacttcg cgttcgccct gctcaacgat gccgtgtcgc | 400 |
| cgtccaacag cctgctcaat ccgctggcga tcaaggaaat cttcaactcc | 450 |
| ggcggcaaca gcctggtgcg cgggatcggc catctggtcg atgacctctt | 500 |
| gcacaacgat ggcttgcccc ggcaagtcac caggcatgca ttcgaggttg | 550 |
| gcaagaccgt cgccaccacc accggcgccg tggtgtttcg caacgagctg | 600 |
| ctggagctga tccaatacaa gccgatgagc gaaaagcagt attccaaacc | 650 |
| gctgctggtg gtgccgccac agatcaacaa gtactacatt tttgacctca | 700 |
| gccccccataa cagcttcgtc cagttcgcgc tcaagaacgg cctgcaaacc | 750 |
| ttcgtcatca gctggcgcaa tccggatgta cgtcaccgcg aatggggcct | 800 |
| gtcgacctac gtcgaagcgg tggaagaagc catgaatgtc tgccgggcaa | 850 |
| tcaccggcgc gcgcgaggtc aacctgatgg gcgcctgcgc tggcgggctg | 900 |
| accattgctg ccctgcaggg ccacttgcaa gccaagcgac agctgcgccg | 950 |
| cgtctccagc gcgacgtacc tggtgagcct gctcgacagc caactggaca | 1000 |
| gcccggccac actcttcgcc gacgaacaga ccctggaggc ggccaagcgc | 1050 |
| cgctcctacc agaaaggtgt gctggaaggc cgcgacatgg ccaaggtttt | 1100 |
| cgcctggatg cgccccaacg atttgatctg gagctacttc gtcaacaatt | 1150 |
| acctgatggg caaggagccg ccggcgttcg acattctcta ctggaacaat | 1200 |
| gacaacacac gcctgccggc cgccctgcat ggtgacttgc tggacttctt | 1250 |
| caagcacaac ccgctgagcc atccgggtgg cctggaagtg tgcggcaccc | 1300 |
| cgatcgactt gcaaaaggtc accgtcgaca gtttcagcgt ggccggcatc | 1350 |
| aacgatcaca tcacgccgtg ggacgcggtg tatcgctcaa ccctgttgct | 1400 |
| cggtggcgag cgtcgctttg tcctggccaa cagcggtcat gtgcagagca | 1450 |
| ttctcaaccc gccgaacaat ccgaaagcca actacctcga aggtgcaaaa | 1500 |
| ctaagcagcg accccagggc ctggtactac gacgccaagc ccgtcgacgg | 1550 |
| tagctggtgg acgcaatggc tgggctggat tcaggagcgc tcgggcgcgc | 1600 |
| aaaaagaaac ccacatggcc ctcggcaatc agaattatcc accgatggag | 1650 |

```
gcggcgcccg ggacttacgt gcgcgtgcgc tga                            1683
```

<210> SEQ ID NO 6
<211> LENGTH: 29
<212> TYPE: DNA
<213> ORGANISM: Artificial Sequence
<220> FEATURE:
<223> OTHER INFORMATION: Primer for PCR multiplication

<400> SEQUENCE: 6

```
ggaccaagct tctcgtctca gggcaatgg                                 29
```

<210> SEQ ID NO 7
<211> LENGTH: 29
<212> TYPE: DNA
<213> ORGANISM: Artificial Sequence
<220> FEATURE:
<223> OTHER INFORMATION: Primer for PCR multiplication

<400> SEQUENCE: 7

```
cgagcaagct tgctcctaca ggtgaaggc                                 29
```

<210> SEQ ID NO 8
<211> LENGTH: 29
<212> TYPE: DNA
<213> ORGANISM: Artificial Sequence
<220> FEATURE:
<223> OTHER INFORMATION: Primer for PCR multiplication

<400> SEQUENCE: 8

```
gtattaagct tgaagacgaa ggagtgttg                                 29
```

<210> SEQ ID NO 9
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 9

```
catccaagct tcttatgatc gggtcatgcc                                30
```

<210> SEQ ID NO 10
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 10

```
cgggatccag taacaagagt aacgatgagt                                30
```

<210> SEQ ID NO 11
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 11

```
cgatctcgag ttaccgttcg tgcacgtacg                                30
```

<210> SEQ ID NO 12
<211> LENGTH: 30
<212> TYPE: DNA

```
<213> ORGANISM: Artificial Sequence
<220> FEATURE:
<223> OTHER INFORMATION: Primer for PCR multiplication

<400> SEQUENCE: 12
cgggatcccg cgataaacct gcgagggagt                                        30

<210> SEQ ID NO 13
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 13
cgatctcgag gcgcacgcgc acgtaagtcc                                        30

<210> SEQ ID NO 14
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 14
cgggatccag taacaagagt aacgatgagt                                        30

<210> SEQ ID NO 15
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 15
cgatctcgag ttaccgttcg tgcacgtacg                                        30

<210> SEQ ID NO 16
<211> LENGTH: 20
<212> TYPE: DNA
<213> ORGANISM: Artificial Sequence
<220> FEATURE:
<223> OTHER INFORMATION: Primer for PCR multiplication

<400> SEQUENCE: 16
tgctggaact gatccagtac                                                   20

<210> SEQ ID NO 17
<211> LENGTH: 23
<212> TYPE: DNA
<213> ORGANISM: Artificial Sequence
<220> FEATURE:
<223> OTHER INFORMATION: Primer for PCR multiplication

<400> SEQUENCE: 17
gggttgagga tgctctggat gtg                                               23

<210> SEQ ID NO 18
<211> LENGTH: 1680
<212> TYPE: DNA
<213> ORGANISM: Pseudomonas cichorii YN2 ; FERM BP-7375

<400> SEQUENCE: 18
atgagtaaca agagtaacga tgagttgaag tatcaagcct ctgaaaacac                  50
cttggggctt aatcctgtcg ttgggctgcg tggaaaggat ctactggctt                 100
```

```
ctgctcgaat ggtgcttagg caggccatca agcaaccggt gcacagcgtc        150
aaacatgtcg cgcactttgg tcttgaactc aagaacgtac tgctgggtaa        200
atccgggctg caaccgacca gcgatgaccg tcgcttcgcc gatccggcct        250
ggagccagaa cccgctctat aaacgttatt tgcaaaccta cctggcgtgg        300
cgcaaggaac tccacgactg gatcgatgaa agtaacctcg cccccaagga        350
tgtggcgcgt gggcacttcg tgatcaacct catgaccgaa gccatggcgc        400
cgaccaacac cgcggccaac ccggcggcag tcaaacgctt tttcgaaacc        450
ggtggcaaaa gcctgctcga cggcctctcg cacctggcca aggatctggt        500
acacaacggc ggcatgccga gccaggtcaa catgggtgca ttcgaggtcg        550
gcaagagcct gggcgtgacc gaaggcgcgg tggtgtttcg caacgatgtg        600
ctggaactga tccagtacaa gccgaccacc gagcaggtat acgaacgccc        650
gctgctggtg gtgccgccgc agatcaacaa gttctacgtt ttcgacctga        700
gcccggacaa gagcctggcg cggttctgcc tgcgcaacaa cgtgcaaacg        750
ttcatcgtca gctggcgaaa tcccaccaag gaacagcgag agtggggcct        800
gtcgacctac atcgaagccc tcaaggaagc ggttgatgtc gttaccgcga        850
tcaccggcag caaagacgtg aacatgctcg gcgcctgctc cggcggcatc        900
acttgcaccg cgctgctggg ccattacgcg gcgattggcg aaaacaaggt        950
caacgccctg accttgctgg tgagcgtgct tgataccacc ctcgacagcg       1000
atgttgccct gttcgtcaat gaacagaccc ttgaagccgc caagcgccac       1050
tcgtaccagg ccggcgtact ggaaggccgc gacatggcga aggtcttcgc       1100
ctggatgcgc cccaacgatc tgatctggaa ctactgggtc aacaattacc       1150
tgctaggcaa cgaaccgccg gtgttcgaca tcctgttctg gaacaacgac       1200
accacacggt tgcccgcggc gttccacggc gacctgatcg aactgttcaa       1250
aaataaccca ctgattcgcc cgaatgcact ggaagtgtgc ggcaccccca       1300
tcgacctcaa gcaggtgacg gccgacatct ttccctggc cggcaccaac       1350
gaccacatca ccccgtggaa gtcctgctac aagtcggcgc aactgtttgg       1400
cggcaacgtt gaattcgtgc tgtcgagcag cgggcatatc cagagcatcc       1450
tgaacccgcc gggcaatccg aaatcgcgct acatgaccag caccgaagtg       1500
gcggaaaatg ccgatgaatg gcaagcgaat gccaccaagc ataccgattc       1550
ctggtggctg cactggcagg cctggcaggc ccaacgctcg ggcgagctga       1600
aaaagtcccc gacaaaactg ggcagcaagg cgtatccggc aggtgaagcg       1650
gcgccaggca cgtacgtgca cgaacggtaa                             1680
```

<210> SEQ ID NO 19
<211> LENGTH: 1683
<212> TYPE: DNA
<213> ORGANISM: Pseudomonas cichorii YN2 ; FERM BP-7375

<400> SEQUENCE: 19

```
atgcgcgata aacctgcgag ggagtcacta cccaccccg ccaagttcat         50
caacgcacaa agtgcgatta ccggcctgcg tggccgggat ctggtttcga        100
cttttgcgcag tgtcgccgcc catggcctgc gccaccccgt gcacaccgcg       150
```

-continued

| | |
|---|---|
| cgacacgcct tgaaactggg tggtcaactg ggacgcgtgt tgctgggcga | 200 |
| caccctgcat cccaccaacc cgcaagaccg tcgcttcgac gatccggcgt | 250 |
| ggagtctcaa tccctttat cgtcgcagcc tgcaggcgta cctgagctgg | 300 |
| cagaagcagg tcaagagctg gatcgacgaa agcaacatga gcccggatga | 350 |
| ccgcgcccgt gcgcacttcg cgttcgccct gctcaacgat gccgtgtcgc | 400 |
| cgtccaacag cctgctcaat ccgctggcga tcaaggaaat cttcaactcc | 450 |
| ggcggcaaca gcctggtgcg cgggatcggc catctggtcg atgacctctt | 500 |
| gcacaacgat ggcttgcccc ggcaagtcac caggcatgca ttcgaggttg | 550 |
| gcaagaccgt cgccaccacc accggcgccg tggtgtttcg caacgagctg | 600 |
| ctggagctga tccaatacaa gccgatgagc gaaaagcagt attccaaacc | 650 |
| gctgctggtg gtgccgccac agatcaacaa gtactacatt tttgacctca | 700 |
| gcccccataa cagcttcgtc cagttcgcgc tcaagaacgg cctgcaaacc | 750 |
| ttcgtcatca gctggcgcaa tccggatgta cgtcaccgcg aatggggcct | 800 |
| gtcgacctac gtcgaagcgg tggaagaagc catgaatgtc tgccgggcaa | 850 |
| tcaccggcgc gcgcgaggtc aacctgatgg gcgcctgcgc tggcgggctg | 900 |
| accattgctg ccctgcaggg ccacttgcaa gccaagcgac agctgcgccg | 950 |
| cgtctccagc gcgacgtacc tggtgagcct gctcgacagc caactggaca | 1000 |
| gcccggccac actcttcgcc gacgaacaga ccctggaggc ggccaagcgc | 1050 |
| cgctcctacc agaaaggtgt gctggaaggc cgcgacatgg ccaaggtttt | 1100 |
| cgcctggatg cgccccaacg atttgatctg gagctacttc gtcaacaatt | 1150 |
| acctgatggg caaggagccg ccggcgttcg acattctcta ctggaacaat | 1200 |
| gacaacacac gcctgccggc cgccctgcat ggtgacttgc tggacttctt | 1250 |
| caagcacaac ccgctgagcc atccgggtgg cctggaagtg tgcggcaccc | 1300 |
| cgatcgactt gcaaaaggtc accgtcgaca gtttcagcgt ggccggcatc | 1350 |
| aacgatcaca tcacgccgtg ggacgcggtg tatcgctcaa ccctgttgct | 1400 |
| cggtggcgag cgtcgctttg tcctggccaa cagcggtcat gtgcagagca | 1450 |
| ttctcaaccc gccgaacaat ccgaaagcca actacctcga aggtgcaaaa | 1500 |
| ctaagcagcg accccagggc ctggtactac gacgccaagc ccgtcgacgg | 1550 |
| tagctggtgg acgcaatggc tgggctggat tcaggagcgc tcgggcgcgc | 1600 |
| aaaaagaaac ccacatggcc ctcggcaatc agaattatcc accgatggag | 1650 |
| gcggcgcccg ggacttacgt gcgcgtgcgc tga | 1683 |

<210> SEQ ID NO 20
<211> LENGTH: 29
<212> TYPE: DNA
<213> ORGANISM: Artificial Sequence
<220> FEATURE:
<223> OTHER INFORMATION: Primer for PCR multiplication

<400> SEQUENCE: 20
ggaccaagct tctcgtctca gggcaatgg                                    29

<210> SEQ ID NO 21
<211> LENGTH: 29
<212> TYPE: DNA
<213> ORGANISM: Artificial Sequence

```
<220> FEATURE:
<223> OTHER INFORMATION: Primer for PCR multiplication

<400> SEQUENCE: 21
cgagcaagct tgctcctaca ggtgaaggc                                29

<210> SEQ ID NO 22
<211> LENGTH: 29
<212> TYPE: DNA
<213> ORGANISM: Artificial Sequence
<220> FEATURE:
<223> OTHER INFORMATION: Primer for PCR multiplication

<400> SEQUENCE: 22
gtattaagct tgaagacgaa ggagtgttg                                29

<210> SEQ ID NO 23
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 23
catccaagct tcttatgatc gggtcatgcc                               30

<210> SEQ ID NO 24
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 24
cgggatccag taacaagagt aacgatgagt                               30

<210> SEQ ID NO 25
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 25
cgatctcgag ttaccgttcg tgcacgtacg                               30

<210> SEQ ID NO 26
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 26
cgggatcccg cgataaacct gcgagggagt                               30

<210> SEQ ID NO 27
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 27
cgatctcgag gcgcacgcgc acgtaagtcc                               30
```